(12) United States Patent
Allen

(10) Patent No.: US 9,610,077 B2
(45) Date of Patent: Apr. 4, 2017

(54) ROUND-FLAT-ROUND SURGICAL BRAIDS

(71) Applicant: EVERESTMEDICA LLC, Erie, PA (US)

(72) Inventor: Brock P. Allen, Erie, PA (US)

(73) Assignee: EverestMedica LLC, Erie, PA (US)

( * ) Notice: Subject to any disclaimer, the term of this patent is extended or adjusted under 35 U.S.C. 154(b) by 0 days.

(21) Appl. No.: 15/063,215

(22) Filed: Mar. 7, 2016

(65) Prior Publication Data
US 2016/0183942 A1 Jun. 30, 2016

Related U.S. Application Data

(63) Continuation-in-part of application No. 14/455,769, filed on Aug. 8, 2014, and a continuation of application No. PCT/US2015/014307, filed on Feb. 3, 2015.

(60) Provisional application No. 62/029,951, filed on Jul. 28, 2014, provisional application No. 61/935,244, filed on Feb. 3, 2014, provisional application No.
(Continued)

(51) Int. Cl.
| | |
|---|---|
| *A61B 17/06* | (2006.01) |
| *A61F 2/08* | (2006.01) |
| *D04C 1/12* | (2006.01) |
| *D04C 3/18* | (2006.01) |
| *D04C 3/30* | (2006.01) |
| *A61B 17/00* | (2006.01) |
| *D04C 3/40* | (2006.01) |
| *D04C 3/48* | (2006.01) |

(52) U.S. Cl.
CPC ...... *A61B 17/06166* (2013.01); *A61F 2/0811* (2013.01); *D04C 1/12* (2013.01); *D04C 3/18* (2013.01); *D04C 3/30* (2013.01); *A61B 2017/00526* (2013.01); *A61B 2017/06171* (2013.01); *A61F 2002/0823* (2013.01); *A61F 2002/0852* (2013.01); *D04C 3/40* (2013.01); *D04C 3/48* (2013.01); *D10B 2509/04* (2013.01)

(58) Field of Classification Search
CPC .... D04C 1/12; D04C 3/30; D04C 3/40; A61B 17/06166
See application file for complete search history.

(56) References Cited

U.S. PATENT DOCUMENTS

| 933,339 A | 9/1909 | Rahm |
|---|---|---|
| 933,340 A | 9/1909 | Rahm |
| 2,148,164 A | 2/1939 | Krippendorf |
| (Continued) | | |

FOREIGN PATENT DOCUMENTS

| DE | 10 2009 020 053 | 11/2010 |
|---|---|---|
| EP | 0 554 653 A2 | 11/1993 |
| JP | 08131450 A | 11/1994 |

OTHER PUBLICATIONS

Branscomb et al., "New Directions in Braiding," Journal of Engineered Fibers and Fabrics, vol. 8, Issue 2, p. 11-24 (2013).
(Continued)

*Primary Examiner* — Shaun R Hurley
(74) *Attorney, Agent, or Firm* — Merchant & Gould P.C.

(57) ABSTRACT

A surgical braid comprising two non-flat sections; a tape section, the tape section being generally flat, the tape section being positioned between the two non-flat sections; and the tape section comprising a single braid, and the two non-flat sections and the tape section being formed with a continuous and gap-less braid.

19 Claims, 100 Drawing Sheets

Related U.S. Application Data

61/863,770, filed on Aug. 8, 2013, provisional application No. 62/097,847, filed on Dec. 30, 2014.

(56) References Cited

U.S. PATENT DOCUMENTS

| | | | |
|---|---|---|---|
| 2,879,687 A | 3/1959 | Leimbach et al. | |
| 3,949,755 A | 4/1976 | Vauquois | |
| 4,321,038 A | 3/1982 | Porteous | |
| 5,540,778 A | 7/1996 | Colligan et al. | |
| 5,931,077 A | 8/1999 | DeYoung | |
| 6,128,998 A | 10/2000 | Freitas et al. | |
| 6,598,510 B1 | 7/2003 | Kim | |
| 6,716,234 B2 | 4/2004 | Grafton et al. | |
| 6,907,810 B2 | 6/2005 | Kim | |
| 6,994,719 B2 | 2/2006 | Grafton | |
| 7,029,490 B2 | 4/2006 | Grafton et al. | |
| 7,892,256 B2 | 2/2011 | Grafton et al. | |
| 7,908,956 B2 | 3/2011 | Dow et al. | |
| 8,088,146 B2 | 1/2012 | Wert et al. | |
| 8,347,772 B2 | 1/2013 | Dow et al. | |
| 8,448,555 B2 | 5/2013 | Dow et al. | |
| 8,794,118 B2 | 8/2014 | Dow et al. | |
| 8,943,941 B2 * | 2/2015 | Dow | D04C 3/00 87/11 |
| 9,038,520 B2 * | 5/2015 | Kang | F16F 1/00 87/9 |
| 2001/0025563 A1 | 10/2001 | Bettger | |
| 2003/0050666 A1 | 3/2003 | Grafton | |
| 2004/0094024 A1 | 5/2004 | Kim | |
| 2007/0135840 A1 | 6/2007 | Schmieding | |
| 2008/0051834 A1 | 2/2008 | Mazzocca et al. | |
| 2009/0188380 A1 * | 7/2009 | Dow | H04N 21/23424 87/11 |
| 2011/0203446 A1 * | 8/2011 | Dow | D04C 1/06 87/11 |
| 2012/0059413 A1 | 3/2012 | Calero et al. | |
| 2013/0167710 A1 | 7/2013 | Dow et al. | |
| 2014/0013931 A1 | 1/2014 | Dow et al. | |
| 2015/0045831 A1 * | 2/2015 | Allen | A61F 2/0811 606/228 |

OTHER PUBLICATIONS

International Search Report and Written Opinion for Application No. PCT/US2014/050435 mailed Jan. 14, 2015.

International Search Report for Application No. PCT/US15/14307 mailed Jun. 24, 2015.

* cited by examiner

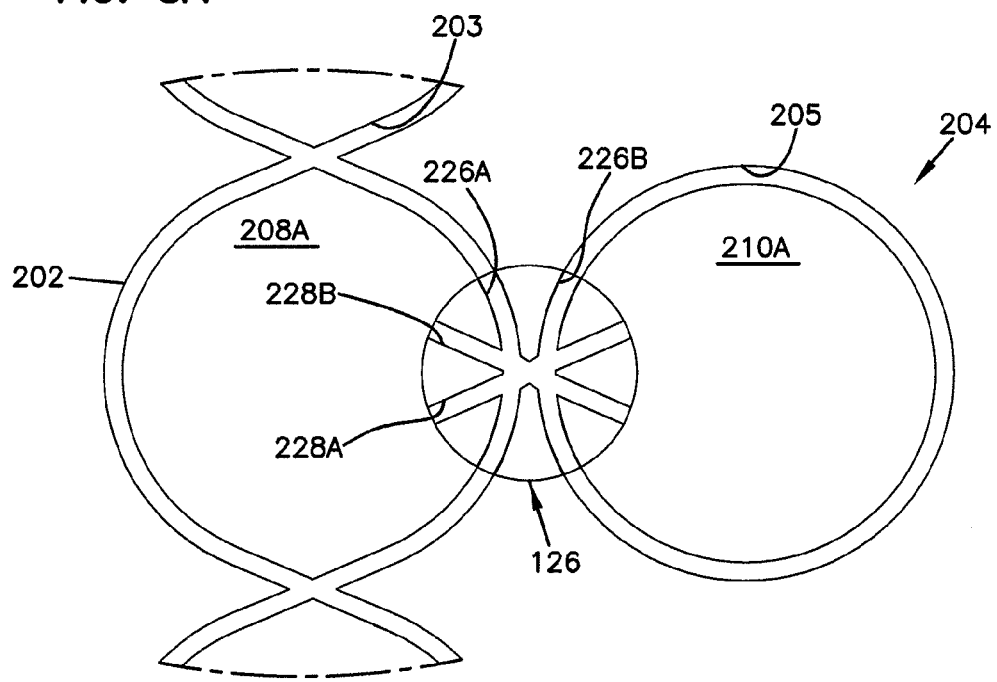
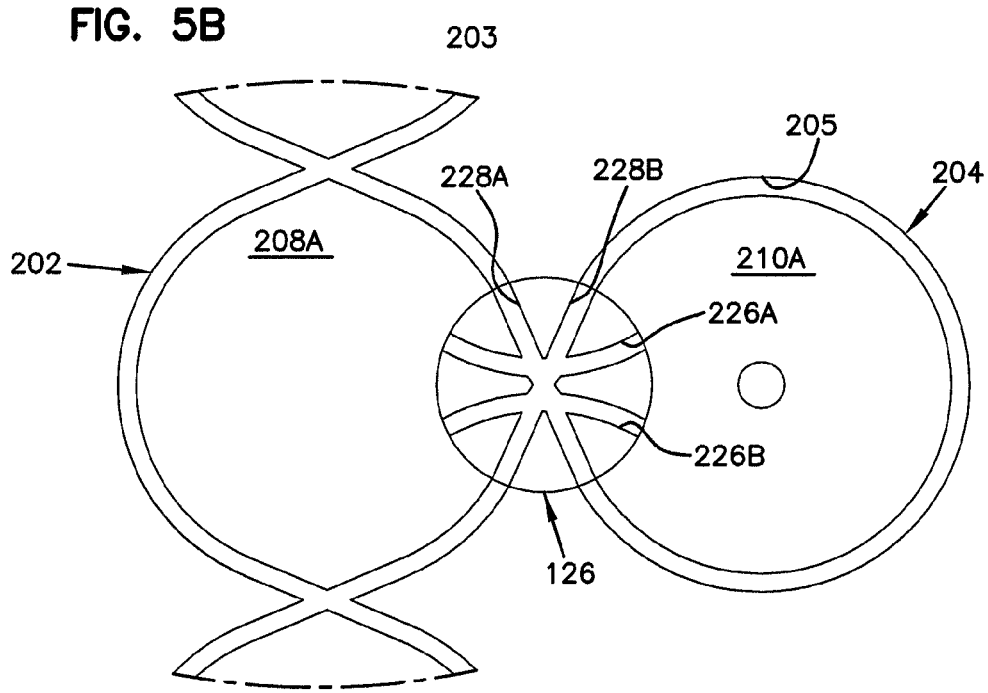

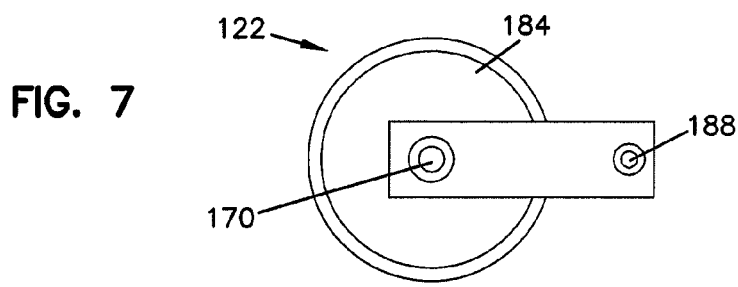
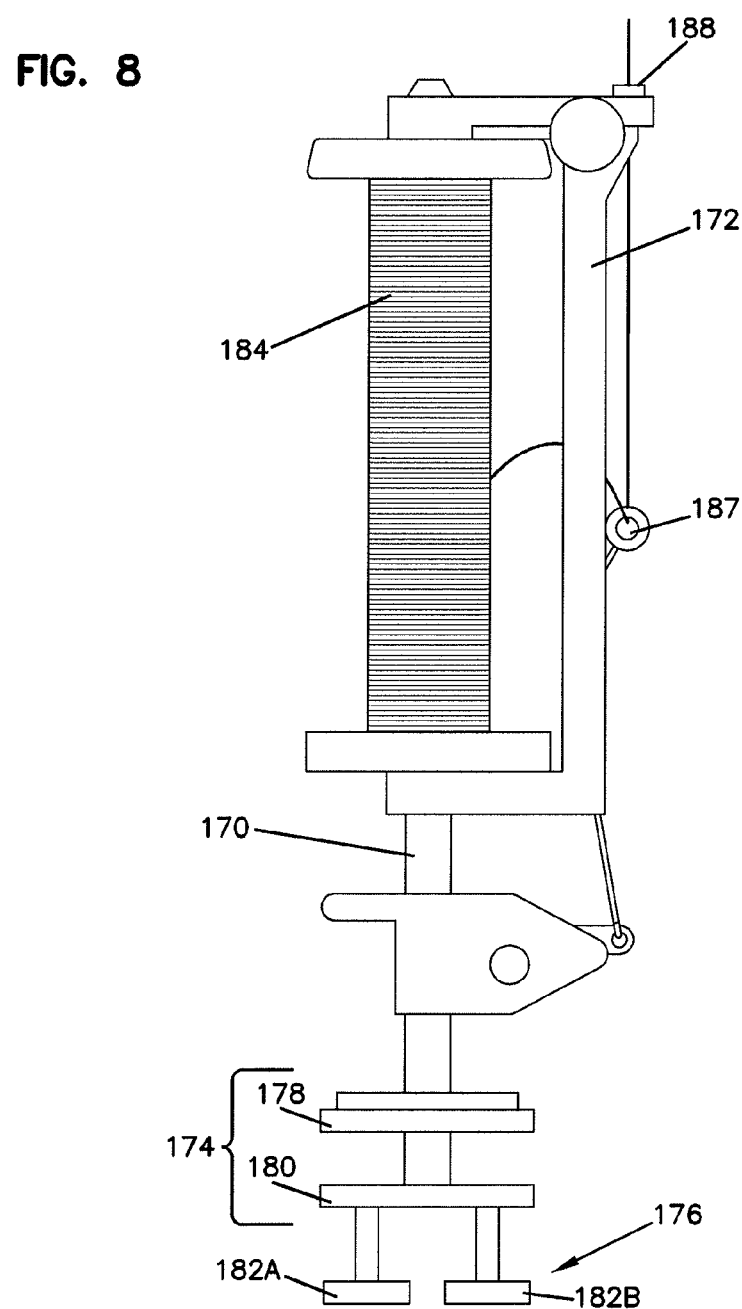

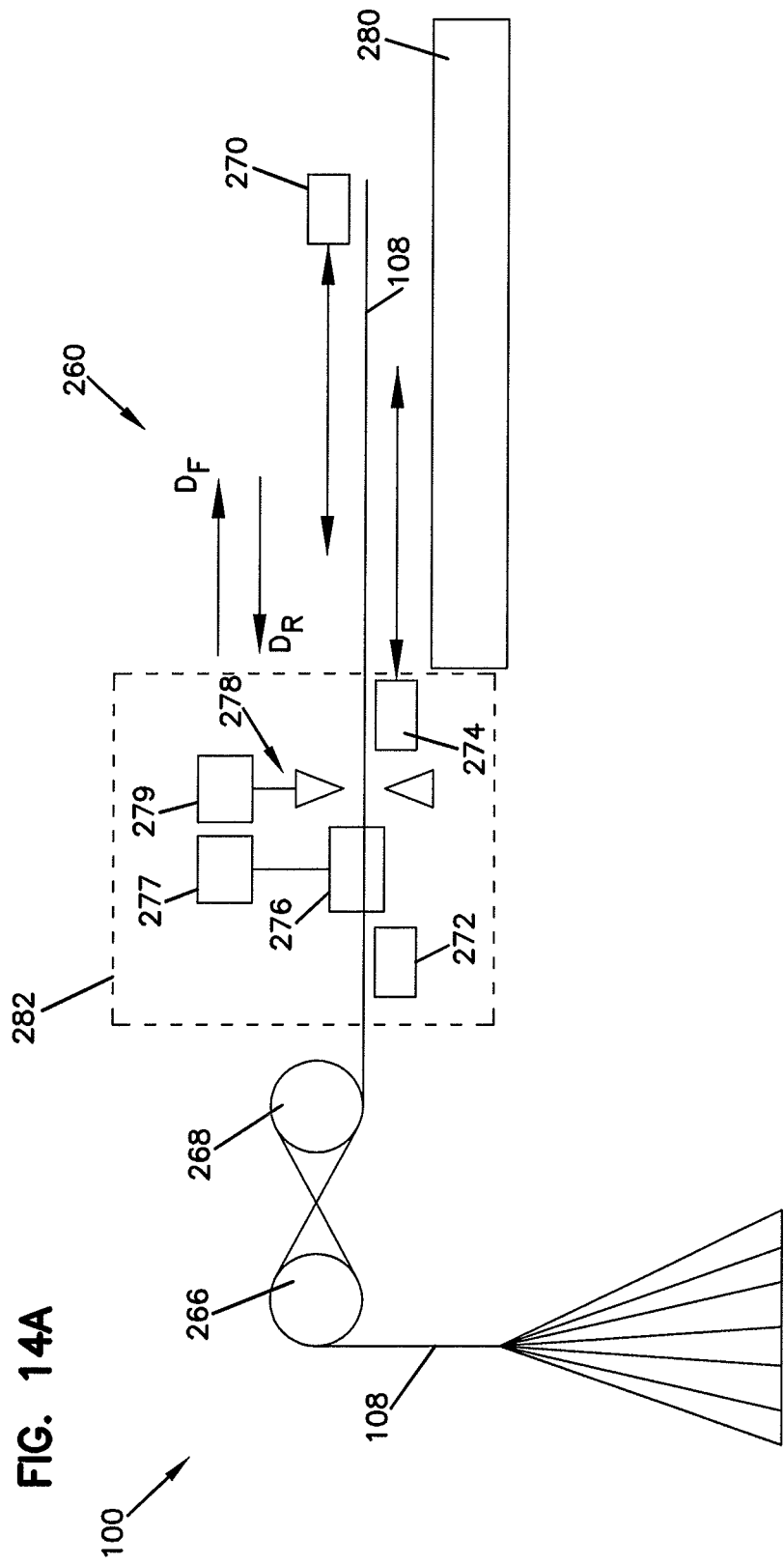

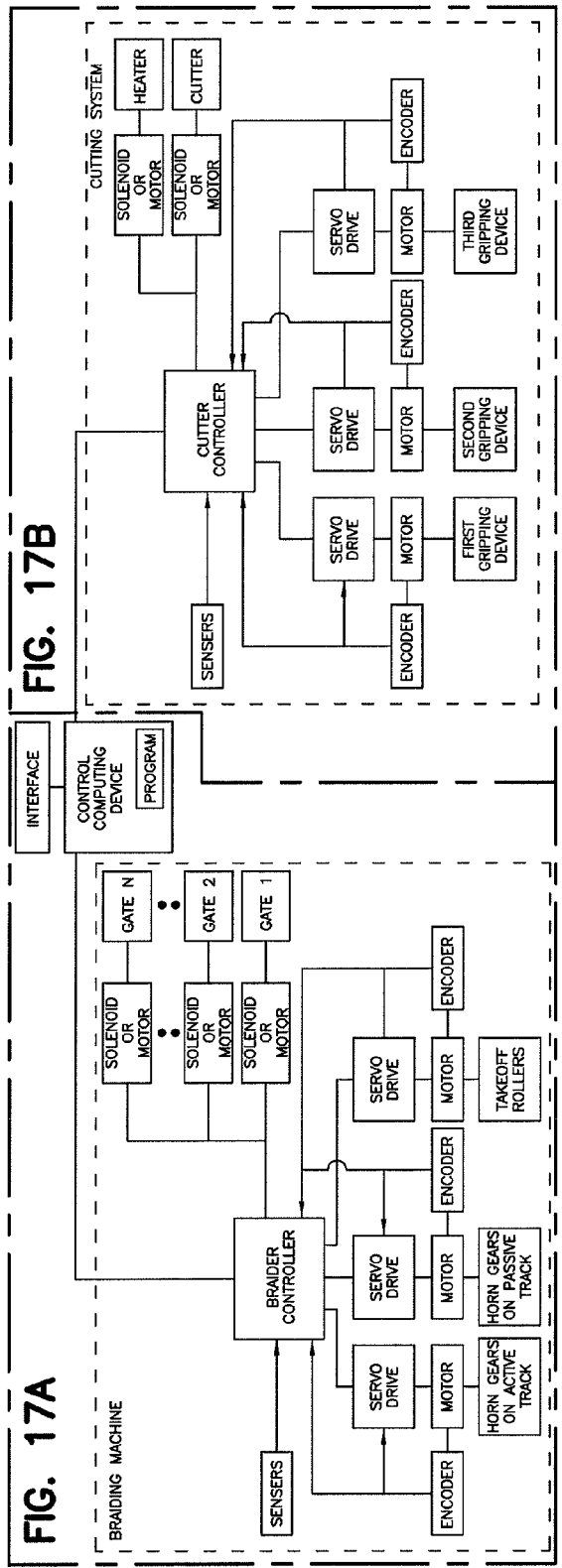

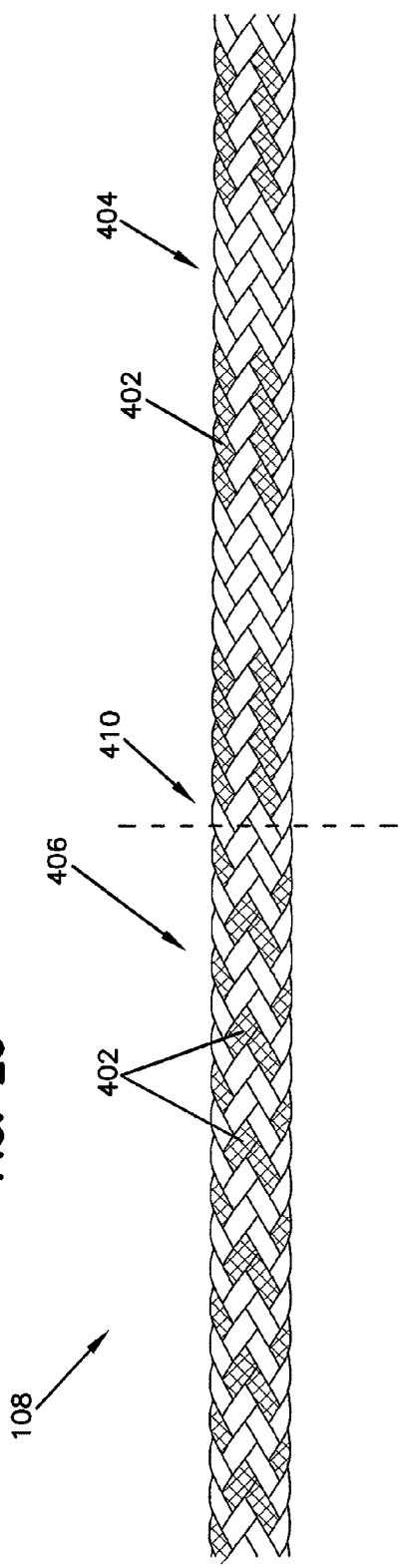
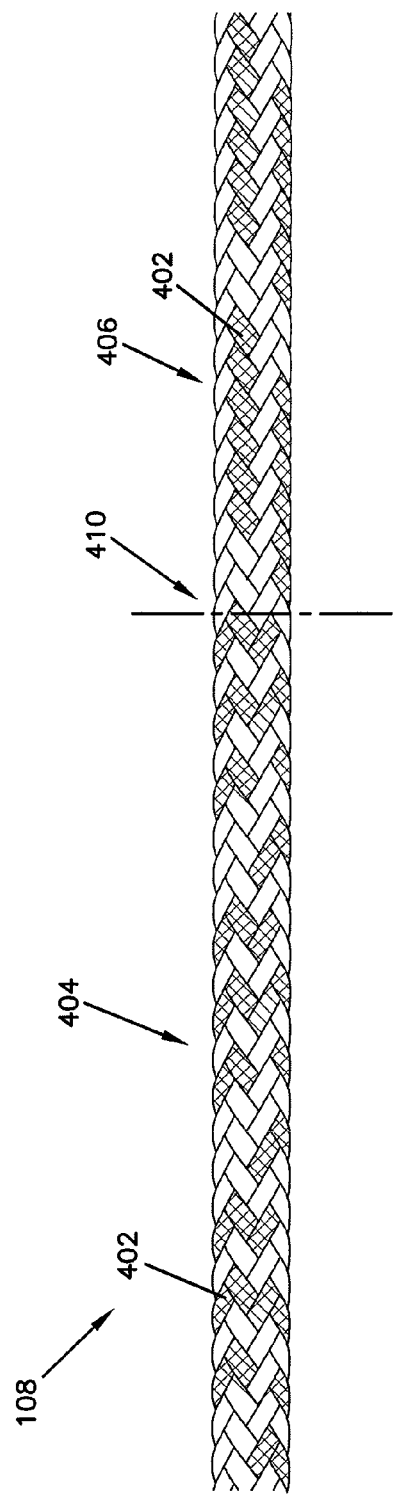
FIG. 20
FIG. 21

[STEP 1]

[STEP 2]

[STEP 3]

[STEP 4]

[STEP 5]

[STEP 6]

[STEP 7]

[STEP 8]

[STEP 9]

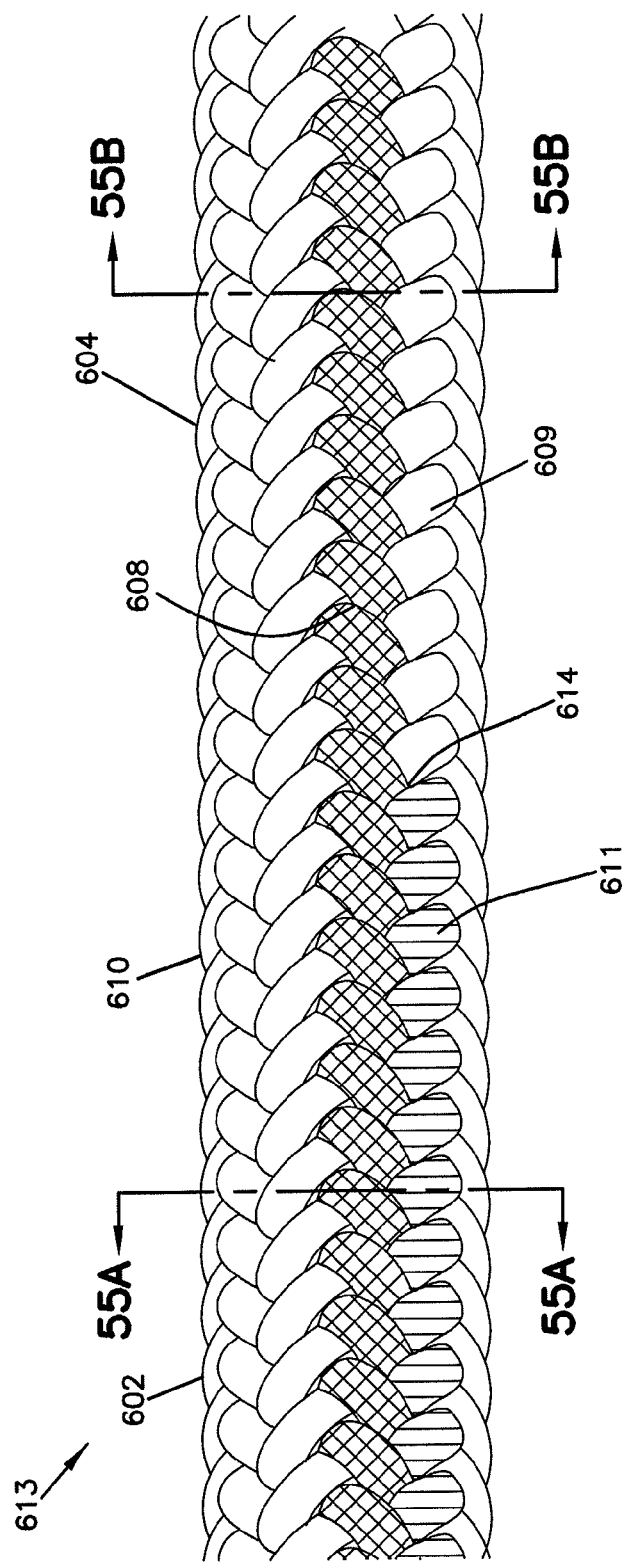

ROUND-FLAT-ROUND SURGICAL BRAIDS

REFERENCE TO COPENDING APPLICATIONS

This application is a continuation-in-part of U.S. Ser. No. 14/455,769 entitled SURGICAL BRAIDS filed Aug. 8, 2014, which claims priority to U.S. Provisional Ser. No. 62/029,951 entitled SURGICAL BRAIDS AND BRAIDING MACHINE filed Jul. 28, 2014, U.S. Provisional Ser. No. 61/863,770 entitled SURGICAL BRAID filed Aug. 8, 2013, and U.S. Provisional Ser. No. 61/935,244 entitled SURGICAL BRAID HAVING COLOR MARKINGS filed Feb. 3, 2014; this application also is a continuation of PCT Application No. PCT/US15/14307 entitled SURGICAL BRAID filed Feb. 3, 2015, which claims priority to U.S. Provisional Ser. No. 62/097,847 entitled SURGICAL BRAID filed Dec. 30, 2014. The entire disclosures of the foregoing applications are hereby incorporated by reference.

BACKGROUND

Surgical braids are generally used by physicians and other medical professionals to close an open wound or otherwise repair tissue, in an effort to facilitate proper healing. Surgical braids are also used by orthopedic surgeons for a variety of purposes such as securing ligaments and muscles to a bone. Surgical braids are typically formed by braiding together several strands of filaments, fibers, yarns, and the like.

During operation, the particular stitch and knot used by a surgeon can be important to the healing process of the wound. If stitched and tied improperly, the surgical braid could damage tissue or not adequately secure the tissue. Surgical braids formed of a single color are often difficult for a medical professional to see and track. In particular, due to the uniform color, medical professionals have difficulty identifying movement and position of the surgical braid.

SUMMARY

In general terms, this patent document is directed to surgical braids, and apparatuses and method for making surgical braids.

One aspect is a surgical braid comprising two non-flat sections. A tape section is positioned between the two non-flat sections and is generally flat. The two non-flat sections and the tape section are formed with a continuous and gap-less braid.

Another aspect of the surgical braid comprises two non-flat sections. A tape section is positioned between the two non-flat sections and is generally flat. The tape section comprises a single braid, and the two non-flat sections and the tape section are formed with a continuous and gap-less braid.

Another aspect of the surgical braid comprises a plurality of strands braided into two non-flat sections and a tape section, the tape section being generally flat and positioned between the two non-flat sections. The surgical braid further comprises first and second end portions, and first and second transition portions. The first end portion is oppositely disposed from the second end portion. Two or more of the strands are continuously braided between the first and second end portions. The first transition portion positioned between one non-flat section and the tape section, the second transition portion positioned between the other non-flat section and the tape section. The tape section comprises first and second edge portions extending between the first and second transition portions, the first edge portion oppositely disposed from the second edge portion. The plurality of strands are interlaced into a single braid and a substantially uniform pattern as they pass through the tape section, the single braid and substantially uniform pattern extends between the first and second transition portions and between the first and second end portions forming a single flat braid between the two non-flat sections.

BRIEF DESCRIPTION OF THE DRAWINGS

FIGS. 5A and 5B illustrate an example operation of the gate of FIGS. 4A and 4B.

FIG. 7 is a top view of the bobbin carrier assembly of FIG. 6.

FIG. 8 is a side view of the bobbin carrier assembly of FIG. 6.

FIG. 14A is a schematic view of another example inline cutting system of FIG. 12, which is configured to be used with a braiding machine.

FIG. 17 is a schematic diagram of an example control system for a braiding machine and a cutting system.

FIG. 20 illustrates an example braid with alternating different patterns defined by four trace strands.

FIG. 21 illustrates an example braid with alternating different patterns defined by six trace strands.

FIG. 54 is a side view schematic diagram of a 16-filament surgical braid showing details of the fibers forming the surgical braid.

DETAILED DESCRIPTION

Figure 1:
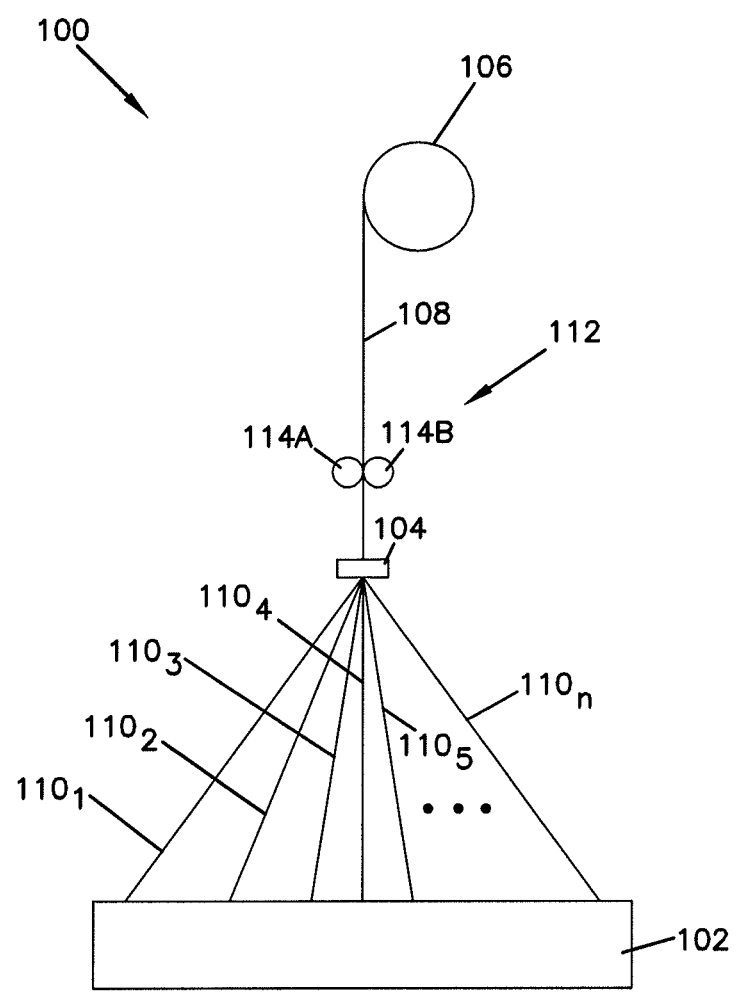
FIG. 1 is a schematic side view of an example braiding machine.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprises," "comprising," "have," "haves," "having," "include," "includes," "including," and "such as" are interchangeable and are not intended to be limiting. For example, the term "including" shall be interpreted to mean "including, but not limited to." All ranges provided herein include the upper and lower values of the range unless explicitly noted. Additionally, unless stated otherwise, or clearly intended otherwise by the content of their use, shapes, configurations, structures, values and the like can vary slightly due to a variety of circumstances such as manufacturing tolerances and variables; variations in material, such as the material's resiliency, density, stiffness, compression; and the like. Additionally terms such as "connected" are not limited to mean that structures are directly linked or fastened together, but rather that they are operationally linked together such that there can be intervening structures.

FIG. 1 is a schematic side view of an example braiding machine 100. In at least some embodiments, the braiding machine 100 includes a braiding assembly 102, a braiding guide mechanism 104, and a take-up mechanism 106. The braiding machine 100 operates to produce a braid 108 from a plurality of strands $110_1$-$110_n$. In some embodiments, the braiding machine 100 can further include a pinching mechanism 112.

The braiding assembly 102 operates to feed the plurality of strands $110_1$-$110_n$ through the guide assembly 104 and rotates the strands $110_1$-$110_n$ to braid them together. In at least some embodiments, the braiding assembly 102 includes horn gear assemblies, bobbin carrier assemblies, and transition mechanisms (e.g., gates). An example braiding assembly 102 is illustrated and described in more detail herein.

The braiding guide 104 defines a hole or opening through which strands $110_1$-$110_n$ pass as they move from the braiding assembly 102 to the take-up mechanism 106. The braiding guide pulls the strands together to form the braid as the braiding assembly 102 moves the strands $110_1$-$110_n$ along a path. In at least some embodiments, the braiding guide mechanism 104 includes an iris that defines the hole through which the strands pass and is capable of adjusting the cross-sectional area of the hole. The braiding guide mechanism 104 can have other embodiments in addition to the embodiments described herein.

The take-up mechanism 106 is configured to wind the braid 108 therearound after the braid 108 passes through the guide assembly 104. In at least some embodiments, the take-up mechanism 106 includes a take-up reel. The braid 108 wound onto the take-up mechanism 106 can be manually delivered to post-braiding processes, such as cleaning or sterilizing the braid, cutting the braid 108 to length to form individual braids, and other processing. In other embodiments, the take-up mechanism 106 can be used to automatically convey the braid 108 to the cutting system, as described and illustrated in more detail herein.

As described in more detail herein, the plurality of strands $110_1$-$110_n$ can include one or more trace strands that have a different color than the rest of the strands. The trace strands can be used to enhance visibility of the braid 108 and help a surgeon distinguish between different sections of the braid 108. In at least some embodiments, the braiding assembly 102 can operate to alternate between braiding the strands $110_1$-$110_n$ into a braid 108 having one pattern of trace strands and braiding the strands $110_1$-$110_n$ into a braid 108 having a different pattern of the trace strands to produce a braid 108 having a plurality of alternating patterns of trace strands. In alternative embodiments, the braiding assembly can operate to alternate between braiding the strands $110_1$-$110_n$ using one color scheme and braiding the strands $110_1$-$110_n$ using a different color scheme. Other alternative embodiments can have a combination of varying patterns and color schemes.

In yet other embodiments, the braid 108 can have a plurality of tubular sections having a generally circular circumference and flat sections. For example, the braiding assembly 102 can operate to alternate between braiding the strands $110_1$-$110_n$ into a generally round, tubular braid and braiding the strands $110_1$-$110_n$ into a flat braid to produce a braid having a plurality of alternating round and flat sections. The braid 108 having the round section and the flat section also can include one or more colored trace strands to provide a pattern, alternating patterns, alternating colors, or combinations thereof.

In some embodiments, the braiding machine 100 can include the pinching mechanism 112 configured to operate to compress the braid 108 to transform a round, tubular section of the braid 108 into an out-of-round section. For braids having a flat section, the pinch rollers also can be used to minimize any curvature along the cross-sectional area of the flat section. In at least some embodiments, the pinching mechanism 112 includes opposing pinch rollers 114A and 114B. The pinching mechanism 112 operates to receive the braid 108 between the pinch rollers 114A and 114B after the braid 108 passes through the braiding guide mechanism 114. The pinch rollers 114A and 114B compress the braid 108 such that the round, tubular section compresses or transforms into the out-of-round section. The pinch rollers 114A and 114B can urge the round, tubular section into a flatter profile.

The pinch rollers 114A and 114B are formed with a soft material having a hardness of about 50 durometers, although other possible embodiments can have a hardness greater than or less than 50 durometers. A soft material compresses the braid 108 more gently than a hard material (e.g., metal or hard plastic) so that the pinch rollers 114A and 114B will compress the round, tubular sections of the braid 108 into the out-of-round sections, but not completely flatten the braid 108 or damage the strands $110_1$-$110_n$. The pinch rollers 114A and 114B can be made from a variety of materials such as a soft polymer. Additionally, a spring assembly (not shown) urges the pinch rollers 114A and 114B towards one another to provide a force sufficient to compress the braid 108. The spring assembly includes springs (not shown) and set screws (not shown) that pass along the center of the springs. The set screws can be rotated to adjust the tension of the springs and the force that each of the pinch rollers 114A and 114B exerts against the braid 108. Other embodiments of the braiding machine 100 do not include the pinching mechanism 112.

Figure 2:
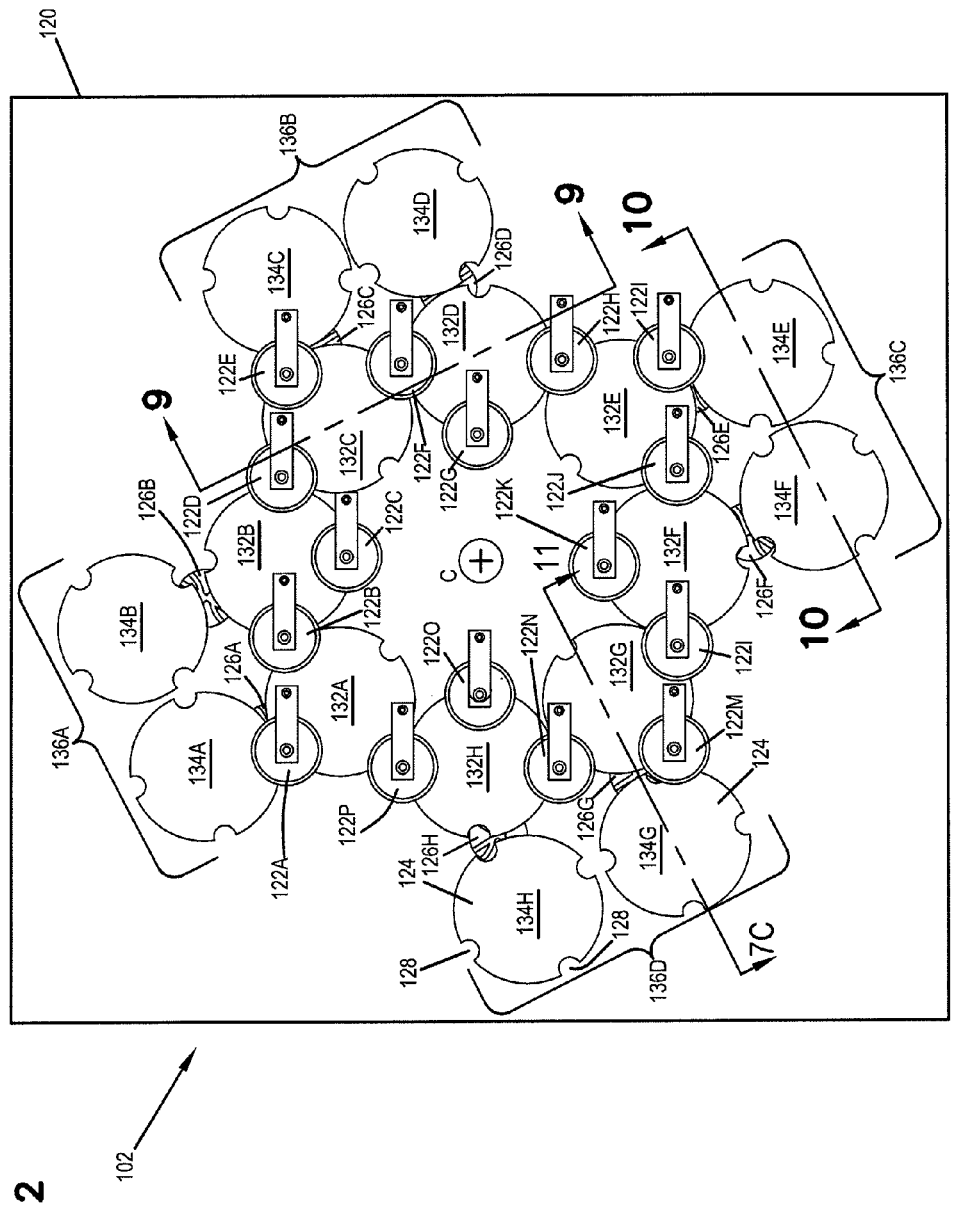
FIG. 2 is a schematic top view of an example braiding assembly.

FIG. 2 is a schematic top view of an example braiding assembly 102. In at least some embodiments, the braiding assembly 102 includes a braiding track plate 120, a plurality of bobbin carrier assemblies 122A-122P, a plurality of horn gear assemblies 132A-132H and 134A-134H, and a plurality of gates 126A-126H.

As describe in more detail herein, the braiding track plate 120 defines one or more tracks 202 and 204 (as illustrated in FIGS. 3a-3f) configured to guide the plurality of bobbin carrier assemblies 122A-122P along defined paths. The plurality of bobbin carrier assemblies 122A-122P operate to carry strands $110_1$-$110_n$ around the braiding machine 100. The plurality of horn gear assemblies 132A-132H support and drive the bobbin carrier assemblies along one or more active paths defined by the active track on the braiding track plate 120. The plurality of horn gear assemblies 134A-134H support and drive the bobbin carrier assemblies along one or more passive paths defined by the passive tracks on the braiding track plate 120. The gates 126A-126H selectively guide the bobbin carrier assemblies 122A-122P from the active track to one or more passive tracks.

In the depicted embodiment, the braiding assembly 102 includes 16 bobbin carrier assemblies 122A-122P to produce a 16-end braid 108. Other embodiment can include any suitable number of bobbin carrier assemblies 122 to make braids having any desired numbers of strands. For example, alternative braiding assemblies could have 8, 24, or 32 bobbin carrier assemblies 122, or any other suitable number of bobbin carrier assemblies 122. The braiding assembly 102 also can have different number of horn gear assemblies 132 and 134 along the active and passive tracks and different number of gates 126 than illustrated in the exemplary shown in FIG. 2.

In at least some embodiments, the horn gear assemblies 124 can include a set of first horn gear assemblies 132A-132H and a set of second horn gear assemblies 134A-134H. In the depicted embodiment, the set of first horn gear assemblies 132A-132H are active track horn gear assemblies and are arranged adjacent one another around a machine axis C. The first horn gear assemblies 132A-132H are operated so that that the bobbin carrier assemblies 122A-122P move across adjacent first horn gear assemblies 132A-132H. The first horn gear assemblies 132A-132H are operated in a manner that two adjacent first horn gear assemblies are rotated in opposite direction. For example, the first horn gear assemblies 132A, 132C, 132E and 132G are rotated counter-clockwise while the second horn gear assemblies 132B, 132D, 132F and 132H are rotated clockwise. In other embodiments, the first horn gear assemblies can be configured to rotate in different manners. As described in more detail herein, the first horn gear assemblies 132 can be mechanically linked and operated together.

The second horn gears 134A-134H are passive track horn gears and are arranged radially outside the set of the first horn gear assemblies 132A-132H and are located adjacent the first horn gear assemblies 132A-132H, respectively. In the depicted embodiment, the set of second horn gear assemblies are paired in quadrants 136A-136D. For example, the passive horn gear assemblies 134A and 134B are paired in a first quadrant 136A and operated to rotate in opposite directions. The passive horn gear assemblies 134A and 134B in the first quadrant 136A are arranged adjacent active horn gear assemblies 132A and 132B, respectively, so that at least one of the bobbin carrier assemblies 122A-122P can selectively move between the active horn gear assemblies 132A and 132B and the passive horn gear assemblies 134A and 134B in the first quadrant 136A. Similarly to the first quadrant 136A, the second horn gear assemblies 134C and 134D are paired in a second quadrant 136B and operated to rotate in opposite direction. The passive horn gear assemblies 134C and 134D are adjacent active horn gear assemblies 132C and 132D. Similarly, the third quadrant 136C includes second horn gear assemblies 134E and 134F, which are adjacent active horn gear assemblies 132E and 132F, respectively. The fourth quadrant 136D includes second horn gear assemblies 134G and 134H, which are adjacent active horn gear assemblies 132G and 132H, respectively.

In at least some embodiments and as described in more detail herein, the passive horn gears 134A-134H in quadrants 136A-136D can be mechanically linked with an arrangement of gears, or any other suitable structure, to be operated together by a single motor connected to one of the second horn gear assemblies 134A-134H. In other embodiments, each pair of passive horn gears 134 in the quadrants 136A-136D can be independently operated by separate motors that are connected to one of the passive horn gears in the pair (e.g., passive horn gear 134A in quadrant 136A). In yet other embodiment, each of the passive horn gears 134A-134H are each connected to a separate motor and can be driven independently from each other.

In at least some embodiments, the plurality of gates 126A-126H can be arranged between the active horn gear assemblies 132A-132H and the passive horn gear assemblies 134A-134H, respectively. The gates 126A-126H can be selectively operated to enable at least one of the bobbin carrier assemblies 122A-122P to move between the active horn gear assemblies 132A-132H and their adjacent passive horn gear assemblies 134A-134H, respectively. The structure and operation of the gates 126A-126H are described in more detail herein.

Figure 3A:
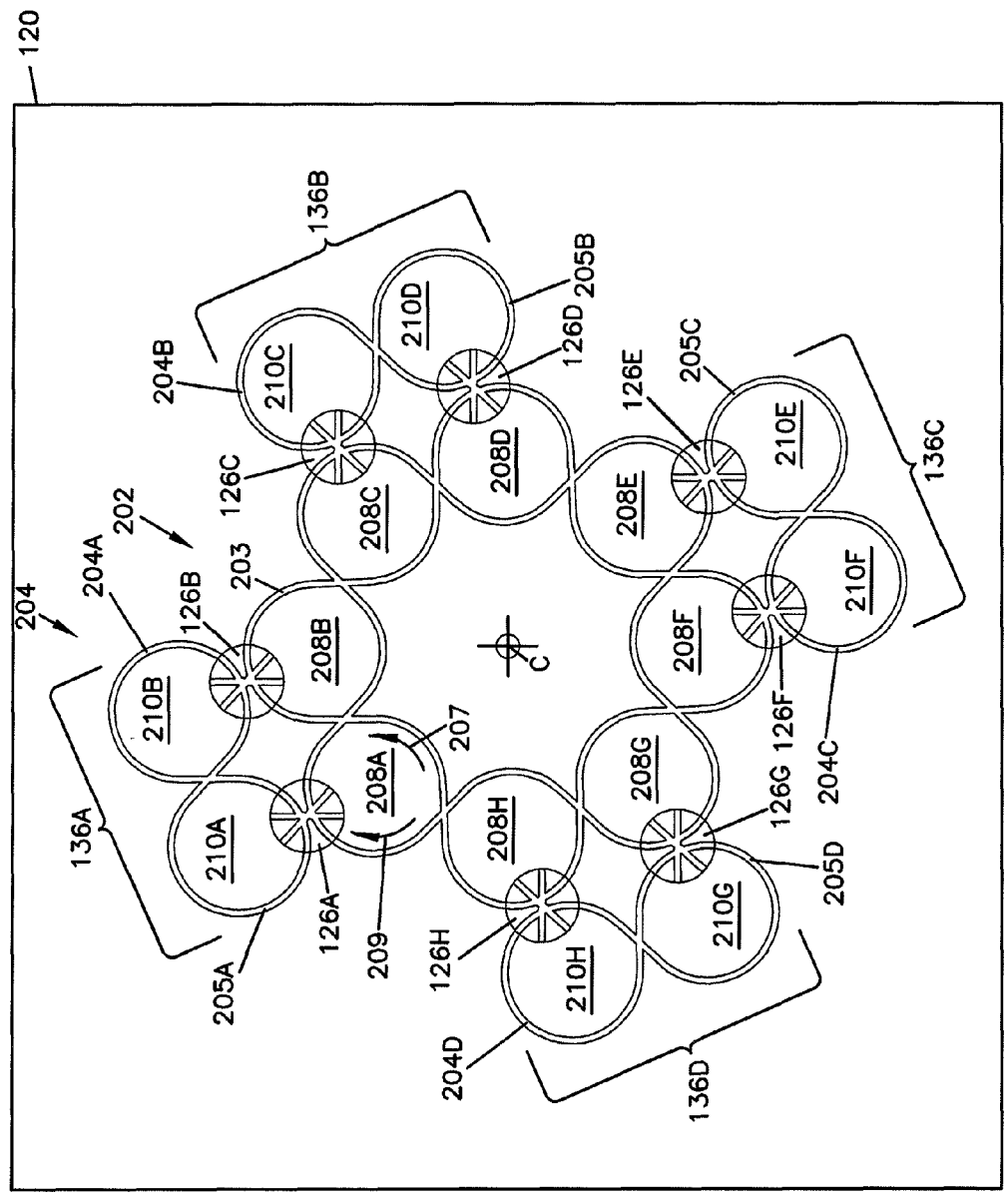
FIGS. 3A-3F illustrate examples of a braiding track plate with example gates engaged.

FIG. 3a illustrates the embodiment of the track plate 120 and active and passive tracks as discussed with reference to FIG. 2. In this embodiment, the track plate 120 is a plate that defines a plurality of slots or grooves 203 that form an active track 202. The active track 202 is formed to correspond to the active horn gear assemblies 132A-132H and guide the bobbin carrier assemblies 122A-122H as they are propelled by the active horn gear assemblies 132A-132H as explained in more detail herein. The active track 202 includes eight first sub-tracks 208A-208H, which correspond to the active horn gear assemblies 132A-132H, respectively. The first sub-tracks 208A-208H are arranged abutted to each other around the machine axis C so that the bobbin carrier assemblies 122A-122H selectively move between adjacent active sub-tracks 208A-208H as they move along the active track 202. The active track 202 provides a clockwise active path 207 and a counter clockwise active path 209, each of which oscillates and are out-of-phase from one another.

A plurality of passive tracks 204A-204D are also formed by grooves or slots 205A-205D, respectively, defined in the braiding track plate 120. The passive track 204A is in quadrant 136A and includes passive sub-tracks 210A and 210B, which are adjacent to active sub-tracks 208A and 208B, respectively. The passive track 204A is in quadrant 136B and includes passive sub-tracks 210C and 210D, which are adjacent to active sub-tracks 208C and 208D, respectively. The passive track 204C is in quadrant 136C and includes passive sub-tracks 210E and 210F, which are adjacent to active sub-tracks 208E and 208F, respectively. The passive track 204D is in quadrant 136D and includes passive sub-tracks 210G and 210H, which are adjacent to active sub-tracks 208G and 208H, respectively. The passive sub-tracks 210A-210G correspond to passive horn gear assemblies 134A-134H, respectively, and guide the bobbin carrier assemblies 122A-122H as they are propelled by the passive horn gear assemblies 134A-134H as explained in more detail herein. Additionally, the bobbin carrier assemblies 122A-122P can selectively move between the active track 202 and one or more of the passive tracks 204A-204D as described in more detail herein.

The gates 126A-126H are positioned between active sub-tracks 208A-208H and passive sub-tracks 210A-210H, respectively. Each gate 126A-126H has an open position and a closed position and define grooves or slots for guiding the bobbin carrier assemblies 122A-122P either between adjacent active and passive sub-tracks (e.g., 208A and 210A), or along the active sub-track and past the adjacent passive sub-tracks (e.g., along 208A and past 210A).

Referring to FIGS. 4a, 4b, 5a, and 5b, each gate 126 includes a gate body 220 that defines inter-track slots or grooves 228A and 228B that form inter-track paths, and intra-track slots or grooves 226A and 226B that form intra-track paths. Each gate 126 has an open position and a closed position.

FIGS. 5a and 5b illustrate the open and closed positions of the gate 126 with respect to active sub-track 208A, passive sub-track 210A, and gate 126A, although the operation described with respect to gate 126A will apply to all of the gates and the subtracks with which they are related. When in the open position as illustrated in FIG. 5b, the inter-track groove or path 228A has one end aligned with and open to the groove 203 of active sub-track 208A and an opposite end aligned with and open to the groove 205 of passive sub-track 210A. Similarly, the inter-track groove or path 228B has one end aligned with and open to the groove 203 of active sub-track 208A and an opposite end of inter-track groove 228A aligned with and open to the groove 205 of passive sub-track 210A. The inter-track paths 228A and 228B provide a bridge to guide bobbin carrier assemblies between an active sub-track (e.g., 208A) and its adjacent passive sub-track (e.g., 210A). In the exemplary embodiment illustrated in FIGS. 5a and 5b, the bobbin carrier assemblies 122 can travel along the active sub-track 208A in one direction (e.g., clockwise or counter clockwise), move to the adjacent passive sub-track 210A, and then travel along the passive sub-track in an opposite direction (e.g., counterclockwise or clockwise), respectively. The intra-track grooves or paths 226A and 226B are not aligned with either the active or passive sub-tracks 208A or 210A when the gate 126A is in the open position.

When in the closed position as illustrated in FIG. 5a, the intra-track groove or path 226A has both ends aligned with and open to opposing segments of the groove 203 of active sub-track 208A. The intra-track groove or path 226A is configured to maintain a continuous path along the active sub-track 208A that bypasses the adjacent passive sub-track 210A, and to guide the bobbin carriers 222 to stay on the active sub-track 208A and move past the adjacent passive sub-track 210A. Similarly, the intra-track groove or path 226B has both ends aligned with and open to opposing segments of the groove 205 of active sub-track 210A. The intra-track groove or path 226B is configured to maintain a continuous path along the passive sub-track 210A that bypasses the adjacent active sub-track 208A and to guide the bobbin carriers 222 to stay on the passive sub-track 210A and move past the adjacent active sub-track 208A. An alternative embodiment of the gates 126 might include only one intra-track groove or path, such as the intra track groove or path 226A to selectively maintain bobbin carrier moving along the active sub-track 208A and past the passive sub-track 210A. The inter-track grooves or paths 228A and 228B are not aligned with either the active or passive tracks when the gate 126 is in the closed position.

In the illustrated embodiment, the gates 126 can be rotatably nested in the braiding track plate 120 such that the top surface 210 of the gate body 220 is flush with the top surface of the braiding track plate 120. In this embodiment, at least the portion of the gates 126 nested in the braiding track plate 120 are cylindrically shaped. The gates 126 can be rotatably supported on the braiding track plate 120 in different manners. In some embodiments, the gates 126 can be held by the gate actuating system 164. In other embodiments, the body 220 of the gates 126 can have a male projection configured to be slidably engaged with a corresponding slot, groove, shoulder, ridge, or similar structure formed in the braiding track plate 120. By defining the length or range of the slot, the range of the rotational movement of the gates 126 can be limited within the slot.

In at least some embodiments, the gates 126 are switched between the open and closed positions by rotating them 90 degrees. In other embodiments, the gates 126 can be movable between the open and closed positions by rotating them with a different angle than 90°. The gates 126 can rotate in one direction to alternately move between the open position and the closed position. For example, when the gates 126 can rotate a certain degree (e.g., 90 degrees) clockwise from the open position, the gate 126 comes to the closed position. As the gates 126 further rotate with the same amount of angle (e.g., 90 degrees), they come to the open position again. In other embodiments, the gates 126 can rotate both directions to move between the open and closed positions. In yet other configurations are possible in alternative embodiments.

Figure 3B:
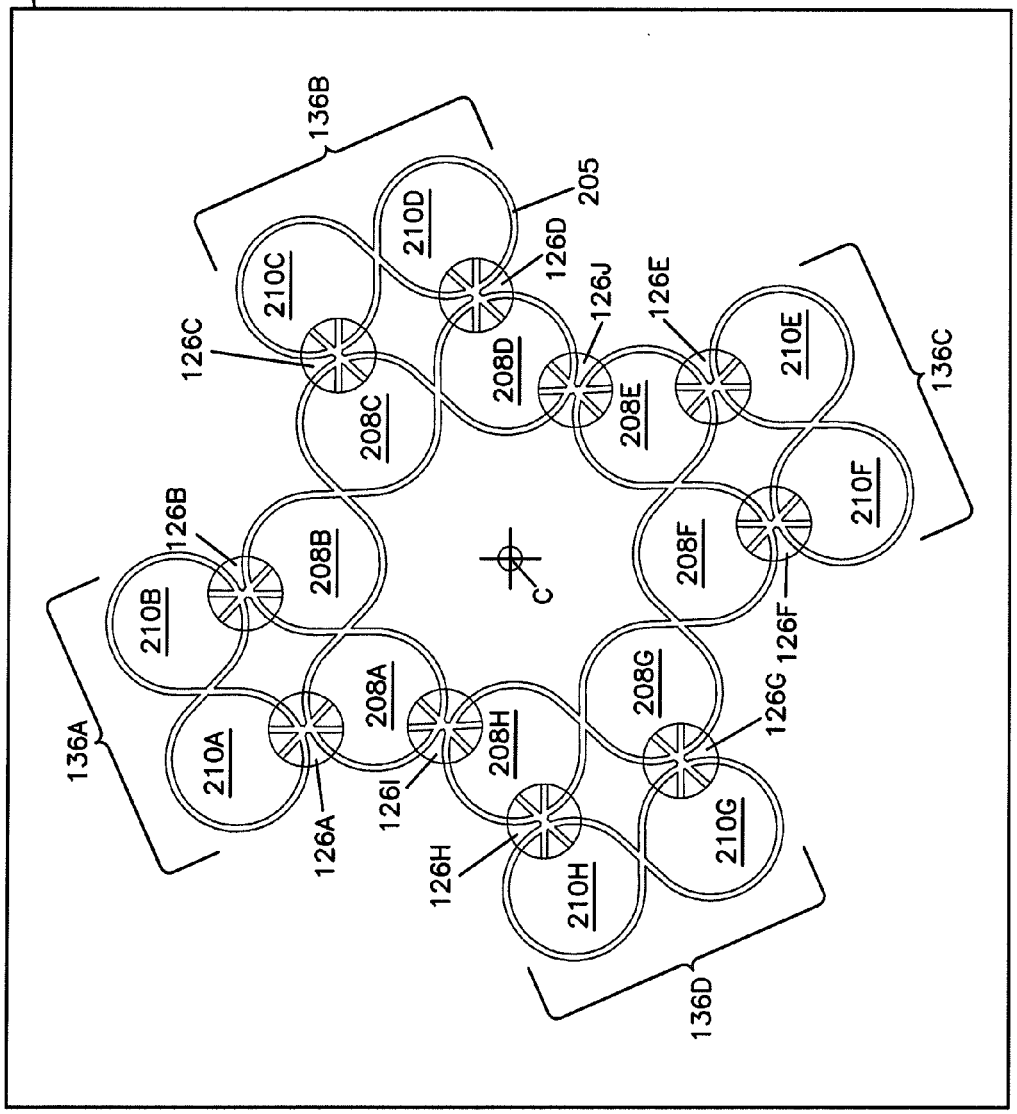
Figure 3C:
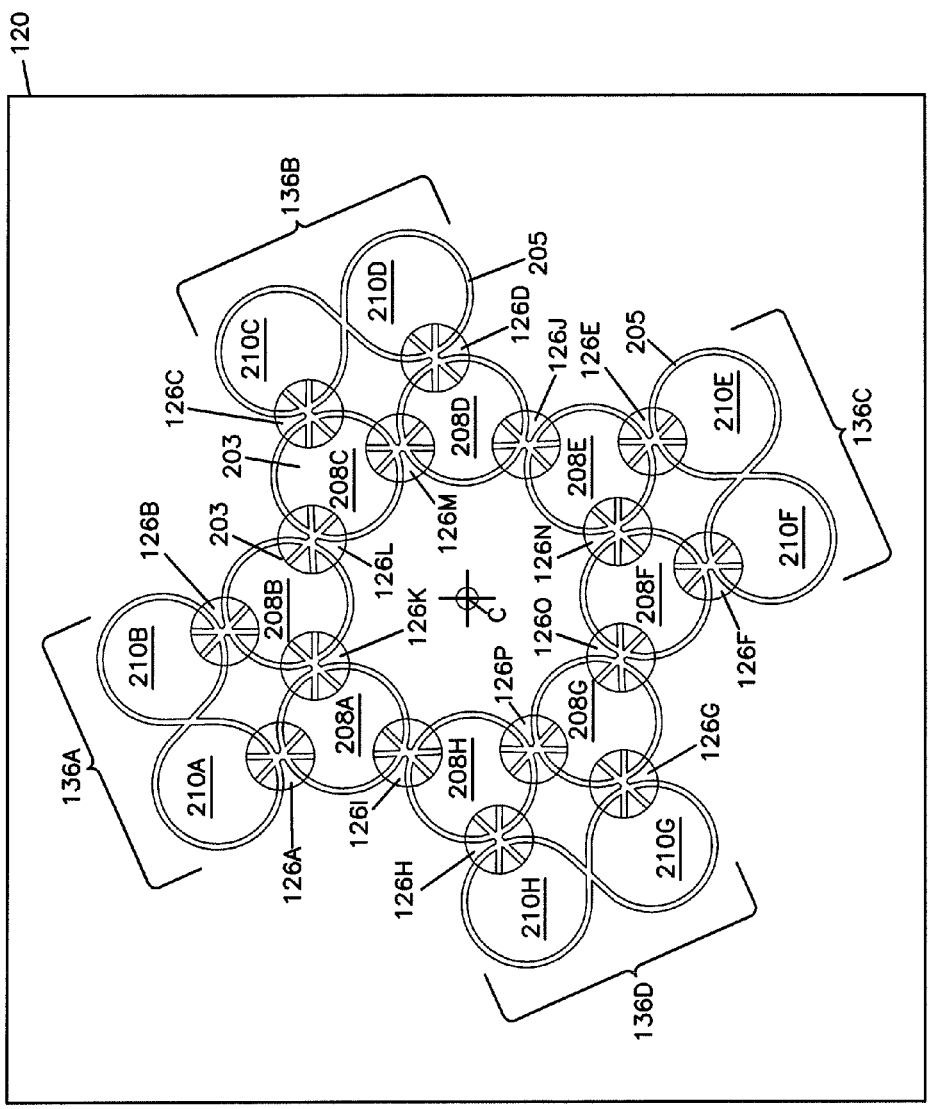
Figure 3D:
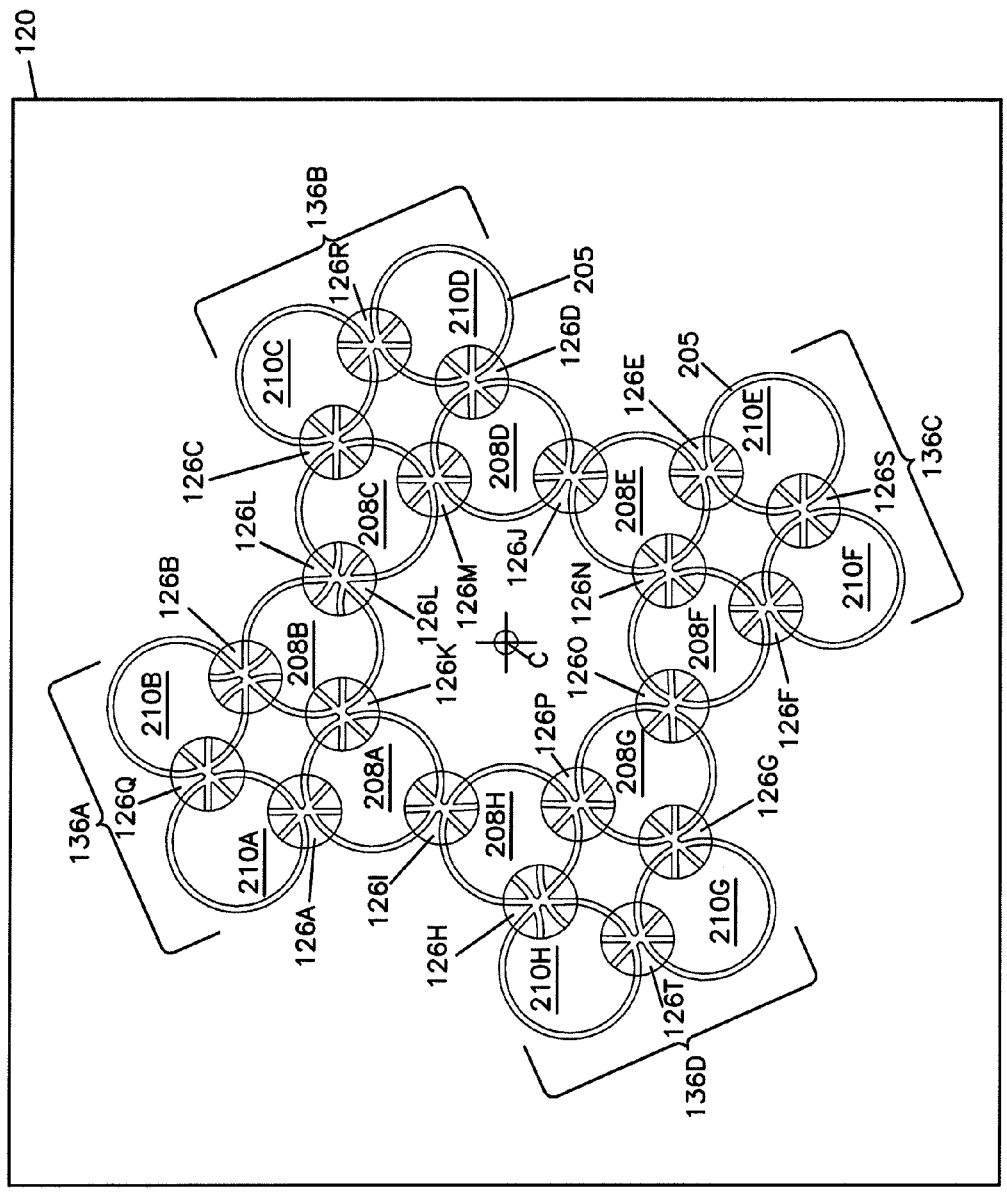

Many alternative embodiments and arrangements of the active tracks, passive tracks, and gates are possible. These alternative embodiments enable greater flexibility for defining different paths for the bobbin carrier assemblies and enables the braider 100 to make a wider variety of different braid structures and configurations. Referring to FIG. 3b, for example, one or more gates can be positioned between adjacent active sub-tracks to enable bobbin carrier assemblies to switch between travelling in the clockwise and counter clockwise directions along the active track. In the alternative embodiment, gate 126I is positioned between active sub-tracks 208A and 208G, and gate 126J is positioned between active sub-tracks 208D and 208E. Having two or more gates positioned between adjacent active sub-gates enables bobbin carrier assemblies to be transported along separate closed or endless paths that traverse the clockwise and counterclockwise paths 207 and 209 of the active track 203. Referring to FIG. 3c, another alternative embodiment includes gates 126I-126P between each of the active sub-tracks. FIG. 3d illustrates yet another possible embodiment in which gates 126 are positioned between the passive sub-tracks 126Q-126T.

Figure 3E:
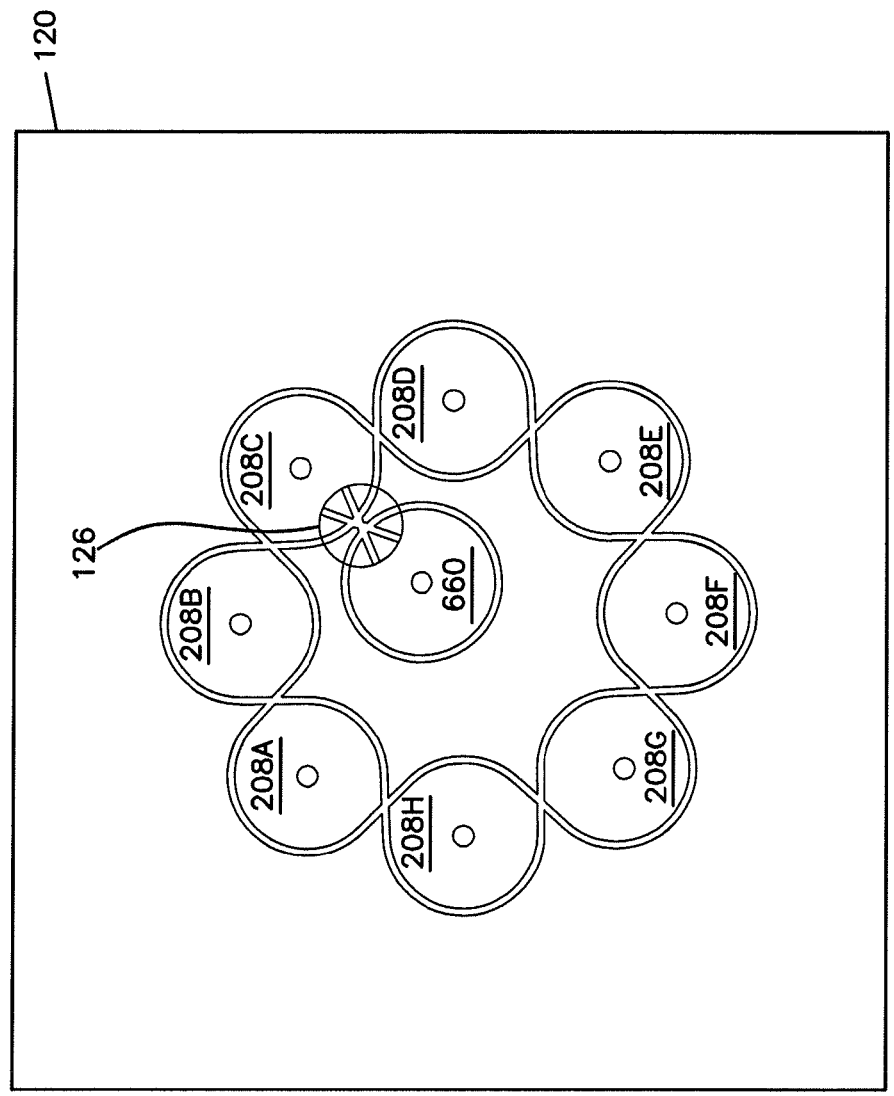
Figure 3F:
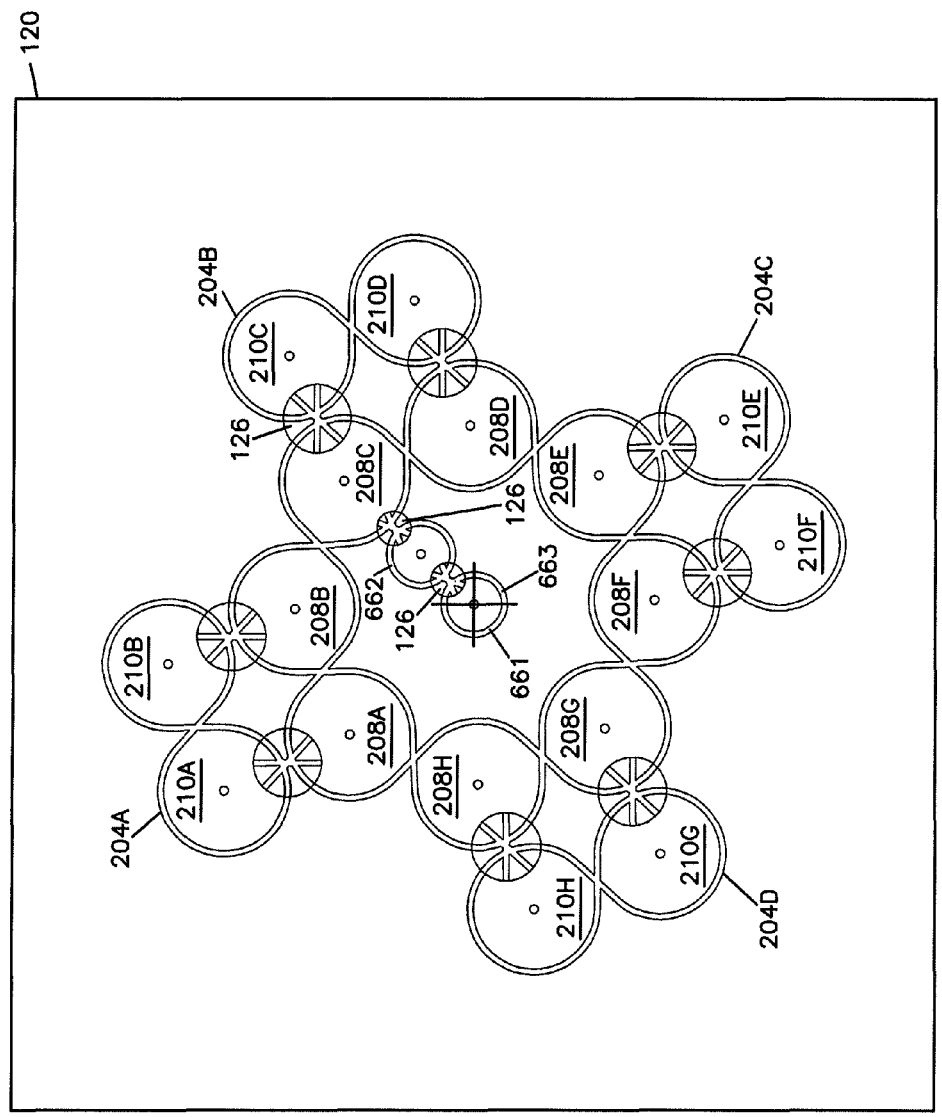
Figure 4A:
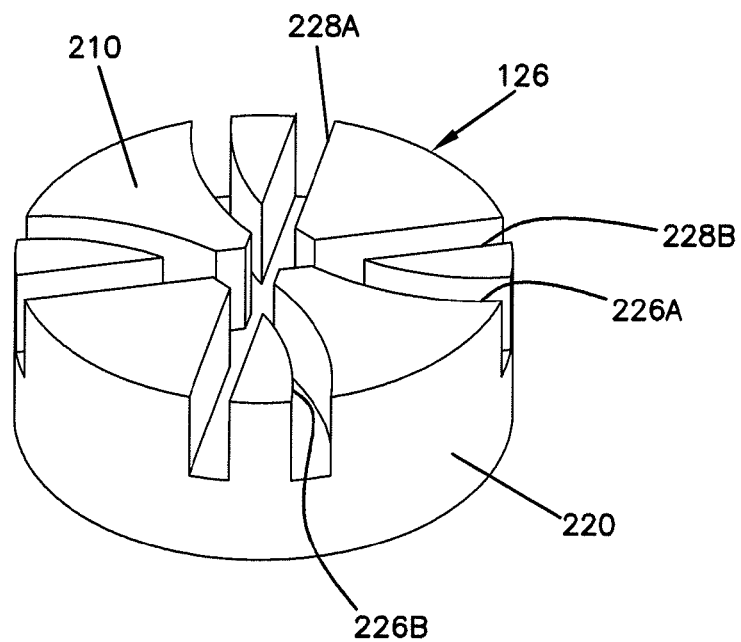
FIGS. 4A and 4B illustrate an example gate.
Figure 4B:
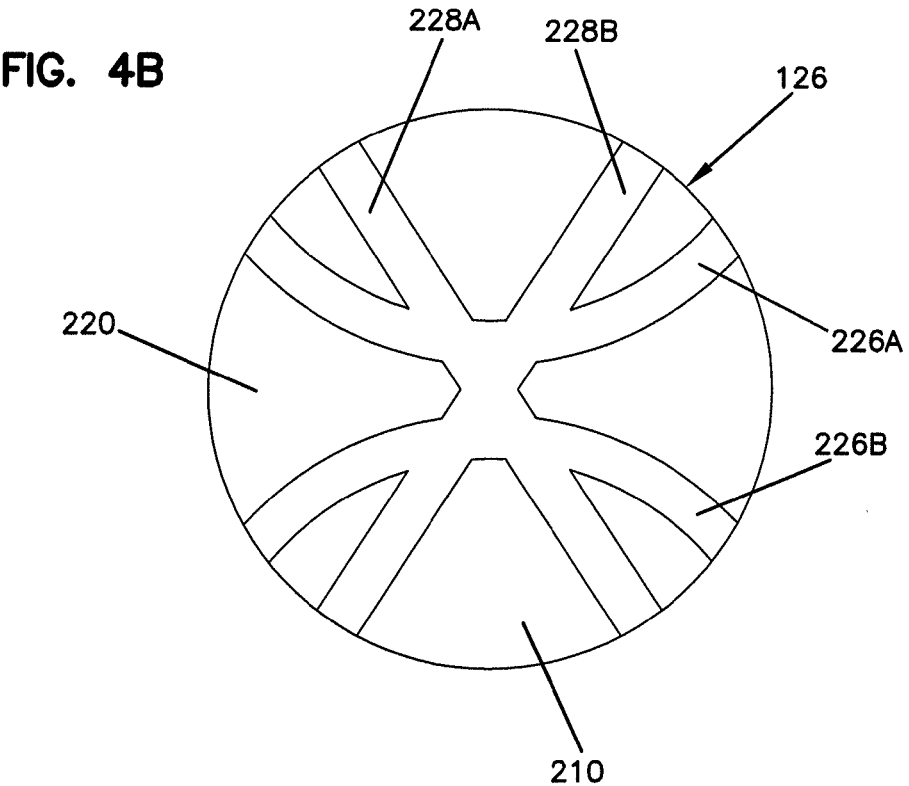

Additionally, alternative embodiments can position the passive tracks in the center of the active track 202, either instead of or in addition to, passive tracks positioned outside of the active track 202 as illustrated in FIGS. 3a-3d. In FIG. 3e, for example, a center passive track 660 is positioned in the center of the active track 202 and is adjacent one of the active sub-tracks (e.g., 208C). A gate 126 is then positioned between the center passive track 660 and the adjacent active sub-track 208C. Alternative embodiments might include more than one passive track in the center of the active track 202. Alternative embodiments also can include center passive tracks that have two or more passive sub-tracks. FIG. 3f illustrates another possible embodiment in which there is an active track 202 and one or more passive tracks 204A-204D arranged on the outside of the active track as illustrated in FIGS. 3a-3d. In these alternative embodiments, a center passive track 661 has one or more passive sub-tracks 662 and 663, which are positioned on the inside of the active track 202 as illustrated in FIG. 3e. Gate 126 are positioned between passive sub-track 662 and active sub-track 208C, and between passive sub-track 662 and passive sub-track 663.

Many different embodiments of the braider track plate, active track, passive tracks, gates, and various sub-tracks are possible in addition to those illustrated and described herein. For example, the active and sub-tracks can be implement with any structure suitable for guiding the bobbin carrier assemblies, including structures other than a braider track having a network of grooves or slots. There can be any number, arrangements, and configurations of the passive tracks, which can have any structure that guides the bobbin carrier assemblies on a path other than the active track and path. For example, the passive tracks can have no sub-tracks or more than two sub-tracks. The passive tracks also can include paths that are not generally circular as illustrated such as oblong, arcuate, and linear paths. Additionally, the gates 126 can be any structure suitable for guiding the bobbin carrier assemblies between the active track and a passive track, or any structure suitable for guiding the bobbin carrier assemblies from one direction to another direction (e.g., between clockwise and counterclockwise directions). Many other embodiments may be possible as well.

Furthermore, certain designs of braids having various patterns and colors, pattern changes, color changes, and structures such as round-flat-round structures, alternating cores, bifurcations, a central braid with legs, and the like are disclosed herein. Additional braids having various combinations of these colors, patterns, and structures can be made using the disclosed braiding machine 100 having active and passive tracks and gates.

Figure 6:
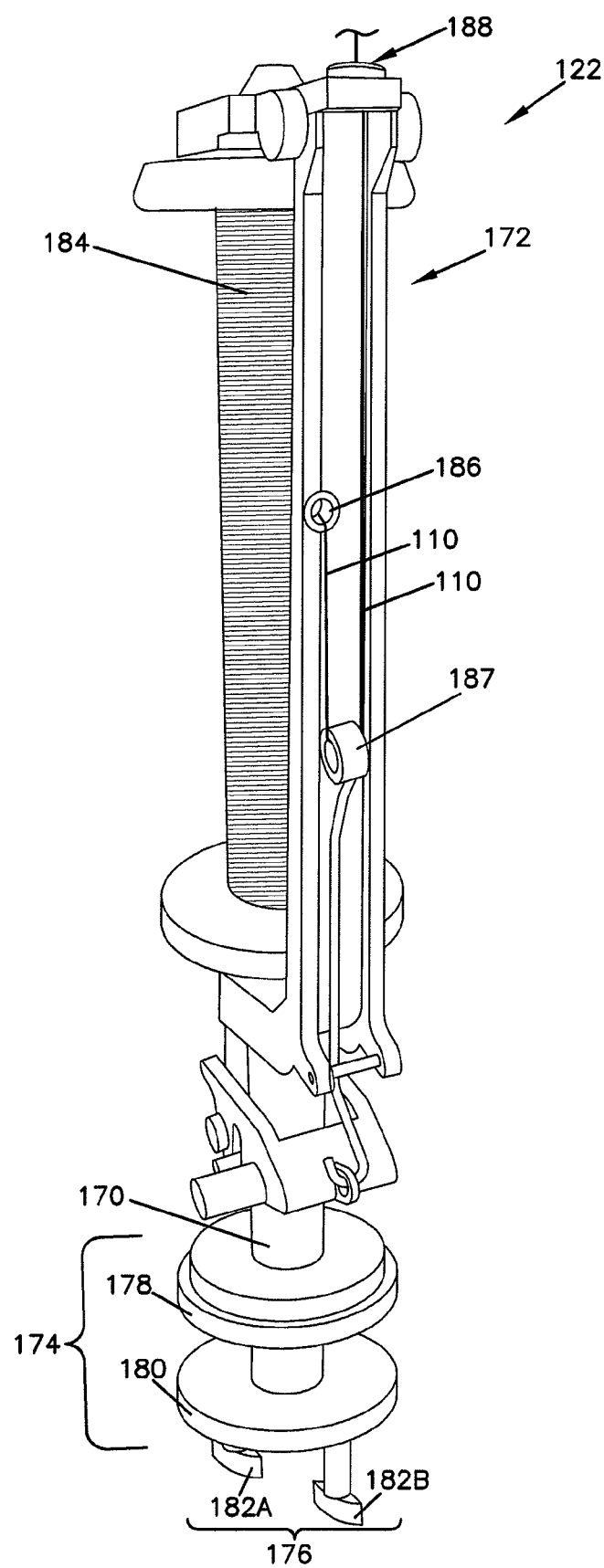
FIG. 6 is a schematic perspective view of an example bobbin carrier assembly.

FIGS. 6-8 illustrate an example bobbin carrier assembly 122. In particular, FIG. 6 is a schematic perspective view of an example bobbin carrier assembly 122. FIG. 7 is a top view of the bobbin carrier assembly 122 of FIG. 6. FIG. 8 is a side view of the bobbin carrier assembly 122 of FIG. 6. In at least some embodiments, the bobbin carrier assembly 122 includes a carrier shaft 170, a bobbin holder 172, a carrier foot 174, and a carrier guide 176.

The bobbin holder 172 is configured to support a bobbin 184 and feed a strand 110 from the bobbin 184. The bobbin holder 172 is supported on the shaft 170 above the carrier foot 174. In some embodiments, the bobbin holder 172 can include a first eyelet 186, a second eyelet 187, and a third eyelet 188. The strand 110 is fed from the bobbin 184, through the first eyelet 186, and then through the second eyelet 187 at a lower portion of the bobbin holder 172. The strand 110 is then routed through the third eyelet 188 and runs out of the bobbin holder 172 to the braiding guide mechanism 104. The strand 110 that is routed from the first eyelet 186, through the second eyelet 187, and through the third eyelet 188 can maintain a proper tension before braiding. In the depicted embodiment, the bobbin 184 is vertically held by the bobbin holder 172. In other embodiments, the bobbin holder 172 can be configured to support the bobbin 184 horizontally or at any other suitable angle or arrangement. In yet other embodiments, the bobbin holder 172 can have any structure suitable for holding the bobbin 184.

The carrier foot 174 is configured to engage the active and passive horn gear assemblies 132A-132H and 134A-134H as disclosed in more detail herein. In at least some embodiments, the carrier foot 174 includes a first foot plate 178 and a second foot plate 180. The first foot plate 178, the second foot plate 180, and the portion of the shaft 170 extending therebetween engage a horn plate of the horn gear assemblies 132A-132H and 134A-134H.

The carrier guide 176 includes one or more keels 182. In the depicted example, the carrier guide 176 includes two keels 182A and 182B. The keels 182 can be supported on and project downward from the bottom of the second foot plate 180. The keels 182A and 182B are inserted into the track defined in the braiding track plate 120 and the gates 126A-126H and guide the bobbin carrier assemblies 122 along the paths defined by the track and the orientation of the gates 126A-126H. The keels 182 are rotatable around their own axis of rotation, which is orthogonal to the second foot plate 182. The keels 182A and 182B smoothly guide the bobbin carrier assemblies 122 along the tracks 202 and 204 and through the gates 126A-126H while preventing the bobbin carrier assembly from spinning around the axis of the carrier shaft 170.

Figure 9:
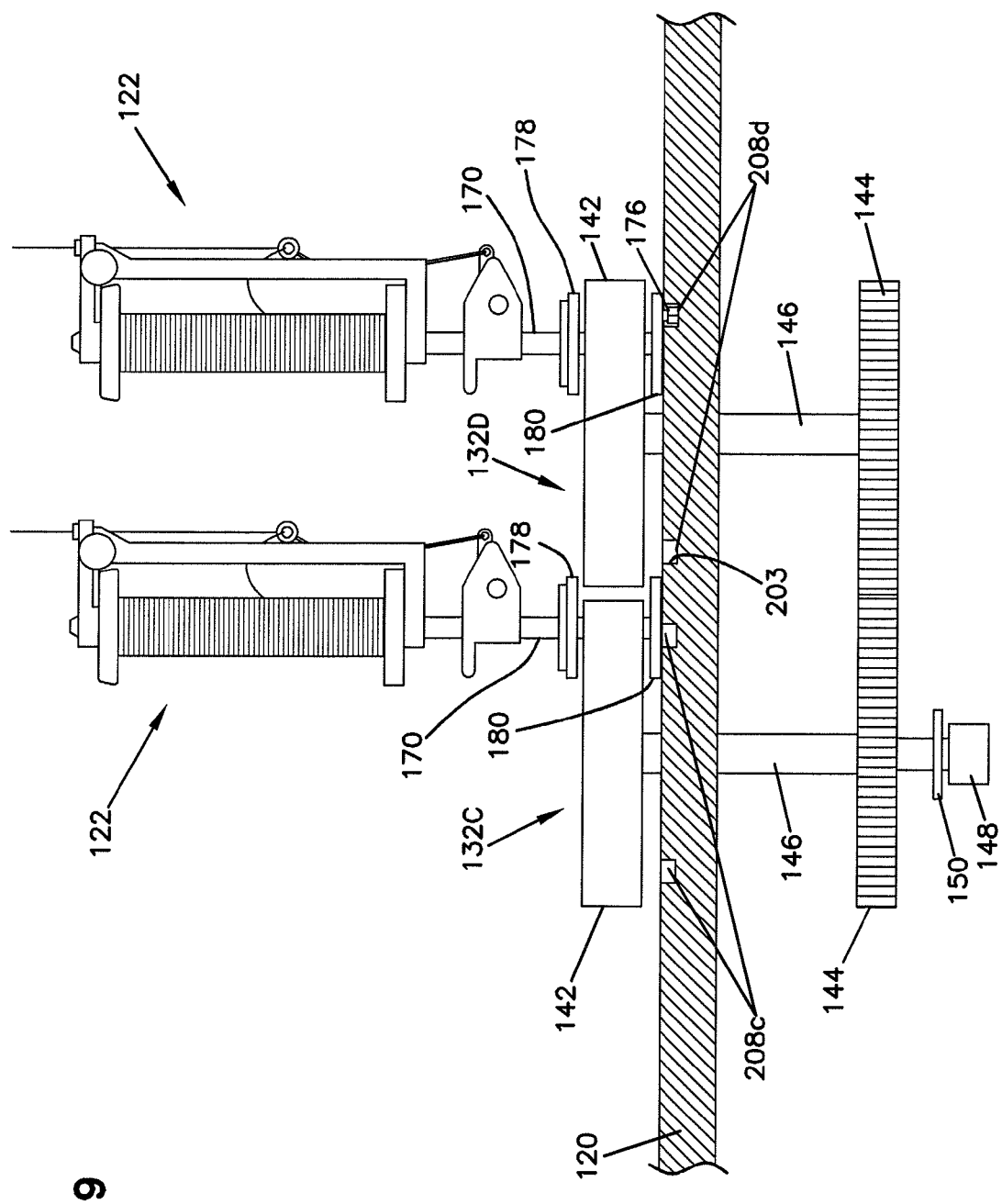
FIG. 9 is a schematic cross-sectional view of the braiding assembly of FIG. 2, illustrating two adjacent first horn gear assemblies.

FIG. 9 is a partial, schematic cross-sectional view of the braiding assembly 102 of FIG. 2 taken along line 9-9, illustrating two adjacent active horn gear assemblies 132C-132D. The other pairs of active horn gear assemblies 132A and 132B, 132E and 132F, and 132G and 132H have similar structures.

In at least some embodiment, each of the active horn gear assemblies 132 can include a horn gear plate 142 and a suitable transmission member such as a gear 144. The horn gear plates 142 are configured to support one or more of the bobbin carrier assemblies 122. The horn gear plate 142 defines one or more notches 128 open to its perimeter and arranged to receive the carrier shaft 170 while the first foot plate 178 rides along the top of the horn gear plate 142 and the second foot plate 180 rides between the horn gear plate 142 and the braiding track plate 120. The keel 182 is positioned within the active groove 203 and slides along the active groove 203 as the horn gear 132 rotates and the horn plate 142 propels the carrier shaft 170.

Each gear 144 is configured to engage the gear 144 of the adjacent active horn gear assemblies 132 so that the active horn gear assemblies rotate simultaneously and at the same rate. The horn gear plate 142 and the gear 144 are connected through a horn gear shaft 146. In some embodiments, the horn gear plate 142 and the gear 144 are arranged on or over different sides of the track plate 120. For example, the carrier support member 142 is arranged over the upper side of the track plate 120 while the gear 144 is arranged on the lower side of the track plate 120. In alternative embodiments, the horn plate 142 and gear 144 are positioned on the same side of the track plate. Other embodiments are possible as well.

An actuating mechanism such as a servo motor 148 is connected to the drive shaft 146 and rotates the active horn gear assembly 132A, and in turn rotates the other active horn gear assemblies 132B-132H through the chain of gears 144. An encoder 150 is also connected to the active horn gear assembly to monitor the operational status and/or conditions of the motor 148 (e.g., the angular locations of the horn gear assemblies 132). Alternative embodiments can use mechanisms other than a servo motor to rotate the active horn gears 132. An example of an alternative mechanism is a stepper motor.

In at least some embodiments, all of the active horn gear assemblies 132 can be operated by one servo motor 148 with one encoder 150 because all of the active horn gear assemblies 132A-132H are interconnected through the gears 144. In some embodiments, the encoder 150 can have a quad channel of about 2000 pulses/channel. Alternative embodiments can have any number of motors 148 to drive the active horn gear assemblies 132A-132H. For example, each active horn gear assembly 132 can be driven by a separate motor. In this embodiment, the active horn gear assemblies 132A-132H do not have the gear 144 because they are all driven independently. In other embodiments individual groups of adjacent active horn gear assemblies 132A-132H are driven by separate motors. For example, active horn gears 132A-132D could be interconnected with one set of gears 144 and driven by one motor 148 and active horn gears 132E-132H could be interconnected with a second set of gears that are not interconnected with the first set of gear and driven by a second motor. Additionally transmission mechanisms other than gears can be used to interconnect and rotate the active horn gear assemblies 132A-132H. Belts are an example of such an alternative transmission mechanism.

Figure 10:
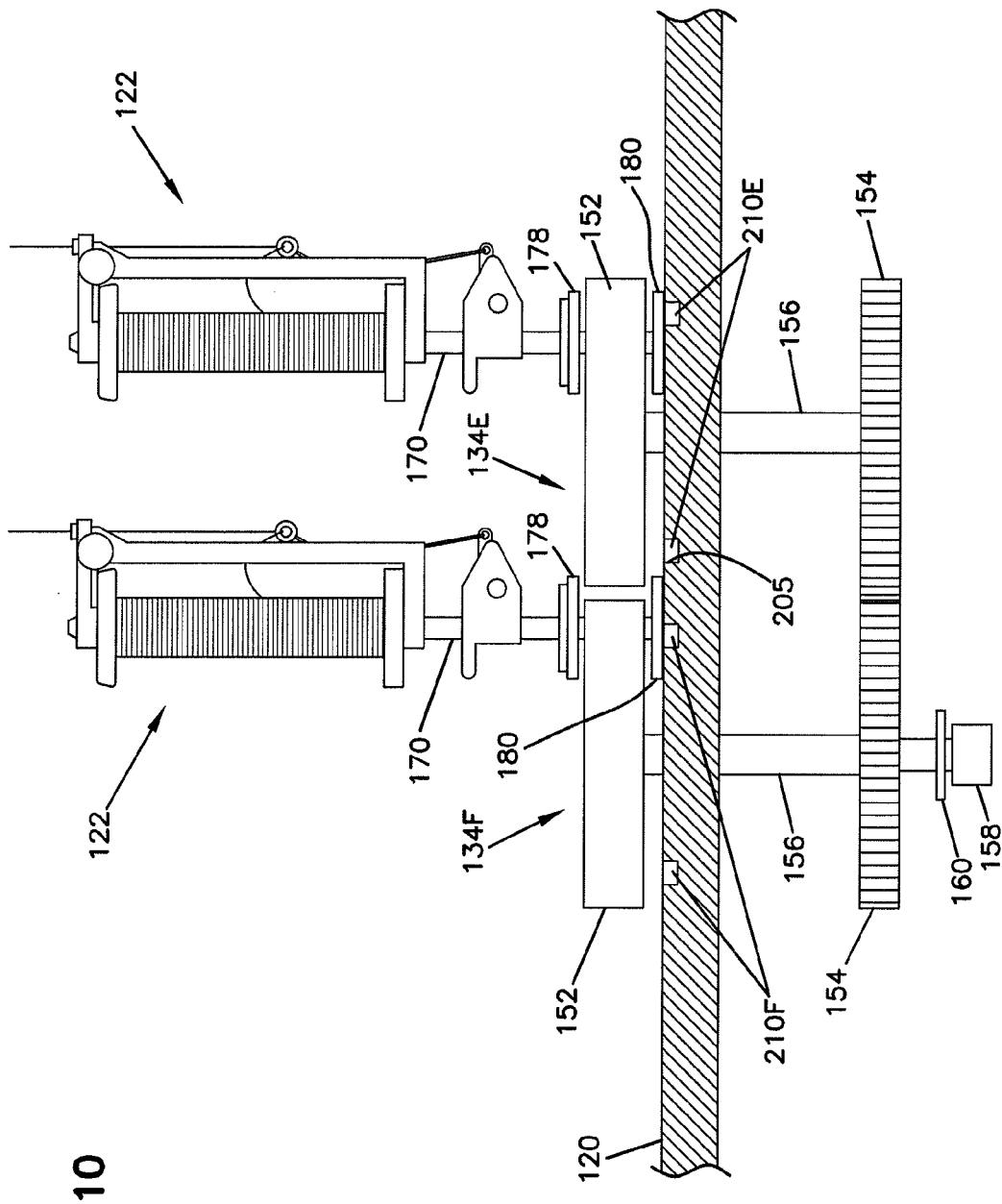
FIG. 10 is a schematic cross-sectional view of the braiding assembly of FIG. 2, illustrating two adjacent second horn gear assemblies.

FIG. 10 is a partial schematic cross-sectional view of the braiding assembly 102 of FIG. 2 taken along line 10-10, illustrating two adjacent passive horn gear assemblies 134E and 134F in quadrant 136C. Passive horn gear assemblies 134E and 134F are substantially similar to active horn gear assemblies 132C and 132D illustrated in FIG. 3, and each include a horn plate 152 similar to horn plate 142, horn gear shaft 156 similar to horn gear shaft 146, and gear 154 similar to gear 144. The gears 154 for passive horn hear assemblies 134E and 134F are interconnected with each other, but are not interconnected with gears of the active horn gear assemblies 132A-132H or the other passive horn gear assemblies 134A-134D or 132G-134H. In this structure, the passive horn gear assemblies 134A-134H operate independently of the active horn gear assemblies 132A-132H and the other passive horn gear assemblies 134A-134D or 132G-134H. The passive horn gear assemblies support and propel the bobbin carrier assemblies 122 along the groove 205 of the passive track in a manner similar to the way the active horn gear assemblies 132 support and propel the bobbin carrier assemblies 122 along the groove 203 of the active track 202.

An actuating mechanism such as a servo motor 158 is connected to the drive shaft 156 and rotates the passive horn gear assembly 134F and in turn rotates passive horn gear assembly 134E through the interconnection of gears 154. In this embodiment, however, the motor 158 connected to the passive horn gear 134F does not cause passive horn gears 134A-134D or 132G-134H to rotate. An encoder 160 also is connected to the passive horn gear assembly 134F to monitor the operational status and/or conditions of the motor 158 and passive horn gears 134F and 134E (e.g., the angular locations of the horn gear assemblies 134F and 134E). In some embodiments, the encoder 160 can have a quad channel of about 2000 pulses/channel. Alternative embodiment can use mechanisms other than a servo motor to rotate the passive horn gears 134F and 134E. An example of an alternative mechanism is a stepper motor. The structure of the other pairs of passive horn gears 134A and 134B, 134C and 134D, and 134G and 134H are substantially similar to the pair of passive horn gears 134E and 134F.

Alternative embodiments can have any number of motors 158 to drive the passive horn gears 134A-134H. For example, all of the passive horn gear assemblies 134A-134H could be interconnected through a common chain of gears or other transmission mechanisms such as belts and then driven by a single motor. In yet other embodiments, each passive horn gear assembly 134A-134H can be driven by a separate motor. In this embodiment, the passive horn gear assemblies 134A-134H do not have the gear 154 because they are all driven independently.

Figure 11:
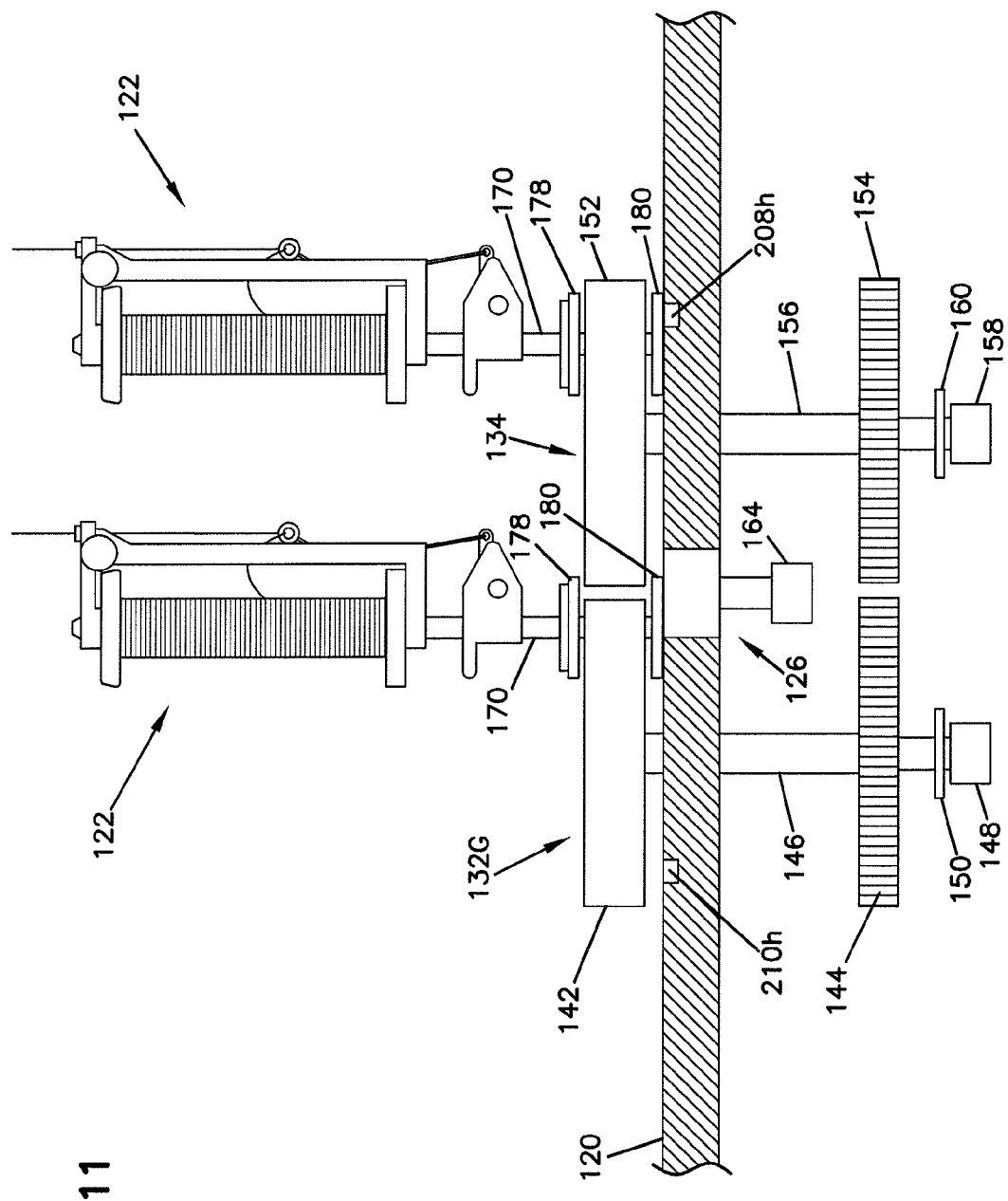
FIG. 11 is a schematic cross-sectional view of the braiding assembly of FIG. 2, illustrating adjacent first and second horn gear assemblies.

FIG. 11 is a partial schematic cross-sectional view of the braiding assembly 102 of FIG. 2 taken along line 11-11, illustrating adjacent active and passive horn gear assemblies 132G and 132F, respectively. Active horn gear assembly 132G is substantially similar to active horn gear assembly 132C, and includes horn plate 142, gear 144, and horn gear shaft 146. Active horn gear assembly 132 is not driven directly by a motor in the illustrated embodiment. Rather the gear 144 of active horn gear assembly 132C is driven by the motor 148, and the rotational motion of the motor 148 is translated to each of the gears 144 in the active horn gear assemblies 132A-132H. Passive horn gear assembly 134G is substantially similar to passive horn gear assembly 134E and includes horn plate 152, gear 154, and horn gear shaft 156. Passive horn gear assembly is not driven directly by a motor in the illustrated embodiment. Rather, the gear 154 of passive horn gear assembly 134G is driven by the motor 158 and the rotational motion of the motor 158 is translated to the passive horn gear assembly 134G by the gears 154 in the passive horn gear assemblies 134G and 134H.

As described herein, the active horn gear assemblies 132A-132H and the passive horn gear assemblies 134A-134H are operated independently from each other. In this configuration, teeth of the gears 144 and 154 do not mesh or otherwise engage each other. In one possible embodiment, the gears 144 and 154 have the same diameter, but the centerline for the horn gear shafts 146 and 156 are separated by a distance greater than the diameter. In an alternative embodiment, the gears 144 and 154 have different diameters.

The gate 126 is positioned between the active and passive horn gear assemblies 132G and 134G. A gate actuating system 164 is connected to the gate 126 and rotates the gate 126 between open and closed positions. In at least some embodiments, the gate actuating system 164 can be a hydraulic operating system. The hydraulic operating system can include a hydraulic motor. Examples of the hydraulic motor include a gear and vane motor, a gerotor motor, an axial plunger motor, a radial piston motor, and other motors of any type suitable for actuating the gate 126. In other embodiments, the gate actuating system 126 can include a linear actuator and linkage configured to rotate the gate 126 between positions. In other embodiments, the gate actuating system 164 can include one or more solenoids of any type, such as electromechanical solenoids, rotary solenoids, rotary voice coils, pneumatic solenoid valves, and hydraulic solenoid valves. In yet other embodiments, the gate actuating system 164 can include a pneumatic operating system. For example, the pneumatic operating system can include a pneumatic indexer, rack and pinion arrangement or a belt. In yet other embodiments, the gate actuating system 164 can include a motor, such as a servo or stepper motor. In this configuration, the angular location of the gate 126 can be monitored through an encoder. In yet other embodiments, the gate 126 can be operated by other arrangement suitable for rotating the gate 126. In yet other embodiments, the gate 126 can be operated by either or both of the active track motor 148 or the passive track motor 158.

Figure 12:
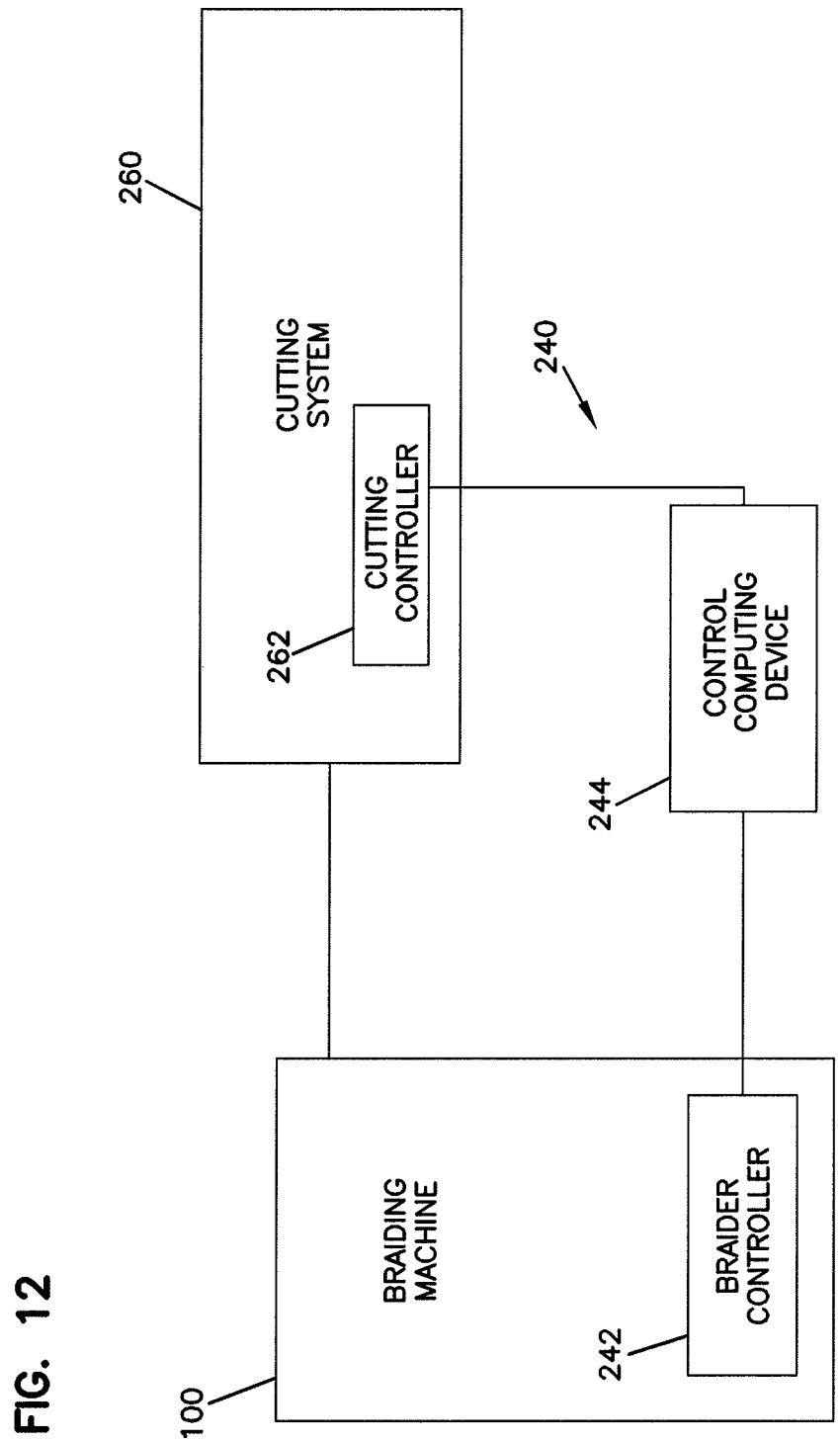
FIG. 12 is a schematic diagram of an example cutting system.

FIG. 12 is a schematic diagram of an example cutting system 260. In at least some embodiments, the cutting system 260 is operated to receive the braid 108 from the braiding machine 100 and cut it to length to form individual braids. The braiding machine 100 and the cutting system 260 can be controlled by a control system 240. The braiding machine 100 includes a braider control system 242, as part of the control system 240, configured to control the braiding machine 100. The cutting system 260 includes a cutter control system 262, as part of the control system 240, configured to control the cutting system 260. In at least some embodiments, the braider control system 242 and the cutter control system 262 are connected to a control computing device 244 configured to integrally control the braiding machine 100 and the cutting system 260. An example control system 240 is illustrated and described in more detail with reference to FIG. 17.

FIGS. 13a-13d are schematic views of an example inline cutting system 260 of FIG. 12, which is configured to be used with a braiding machine 100. The inline cutting system 260 is configured to precisely cutting a transition braid 108 produced and fed from the braiding machine 100. In at least some embodiments, the inline cutting system 260 includes a set of spools including a first spool 266 and a second spool 268, a set of gripping devices including a first gripping device 270, a second gripping device 272 and a third gripping device 274, a heating device 276, a cutting device 278, and a tray 280.

The first and second spools 266 and 268 are configured to draw the braid 108 from the braiding machine 100 and retain them for the subsequent cutting process by the cutting system 260. In at least some embodiments, one of the first and second spools 266 and 268 operates to take off the braid 108 from the braiding machine 100, thereby being referred to as a takeoff roller or spool. In at least some embodiments, the takeoff spool is powered by a servo motor to control the angular speed of the spool. The other spool of the first and second spools 266 and 268 is not operated by a separate power source and configured to freely spin. This spool can also be referred to herein as an idler spool. As depicted, the first and second spools 266 and 268 are bound by the wrapped braid 108 and thus the idler spool rotates at the same rate as the takeoff spool, which is operated by the servo motor. In at least some embodiments, the takeoff spool is operated by a stepper motor.

In at least some embodiments, the braid 108 wraps around the set of the spools 266 and 268 multiple times to reduce a tension T1 on the braid 108 until the braid 108 has a predetermined exit tension T2 at the outlet of the set of the spools 266 and 268. The predetermined exit tension T2 can be selected to be suitable for the cutting process by the cutting system 260. In general, the wraps of the braid 108 increase around the spools 266 and 268, the exit tension T2 of the braid 108 decreases. The spools 266 and 268 wrap the braid 108 to constantly maintain the exit tension T2 less than the original tension T1 on the braid 108. In at least some embodiments, the braid 108 is wrapped between 2 to 10 times to provide a proper exist tension. In other embodiments, the braid 108 is wrapped 4 or 5 times. In yet other embodiments, the braid 108 is wrapped around the spools.

The gripping devices 270, 272 and 274, along with a linear rail or actuator 267 of the cutting system 260, are used to keep tension on the braid during heating and cutting operations. In at least some embodiments, at least one of the gripping devices 270, 272 and 274 can be operated to move at the speed of the braid, which can be calculated from the takeoff speed.

The gripping devices 270, 272 and 274 are operated by actuating mechanisms 271, 273 and 275, respectively. In at least some embodiments, the actuating mechanisms 271, 273 and 275 can include servo motors. The servo motors can include encoders 291, 293 and 295 configured to monitor the operational status and/or conditions of the servo motor. In other embodiments, the actuating mechanisms 271, 273 and 275 can include stepper motors.

The first gripping device 270 is configured to move along a conveying line L and operates to pull the braids 108 to predetermined points and/or with predetermined tensions on the braid 108 as the braid 108 exits from the first and second spools 266 and 268. In at least some embodiments, the first gripping device 270 operates to contact the braid 108 and create pressure onto the braid 108 so that the braid 108 does not slip along the conveying line L. In at least some embodiments, the first gripping device 270 is controlled by a linear actuator driven by a servo motor. In other embodiments, the first gripping device 270 is operated by a stepper motor. In at least some embodiments, this motor is configured as a slave of the motor that operates the takeoff spool as illustrated above. By taking input from the motor of the takeoff spool, the first gripping device 270 is operated at the same speed as the braid 108 and, thus, the exit tension of the braid 108 can be maintained properly to continue a consistent braid. Further, this configuration allows controlling the position of the transition braid 108 accurately.

In at least some embodiments, the second and third gripping devices 272 and 274 can be stationary while the first gripping device 270 is configured to be linearly movable. In other embodiments as described in more detail herein, one of the second and third gripping devices 272 and 274 can move while the first gripping device 270 is movable in order to prevent interference to the braiding machine 100 during cutting process. In yet other embodiments, both of the second and third gripping devices 272 and 274 can move, either independently or as a unit, as the first gripping device 270 is movable.

The heating device 276 is operated by a heater actuating mechanism 277. In at least some embodiments, the heater actuating mechanism 277 can include a hydraulic operating system. The hydraulic operating system can include a hydraulic motor. Examples of the hydraulic motor include a gear and vane motor, a gerotor motor, an axial plunger motor, a radial piston motor, and other motors of any type suitable for actuating the gate 126. In other embodiments, the heater actuating mechanism can include one or more solenoids of any type, such as electromechanical solenoids, rotary solenoids, rotary voice coils, pneumatic solenoid valves, and hydraulic solenoid valves. In yet other embodiments, the heater actuating mechanism can include a pneumatic operating system. For example, the pneumatic operating system can include a pneumatic indexer, rack and pinion arrangement or a belt, and a stepper motor or servo motor arrangement. In yet other embodiments, the heater actuating mechanism can include a motor, such as a servo motor. In this configuration, the angular location of the motor can be monitored through a motor encoder. In yet other embodiments, the motor can be a stepper motor. In yet other embodiments, the heating device 276 can be operated by other arrangement suitable for actuating the heating device 276.

The cutting device 278 can be operated by a cutter actuating mechanism 279. The cutter actuating mechanism 279 can be configured in a similar manner to the actuation of the heating device 276. Thus, the description for the cutter actuating mechanism 279 is omitted for brevity purposes.

Figure 13A:
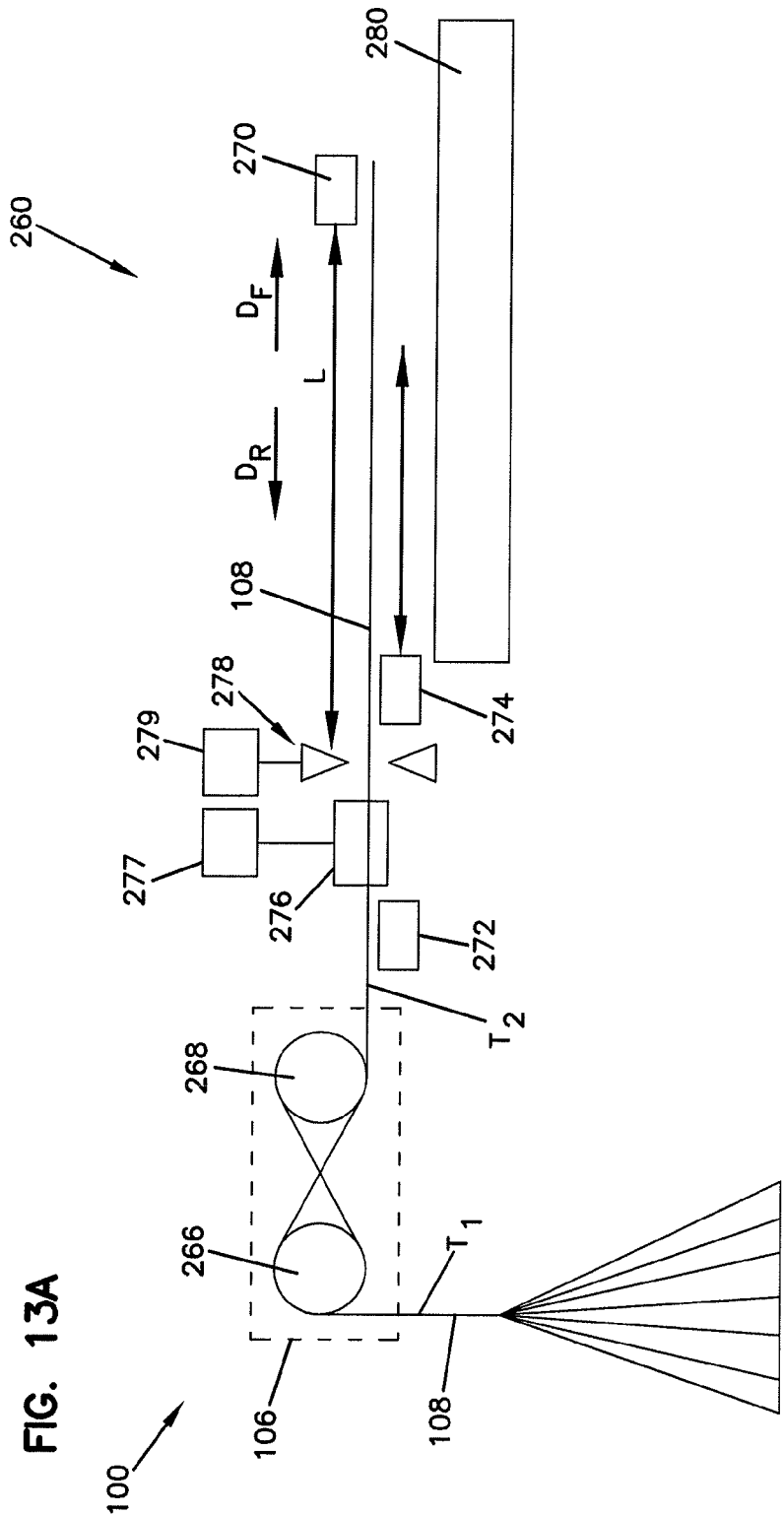
FIGS. 13A-13D are a schematic view of an example inline cutting system of FIG. 12, which is configured to be used with a braiding machine.
Figure 13B:
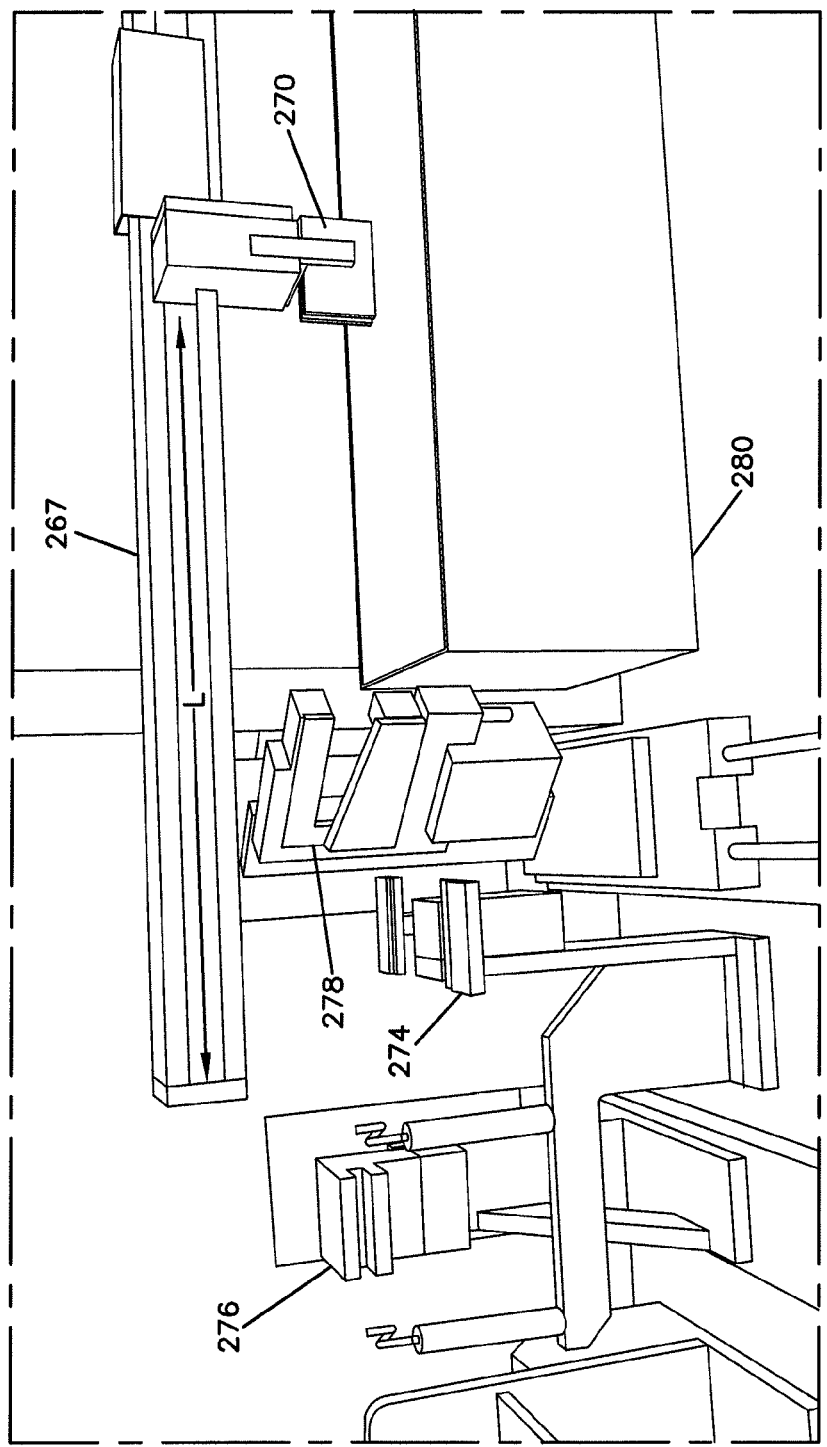
Figure 13C:
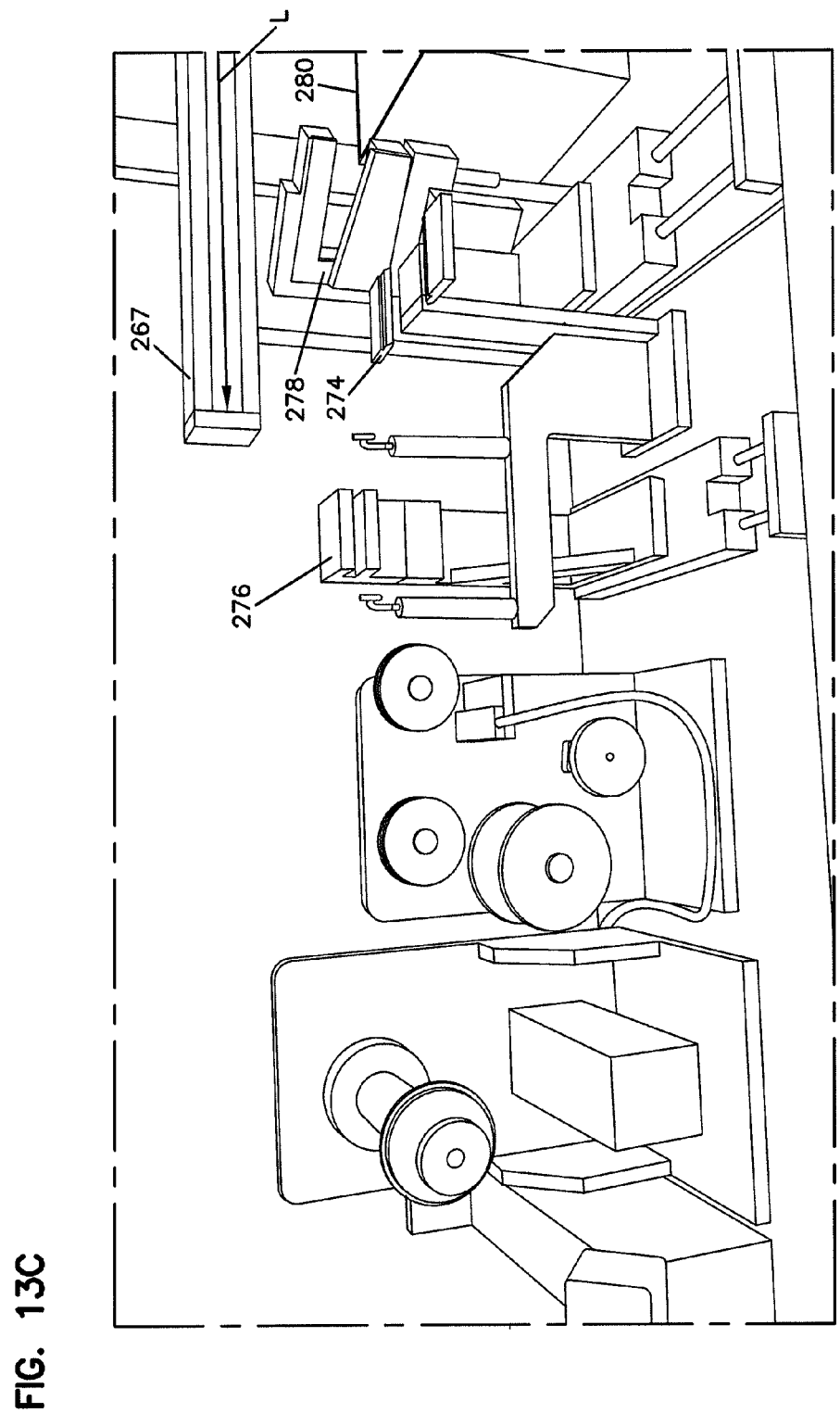
Figure 13D:
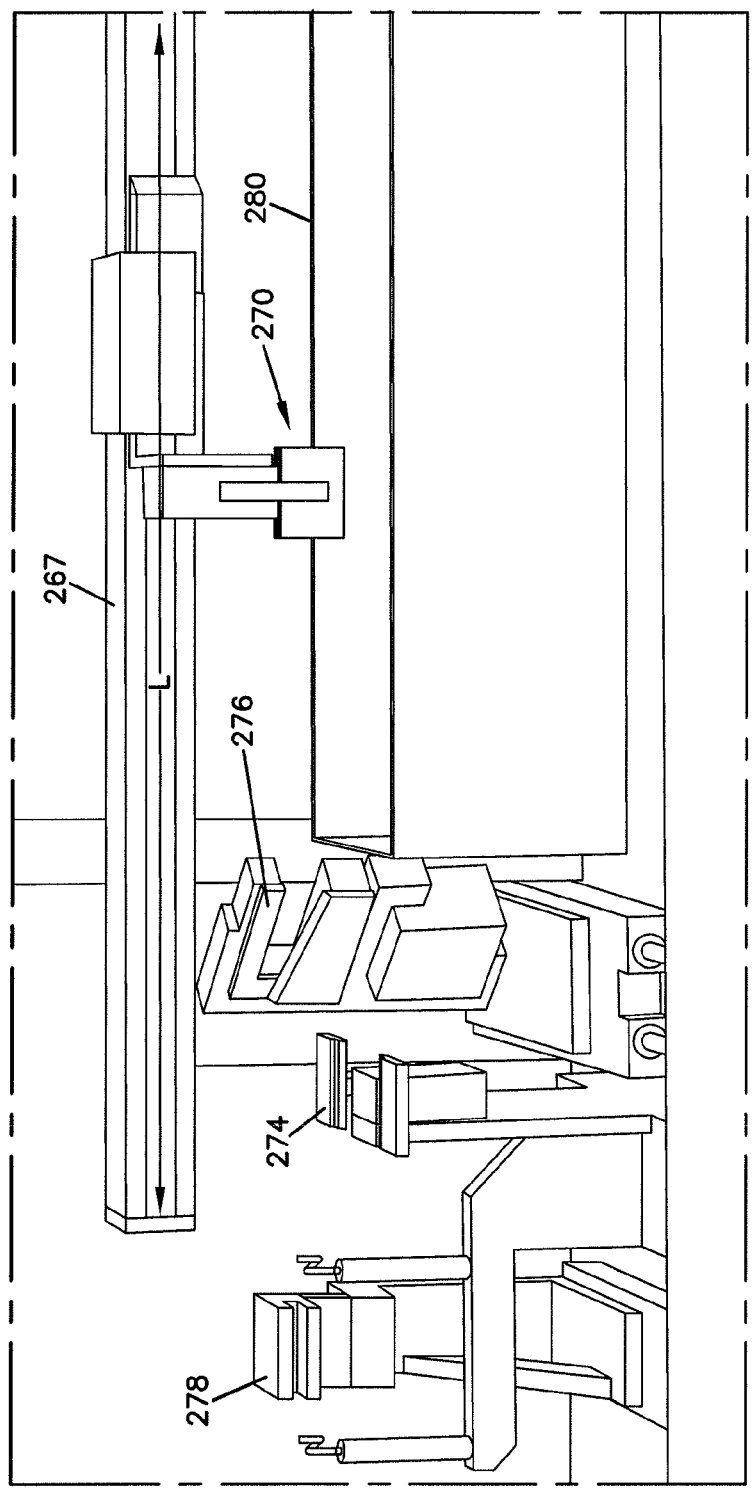
Figure 13E:
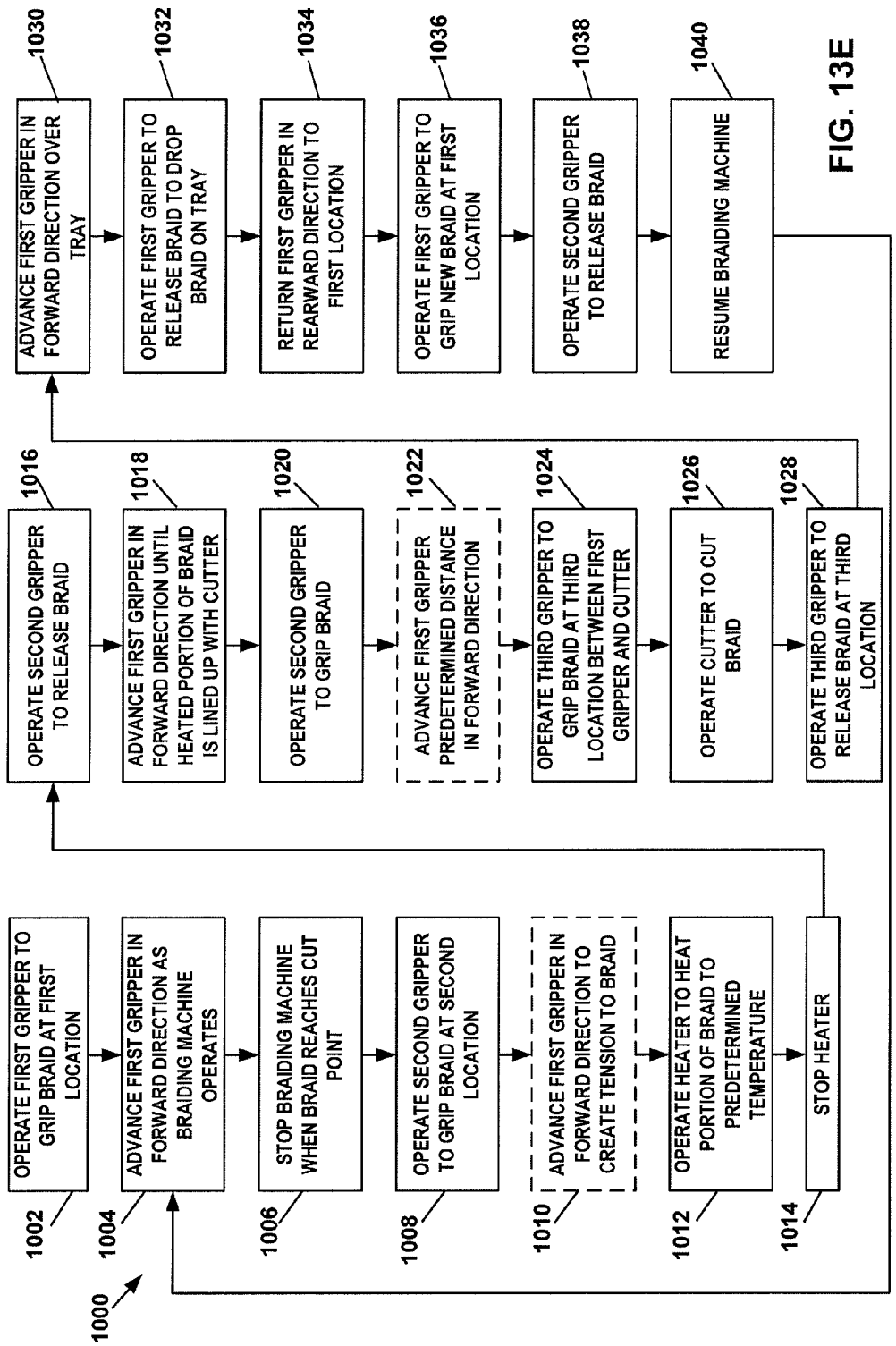
FIG. 13E is a flowchart illustrating an example method of operating the cutting system of FIGS. 13A-13D.

FIG. 13e is a flowchart illustrating an example method 1000 of operating the cutting system 260 of FIGS. 13a-13d. In the depicted embodiment, the method 1000 may include operations 1002, 1004, 1006, 1008, 1010, 1012, 1014, 1016, 1018, 1020, 1022, 1024, 1026, 1028, 1030, 1032, 1034, 1036, 1038, and 1040.

The method 1000 typically begins at the operation 1002 where the first gripping device 270 is operated to grip the braid 108 at a first location 281. In at least some embodiments, the first location 281A is located between the take-up reel 106 (including the first and second spools 266 and 268) and the second gripping device 272. In other embodiments, the first location 281A can be defined at a different position.

At the operation 1004, the first gripping device 270 is advanced in a forward direction $D_F$ along the conveying line L as the braiding machine 100 operates. In at least some embodiments, the first gripping device 270 can be operated at the same speed as the takeoff speed of the braid 108 (i.e., the speed at which the braid 108 is drawn at the takeoff spool) to maintain a proper tension on the braid 108. In other embodiments, the speed of the first gripping device 270 can be adjusted based upon different factors.

At the operation 1006, the braiding machine 100 is stopped when the braid 108 reaches a predetermined braid length or cut point. The predetermined braid length or cut point can be set and input by an operator, or automatically calculated by the control system based upon other operational parameters input by the operator. For example, as described herein, the braid length can be calculated from the takeoff speed, which can be determined by a given pick count and a given table speed.

At the operation 1008, the second gripping device 272, which is stationary, can operate to grip the braid 108 at a second position 281B. At this operation, the second position 218B is located between the set of the spools 266 and 268 (i.e., the take-up reel 106) and the first gripping device 270. In at least some embodiments, the second gripping device 272 is arranged between the take-up reel 106 (including the first and second spools 266 and 268) and the heating device 276. In other embodiments, the second gripping device 272 can be positioned between the take-up reel 106 and the cutting device 278. In yet other embodiments, the second gripping device 272 can be arranged at a different position.

At the operation 1010, which is optional, the first gripping device 270 can be operated to advance in the forward direction $D_F$ to create a predetermined tension of the braid 108. The operation can be a preliminary step at which the braid 108 is properly stretched out over the heating device 276 by the first and second gripping device 270 and 272 before the braid 108 is heated at the operation 1012.

At the operation 1012, the heating device 276 is operated to heat a portion of the braid 108 that is to be cut by the cutting device 278. In at least some embodiments, the heating device 276 is moved around the portion of the braid 108 and operates for a predetermined period of time at a set temperature. In at least some embodiments, the heating device 276 is arranged between the first gripping device 270 and the second gripping device 272. In at least some embodiments, the heating device 276 is a non-contact heat block. Once the braid 108 is heated at the set temperature, the heating device 276 can retract.

At the operation 1016, the second gripping device 272 operates to open to release the braid 108. At the operation 1018, the first gripping device 270 is operated to advance in the forward direction $D_F$ until the heated portion of the braid 108 is lined up with the cutting device 278. In at least some embodiments, the cutting device 278 can be arranged between the heating device 276 and the first gripping device 270. In other embodiments, the cutting device 278 can be arranged at different locations.

At the operation 1020, the second gripping device 272 is operated to grip the braid 108 when the braid 108 is in a predetermined position for cutting with respect to the cutting device 278. At the operation 1022, which is optional, the first gripping device 270 is operated to advance a predetermined distance in the forward direction $D_F$. This operation can be performed to provide a predetermined tension to the braid 108 to stretch out the braid 108 between the first and second gripping devices 270 and 272 before the braid 108 is cut at the operation 1026.

At the operation 1024, the third gripping device 274 is operated to grip the braid 108 at a third location 281C. In at least some embodiments, the third location 281C is located between the cutting device 274 and the first gripping device 270. In other embodiments, the third location 281C is arranged in different positions.

At the operation 1026, the cutting device 278 is operated to cut the braid 108 between the first and third gripping devices 270 and 274. In at least some embodiments, the cutting device 278 operates to move around the braid 108 and shear the braid 108. At the operation 1028, the third gripping device 274 operates to open to release the braid 108 at the third location 281C after the braid 108 is sheared. At the operation 1030, the first gripping device 270 operates to advance in the forward direction $D_F$ to place the sheared braid 108 over the tray 280. At the operation 1032, the first gripping device 270 operates to release the braid 108 to drop the braid 108 into the tray 280. At the operation 1034, the first gripping device 270 returns in the rearward direction $D_R$ to the first location 281A.

At the operation 1036, the first gripping device 270 operates to grip a new braid 108 at the first location 281A. Since the operation 1020, the second gripping device 272 can remain closed to maintain the proper exit tension of the braid 108 until the first gripping device 270 moves back to the first location 281A adjacent the second gripping device 272 to grip a new portion of the braid 108.

At the operation 1038, the second gripping device 272 operates to open and release the braid 108 when the first gripping device 270 returns and grips the braid 108 near the second gripping device 272. At the operation 1040, the braiding machine 100 resumes its operation and continues the braiding process. Then, the method 1000 returns to the operation 1004.

Although the second and third gripping devices 272 and 274 are stationary in this embodiment, either or both of the second and third gripping devices 272 and 274 can be configured to move. In some embodiments, the third gripping devices 274 can be linearly operated as the first gripping device 270 moves. In this configuration, the first gripping device 270 and the third gripping device 274 can be alternately operated to grip and convey the braid 108 in the forward direction $D_F$. For example, when the first gripping device 270 grips the braid 108 and moves it away from the cutting device 278 in the conveying direction L, the third gripping device 274 can stay adjacent the cutting device 278. Then, as the first gripping device 270 returns close to the cutting device 278 after dropping the braid 108 onto the tray 280, the third gripping device 274 can be operated to grip another braid 108 and move it from the cutting device 278 in the forward direction $D_F$. In this case, the alternating movements of the first and third gripping device 270 and 274 can enable the operation of the braiding machine 100 without interruption or pause during cutting process. In other embodiments, the second gripping device 272 can be selectively operated to move, depending on the movement and/or location of the first gripping device 270. The second gripping device 272 can move at a lower speed than the first gripping device 270.

In some embodiments, the cutting system 260 does not employ either of the second gripping device 272 and the third gripping device 274. In other embodiments, the cutting system 260 can only use the first gripping device 270 to perform the same or similar operations as described herein.

FIG. 14a is a schematic view of another example inline cutting system 260 of FIG. 12, which is configured to be used with a braiding machine 100. In this embodiment, a carrier 282 is provided to avoid pausing the operation of the braiding machine 100 and allow the braiding machine 100 to continue to operate without interruption while the cutting process of the cutting system 260. In at least some embodiments, the carrier 282 is configured to move a set of the second gripping device 272, the third gripping device 274, the heating device 276, and the cutting device 278, and is configured to linearly moveable along the conveying line L.

The cutting system 260 in this embodiment may be operated in the same manner as in FIG. 13, except that the carrier 282 is operated to move in a forward direction $D_F$ so that the braiding machine 100 continues to braid without interruption. The carrier 282 moves in the forward direction $D_F$ until the first gripping device 270 moves back in a rearward direction $D_R$ to grip a new section of the braid 108 after one cycle of cutting process. When the first gripping device 270 grips the braid 108, the carrier 282 can move back in the rearward direction $D_R$ to return to its original position. An example operation of the cutting system 260 with the carrier 282 is illustrated in more detail with reference to FIG. 14b.

Figure 14B:
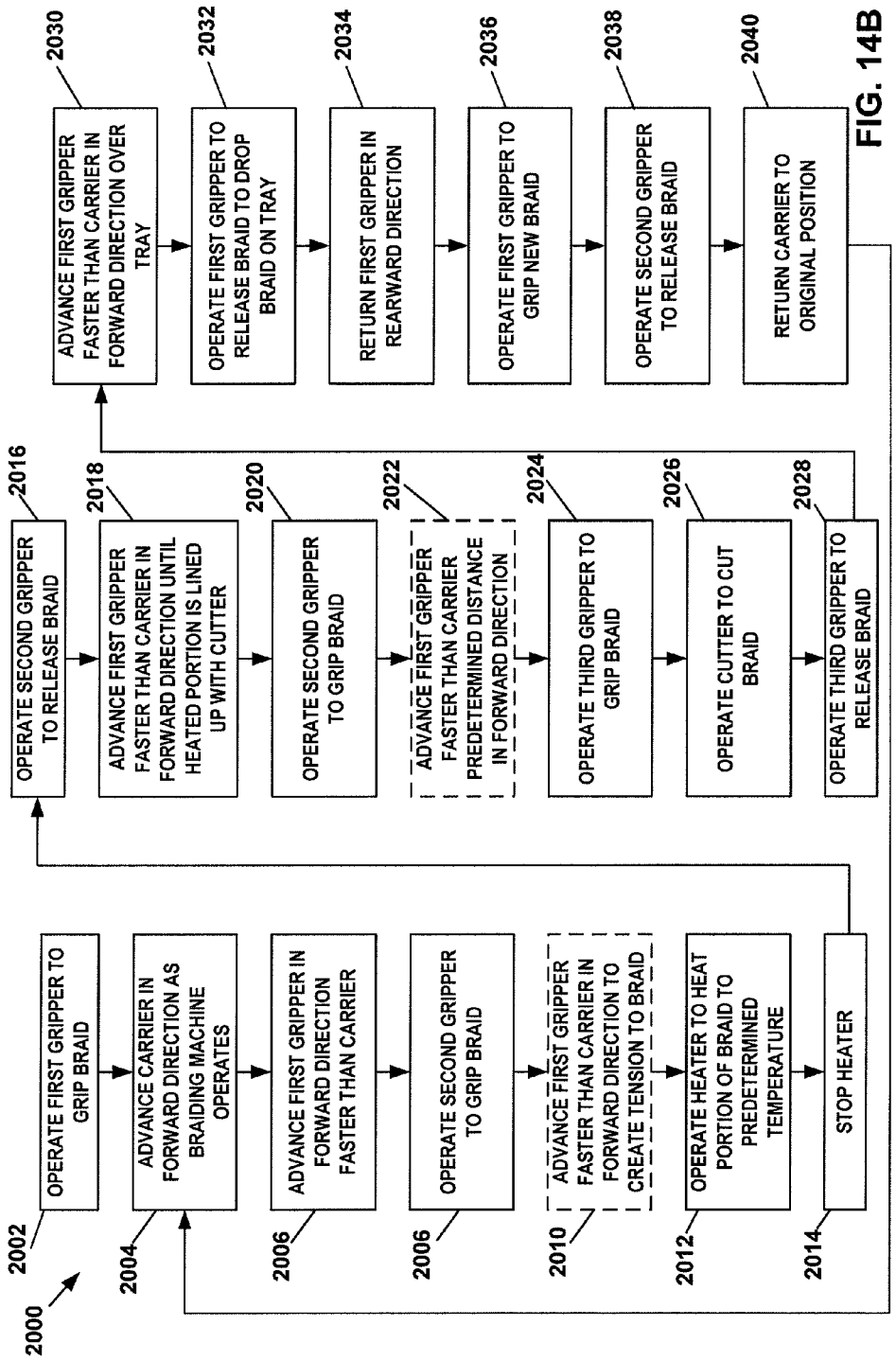
FIG. 14B is a flowchart illustrating an example method of operating the cutting system in accordance with the example operation of FIG. 14A.

FIG. 14b is a flowchart illustrating an example method 2000 of operating the cutting system 260 in accordance with the example operation of FIG. 14a. In the depicted embodiment, the method 2000 may include operations 2002, 2004, 2006, 2008, 2010, 2012, 2014, 2016, 2018, 2020, 2022, 2024, 2026, 2028, 2030, 2032, 2034, 2036, 2038, and 2040.

The method 2000 typically begins at the operation 2002 where the first gripping device 270 is operated to grip the braid 108. In at least some embodiments, the first gripping device 270 first grips the braid 108 between the take-up reel 106 (including the first and second spools 266 and 268) and the second gripping device 272. In other embodiments, the first gripping device 270 can grip the braid 108 at a different position.

At the operation 2004, the carrier 282 is advanced in a forward direction $D_F$ along the conveying line L as the braiding machine 100 operates. In at least some embodiments, the carrier 282 can be operated at the same speed as the takeoff speed of the braid 108 (i.e., the speed at which the braid 108 is drawn at the takeoff spool) to maintain a proper tension on the braid 108. In other embodiments, the speed of the carrier 282 can be adjusted based upon different factors.

At the operation 2006, the first gripping device 270 is operated to advance in the forward direction $D_F$ faster than the carrier 282 as the carrier 282 continue to move in the forward direction $D_F$. At the operation 2008, the second gripping device 272, which is moving as part of the carrier 282, can operate to grip the braid 108 when the braid 108 reaches a predetermined braid length or cut point. The predetermined braid length or cut point can be set and input by an operator, or automatically calculated by the control system based upon other operational parameters input by the operator. For example, as described herein, the braid length can be calculated from the takeoff speed, which can be determined by a given pick count and a given table speed.

The second gripping device 272 at the operation 2008 can grip the braid 108 between the set of the spools 266 and 268 (i.e., the take-up reel 106) and the first gripping device 270. In at least some embodiments, the second gripping device 272 is arranged between the take-up reel 106 (including the first and second spools 266 and 268) and the heating device 276. In other embodiments, the second gripping device 272 can be positioned between the take-up reel 106 and the cutting device 278. In yet other embodiments, the second gripping device 272 can be arranged at a different position.

At the operation 2010, which is optional, the first gripping device 270 can be operated to advance in the forward direction $D_F$ to create a predetermined tension of the braid 108. The operation can be a preliminary step at which the braid 108 is properly stretched out over the heating device 276 by the first and second gripping device 270 and 272 before the braid 108 is heated at the operation 2012. At the operation 2012, the heating device 276 is operated to heat a portion of the braid 108 that is to be cut by the cutting device 278. In at least some embodiments, the heating device 276 is moved around the portion of the braid 108 and operates for a predetermined period of time at a set temperature. In at least some embodiments, the heating device 276 is arranged between the first gripping device 270 and the second gripping device 272. In at least some embodiments, the heating device 276 is a non-contact heat block. Once the braid 108 is heated at the set temperature, the heating device 276 can retract.

At the operation 2016, the second gripping device 272 operates to open to release the braid 108. At the operation 2018, the first gripping device 270 is operated to advance faster than the carrier 282 in the forward direction $D_F$ until the heated portion of the braid 108 is lined up with the cutting device 278. In at least some embodiments, the cutting device 278 can be arranged between the heating device 276 and the first gripping device 270. In other embodiments, the cutting device 278 can be arranged at different locations.

At the operation 2020, the second gripping device 272 is operated to grip the braid 108 when the braid 108 is in a predetermined position for cutting with respect to the cutting device 278. At the operation 2022, which is optional, the first gripping device 270 is operated to advance faster than the carrier 282 a predetermined distance in the forward direction $D_F$. This operation can be performed to provide a predetermined tension to the braid 108 to stretch out the braid 108 between the first and second gripping devices 270 and 272 before the braid 108 is cut at the operation 2026.

At the operation 2024, the third gripping device 274 is operated to grip the braid 108. In at least some embodiments, the third gripping device 274 grips the braid 108 between the cutting device 274 and the first gripping device 270. In other embodiments, the third gripping device 274 is arranged to grip the braid 108 in different positions.

At the operation 2026, the cutting device 278 is operated to cut the braid 108 between the first and third gripping devices 270 and 274. In at least some embodiments, the cutting device 278 operates to move around the braid 108 and shear the braid 108. At the operation 2028, the third gripping device 274 operates to open to release the braid 108 at the third location 281C after the braid 108 is sheared. At the operation 2030, the first gripping device 270 operates to advance faster than the carrier 282 in the forward direction $D_F$ to place the sheared braid 108 over the tray 280. At the operation 2032, the first gripping device 270 operates to release the braid 108 to drop the braid 108 into the tray 280. At the operation 2034, the first gripping device 270 returns in the rearward direction $D_R$ to the first location 281A.

At the operation 2036, the first gripping device 270 operates to grip a new braid 108. In at least some embodiments, the first gripping device 270 can grip the braid 108 between the take-up reel 106 and the second gripping device 272. In other embodiments, the first gripping device 270 can grip the braid 108 at a different position.

Since the operation 2020, the second gripping device 272 can remain closed to maintain the proper exit tension of the braid 108 until the first gripping device 270 moves back to the first location 281A adjacent the second gripping device 272 to grip a new portion of the braid 108. At the operation 2038, the second gripping device 272 operates to open and release the braid 108 when the first gripping device 270 returns and grips the braid 108 near the second gripping device 272. At the operation 2040, the carrier 282 returns to its original location. Then, the method 2000 returns to the operation 2004.

Figure 15:
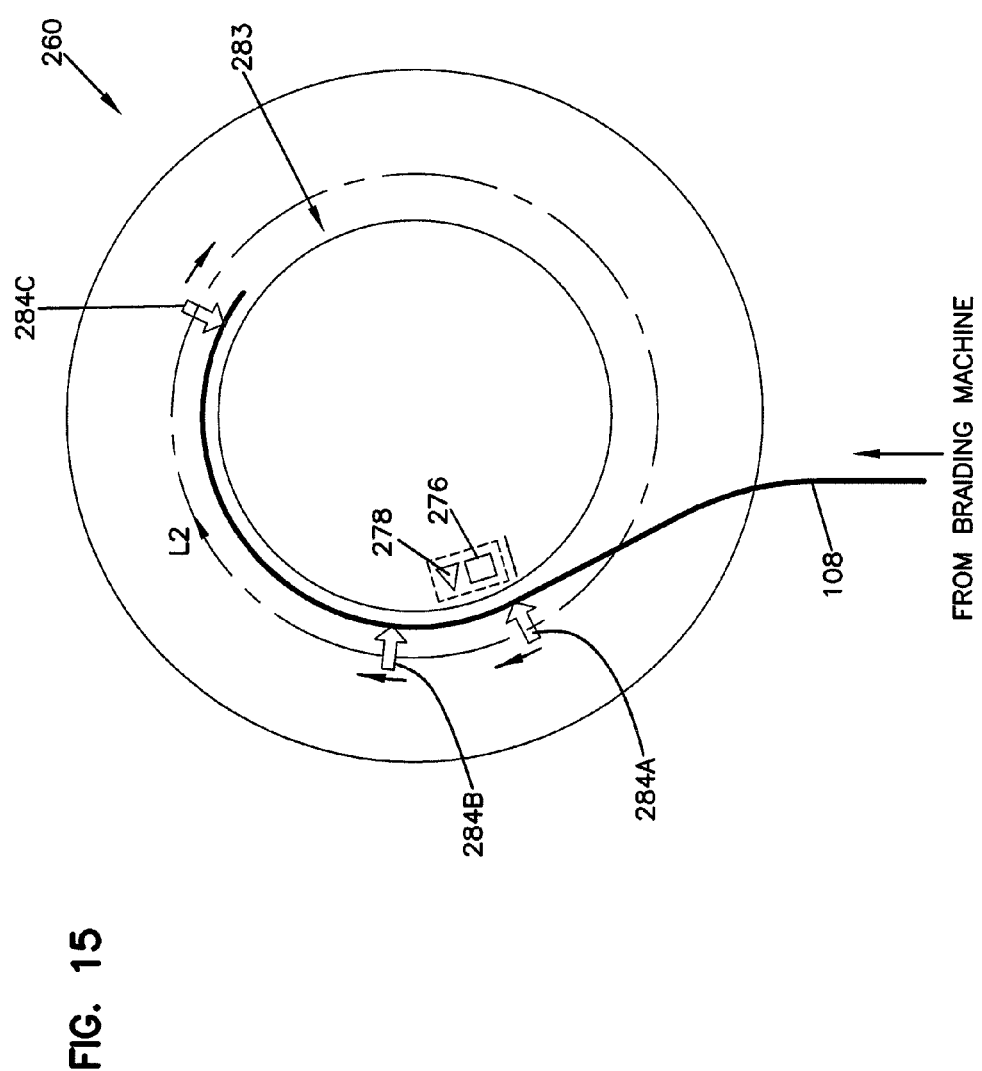
FIG. 15 is a schematic view of yet another example inline cutting system of FIG. 12, which is configured to be used with a braiding machine.

FIG. 15 is a schematic view of yet another example inline cutting system 260 of FIG. 12, which is configured to be used with a braiding machine 100. In this embodiment, the cutting system 260 is configured as a circular track 283 to continuously perform cutting process while allowing the braiding machine 100 to continue to operate without pause.

The braid 108 can be fed from the braiding machine 100 to the circular track 283 to route therearound. The cutting system 260 can include one or more gripping devices 284. In the depicted embodiment, the cutting system 260 includes three gripping devices 284A, 284B and 284C. The gripping devices 284 can independently move along the circular track 283 in a conveying direction L2.

In at least some embodiments, the heating device 276 and the cutting device 278 is movably arranged out of the circular track 283. For example, the heating device 276 and/or the cutting device 278 can be extended to the circular track 283 when the braid 108 is arranged in position on the circular track 283 for heating and/or shearing. In other embodiments, the heating and/or cutting devices 276 and 278 can be operated in different manners.

The principle of the operation of the cutting system 260 in this embodiment is similar to the cutting system illustrated in FIG. 13, except that the three gripping devices 284A-284C alternately change their roles as the first, second and third gripping devices 270, 272 and 274 as illustrated in FIG. 13. For example, once the gripping devices 284C, 284A and 284B operate as the first, second and third gripping devices 270, 272 and 274, respectively, to complete one cycle of the cutting process, the gripping device 284C moves around the circular track 283 and functions as the second griping device 272. In this case, the gripping device 284B becomes to work as the first gripping device 270 and the griping device 284A operates as the third gripping device 272 to perform the next cycle of the cutting process. In other embodiments, other configurations are possible.

Figure 16:
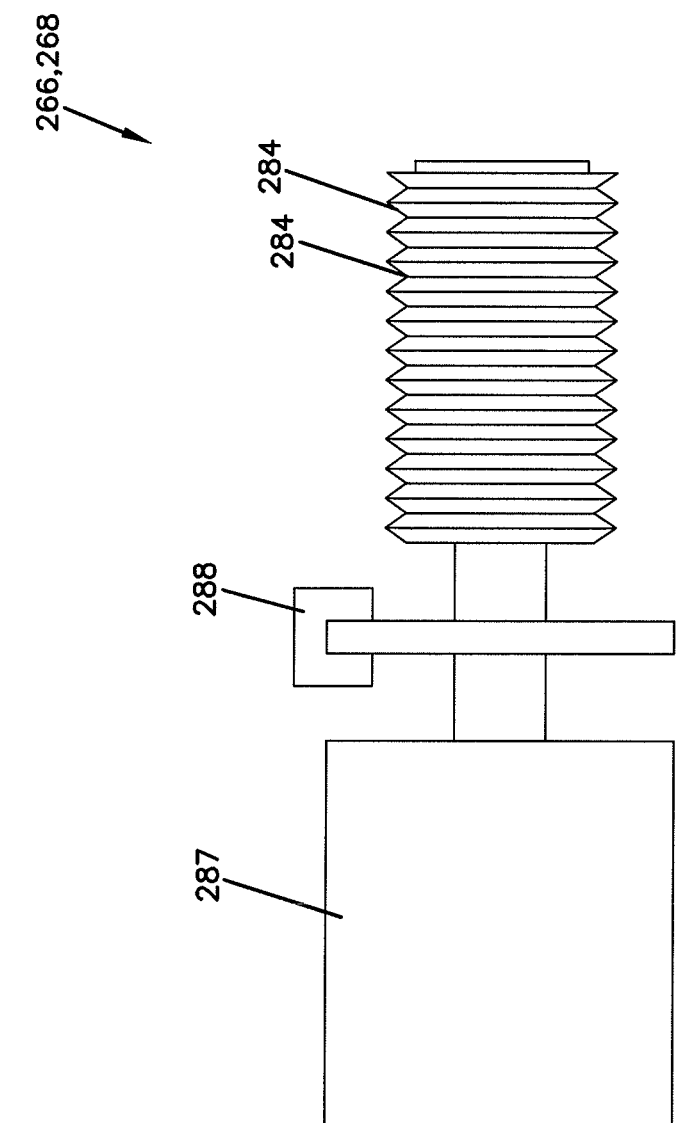
FIG. 16 shows an example spool.

FIG. 16 shows an example spool 266 or 268. In at least some embodiments, the spools 266 and 268 have a plurality of grooves 464. The grooves 464 are configured to organize the braid 108 wrapped therearound. In at least some embodiments, the grooves 464 are shapes in a "V" configuration.

One of the spools 266 and 268 are driven by a spool actuating mechanism 286. In at least some embodiments, the spool actuating mechanism 286 can include a servo motor 287. The operational status and/or conditions of the servo motor 287 can be monitored a spool motor encoder 288 attached to the spool motor 287. The status and/or conditions (e.g., the angular location of the motor 286 or the takeoff spool) obtained by the spool motor encoder 288 is fed back to the cutter control system 262 and used to control the cutting system 260. In other embodiments, the spool motor 286 is a stepper motor. In yet other embodiments, the spool actuating mechanism 286 can be configured in different manners.

The spool motor 286 can be controlled independently from the active track and passive track motors 148 and 158 in order to allow changing the pick count of the braid. In at least some embodiments, the pick counts and the horn gear rotations (i.e., table speeds) can be used to calculate the length of the braid, which can be used in the cutting system 260.

Figure 17A:
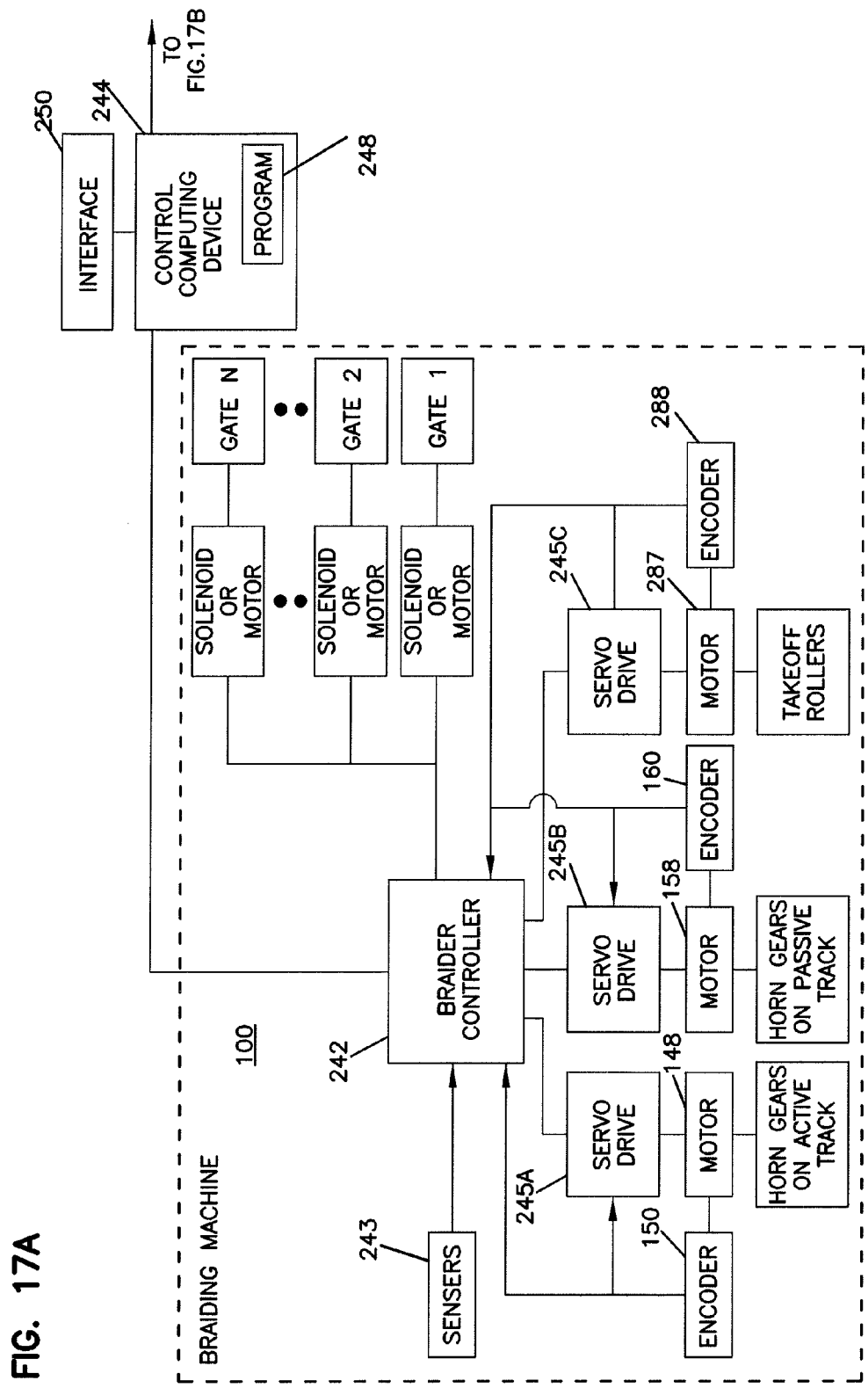
FIG. 17A is a schematic diagram of the control system of FIG. 17 for a braiding machine.
Figure 17B:
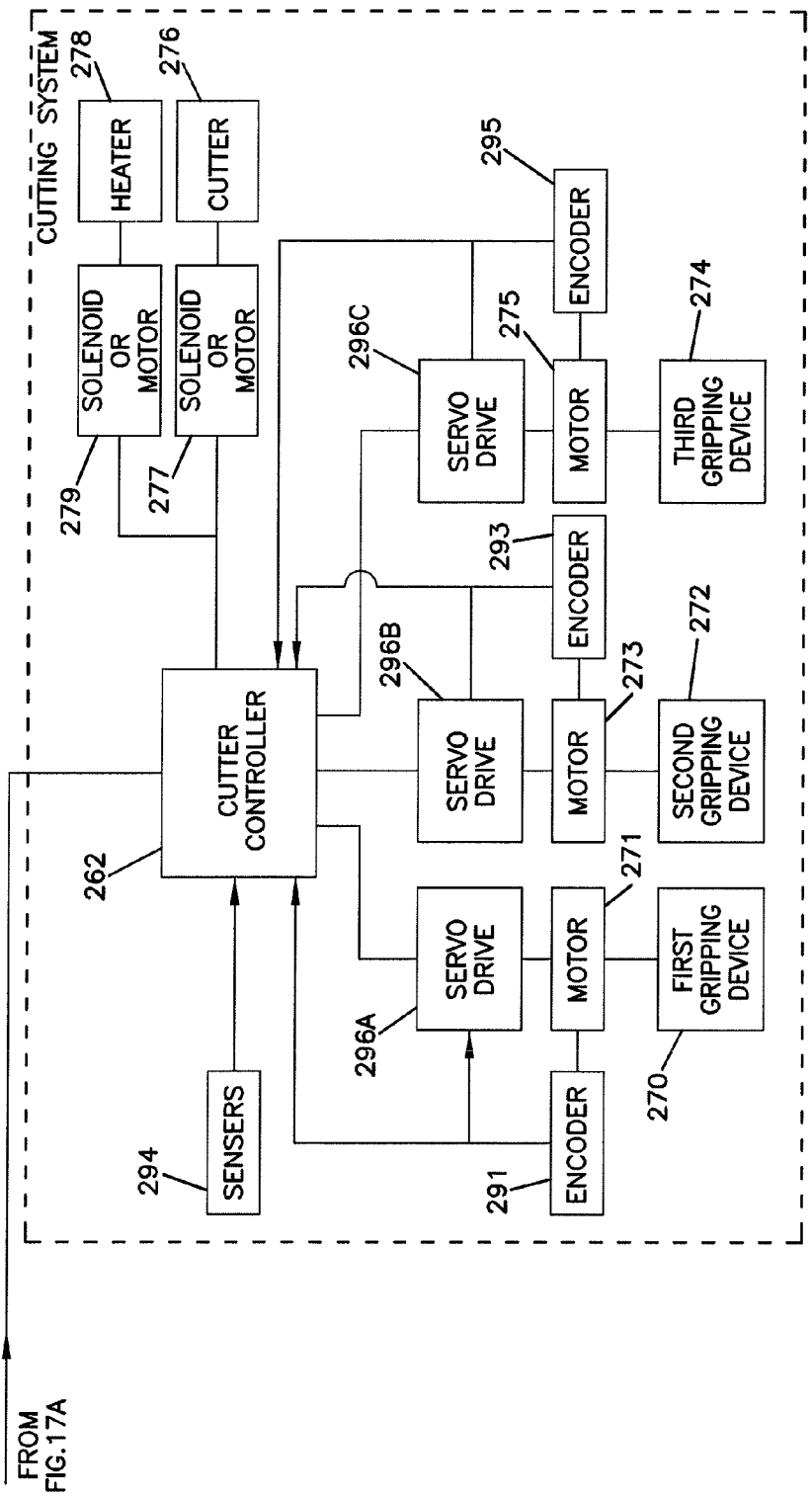
FIG. 17B is a schematic diagram of the control system of FIG. 17 for a cutting system.

FIG. 17 is a schematic diagram of an example control system 240 for the braiding machine 100 (FIG. 17A) and the cutting system 260 (FIG. 17B). In at least some embodiments, the control system 240 includes a braider controller 242, one or more braider sensors 243, servo drives 245, a control computing device 244, a program 248, a user interface 250, a cutter controller 262, one or more cutter sensors 294, and servo drives 296.

The braider controller 242 is configured to control at least some of the components of the braiding system 100. Examples of the braider controller 242 include a programmable logic controller (PLC) and a computer numerical control (CNC). Although the depicted embodiment of the braider controller 242 is primarily illustrated as a PLC, the braider controller 242 can be of any type suitable for controlling the braiding machine 100 as desired.

The braider controller 242 is connected to the servo drives 245 and communicates with the servo drives 245 to control the servo motors 148, 158 and 278.

The braider sensors 243 operate to monitor the status, position, and/or operation of the components of the braiding machine 100. For example, the sensors 243 can be used to detect the relative positions of the bobbin carrier assemblies 122, the horn gear assemblies 124, and/or the gates 126. Examples of the sensors 243 include proximity sensors and cameras.

The servo drives 245 are configured to operate the motors 148, 158 and 278 based upon signals from the braider controller 242. For example, the servo drives 245 can operate to receive a command signal from the braider controller 242, amplify the signal, and transmit electric current to the servo motors 148, 158 and 278 in order to produce motion of the motors proportional to the command signal. Other configurations are also possible. The encoders 150, 160 and 288 attached to the motors 148, 158 and 278 operates to report the motors' actual status back to the servo drives 245 and/or the braider controller 242. Then, the servo drives 245 can compare the actual motor status with the command motor status and alter the voltage frequency or pulse with to the motors so as to correct for any deviation from the commanded status.

The control computing device 244 operates to manage both of the braider controller 242 and the cutter controller 262. An example of the control computing device 244 is illustrated and described in more detail with reference to FIG. 18.

The program 248 is executed in the control computing device 244 to control the braider controller 242 and the cutter controller 262. The program 248 contains a variety of algorithms for different operations of the braiding machine 100 and the cutting system 260. In at least some embodiments, the control computing device 244 can be provided with different programs 248 for different types of braid 108, such as different patterns of one or more trace strands and/or alternating flat/round sections, as described herein. The programs 248 are composed based upon a plurality of operational parameters, which are described herein.

The user interface 250 provides an interface for an operator to interact with to input user instructions and commands to the control computing device 244, and to monitor the status of the braiding machine 100 and the cutting system 260.

The cutter controller 262 is configured to control at least some of the components of the cutting system 260. Examples of the braider controller 262 include a programmable logic controller (PLC) and a computer numerical control (CNC). Although the depicted embodiment of the cutter controller 262 is primarily illustrated as a PLC, the cutter controller 262 can be of any type suitable for controlling the braiding machine 100 as desired.

The cutter sensors 294 operate to monitor the status, position, and/or operation of the components of the cutting system 260. For example, the cutter sensors 294 can be used to detect the relative positions of the gripping devices 270, 272 and 274, the heating device 274, and/or the cutting device 276. Examples of the sensors 243 include proximity sensors and cameras.

The servo drives 296 (including 296A-296C) are configured to operate the motors 271, 273 and 275 upon signals from the cutter controller 262. For example, the servo drives 296 can operate to receive a command signal from the cutter controller 262, amplify the signal, and transmit electric current to the servo motors 271, 273 and 275 in order to produce motion of the motors proportional to the command signal. Other configurations are also possible. The encoders 291, 293 and 295 attached to the motors 271, 273 and 275 operates to report the motors' actual status back to the servo drives 296 and/or the cutter controller 262. Then, the servo drives 296 can compare the actual motor status with the command motor status and alter the voltage frequency or pulse with to the motors so as to correct for any deviation from the commanded status.

In at least some embodiments, the braiding machine 100 and the cutting system 260 can be controlled depending on a plurality of operational parameters. An operator of the system can interact with the user interface 250 to input one or more of the operational parameters. Examples of the operational parameters include transition points of pattern, pick counts, take-off speeds, table speeds (i.e., the rotation speeds of the horn gear assemblies or the motors thereof), braid lengths, cut locations, temperatures of the heating device 276, a heating time, and the total number of parts per lot. The braid transition points indicate points of the braid 108 at which the patterns of the braid 108 and/or the braiding types of the braid 108 change. The pick counts indicate the number of crossovers of alternate endings in a given length of the braid 108. The pick counts can change as the patterns and/or types vary. The take-off speeds is a speed of the braid 108 that takes off from the braiding machine 100. For example, the take-off speeds can be calculated from the operation of one or both of the first and second spools 266 and 268 (i.e., the take-up reel 106). In at least some embodiments, the braid lengths are used to determine the cut locations of the braid 108 to produce desired lengths of individual braids. The cut locations can be used to determine the locations of the cutting device 260.

The pick counts, the take-off speeds, the table speeds, and the braid lengths are all related. For example, the take-off speeds can be calculated from the pick counts and the table speeds. Also, the braid lengths can be calculated from the take-off speeds. In at least some embodiments, therefore, the operator can input the pick counts and the table speeds into the control computing device 244 via the user interface 250 to adjust the take-off speeds (and thus the braid lengths).

The cutter controller 262 is also operated based upon the operational parameters input to the control computing device 244. In at least some embodiments, based upon these parameters, the cutter controller 262 can control the linear rail speeds, the movements and/or positions of the gripping devices, the cut locations, the temperatures of the heating device 276, the number of heating processes, and/or the number of cutting cycles.

In at least some embodiments, the braider controller 242 and the cutter controller 292 can be separately controlled by a single control computing device or multiple control computing devices.

Figure 18:
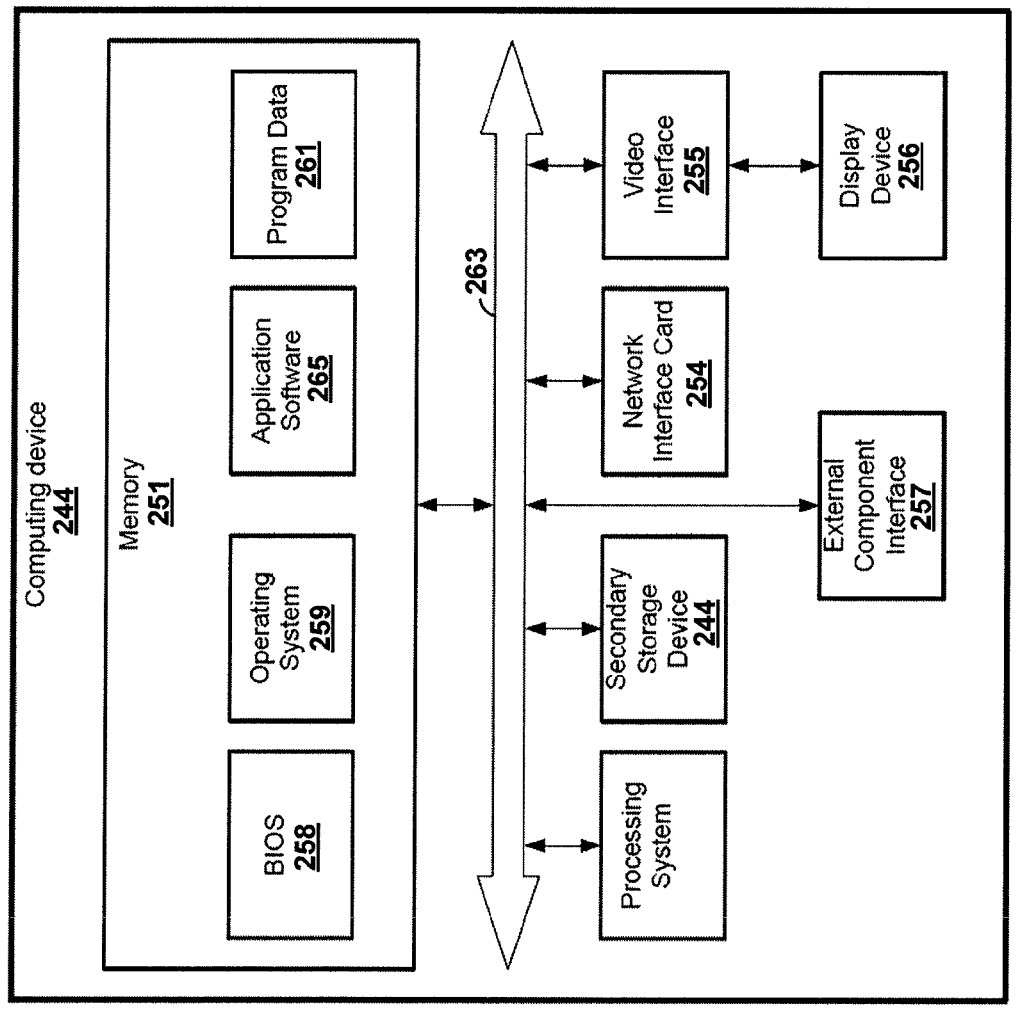
FIG. 18 is a block diagram illustrating an example computing device.

FIG. 18 is a block diagram illustrating an example computing device 244. In some embodiments, the database system 100 and/or a device with the operating system 110 are implemented as one or more computing devices like the computing device 244. It should be appreciated that in other embodiments, the database system 100 and/or a device with the operating system 110 are implemented using computing devices having hardware components other than those illustrated in the example of FIG. 18.

The term computer readable media as used herein may include computer storage media and communication media. As used in this document, a computer storage medium is a device or article of manufacture that stores data and/or computer-executable instructions. Computer storage media may include volatile and nonvolatile, removable and non-removable devices or articles of manufacture implemented in any method or technology for storage of information, such as computer readable instructions, data structures, program modules, or other data. By way of example, and not limitation, computer storage media may include dynamic random access memory (DRAM), double data rate synchronous dynamic random access memory (DDR SDRAM), reduced latency DRAM, DDR2 SDRAM, DDR3 SDRAM, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Accordingly, in the embodiments contemplated herein, computer storage media includes at least some tangible medium or device. In certain embodiments, computer storage media includes non-transitory media and/or devices. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

In the example of FIG. 18, the computing device 244 includes a memory 251, a processing system 252, a secondary storage device 253, a network interface card 254, a video interface 255, a display unit 256, an external component interface 257, and a communication medium 263. The memory 251 includes one or more computer storage media capable of storing data and/or instructions. In different embodiments, the memory 251 is implemented in different ways. For example, the memory 251 can be implemented using various types of computer storage media.

The processing system 252 includes one or more processing units. A processing unit is a physical device or article of manufacture comprising one or more integrated circuits that selectively execute software instructions. In various embodiments, the processing system 252 is implemented in various ways. For example, the processing system 252 can be implemented as one or more processing cores. In another example, the processing system 252 can include one or more separate microprocessors. In yet another example embodiment, the processing system 252 can include an application-specific integrated circuit (ASIC) that provides specific functionality. In yet another example, the processing system 252 provides specific functionality by using an ASIC and by executing computer-executable instructions.

The secondary storage device 253 includes one or more computer storage media. The secondary storage device 253 stores data and software instructions not directly accessible by the processing system 252. In other words, the processing system 252 performs an I/O operation to retrieve data and/or software instructions from the secondary storage device 253. In various embodiments, the secondary storage device 253 includes various types of computer storage media. For example, the secondary storage device 253 can include one or more magnetic disks, magnetic tape drives, optical discs, solid state memory devices, and/or other types of computer storage media.

The network interface card 254 enables the computing device 244 to send data to and receive data from a communication network. In different embodiments, the network interface card 254 is implemented in different ways. For example, the network interface card 254 can be implemented as an Ethernet interface, a token-ring network interface, a fiber optic network interface, a wireless network interface (e.g., WiFi, WiMax, etc.), or another type of network interface.

The video interface 255 enables the computing device 244 to output video information to the display unit 256. The display unit 256 can be various types of devices for displaying video information, such as a cathode-ray tube display, an LCD display panel, a plasma screen display panel, a touch-sensitive display panel, an LED screen, or a projector. The video interface 255 can communicate with the display unit 256 in various ways, such as via a Universal Serial Bus (USB) connector, a VGA connector, a digital visual interface (DVI) connector, an S-Video connector, a High-Definition Multimedia Interface (HDMI) interface, or a DisplayPort connector.

The external component interface 257 enables the computing device 244 to communicate with external devices. For example, the external component interface 257 can be a USB interface, a FireWire interface, a serial port interface, a parallel port interface, a PS/2 interface, and/or another type of interface that enables the computing device 244 to communicate with external devices. In various embodiments, the external component interface 257 enables the computing device 244 to communicate with various external components, such as external storage devices, input devices, speakers, modems, media player docks, other computing devices, scanners, digital cameras, and fingerprint readers.

The communications medium 263 facilitates communication among the hardware components of the computing device 244. In the example of FIG. 18, the communications medium 263 facilitates communication among the memory 251, the processing system 252, the secondary storage device 253, the network interface card 254, the video interface 255, and the external component interface 257. The communications medium 263 can be implemented in various ways. For example, the communications medium 263 can include a PCI bus, a PCI Express bus, an accelerated graphics port (AGP) bus, a serial Advanced Technology Attachment (ATA) interconnect, a parallel ATA interconnect, a Fiber Channel interconnect, a USB bus, a Small Computing system Interface (SCSI) interface, or another type of communications medium.

The memory 251 stores various types of data and/or software instructions. For instance, in the example of FIG. 18, the memory 251 stores a Basic Input/Output System (BIOS) 258 and an operating system 259. The BIOS 258 includes a set of computer-executable instructions that, when executed by the processing system 252, cause the computing device 244 to boot up. The operating system 259 includes a set of computer-executable instructions that, when executed by the processing system 252, cause the computing device 244 to provide an operating system that coordinates the activities and sharing of resources of the computing device 244. Furthermore, the memory 251 stores application software 265 including the program 248. The application software 265 includes computer-executable instructions, that when executed by the processing system 252, cause the computing device 244 to provide one or more applications. The memory 251 also stores program data 261. The program data 261 is data used by programs that execute on the computing device 244.

Referring to FIG. 19-22, the braiding machine described herein can be used to make a variety of different surgical braid that have different patterns and structures. The braids illustrated herein are braided using a 1-over-1 configurations, although alternative embodiment can use braid configurations other than a 1-over-1 braid. Additionally, the braiding machine can be used to make braids having different structures such as a generally tubular structure in which strands 110 follow a generally spiral path for a full 360 degrees, a braid having a flat section, braids having bifurcations, and other braid structures. The braiding machine 102 also can be controlled to make braids can be made with or without a core, spine, or reinforcing member running along the length of the braid. Various embodiments of the braiding machine 100 disclosed herein can make surgical braids having these structures and surgical braids having combinations of these structures.

The braiding machine 100 also can be used to make surgical braids formed with a continuous braid along the entire length of the braid without requiring weaving, splicing, or gluing. For example, the surgical braid can have a continuous braid through transitions between different structures such as the transition from a tubular braid to a flat or tape braid, or through a change in strands used to form a core. Some alternative embodiment might still use fastening techniques such as gluing, weaving, or splicing to form certain aspects of the surgical braids.

Additionally, braids can be made using trace strands 402 that different colors than the rest of the strands 110 used in the braid 108 to further enhance visibility of the surgical braid 300. For example, the braid 108 can include a plurality of white strands 110 and one or more colored trace strands 402 that visually stands out from the rest of the strands 110. When trace strands are used, braids can be made having changing colors and changing patterns for the trace stands. Example colors that can be used for the strands 402 include blue, green, violet, brown, purple, black, white, or any other suitable color.

The braids 108 can be used as surgical braids. Example materials that can be used for strands 110 in the surgical braid include polypropylene, polyethylene, polyethylene terephthalate (PET), silk, nylon, thermoplastic fluoropolymers such as polyvinylidene fluoride, polyvinylidene difluoride (PVDF), or any combination thereof. Advantages of such materials include added tensile strength, which reduces stretching when pulled and an axial load is applied to the braid. In at least some possible embodiments, the surgical braid is braided with 16 strands in a 1-over-1 configuration. Other embodiments are possible. For example, the surgical braid can be braided with more or less than 16 strands, and configurations other than a 1-over-1 configuration. Additionally, the surgical braid can include strands formed with ultra-high-molecular weight polyethylene (UHMWPE). In some possible embodiment, less than about 90% of the strands in the surgical braid are UHMWPE. In other possible embodiments, less than about 75% of the strands 306 in the surgical braid are UHMWPE. The strands can have a range of linear mass densities. For example, in at least some embodiments, the strands have a linear mass density greater than 110 deniers. Other embodiments can have strands with a linear mass density about 110 deniers or lower. Yet other embodiments have an average of about 100 deniers. Alternative embodiments also can include multifilament fibers, monofilament fibers, yarns, strands formed with braided or twisted fibers, individual fibers, or a combination thereof. In at least some possible embodiments, the trace strand is formed using a stronger material than the material used for the other strands of the surgical braid. Additionally, although surgical braids are disclosed, the braiding machine 102 and methods disclosed herein can be used to make other types of braids such as ropes, wires, and cables, and can use strands made from any type of suitable material including metals, plant-based fibers, and chemical-based fibers.

Figure 19:
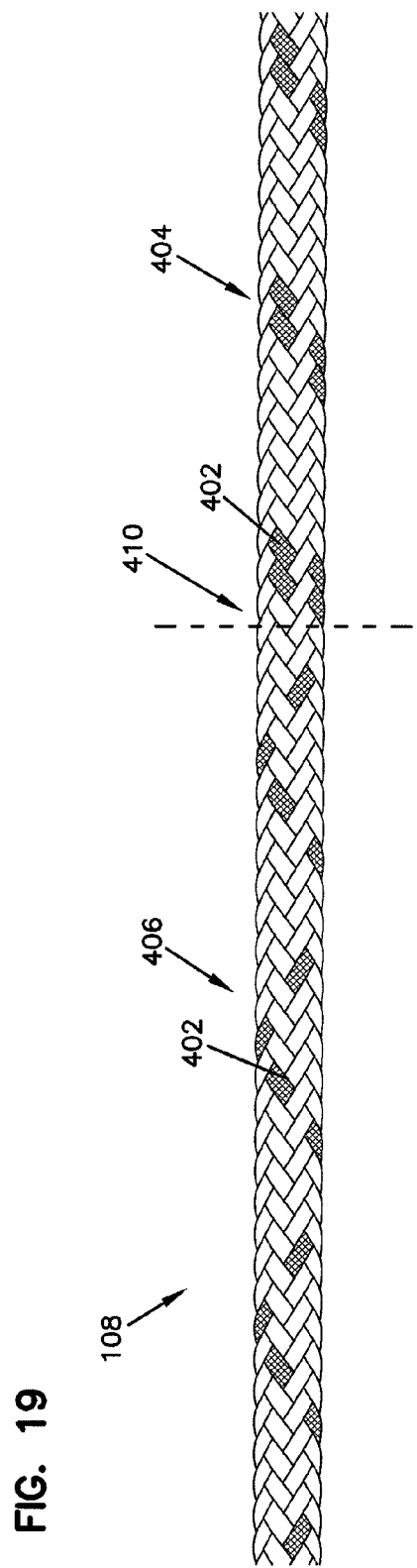
FIG. 19 illustrates an example braid with alternating different patterns defined by two trace strands.
Figure 22:
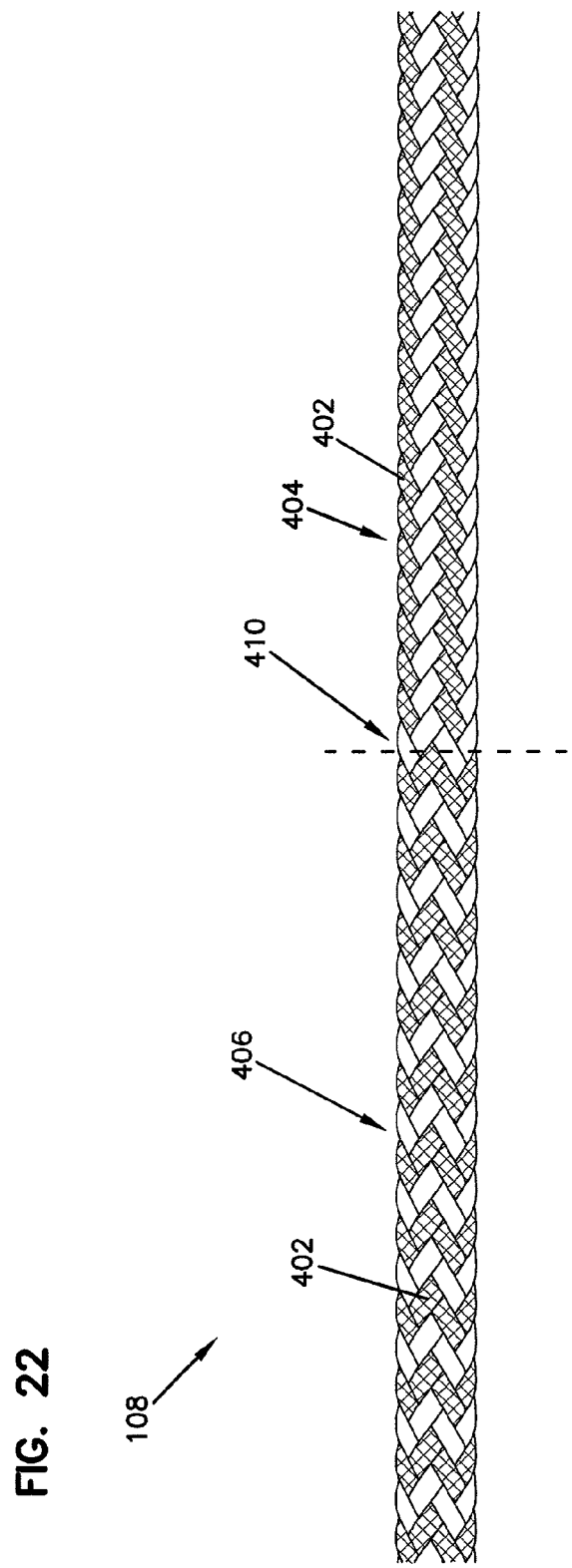
FIG. 22 illustrates an example braid with alternating different patterns defined by eight trace strands.

FIGS. 19-22 illustrate braids having changing patterns of color traces, which can be made using a braiding machine having active and passive tracks as disclosed and taught herein. FIG. 19 illustrates an exemplary braid having two trace strands 402. As illustrated, the braid 108 is substantially tubular and has first and second sections 404 and 406 such that the trace strands have one pattern in the first section and a different pattern in the second section 406. In the illustrated embodiment, the braid 108 has a striped pattern in the first section 404 and a cross pattern in the second section 406. FIG. 20 illustrates an example braid 108 with alternating different patterns defined by four trace strands 402. In the depicted embodiment, the braid 108 can include a cross pattern in the section 404 and a striped pattern in the section 406. FIG. 21 illustrates an example braid 108 with alternating different patterns defined by six trace strands 402. In the depicted embodiment, the braid 108 can include a striped pattern in the section 404 and a cross pattern in the section 406. FIG. 22 illustrates an example braid 108 with alternating different patterns defined by eight trace strands 402. In the depicted embodiment, the braid 108 can include a cross pattern in the section 404 and a striped pattern in the section 406.

In different embodiments, the trace strands in the embodiments illustrated in FIGS. 19-22 can each have the same color, each have a different color, or can have different combinations of two or more colors such that one group of trace fibers have one color and other group(s) of trace fibers have a different color(s). Additionally, the braid can be formed with different patters than the stripped and crossing patterns as illustrated. Yet other embodiment might have more than two sections such that the patters alternate along the length of the fiber or such that each section has a different pattern.

When making braids having a changing patter as illustrated in FIGS. 19-22, the bobbin carrier assemblies travel along clockwise and counterclockwise paths 207 and 209 of the active track 202 during which the trace strands are braided into a first pattern. To transition the traces to a second pattern, the bobbin carrier assemblies 222 are moved along a combination of the active and passive tracks 202 and 204A-204D as illustrated in FIGS. 23-31. For purposes of illustration, the steps and bobbin carrier positions in FIGS. 23-31 are shown using the arrangement of active and passive tracks, active and passive horn gears, and gates illustrated in FIGS. 2 and 3a, although the steps or operations described herein can be implemented with alternative arrangements of the active and passive tracks, active and passive horn gears, and gates.

Figure 33:
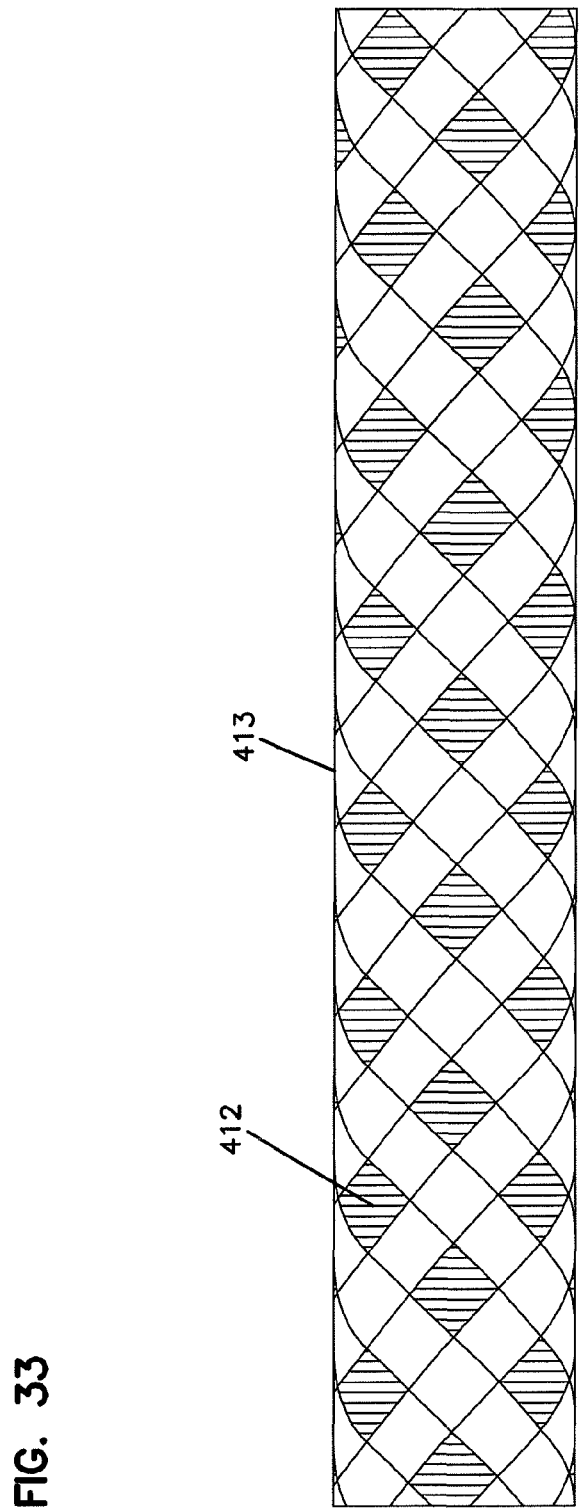
FIG. 33 illustrates an example braid with a cross-striped pattern.

As illustrated in FIGS. 23-31, the horn gears 132A-132H and 134A-134H operate to carry the bobbin carriers 1A, 1B, 2A, 2B, 3A, 3B, 4A, 4B, 5A, 5B, 6A, 6B, 7A, 7B, 8A, and 8B, which roughly correspond to bobbin carriers 122A-122P. As described below, the horn gears also operate to selectively transfer at least one of the bobbin carriers between adjacent horn gears as the horn gears rotate. In at least some embodiments, shifts of the bobbin carriers between adjacent active horn gears occur at transition positions GA1-GA8. Shifts of the bobbin carriers between active horn gears and adjacent passive horn gears occur at transition points GP1-GP4 to forms continuous paths (such as paths 312, 314, 316 and 318 as illustrated in FIG. 33). The bobbins can be selectively shifted between the active and passive tracks 202 and 204 through gates GPA1-GPA8, which correspond to gates 126A-126H in FIGS. 2 and 3a. The transition mechanisms GPA1-GPA8 are configured to selectively guide the bobbin carriers 122 between the active and passive tracks 202 and 204A-204D. In at least some embodiments, at least one of the transition mechanisms GPA1-GPA8 are implemented with the gates 126.

When making the braid having two trace strands as illustrated in FIG. 19, the bobbin carrier assemblies 1A and 2B are loaded with trace strands and the remaining bobbin carriers are loaded with white stands. When making the braid having four trace strands as illustrated in FIG. 20, the bobbin carrier assemblies 1A, 2A, 5A, and 6A are loaded with trace strands and the remaining bobbin carriers are loaded with white stands. When making the braid having six trace strands as illustrated in FIG. 21, the bobbin carrier assemblies 1A, 2B, 5A, 6B, 7A, and 4B are loaded with trace strands and the remaining bobbin carriers are loaded with white stands. When making the braid having eight trace strands as illustrated in FIG. 22, the bobbin carrier assemblies 1A, 2A, 5A, 6A, 7A, 8A, 3A, and 4A are loaded with trace strands and the remaining bobbin carriers are loaded with white stands.

Figure 23:
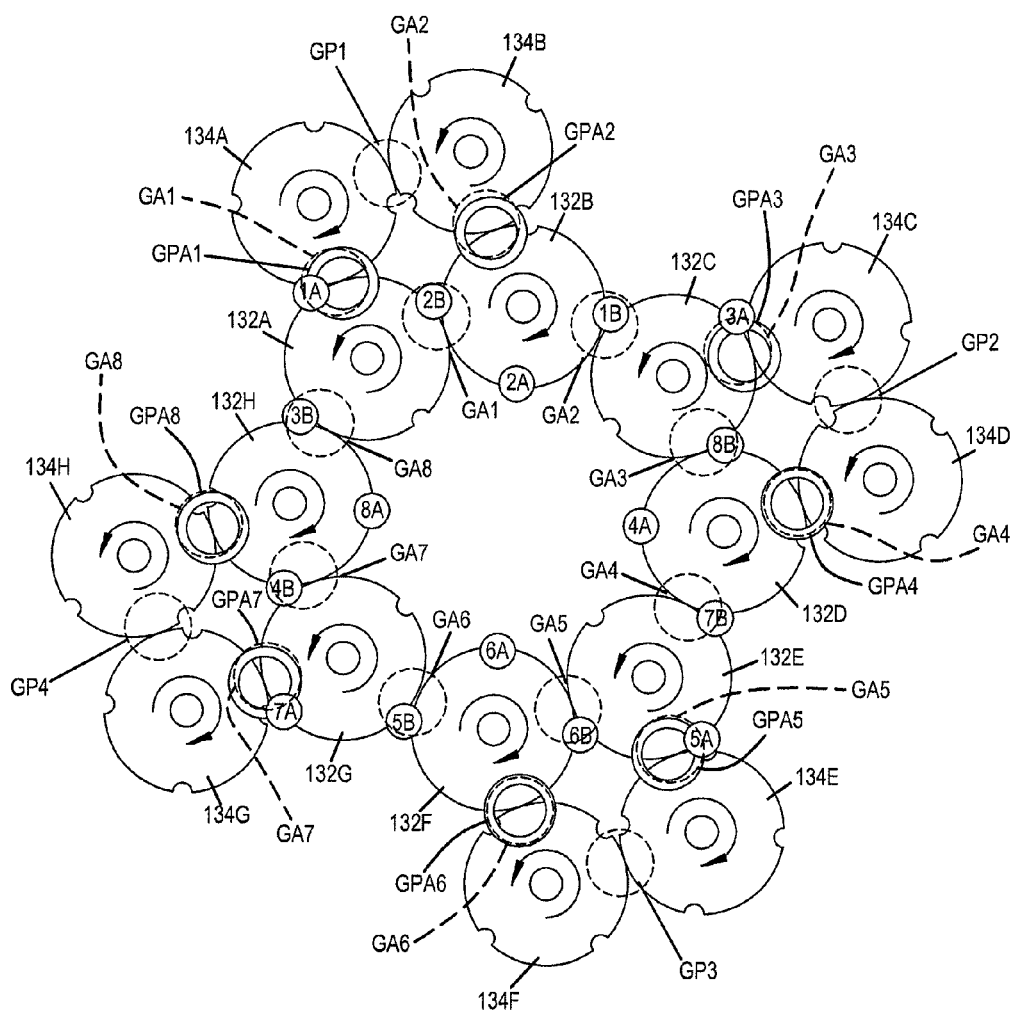
FIG. 23 illustrates an example configuration of the braiding machine when a surgical braid is made to a certain length.

In FIG. 23 illustrates a starting position (Step 1) of the bobbin carriers 222, all of the bobbin carriers 1A, 1B, 2A, 2B, 3A, 3B, 4A, 4B, 5A, 5B, 6A, 6B, 7A, 7B, 8A, and 8B are located on the active track 202. To move the bobbin carrier assemblies to the next position (Step 2 in FIG. 24), the transition mechanisms GPA2, GPA4, GPA6, and GPA8, which are collectively referred to as Gate Set A, are opened to transfer select bobbin carriers from the active track 202 to the passive track 204. Then, the braiding machine 100 operates to rotate all of the horn gears 132A-132H and 134A-134H about 90 degrees to transfer the bobbin carriers 2B, 4B, 6B and 8B from the active track horn gears 132B, 132H, 132F and 132D to the passive track horn gears 134B, 134H, 134F and 134D, respectively. The bobbin carriers 1B, 3B, 5B and 7B remain on the active track 202. Further, the bobbin carriers 1A, 2A, 3A, 4A, 5A, 6A, 7A and 8A remains on the active track 202 and are transferred counter-clockwise between adjacent active track horn gears 132A-132H.

Figure 24:
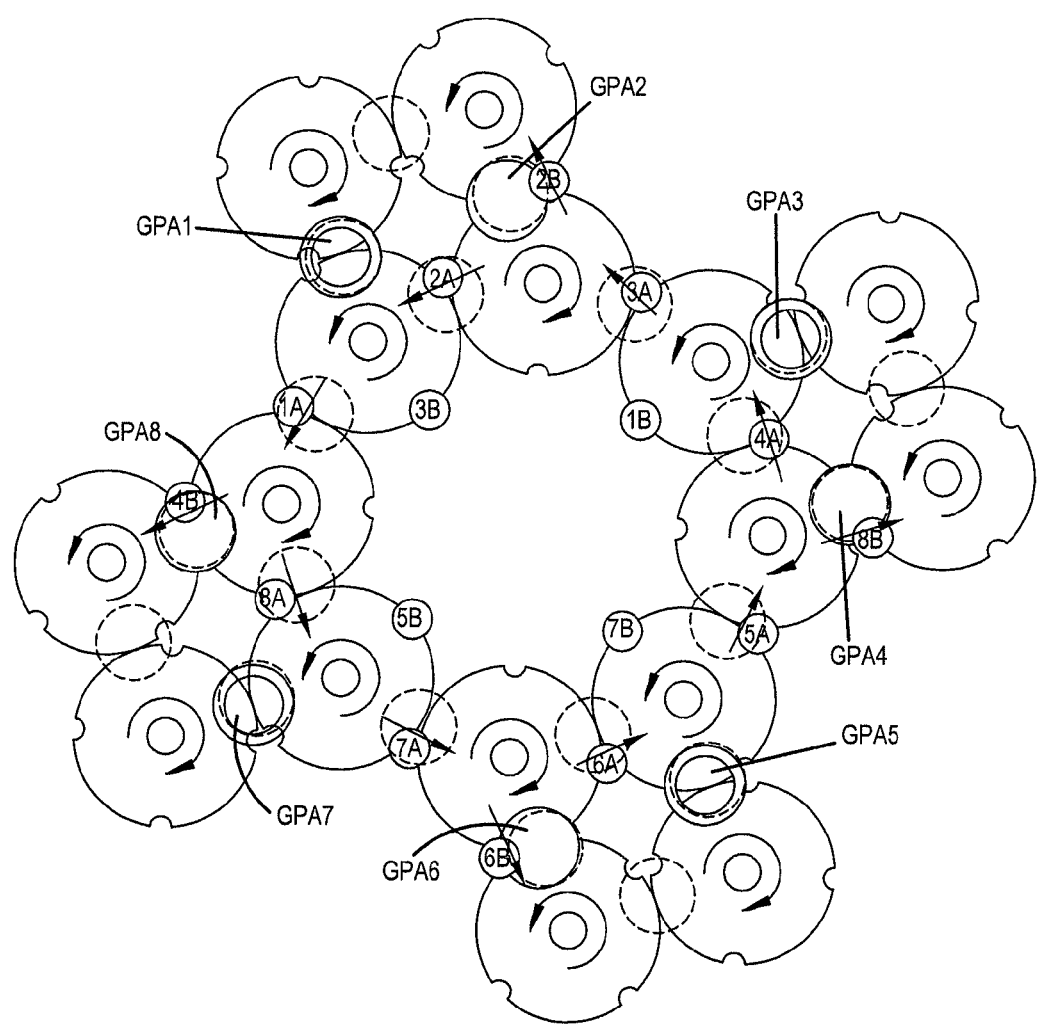
FIG. 24 illustrates the positions of the bobbin carriers at step 2 when the horn gears rotate 90 degrees about their rotational axes, respectively, from the positions of FIG. 23.
Figure 25:
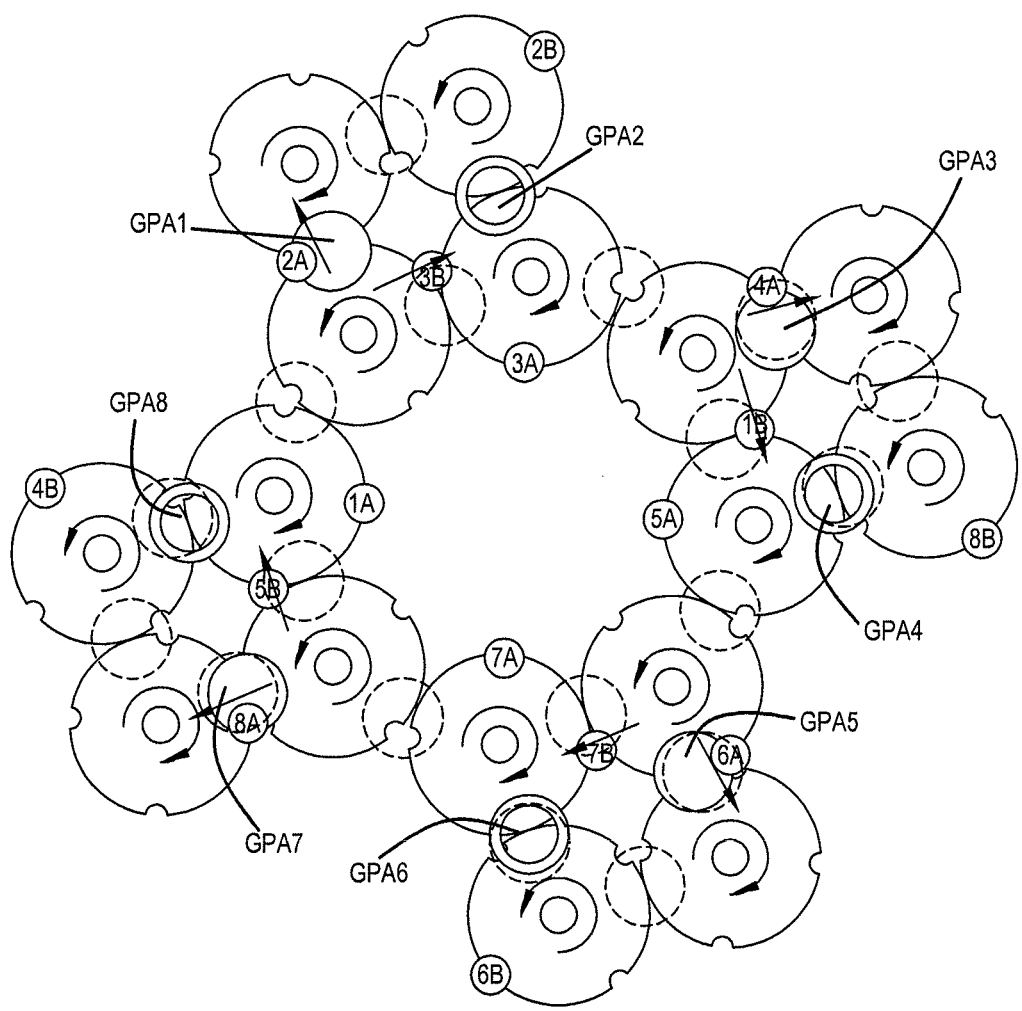
FIG. 25 illustrates the positions of the bobbin carriers at step 3 when the horn gears rotate 90 degrees about their rotational axes, respectively, from the positions of FIG. 24.

To move the bobbin carrier assemblies from the positions illustrated in FIG. 24 to the positions illustrated in FIG. 25 (Step 3), the transition mechanisms GPA1, GPA3, GPA5 and GPA7, which are collectively referred to as Gate Set B, are opened to transfer select associated bobbin carriers from the active track 202 to the passive track 204. Then the braiding machine operates to rotate the horn gears 132A-132H and 134A-134H about 90 degrees to transfer the bobbin carriers 2A, 4A, 6A and 8A from the active track horn gears 132A, 132C, 132E and 132G to the passive track horn gears 134A, 134C, 134E and 134G, respectively, at the transition positions GA1, GA3, GA5 and GA7, respectively. The bobbin carriers 2B, 4B, 6B and 8B remain on the passive track 204. Further, the bobbin carriers 1A, 2A, 3A, 4A, 5A, 6A, 7A and 8A remain on the active track 202. However, the active track bobbin carriers 1B, 3B, 5B and 7B are transferred counter-clockwise between adjacent active track horn gears 132A-132H. In particular, the bobbin gear 1B is shifted from the horn gear 132C to the horn gear 132D, the bobbin gear 3B is shifted from the horn gear 132A to the horn gear 132B, the bobbin gear 5B is shifted from the horn gear 132G to the horn gear 132H, and the horn gear 7B is shifted from the horn gear 132E to the horn gear 132F.

Figure 26:
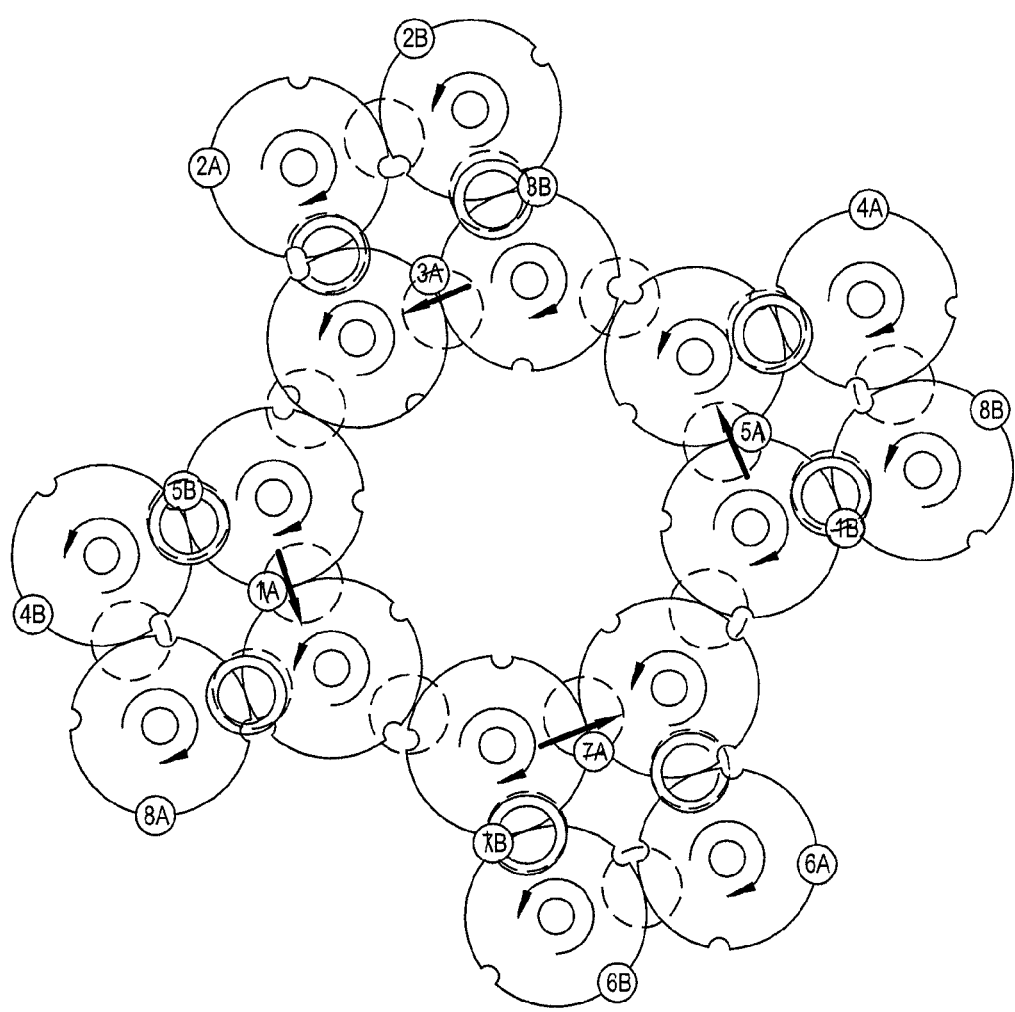
FIG. 26 illustrates the positions of the bobbin carriers at step 4 when the horn gears rotate 90 degrees about their rotational axes, respectively, from the positions of FIG. 25.

To move the bobbin carrier assemblies from the positions illustrated in FIG. 25 to the positions illustrated in FIG. 26 (Step 4), all of the transition mechanisms are closed after the bobbin carriers are moved into their positions illustrated in FIG. 25. The braiding machine 100 then operates to rotate all of the horn gears about 90 degrees. Because all of the transition mechanisms are closed, no bobbin carriers are transferred between adjacent horn gears. The eight bobbin carriers 2A, 2B, 4A, 4B, 6A, 6B, 8A and 8B stay on the passive track 204, and the other eight bobbin carriers 1A, 1B, 3A, 3B, 5A, 5B, 7A and 7B stay on the active track 202. As the horn gears rotate during step 4, some of the bobbin carriers move across adjacent horn gear assemblies on the active track through the transition positions GA2, GA4, GA6 and GA8. Further, some of the bobbin carriers move across the passive track transition positions GP1, GP2, GP3 and GP4.

Figure 27:
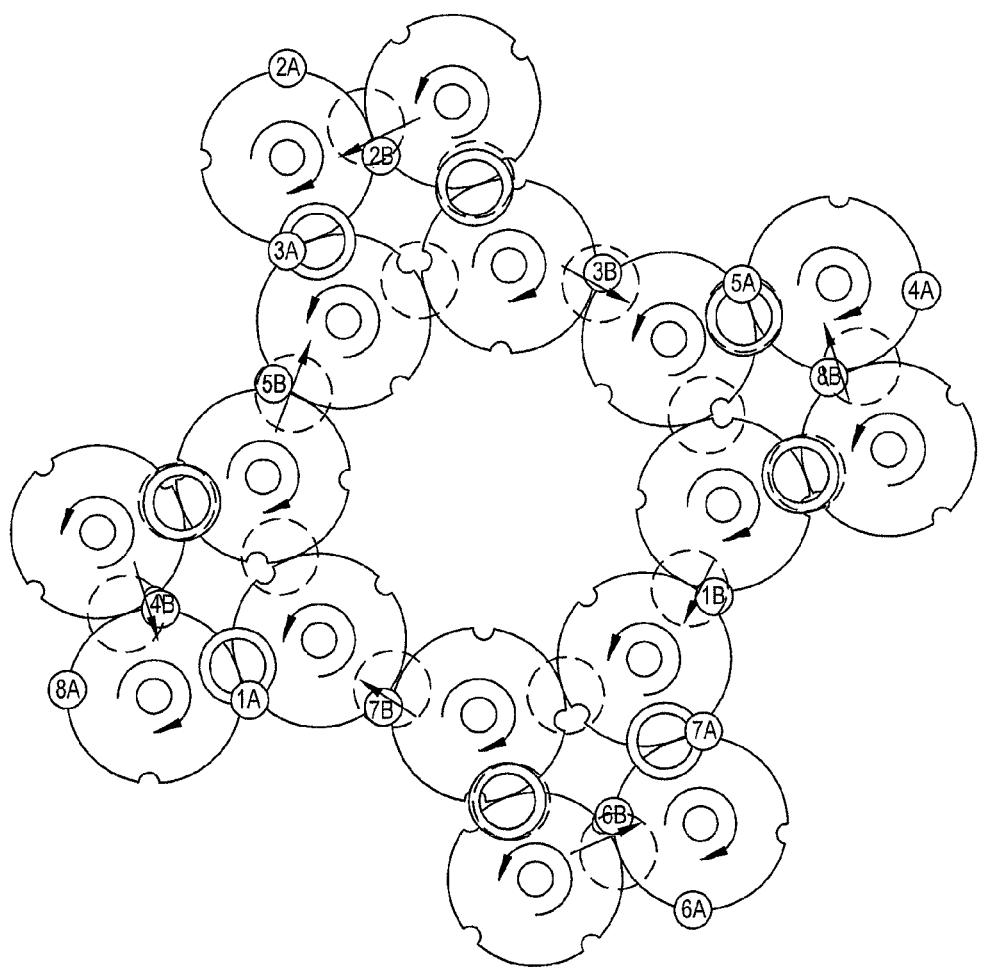
FIG. 27 illustrates the positions of the bobbin carriers at step 5 when the horn gears rotate 90 degrees about their rotational axes, respectively, from the positions of FIG. 26.

To move the bobbin carrier assemblies from the positions illustrated in FIG. 26 to the positions illustrated in FIG. 27 (Step 5), the horn gears rotate an additional 90 degrees about their rotational axes, respectively. The bobbin carriers 1B, 3B, 5B and 7B are transferred between adjacent horn gears on the active track 202, and the bobbin carriers 2B, 4B, 6B and 8B are transferred between adjacent horn gears on the passive track 204. In particular, the bobbin carrier 1B is shifted from the horn gear 132D to the horn gear 132E, the bobbin carrier 3B is shifted from the horn gear 132B to the horn gear 132B, the bobbin carrier 5B is shifted from the horn gear 132H to the horn gear 132A, and the bobbin carrier 7B is shifted from the horn gear 132F to the horn gear 132G. The bobbin carrier 2B is shifted from the horn gear 134B to the horn gear 134A, the bobbin carrier 4B is shifted from the horn gear 134H to the horn gear 134G, the bobbin carrier 6B is shifted from the horn gear 134F to the horn gear 134E, and the bobbin carrier 8B is shifted from the horn gear 134D to the horn gear 134C.

Figure 28:
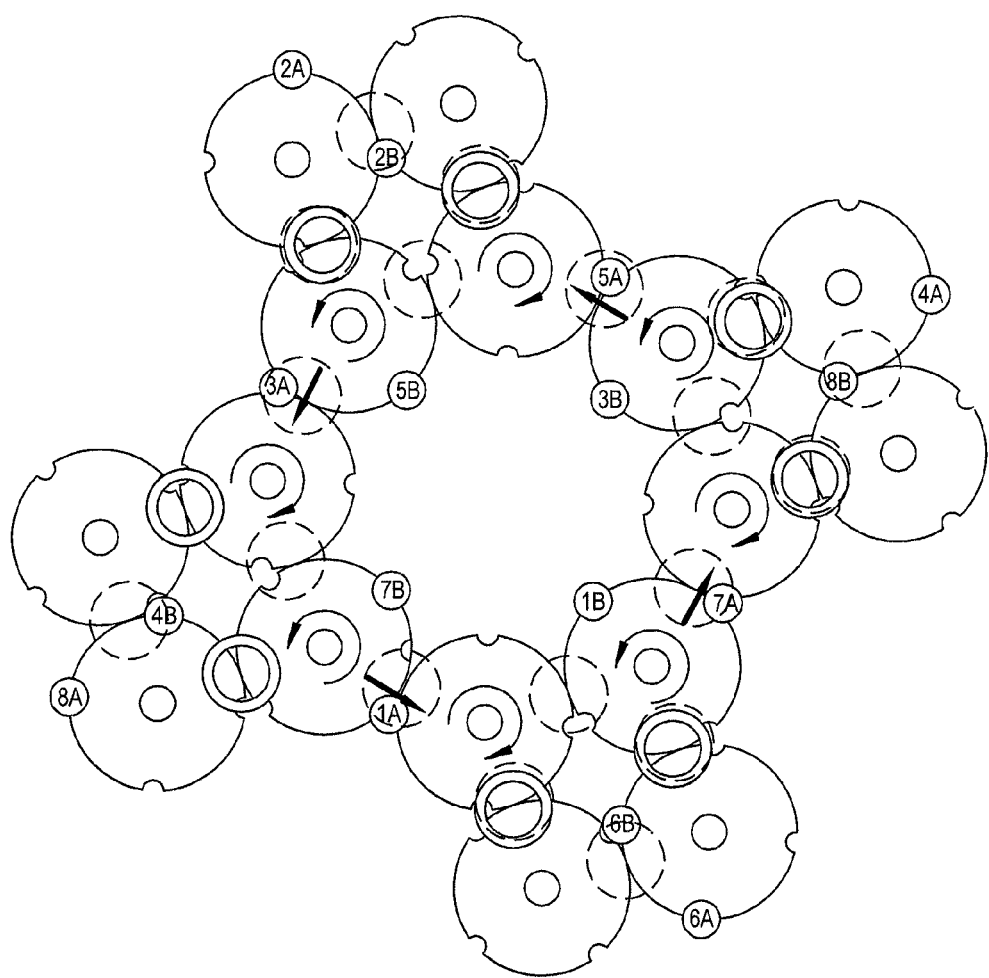
FIG. 28 illustrates the positions of the bobbin carriers at step 6 when the active track horn gears rotate 90 degrees, while the passive track horn gears remain still, from the positions of FIG. 27.

To move the bobbin carrier assemblies from the positions illustrated in FIG. 27 to the positions illustrated in FIG. 28 (Step 6), the active track horn gears 132A-132H are rotated 90 degrees while the passive track horn gears 134A-134H do not rotate and remain still. Accordingly, the bobbin carrier assemblies 2A, 2B, 4A, 4B, 6A, 6B, 8A, and 8B remain in the same position along the passive tracks.

Figure 29:
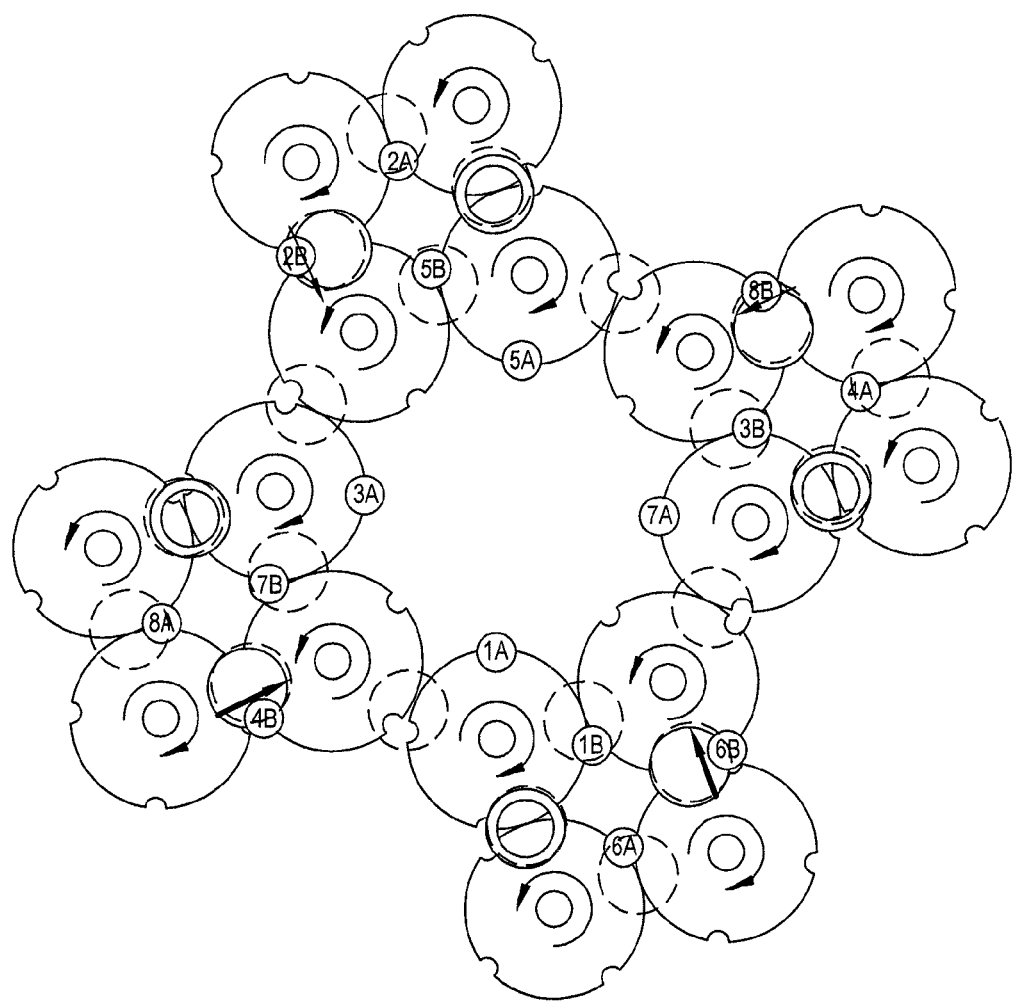
FIG. 29 illustrates the positions of the bobbin carriers at step 7 when the horn gears rotate 90 degrees about their rotational axes, respectively, from the positions of FIG. 28.

To move the bobbin carrier assemblies from the positions illustrated in FIG. 28 to the positions illustrated in FIG. 29 (Step 7), the braiding machine 100 operates to rotate all of the horn gears 132A-132H and 134A-134H about 90 degree until the step 7 as shown in FIG. 29.

To move the bobbin carrier assemblies from the positions illustrated in FIG. 28 to the positions illustrated in FIG. 29 (Step 7), the transition mechanisms GPA1, GPA3, GPA5, and GPA7 (Gate Set B) are then opened so that bobbin carriers 2B, 4B, 6B and 8B on the passive track 204 can be transferred to the active track 202. The horn gears 132A-132H and 134A-134H are then rotated about 90 degrees. The bobbin carriers 2B, 4B, 6B and 8B are transferred from the passive track 204 to the active track 202. The bobbin carriers 2B, 4B, 6B and 8B return to the active track 204 for the first time since the step 1, but enter the slots of the active track horn gears in which the bobbin carriers 2A, 4A, 6A and 8A had been placed before they were transferred from the active track 202 to the passive tracks 204 in the step 3. In particular, the bobbin carrier 2B moves from the horn gear 134A to the horn gear 132A, the bobbin carrier 4B moves from the horn gear 134G to the horn gear 132G, the bobbin carrier 6B moves from the horn gear 134E to the horn gear 132E, and the bobbin carrier 8B moves from the horn gear 134C to the horn gear 132C.

Figure 30:
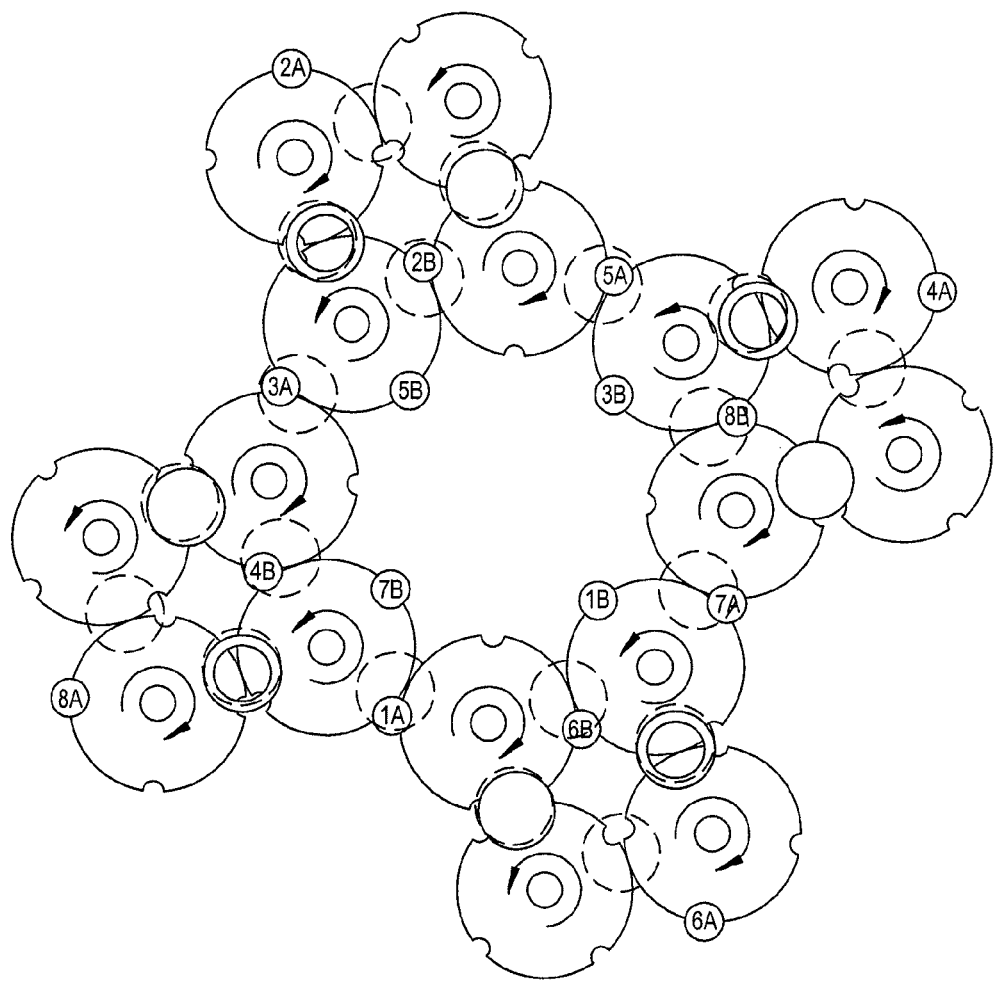
FIG. 30 illustrates the positions of the bobbin carriers at step 8.

To move the bobbin carrier assemblies from the positions illustrated in FIG. 29 to the positions illustrated in FIG. 30 (Step 8), all of the horn gears are rotated about 20 degrees about their rotational axes to clear all transition mechanism locations (Step 8A). After the horn gears are rotated 20 degrees, the transition mechanisms GPA1, GPA3, GPA5 and GPA7 (Gate Set B) are closed and then all of the horn gears are rotated about 90 degrees in the reverse direction (Step 8B).

Figure 31:
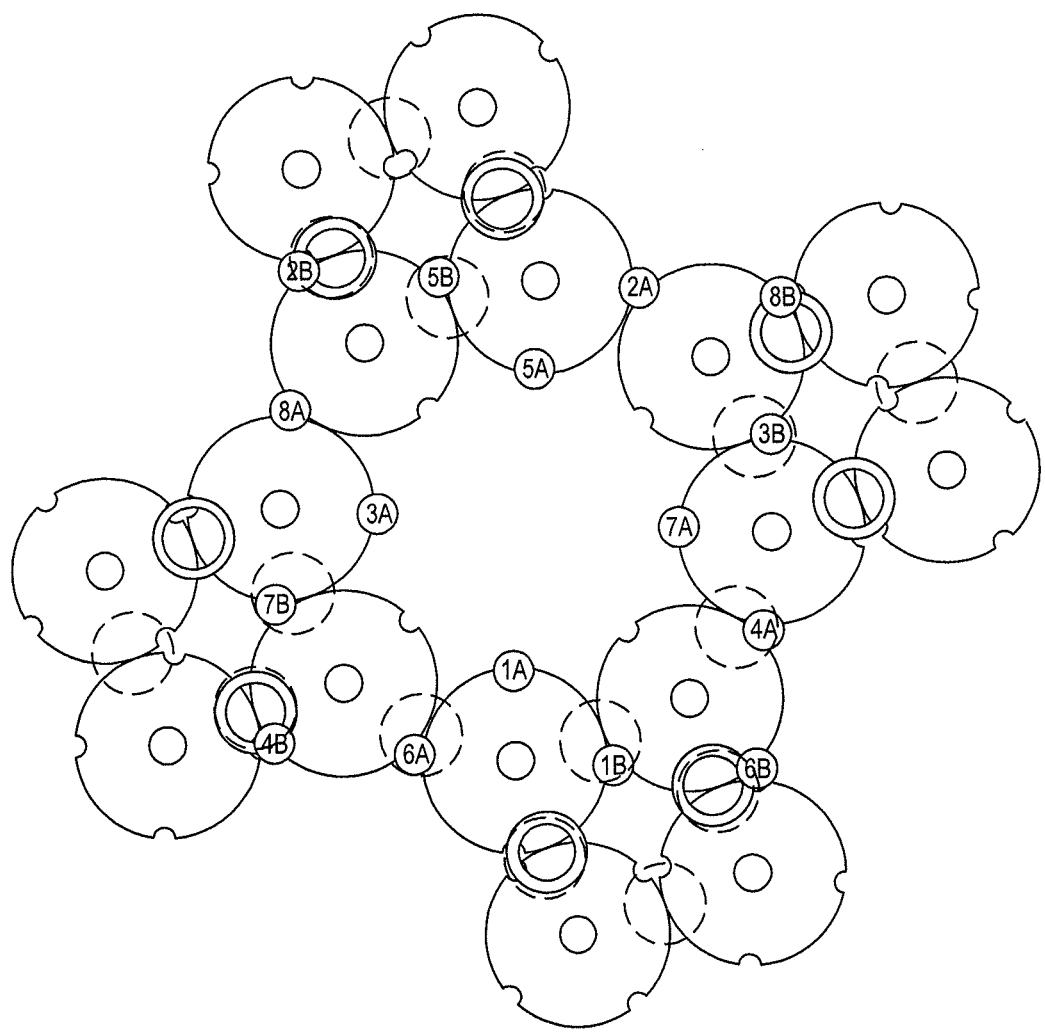
FIG. 31 illustrates the positions of the bobbin carriers at step 9.

To move the bobbin carrier assemblies from the positions illustrated in FIG. 30 to the positions illustrated in FIG. 31 (Step 9), the transition mechanisms GPA2, GPA4, GPA6 and GPA8 (Gate Set A) are opened and the active track horn gears 132A-132H are rotated about 60 degrees in the reverse direction while the passive track horn gears 134A-134H do not rotate and remain stationary (Step 9A). Then the passive track horn gears 134A-134H rotate about 120 degrees in the original direction (Step 9B). The active and passive tracks are then interlocked electronically, and are rotated together about 150 degrees in the original direction (Step 9C). Once this process is complete, the braiding machine 100 operates to close the transition mechanisms GPA2, GPA4, GPA6 and GPA8 (Gate Set A) and continue the braiding process until the next transition is required.

Figure 32:
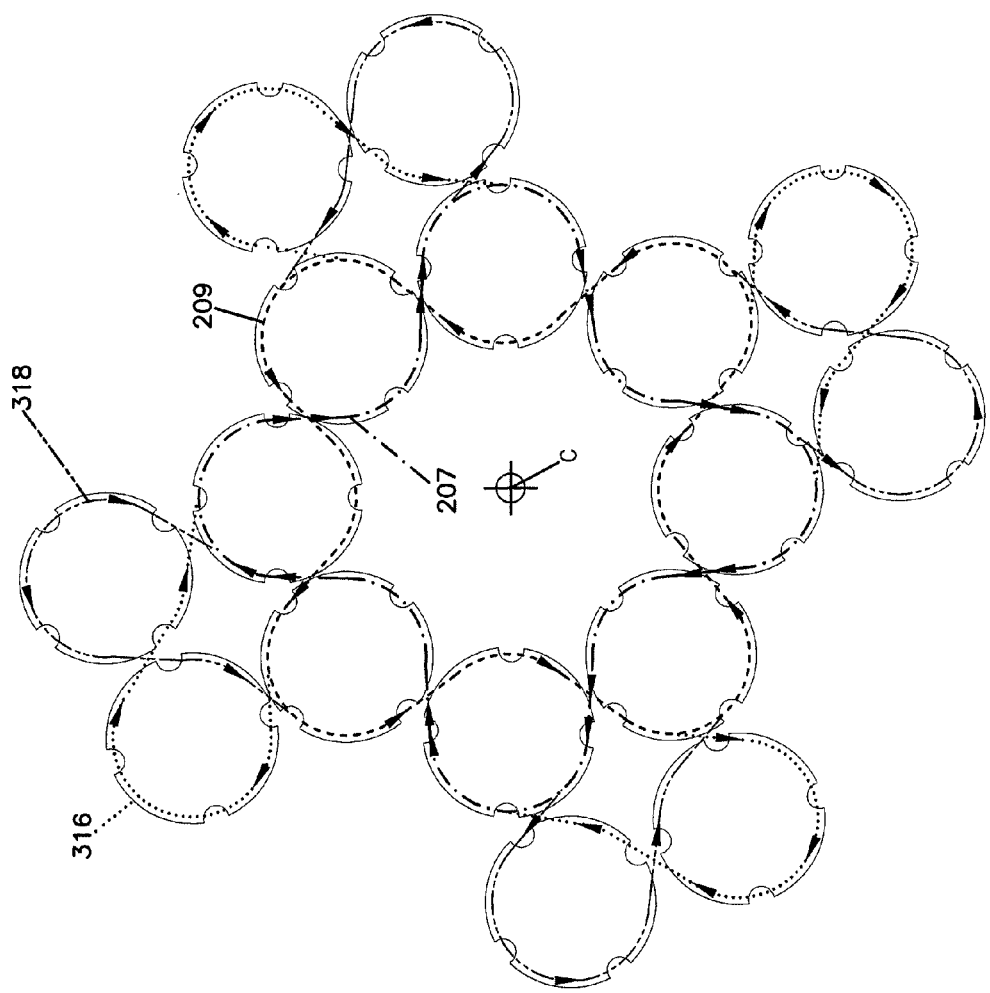
FIG. 32 is a diagram illustrating example paths of the bobbin carrier assemblies.

FIG. 32 illustrates the paths of the bobbin carrier assemblies 122 as they move through the positions illustrated in FIGS. 23-31 and the trace strands transition between patterns. In the illustration, the active track 202 defines a counterclockwise path 209 (as designated with a single arrow) and a clockwise carrier path 207 (as designated with a double arrow), both of which are arranged around a center (axis C) of the active track 202. The clockwise and counterclockwise paths 207 and 209 are both closed or endless paths, are oscillating, and are out-of-phase from each other. The passive tracks 204A-204D each define a first transition path 316 (as designated with a striped line) and a second transition path 318 (as designated with a dotted line). The first transition path 316 is configured to move the bobbin carrier assemblies 122 from the counterclockwise carrier path 209 to the clockwise carrier path 207, thereby reversing the direction of the bobbin carrier assemblies 122. The second transition path 318 is configured to move the bobbin carrier assemblies 122 from the clockwise carrier path 207 to the counterclockwise carrier path 209 also the direction of the bobbin carrier assemblies 122 in the opposite direction.

The movement and positioning of the horn gear assemblies and the bobbin carrier assemblies as they transition the trace strands from one pattern to another as illustrated in FIGS. 23-31 is documented in Table 1—Operational Sequence of Horn Gear Assemblies.

TABLE 1

Operational Sequence of Horn Gear Assemblies

| Step | Start Position on Active Track | Start Position on Passive Track | Amount of Rotation on Active Track | Amount of Rotation on Passive Track | Stop Position on Active Track | Stop Position on Passive Track | Total Rotation on Active Track | Total Rotation on Passive Track | Position of Gate Set A | Position of Gate Set B |
|---|---|---|---|---|---|---|---|---|---|---|
| 1  | 0   | 0   | 0   | 0   | 0   | 0   | 0   | 0   | Closed | Closed |
| 2  | 0   | 0   | 90  | 90  | 90  | 90  | 90  | 90  | Open   | Closed |
| 3  | 90  | 90  | 90  | 90  | 180 | 180 | 180 | 180 | Open   | Open   |
| 4  | 180 | 180 | 90  | 90  | 270 | 270 | 270 | 270 | Closed | Open   |
| 5  | 270 | 270 | 90  | 90  | 0   | 0   | 360 | 360 | Closed | Closed |
| 6  | 0   | 0   | 90  | 0   | 90  | 0   | 450 | 360 | Closed | Open   |
| 7  | 90  | 0   | 90  | 90  | 180 | 90  | 540 | 450 | Closed | Open   |
| 8A | 180 | 90  | 20  | 20  | 200 | 110 | 560 | 470 | Closed | Closed |
| 8B | 200 | 110 | −90 | −90 | 110 | 20  | 650 | 560 | Closed | Open   |
| 9A | 110 | 20  | −60 | 0   | 50  | 20  | 700 | 560 | Open   | Closed |
| 9B | 50  | 20  | 0   | 120 | 50  | 140 | 700 | 680 | Closed | Closed |
| 9C | 50  | 140 | 150 | 150 | 200 | 290 | 850 | 830 | Closed | Closed |

The start position on the active track (the first column) indicates an angular location of the horn gear assemblies 124 of the active track 202 relative to the first location of the horn gear assemblies 124. Similarly, the start position on the passive track (the second column) indicates an angular location of the horn gear assemblies 124 of the passive track 204 relative to the first location of the horn gear assemblies 124. The amount of the rotation on the active track (the third column) indicates an amount of the rotation of the active track motor 148. Similarly, the amount of the rotation on the passive track (the fourth column) indicates an amount of the rotation of the passive track motor 158. The stop position on the active track (the fifth column) indicates the end position of the horn gear assemblies 124 of the active track 202 after the horn gear assemblies 124 rotates by the amount of the rotation on the active track from the start position on the active track. Similarly, the stop position on the passive track (the sixth column) indicates the end position of the horn gear assemblies 124 of the passive track 204 after the horn gear assemblies 124 rotates by the amount of the rotation on the passive track from the start position on the passive track. The total rotation on the active track (the seventh column) indicates the cumulative amount of rotation of the horn gear assemblies 124 of the active track 202. Similarly, the total rotation on the passive track (the eighth column) indicates the cumulative amount of rotation of the horn gear assemblies 124 of the passive track 204. The position of the gate set A (the ninth column) indicates the position (either open of closed) of the gates GPA2, GPA4, GPA6, and GPA8. The position of the gate set B (the tenth column) indicates the position (either open of closed) of the gates GPA1, GPA3, GPA5, and GPA7.

In at least some embodiments, the encoders 150 and 160 attached to the motors 148 and 158 (e.g., servo motors) are used to enable the motor 148 on the active track 202 to be the master motor and the motor 158 on the passive track 204 to be the slave motor by electrically gearing the two motors 148 and 158. In other embodiments, can use different types of sensor devices to monitor the relative positions of the horn gear assemblies 124 and/or the relative positions of the bobbin carrier assemblies 122 on the active track 202 and/or the passive track 204. Examples of alternative sensor devices include proximity sensors and cameras.

Figure 34:
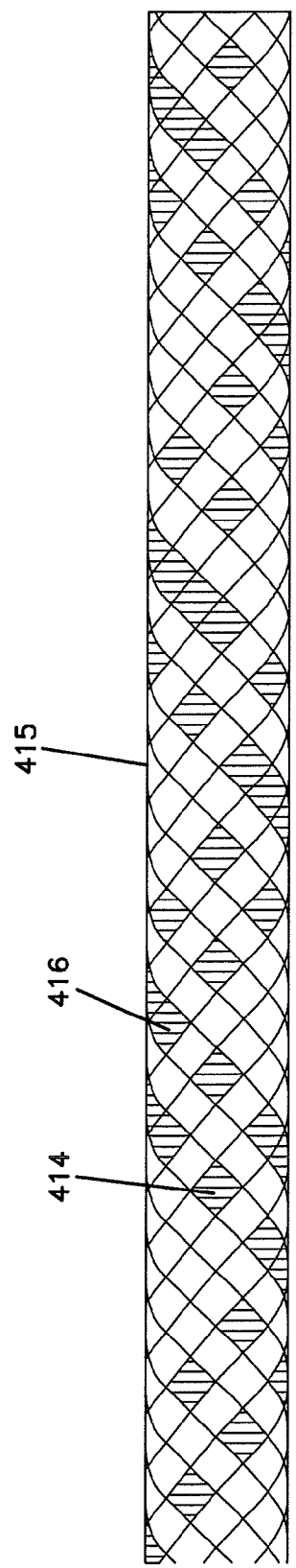
FIG. 34 illustrates an example braid with a parallel-striped pattern.
Figure 35:
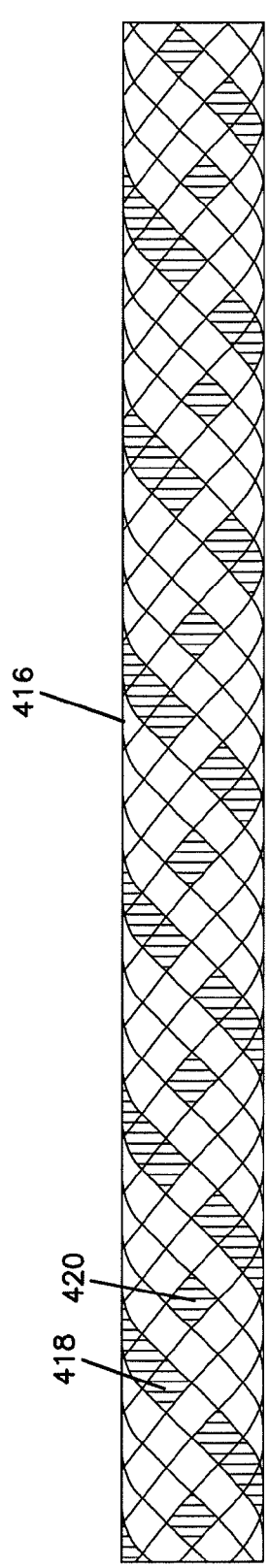
FIG. 35 illustrates an example braid with a crossing pattern.

FIGS. 33-35 illustrate example braids 413, 415, and 417 with different patterns of one or more trace strands 402. In some embodiments, the trace strands 402 can have the same color. In other embodiments, the trace strands 420 can have different colors.

In these embodiments, each of the braids 413, 415, and 417 has a consistent pattern along the length thereof. In other embodiment, the braids 413, 415, and 417 can have two or more different patterns that alternate along the length thereof. Similar to the example braids in FIGS. 19-22, the braids 413, 415, and 417 have no core running therealong.

FIG. 33 illustrates an example braid 413 with a cross-striped pattern. The cross-striped pattern is defined by one or more trace strands 412. In at least some embodiments, the cross-striped pattern is generated by using a single colored trace strand 412. In other embodiments, the cross-striped pattern is generated by using one or more colored trace strands 412. The plurality of colored trace strands 412 can have an identical color. In other embodiments, the plurality of colored trace strands 412 can have different colors to define a multi-colored pattern. Other features of the trace strand(s) 412 and the braid 413 in this embodiment are the same as those in FIGS. 19-22.

FIG. 34 illustrates an example braid 415 with a parallel-striped pattern. The parallel-striped pattern can be defined by two or more trace strands 414 and 416. In at least some embodiments, the parallel-striped pattern is generated by using two trace strands 414 and 416 having the same color. In other embodiments, the trace strands 414 and 416 can have different colors. Other features of the trace strands 414 and 416 and the braid 415 in this embodiment are the same as those in FIGS. 19-22.

FIG. 35 illustrates an example braid 417 with a crossing pattern. The crossing pattern can be defined by two trace strands 418 and 420. In at least some embodiments, the two trace strands 418 and 420 have the same color. In other embodiments, the trace strands 418 and 420 can have different colors. Other features of the trace strands 418 and 420 and the braid 417 in this embodiment are the same as those in FIGS. 19-22.

Figure 36:
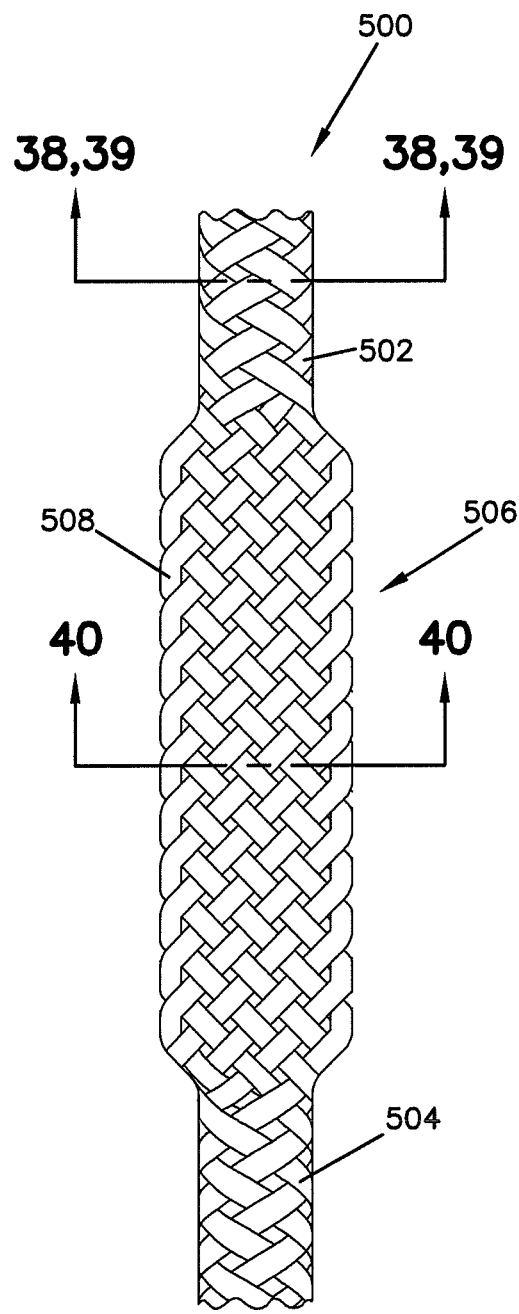
FIG. 36 is a top plan view of a surgical braid showing some details of the fibers forming the surgical braid.
Figure 37:
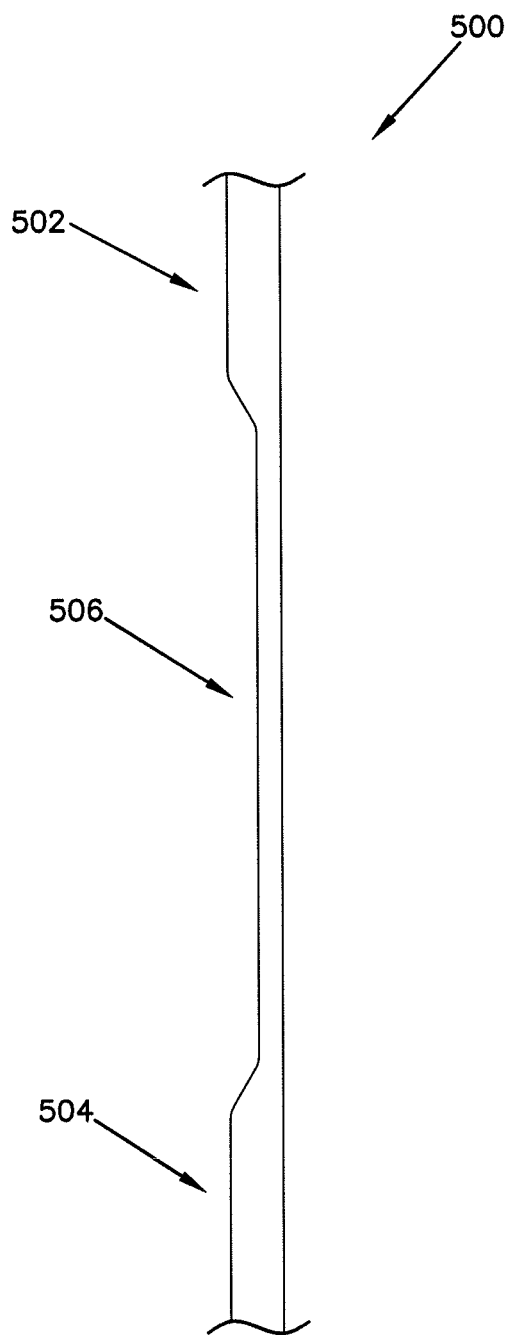
FIG. 37 is a side plan view showing the general shape of the surgical braid illustrated in FIG. 36 without the details of the fibers forming the braid.

FIGS. 36-40 illustrate an example surgical braid having tubular sections and a flat section that does not include a bifurcation. Referring now to FIGS. 36 and 37, a surgical braid 500 has two non-flat sections 502 and 504 and a flat section 506 therebetween. In at least some embodiments, the non-flat sections 502 and 504 are configured to be out-of-round or cylindrical. In other embodiments, the non-flat sections 502 and 504 are round sections. A flat or tape section 506 is positioned between the two non-flat sections 502 and 504. The first and second non-flat sections 502 and 504 and the tape section 506 are formed with a plurality of strands 508 braided into a continuous braid. In at least some embodiments, there is no interruption in the braiding at the transition between the non-flat sections 502 and 504 and the tape section 506. Nor is there any splicing, gluing, or other fastening between the non-flat sections 502 and 504 and the tape section 506.

The strands 508 are braided using a 1-over-1 configuration such that the strands 508 in the non-flat sections 502 and 504 follow a generally helical or otherwise spiral path for a full 360°. When the strands 508 transition to the tape section 506, the strands 508 in the braid follow a helical or otherwise spiral path over an arc that is less than 360°. As they are being braided, the strands 508 in the tape section 506 reverse direction, relative to the width of the braid, as they reach each end of the arc.

In the illustrated embodiment, the surgical braid 500 does not have any bifurcated sections or gaps in either the non-flat sections 502 and 504 or the tape section 506. Additionally, there is no core running through the non-flat sections 502 and 504 or spine running along or otherwise reinforcing the tape section 506. In some cases, gaps in the braid can reduce the surface area over which the surgical braid 500 exerts force against tissue and thus reduce the distribution of force. Additionally, there is a risk that tissue opposing a gap can enter the gap and be pinched further increasing the risk to trauma. Similarly, a core or spine running along the surgical braid 500 can create a line where force exerted against the tissue is increased. Eliminating bifurcations, gaps, cores, spines, reinforcing members, and the like enables force exerted against tissue by the surgical braid 500 to be distributed over a larger area and more evenly and also prevents pinching of the tissue thereby reducing trauma.

Figure 38:
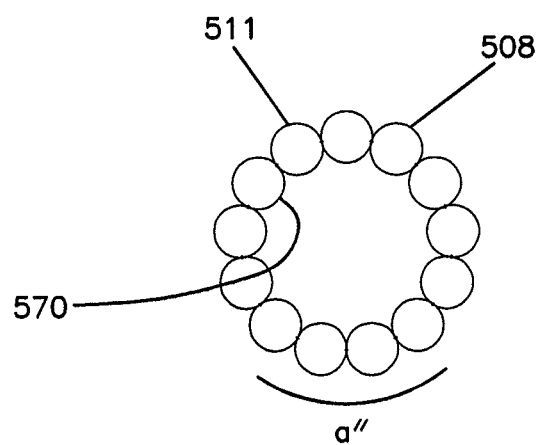
FIG. 38 is a cross-sectional view of the surgical braid illustrated in FIG. 36, showing the surgical braid before it passes through pinch rollers.
Figure 39:
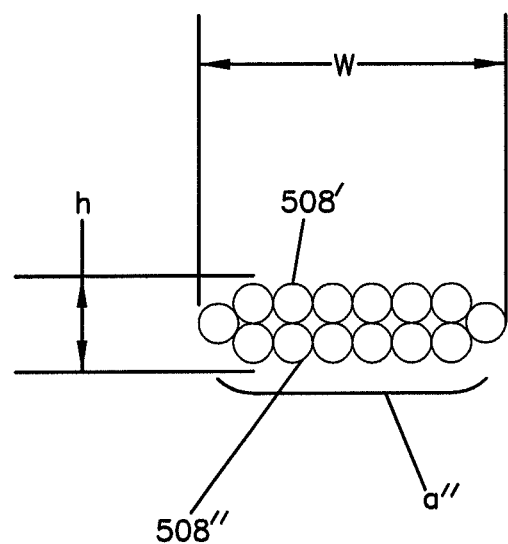
FIG. 39 is a cross sectional view of the surgical braid illustrated in FIG. 36, showing the surgical braid after it passes through pinch rollers.

Referring now to FIG. 38, the circumference of the non-flat sections 502 and 504 are initially tubular and have a generally round circumference when initially braided. When in this state, the non-flat sections 502 and 504 define an inner channel 510. As explained in more detail herein, the surgical braid 500 can be compressed during manufacturing by the pinch rollers 114A and 114B which reshapes the non-flat sections 502 and 504 from a generally round circumference to an oblong circumference. The compression increases the width and decreases the height of the non-flat section. A cross-section for an exemplary embodiment of the non-flat sections 502 and 504 is illustrated in FIG. 39. The out-of-round circumference has a width (w) greater than its height (h), and can have a variety of different shapes such as oblong, oval, elliptical, and the like. Additionally, compressing the non-flat sections 502 and 504 urges opposing strands 508' and 508" in the braid together and substantially closes the inner channel 510. In this embodiment, the non-flat sections 502 and 504 are not tubular and do not define an inner channel. Other embodiments are possible. For example, in at least some alternative embodiments, the non-flat sections 502 and 504 are not compressed by the pinch rollers 114A and 114B and have an open inner channel and are generally tubular.

The increased width and oblong shape of the non-flat sections 502 and 504 have several functions. For example, this increased width provides a surface area (a') that is pressed against tissue. The surface area (a') of the non-flat sections 502 and 504 is larger than the surface area (a") of a surgical braid 500 having a circular circumference when pressed against the tissue. The surface area (a') of the non-flat sections 502 and 504 of the surgical braid 500 provides a distribution of force against tissue that is greater than the distribution of force provided by a circular braid, and this greater distribution of force reduces trauma to tissue. In another example, the oblong shape increases the ability of the non-flat sections 502 and 504 to maintain a knot when they are tied together during a medical procedure and decreases the risk that the knot will become inadvertently untied.

Figure 40:
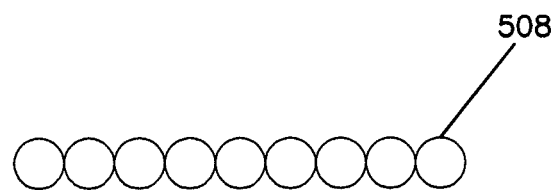
FIG. 40 is a cross-sectional view of the surgical braid illustrated in FIG. 36

Referring to FIGS. 36, 37, and 40 the tape section 506 is substantially flat, although the structure of the braid may result in some slight curvature along the cross section of the tape section 506. The tape section 506 is substantially wider than the non-flat sections 502 and 504. This flat, wide configuration provides greater distribution of force when the tape section 506 is bound against tissue, which reduces trauma to the tissue. As noted herein, having no bifurcation or gaps in the braiding of the tape section 506 further reduces the risk of trauma to tissue.

Figure 41:
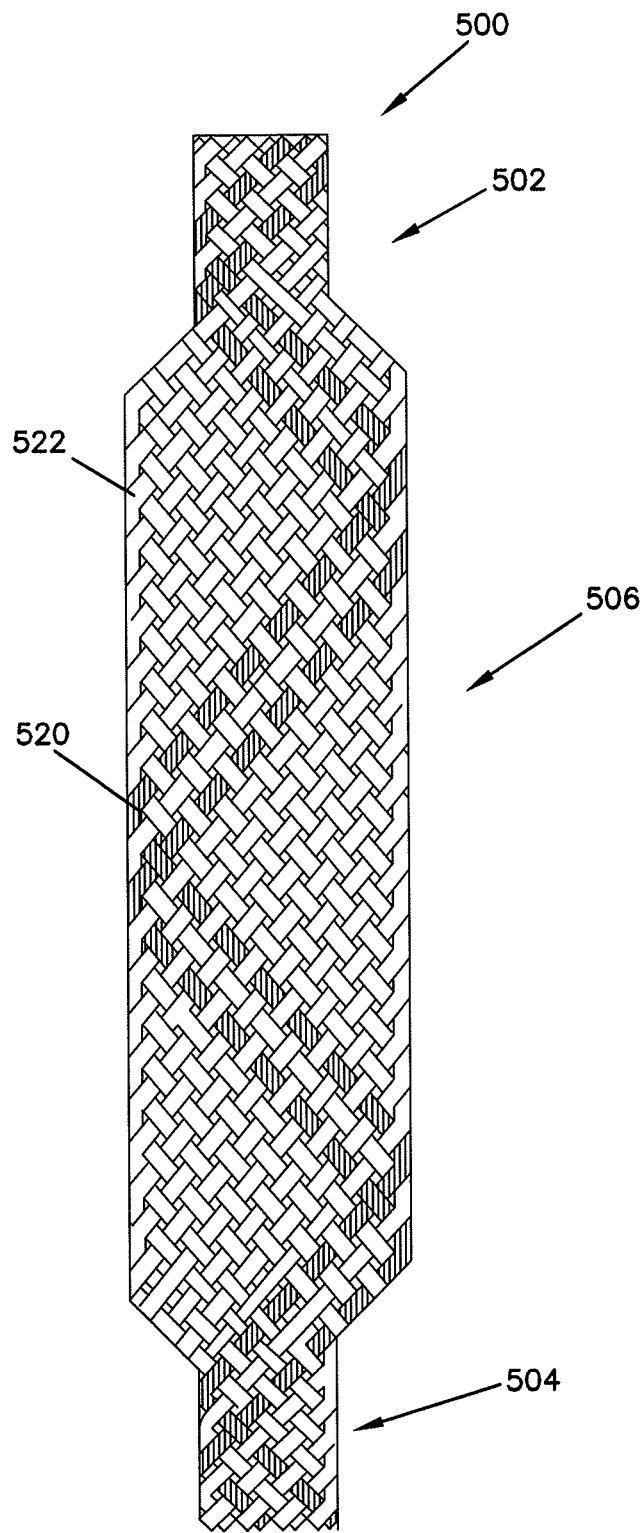
FIG. 41 illustrates the surgical braid of FIG. 36 with one or more trace strands.

FIG. 41 illustrates an alternative embodiment of the surgical braid 500 shown in FIG. 36. In this embodiment, the surgical braid 500 has one or more trace strands 520. The trace strands 520 are braided into the surgical braid 500 to increase visibility of the surgical braid 500. A trace strand 520 has a different color than the majority of strands 508 used in the surgical braid 500. For example, the surgical braid 500 can include a plurality of white strands 522 and one or more color strands 520 that visually stand out from the rest of the strands. Examples of the color strands include blue strands, green strands, and red strand, and any combination thereof. In the depicted example of FIG. 41, the braid 500 includes a parallel pattern of two colored strands 520. In at least some embodiments, the trace strands can be braided into a variety of different patterns. Additionally, some alternative embodiments will use both the active track and one or more of the passive tracks during manufacturing to transition the trace strands between two or more different patters along the length of the braid.

Figure 42:
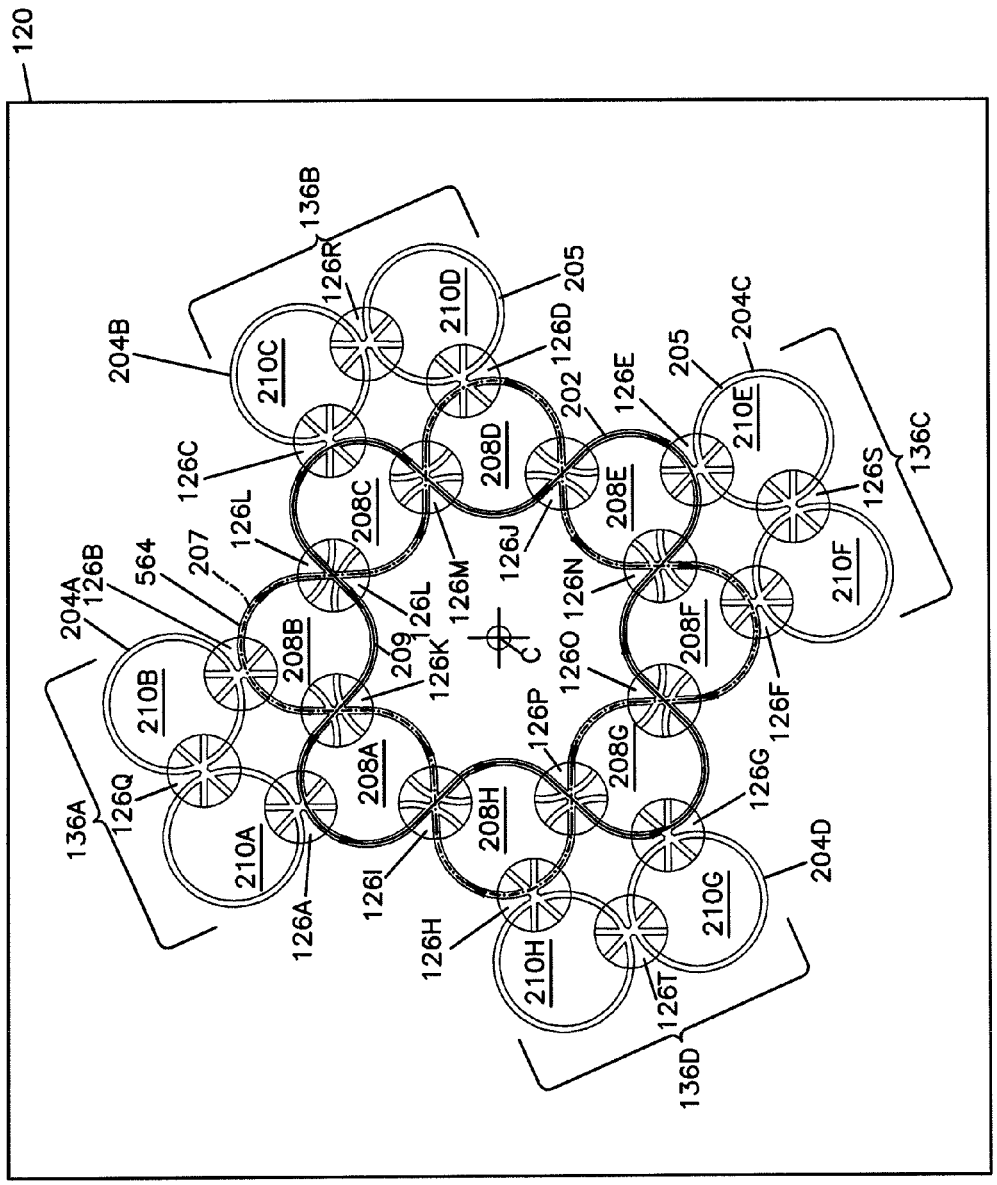
FIG. 42 illustrates the position of gates and the path of bobbin carrier assemblies when making the surgical braid illustrated in FIGS. 36-40.
Figure 43:
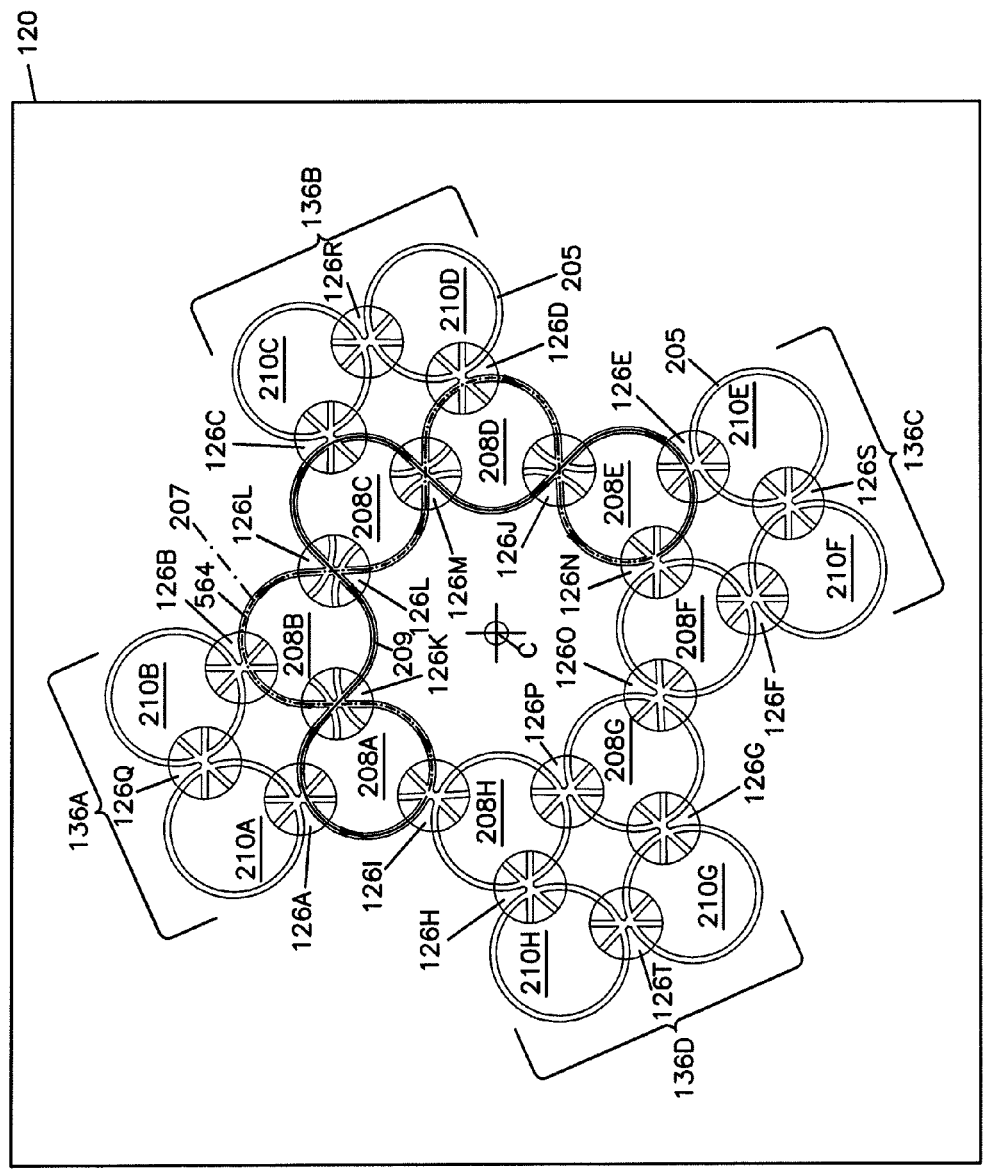
FIG. 43 illustrates the position of gates and the path of bobbin carrier assemblies when making the surgical braid illustrated in FIGS. 36-40.

FIGS. 42 and 43 illustrate the position of the gates 126 and the path of the bobbin carrier assemblies when using the arrangement of active tracks, passive tracks, and gates as illustrated in FIG. 3d to make the surgical braid illustrated in FIGS. 36-40. The path is illustrated using the configuration of active tracks, passive tracks, and gates illustrated in FIG. 3d. When braiding the non-flat sections 502 and 504, gates 126A-126H are closed and gates 126I-126P are open so that half of the bobbin carrier assemblies travel along the clockwise path 207 of the active track and the other half of the bobbin carrier assemblies travel along the counterclockwise path 209 of the active track (FIG. 42). To transition to braiding the flat section 506, the gates 126I and 126J are moved to the closed position so that the intra-bridge path of the gates will guide the bobbin carrier assemblies between the clockwise and counterclockwise paths of the active track (FIG. 43). To transition back to braiding the non-flat sections 502 and 506, the gates are moved back to their open positions so that the inter-track paths of the gates will guide the bobbin carrier assemblies along the same path and between the adjacent active sub-tracks.

Figure 44:
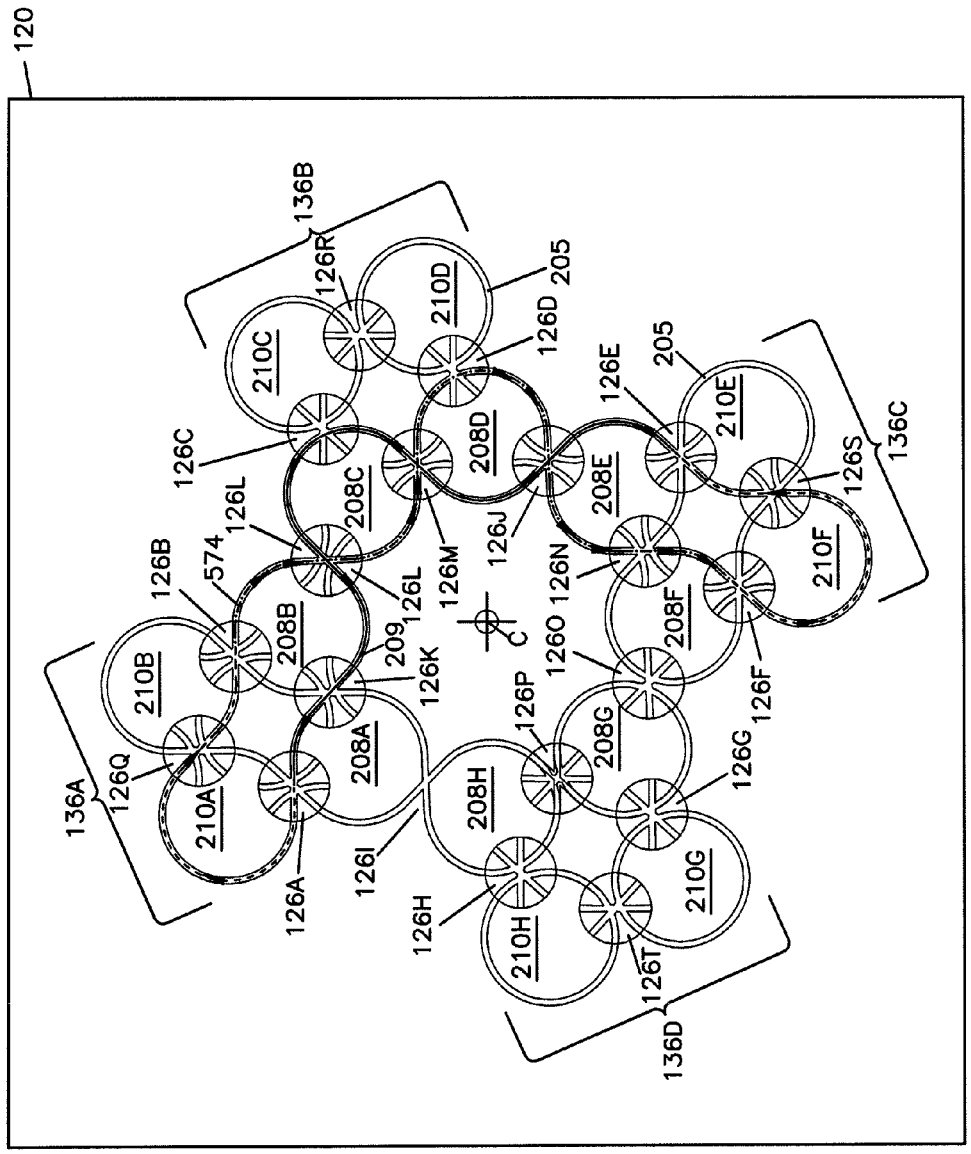
FIG. 44 is a diagram illustrating an example path of the bobbin carrier assemblies on the braiding track plate.

FIG. 44 illustrates an alternative positioning of the gates 126 and path of the bobbin carrier assemblies for braiding the flat section when using the arrangement of active tracks, passive tracks, and gates illustrated in FIG. 3d. In this arrangement, the gates 126E and 126F (as well as the gates 126K, 126L, 126M, 126J, 126N, and 126S) are in the open position and the bobbin carriers traveling along the clockwise path of the active track will be guided to the passive sub-track, to the next passive sub-track, and back to the counterclockwise path of the active track. Similarly, the gates 126A and 126B (as well as the gates 126K, 126L, 126M, 126J, 126N, and 126Q) are in the open position and the bobbin carriers traveling along the counterclockwise path of the active track will be guided to the passive sub-track, to the next passive sub-track, and back to the clockwise path of the active track.

Figure 45:
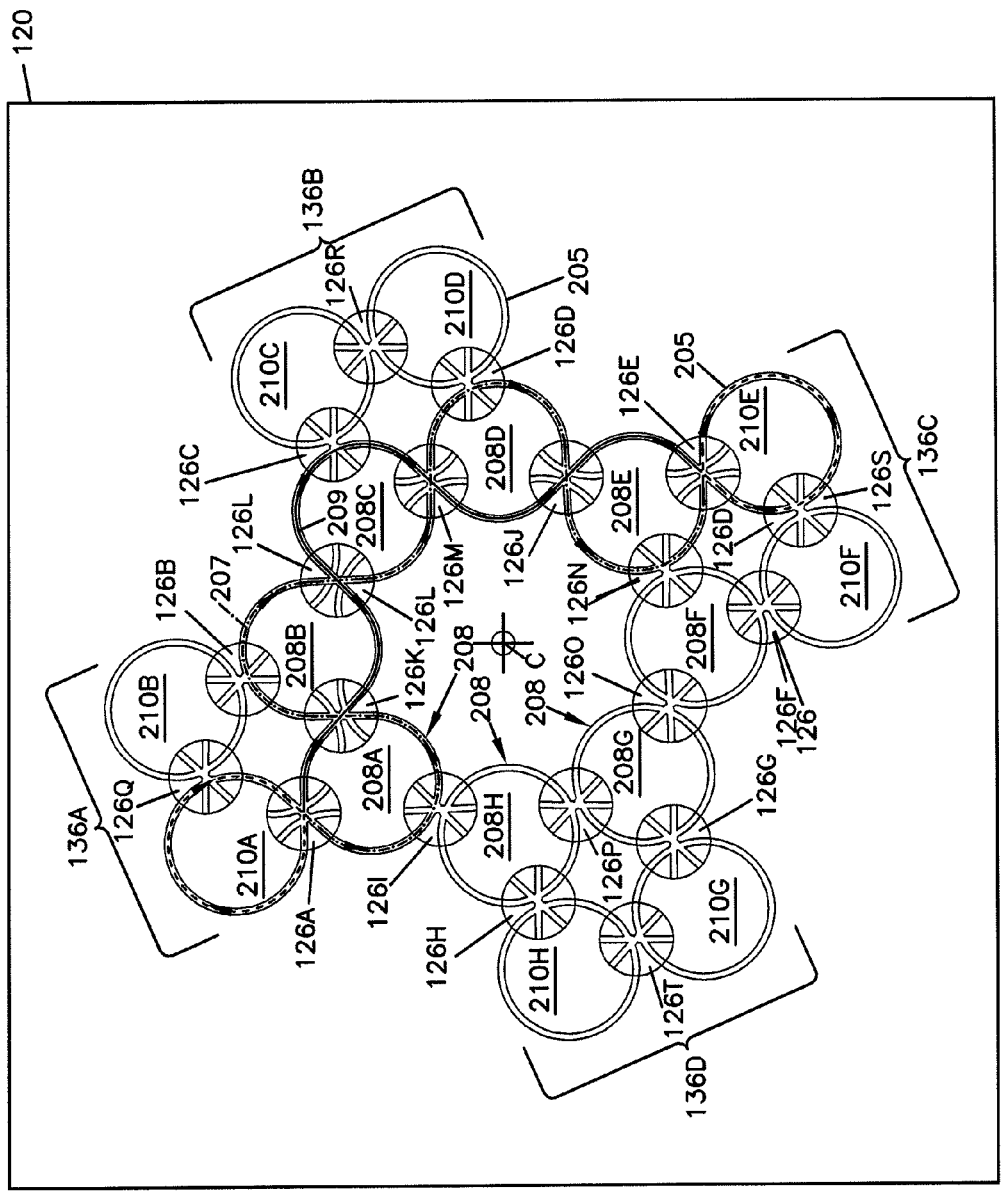
FIG. 45 is a diagram illustrating an example path of the bobbin carrier assemblies on the braiding track plate.

FIG. 45 illustrates yet another alternative positioning of the gates 126 and path of the bobbin carrier assemblies for braiding the flat section when using the arrangement of active tracks, passive tracks, and gates illustrated in FIG. 3d. In this arrangement, the gate 126E, as well as the gates 126K, 126L, 126M, and 126J, are moved to the open position and the gates 126N and 126S are in the closed position so that they will guide bobbin carriers traveling along the clockwise path of the active track to the passive sub-track and then back to the counterclockwise path of the active track. Similarly, the gate 126A is open (as well as the gates 126K, 126L, 126M, and 126J) and the gates 126I and 126Q are in the closed position so that they will guide bobbin carriers traveling along the counterclockwise path of the active track to the passive sub-track and then back to the clockwise path of the active track.

Figure 46:
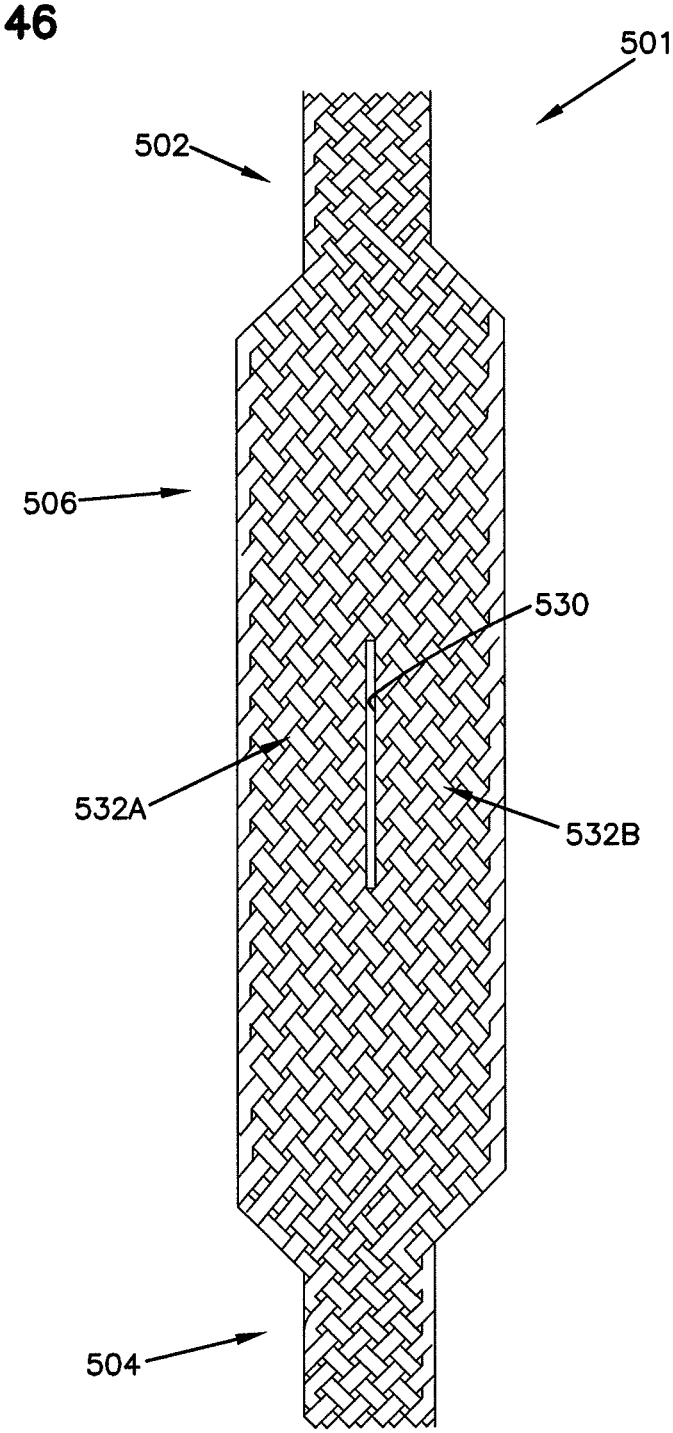
FIG. 46 illustrates the surgical braid of FIG. 36 with one or more bifurcated sections.

FIG. 46 illustrates another alternative embodiment of the surgical braid having tubular and flat sections. In this embodiment surgical braid 501 is substantially similar to surgical braid 500 illustrated in FIGS. 36-40 and also includes two non-flat sections 502 and 504 and a flat section 506 therebetween. However, the flat section 506 defines a bifurcation or gap 530 that divides the flat section 506 into bifurcated arms 530A and 530B. In at least some embodiments, the surgical braid 500 is braided with 16 total strands and each of the two bifurcation arms 532A and 532B are braided with 8 strands. Although the surgical braid 500 is illustrated having a single bifurcation with two bifurcation arms 532 of an equal number of strands. Other embodiment can include more than one bifurcation. Alternative embodiment might also braid the bifurcation arms with an unequal number of strands, which may change the position of the bifurcation along the width of the braid. For example, where the surgical braid 500 has two bifurcation arms, one of the bifurcation arms is braided with 4 strands, and the other is braided with 12 strands. Additionally, the bifurcated braid illustrated in FIG. 46 can include one or more trace strands having a consistent pattern or a changing pattern as described in more detail herein.

The arrangement of active tracks, passive tracks, and gates to braid the non-flat sections 502 and 504 and the flat section 506 of the surgical braid 501 is substantially the same as illustrated in FIGS. 42 and 43. However, when braiding the bifurcations arms 532A and 532B, a second set of gates along the active path are closed to form two closed or endless paths along the active track. The number of bobbin carrier assemblies traveling along each endless path will correspond to the number of strands in each of the bifurcation arms 532A and 532B. In alternative embodiments, the passive tracks can be used similar to the arrangements illustrated in FIGS. 44 and 45 to form the two endless paths for the two groups of bobbin carrier assemblies.

Figure 47:
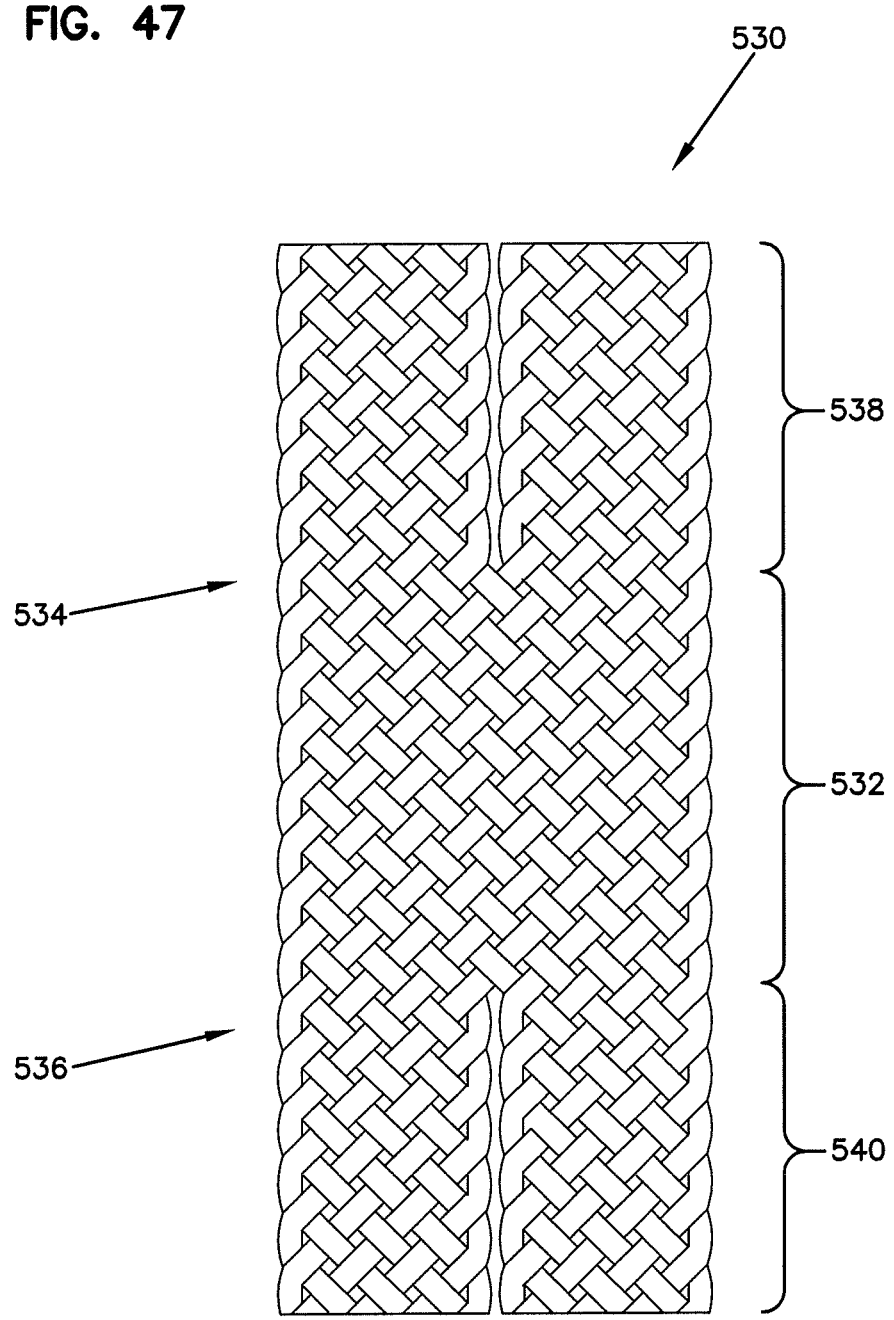
FIG. 47 illustrates an example surgical braid with a plurality of leg sections.

FIG. 47 illustrates another alternative embodiment of a surgical braid having a plurality of leg sections that can be made with braiding machine 100 as described herein. In this embodiment, a surgical braid 530 has a center section 532 having first and second ends 534 and 536. A plurality of bifurcated leg sections 538A and 538B are connected to the first end 534 of the center section 532, and a second plurality of bifurcated leg sections 540A and 540B are connected to the second end 536 of the center section 532. In at least some embodiments, the leg sections 538A and 538B, 540A and 540B are flat or tape-like braids. In various embodiments, the center section 532 can be formed as a non-flat tubular braid or can be a flat or tape-like section. The surgical braid 530 can include one or more trace strands having a consistent pattern or a changing pattern as described in more detail herein. The center section and the bifurcated legs can be made using various arrangements of active tracks, passive tracks, and gates as described herein to form tubular braids, flat braids, and bifurcated braids.

FIGS. 48-59 illustrate an example surgical braid 600 with sections having different patterns of colors on markings. As described below, the surgical braid 600 may have different patterns and/or colors of one or more trace strands. Examples of such patterns and/or colors of the trace strand 608 are described and illustrated with reference to FIGS. 48-59.

Figure 48:
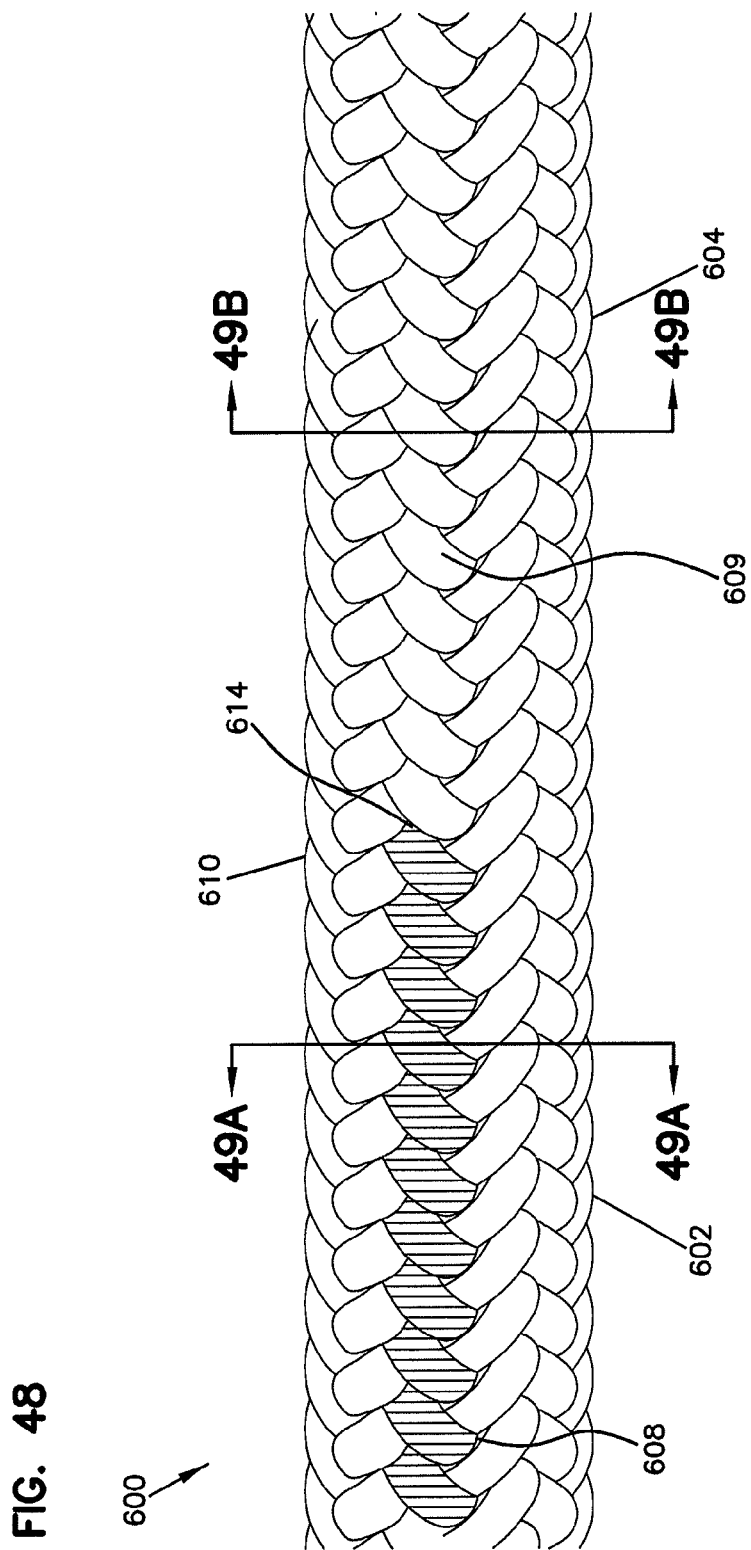
FIG. 48 is a side view schematic diagram of a 16-filament surgical braid showing details of the fibers forming the surgical braid.

Referring now to FIG. 48, the surgical braid 600 comprises two tubular sections 602 and 604 respectively, which form an outer wall 610 of the surgical braid 600. A first section 602 and a second section 604 are formed of a plurality of strands 606 braided into a continuous braid. The outer wall 610 of each section 602 and 604 is additionally braided around a core section (see FIGS. 49a and 49b). In the embodiment illustrated, there is no substantial interruption in the braiding at the transition 614 between sections 602 and 604. Nor is there any splicing, gluing, or other fastening between sections 602 and 604, however in at least some alternative embodiments, other configurations are possible.

The strands 606 can be braided using a 1-over-1 configuration such that the strands 606 in the out-of-round sections 602 and 604 follow a generally helical or otherwise spiral path for a full 360 degrees. As used herein, a strand 606 can have a variety of possible structures such as individual strands or filaments; strands formed with braided or twisted strands or filaments; and the like. Example materials that can be used for strands in the surgical braid 600 include those used in the strands 100 for the braid 108.

In this embodiment, the surgical braid 600 does not have any bifurcated sections or gaps in either the out-of-round sections 602 and 604. However, in other embodiments, such bifurcations are possible, as illustrated in FIGS. 46 and 47. Additionally, a core 612 (shown in FIGS. 49a and 49b) runs through the out-of-round sections 602 and 604 and a transition area 614. The core 612 is described in more detail herein.

As shown in FIG. 48, the surgical braid 600 includes a trace strand 608. A trace strand 608 is a different color than the majority of strands 606 used in the surgical braid 600. A surgical braid can include one or more trace strands to further enhance visibility of the surgical braid 600. For example, the surgical braid 600 can include a plurality of white strands and a color trace strand that visually stands out from the rest of the strands. In other embodiments, the surgical braid 600 includes a plurality of white strands, two color strands. In yet other embodiments, the surgical braid 600 includes any combination of a plurality of strands, each having a contrasting color to enhance visibility. Example colors used for the trace strand 608 include blue, green, violet, brown, purple, black, white, or any other suitable color.

As shown in FIG. 48, the surgical braid is formed of 16 strands interbraided in a pattern as described herein. The trace strand 608 is braided into the outer wall 610 of first section 602 to increase visibility of the surgical braid 600. The trace strand 608 then transitions, at a transition point 614, to form the section of the core 612 running along the second section 604. The outer wall 610 of the second section 604 is braided around the core (the trace strand 608) of the second section 604, thereby forming a continuous, surgical braid 600. In embodiments described in further detail herein, surgical braids 600 can be formed using one or more trace strands 608. In this example embodiment, the trace strands 608 do not require splicing, gluing or fastening between sections 602 and 604, however these methods are possible in alternative embodiments. Additionally, in at least one of the possible embodiments, the surgical braid 600 has a length of about 36 inches so that the first and second sections 602 and 604 each have a length of about 18 inches. Other embodiments can have different lengths.

Figure 49A:
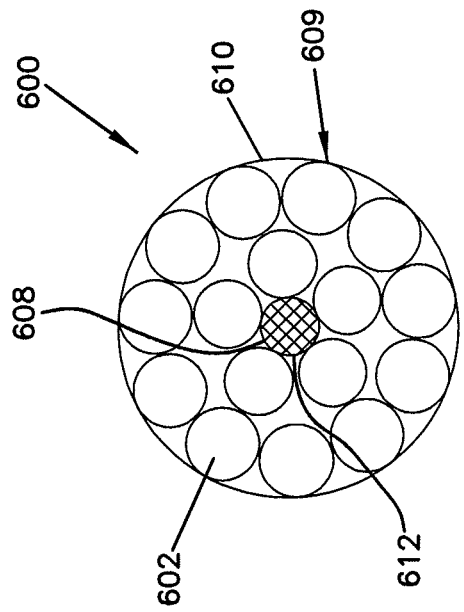
FIG. 49A is a cross-sectional view of the surgical braid illustrated in FIG. 48.
Figure 49B:
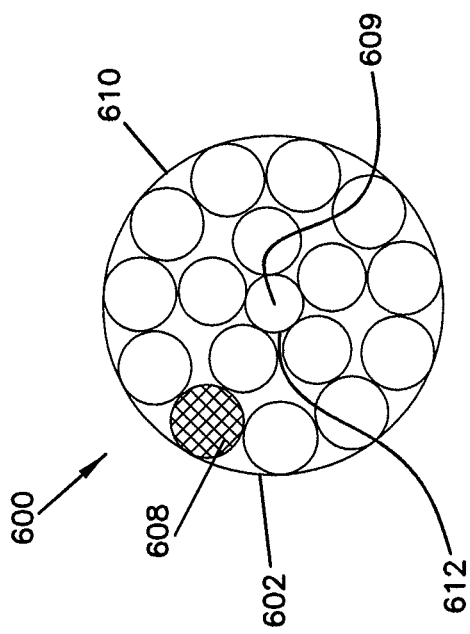
FIG. 49B is a cross-sectional view of the surgical braid illustrated in FIG. 48.

FIGS. 49a and 49b show a cross-sectional view of the first section 602 and second section 604, respectively, of the surgical braid 600 illustrated in FIG. 48. The surgical braid 600 is tubular and has a generally round circumference. Other possible embodiments include flattened, oval, or other generally oblong cross-sectional shapes. As shown, sections 602 and 604 are each formed using 16 strands interbraided as described with reference to FIG. 48. As shown in FIG. 49a, the single trace strand 608 is braided into the outer wall 610 of the first section 602 and at the transition point 614, the trace strand 608 is transitioned to form the core 612 of the second section 604. Additionally illustrated in FIG. 48, strand 609 with white, or no distinguishing color is braided into the outer wall 610 of the second section 604 and at the transition point 614, the strand 609 is transitioned to form the core 612 running along the first section 602. As such, the surgical braid 600 shown in FIG. 48 is a continuous braid having a single trace strand 608 that transitions from the outer wall 610 to the core 612.

Figure 50:
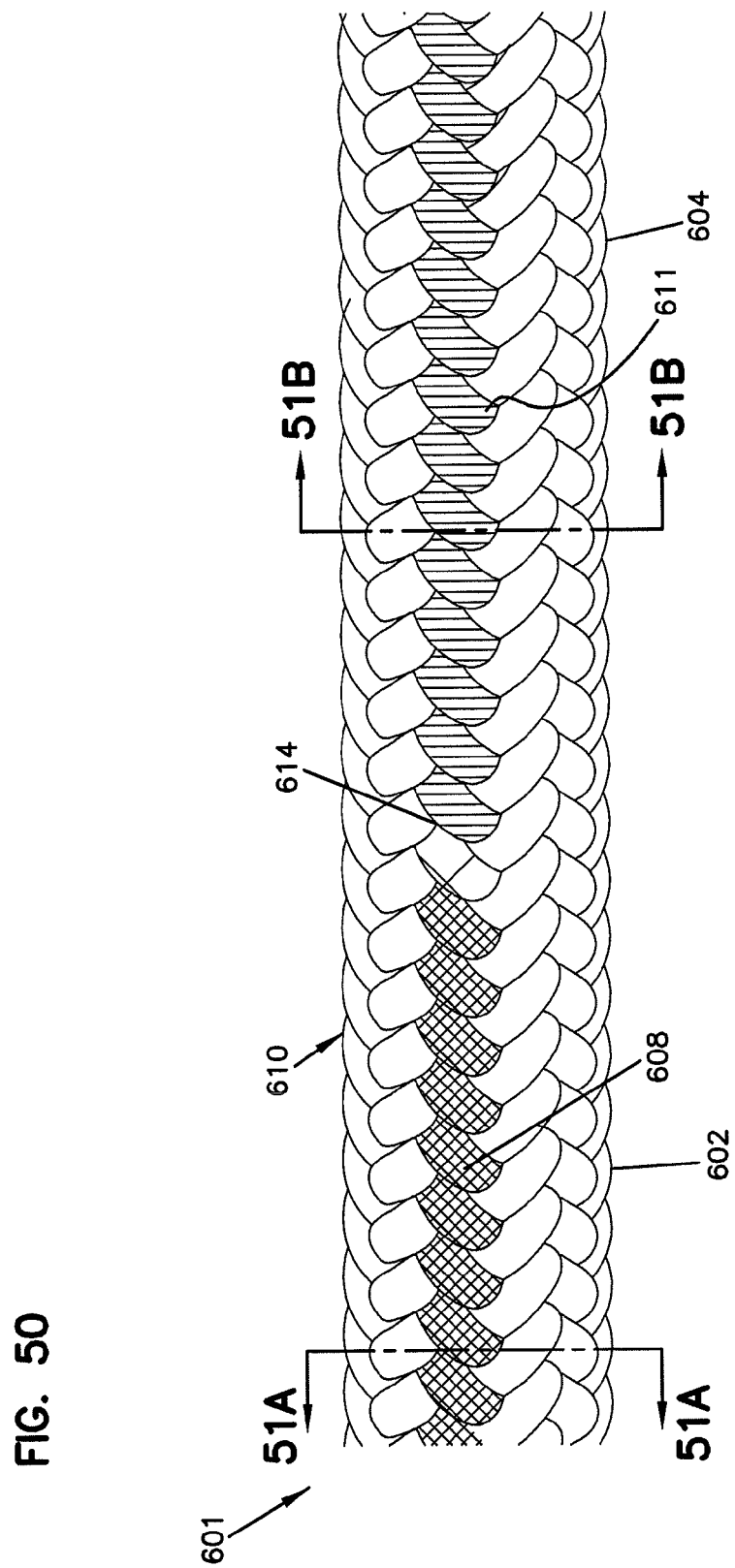
FIG. 50 is a side view schematic diagram of a 16-filament surgical braid showing details of the fibers forming the surgical braid.
Figure 51A:
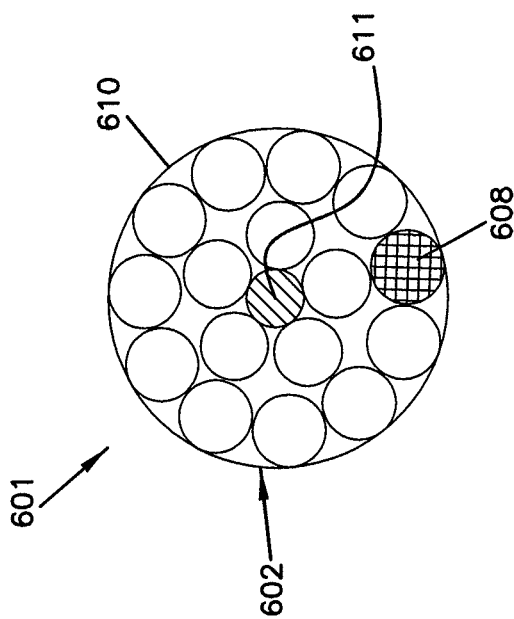
FIG. 51A is a cross-sectional view of the surgical braid illustrated in FIG. 50.
Figure 51B:
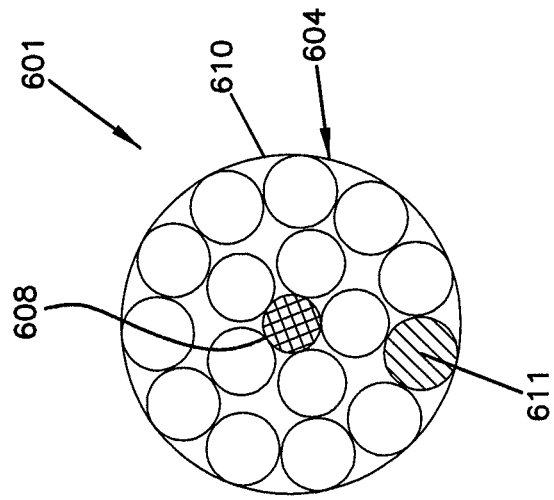
FIG. 51B is a cross-sectional view of the surgical braid illustrated in FIG. 50.
Figure 52:
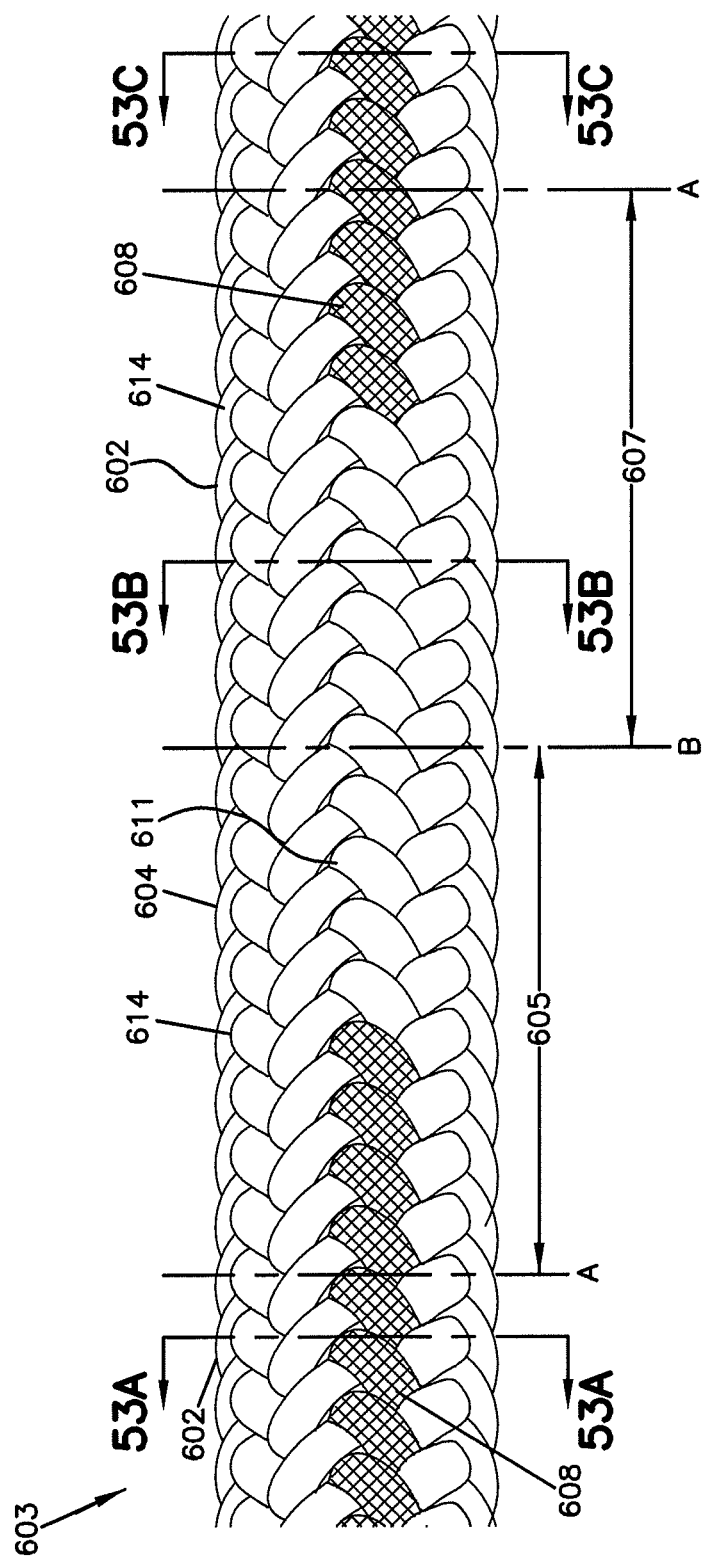
FIG. 52 is a side view schematic diagram of a 16-filament surgical braid showing details of the fibers forming the surgical braid.
Figure 53C:
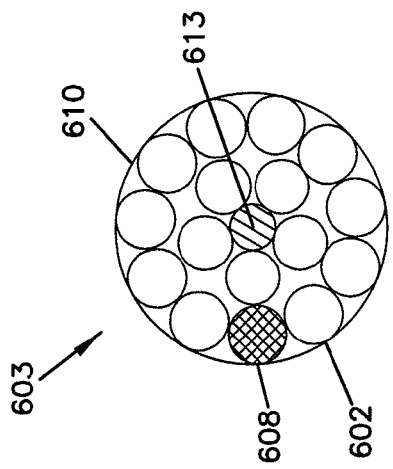
FIG. 53C is a cross-sectional view of the surgical braid illustrated in FIG. 52.
Figure 53B:
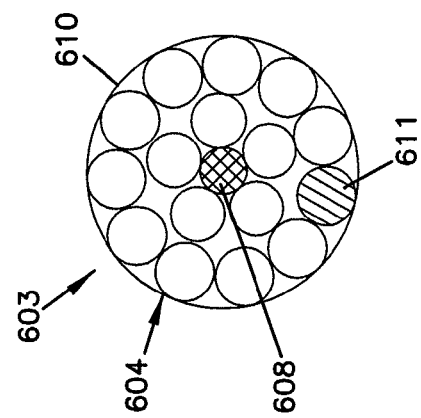
FIG. 53B is a cross-sectional view of the surgical braid illustrated in FIG. 52.
Figure 53A:
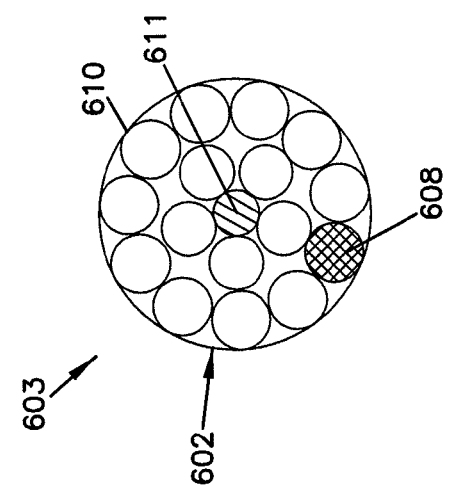
FIG. 53A is a cross-sectional view of the surgical braid illustrated in FIG. 52 taken along line 5-5.

FIGS. 50, 51a and 51b show an alternative embodiment of the 16-filament surgical braid 600 shown in FIG. 48. The surgical braid 601 is substantially similar to surgical braid 600 of FIG. 48, however, the white strand 609 is replaced with a trace strand 611, which is of a contrasting color.

FIGS. 52 and 53a-53c show an alternative embodiment of the 16-filament surgical braid 600 shown in FIG. 48. The surgical braid 603 is substantially similar to surgical braid 600 of FIG. 48. However, shown is an elongated version of the surgical braid 600 including two first sections 602 alternating with the second section 604. After manufacture, the surgical braid 603 may be cut into smaller surgical braids at lines A and B to form shorter individual surgical braids 605 and 607 having a first trace strand 608 and a second trace strand 611. This pattern of alternating sections 602 and 604 and alternating cut lines A and B can continue during manufacturing while the strands are being braided and wound onto a take-up reel. The braid is then cut into the surgical braids 601 (as shown in FIG. 46) at a later manufacturing stage.

Figure 55B:
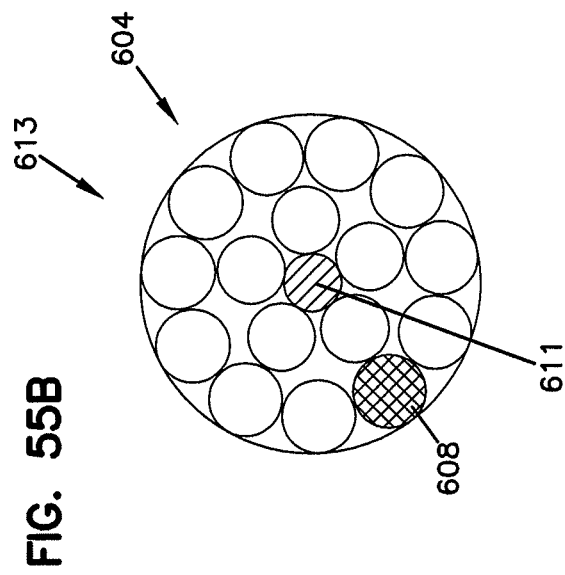
FIG. 55B is a cross sectional view of the surgical braid illustrated in FIG. 54.
Figure 55A:
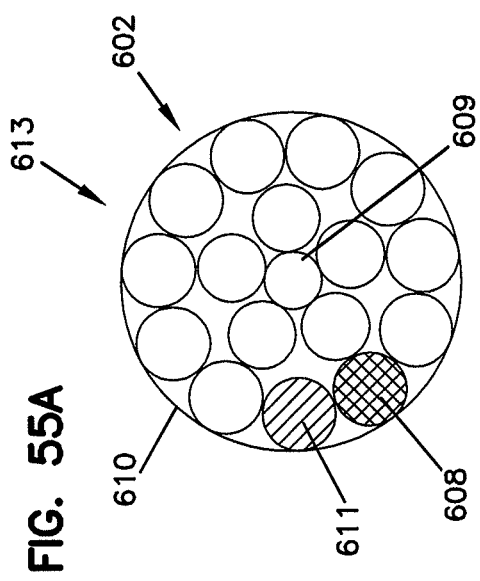
FIG. 55A is a cross sectional view of the surgical braid illustrated in FIG. 54.

FIGS. 54, 55a and 55b show an alternative embodiment of the 16-filament surgical braid 600 shown in FIG. 48. A surgical braid 613 is substantially similar to the surgical braid 600 of FIG. 48. However, the trace strand 608 is braided into the entire length of the outer wall 610 of the surgical braid 613. A second trace strand 611 is additionally braided into the outer wall 610 of the first section 602 and at a transition point 614, the strand 611 transitions to form the core 612 of the second section 604. Additionally, a strand 609 is transitioned, at the transition point 614, from the core of the first section 602 to the outer wall of the second section 604.

Figure 56:
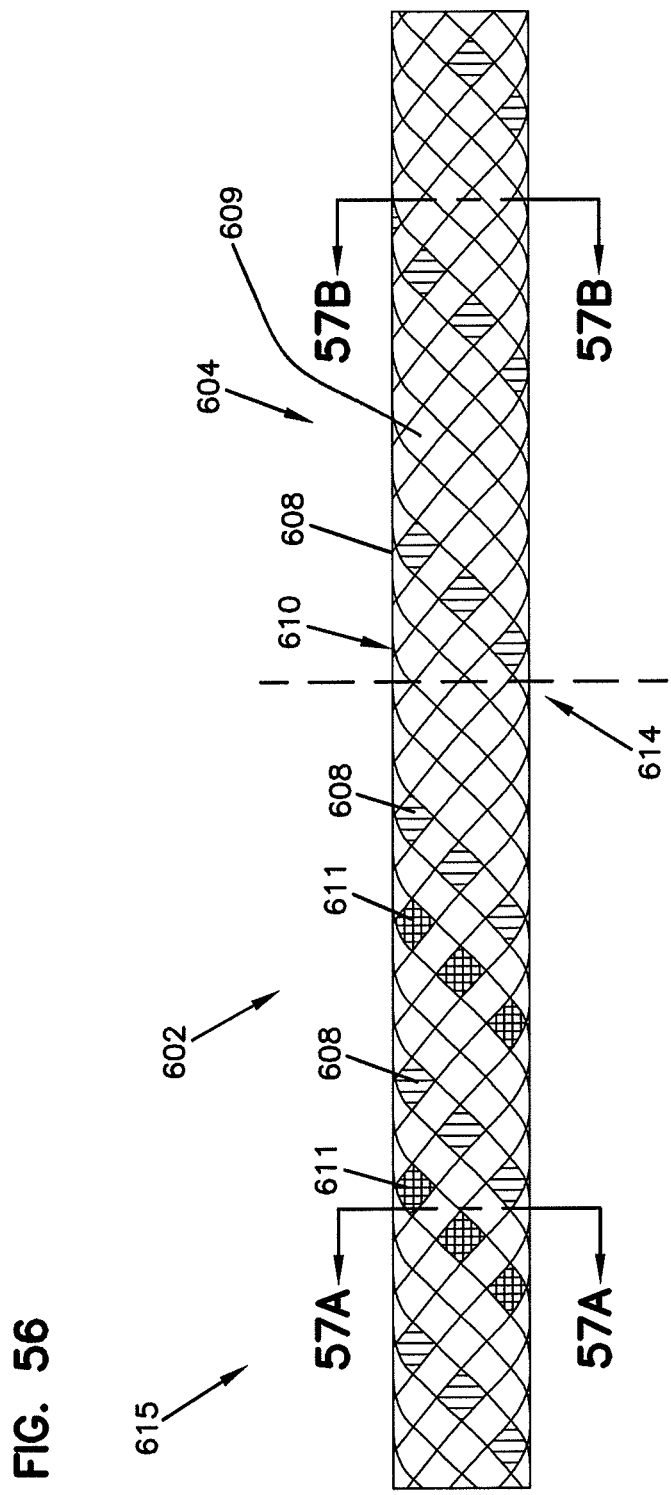
FIG. 56 is a side view schematic diagram of a 16-filament surgical braid showing details of the fibers forming the surgical braid.
Figure 57B:
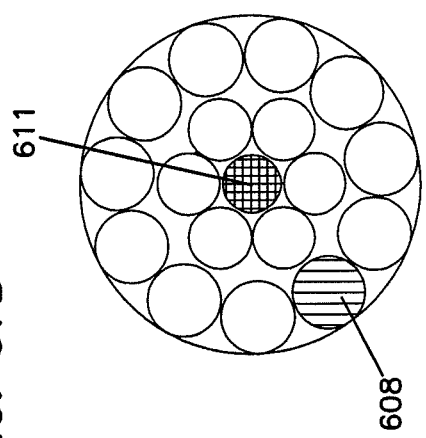
FIG. 57B is a cross sectional view of the surgical braid illustrated in FIG. 56.
Figure 57A:
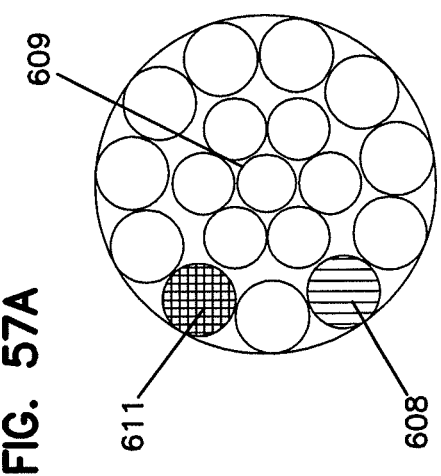
FIG. 57A is a cross sectional view of the surgical braid illustrated in FIG. 56.

FIGS. 56, 57a and 57b show and alternative embodiment of the surgical braid 613 illustrated in FIGS. 54, 55a, and 55b. In this embodiment, a surgical braid 615 has a different pattern for the first and second trace strands 608 and 611.

The first trace strand 608 is braided into the entire length of the outer wall 610 of the surgical braid 613 to form a spiral pattern. The second trace strand 611 is also braided into the outer wall 610 of the first section 602 to form a spiral pattern parallel to the first trace strand 608. At the transition portion 614, the second trace strand 611 transitions to form the core 612 of the second section 604. Additionally, the strand 609 is transitioned, at the transition point 624, from the core of the first section 602 to the outer wall of the second section 604.

Figure 58:
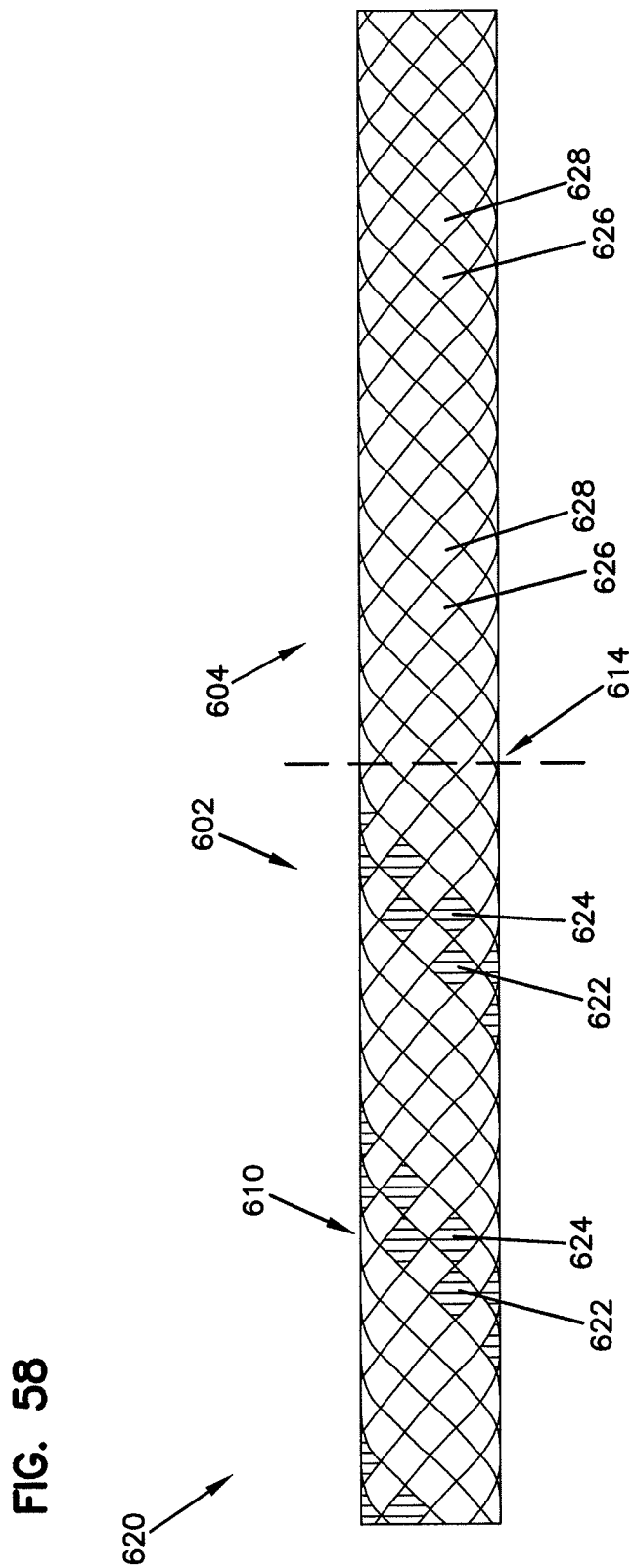
FIG. 58 is a side view schematic diagram of a 16-filament surgical braid showing details of the fibers forming the surgical braid.
Figure 59B:
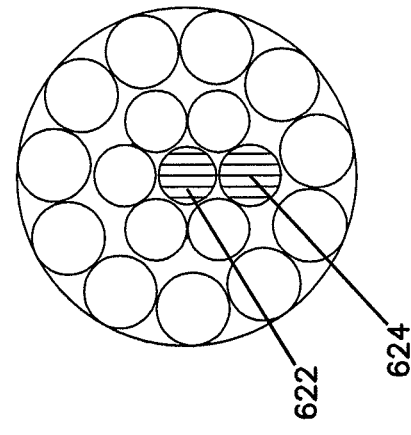
FIG. 59B is a cross sectional view of the surgical braid illustrated in FIG. 58.
Figure 59A:
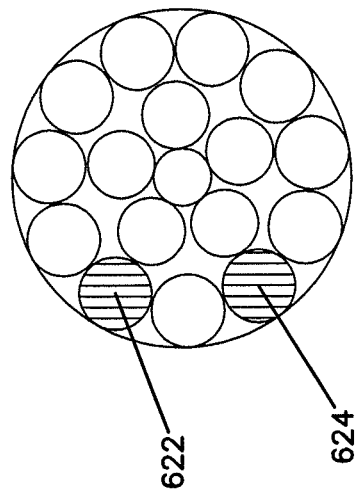
FIG. 59A is a cross sectional view of the surgical braid illustrated in FIG. 58.

FIGS. 58, 59a and 59b illustrate an example surgical braid 620, which is an alternative embodiment of the surgical braid 600 of FIG. 48. The surgical braid 620 is substantially similar to the surgical braid 600 of FIG. 48, except that two trace strands 622 and 624 with contrasting color are braided in a pattern. For example, the two trace strands 622 and 624 are braided into the outer wall 610 of the first section 602 to form parallel spiral patterns. The trace strands 622 and 624 then transition at the transition area 614 to form two cores running along the second section 604. The outer wall 610 of the second section 604 is braided around the core formed by the two trace strands 622 and 624. Strands 626 and 628 with white or a color indistinguishable from other strands (except the trace strands 622 and 624) are braided into the outer wall 610 of the second section 604. In at least some embodiments, the white strands 626 and 628 are transitioned at the transition area 614 to form a core running along the first section 602.

Figure 60:
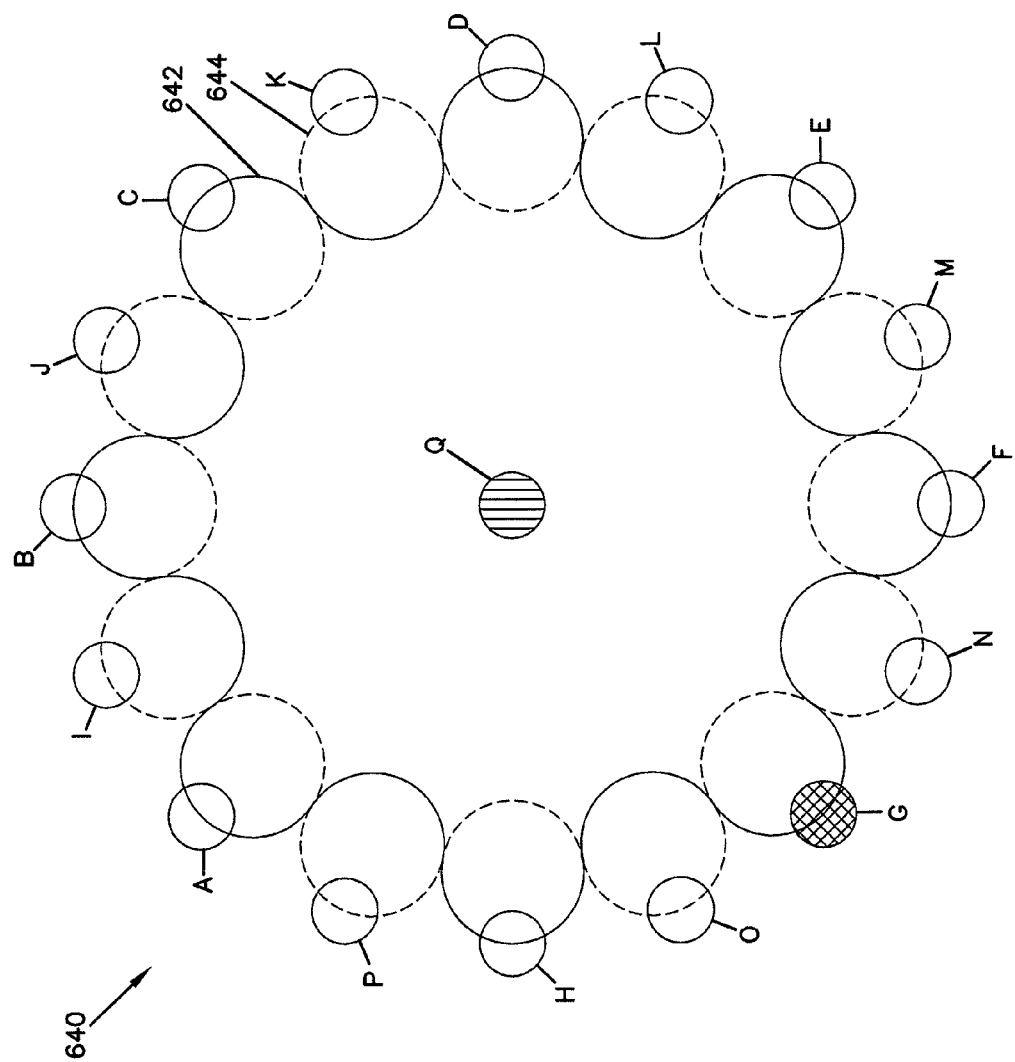
FIG. 60 is a top diagrammatic view of a 16 bobbin carrier and track.
Figure 61:
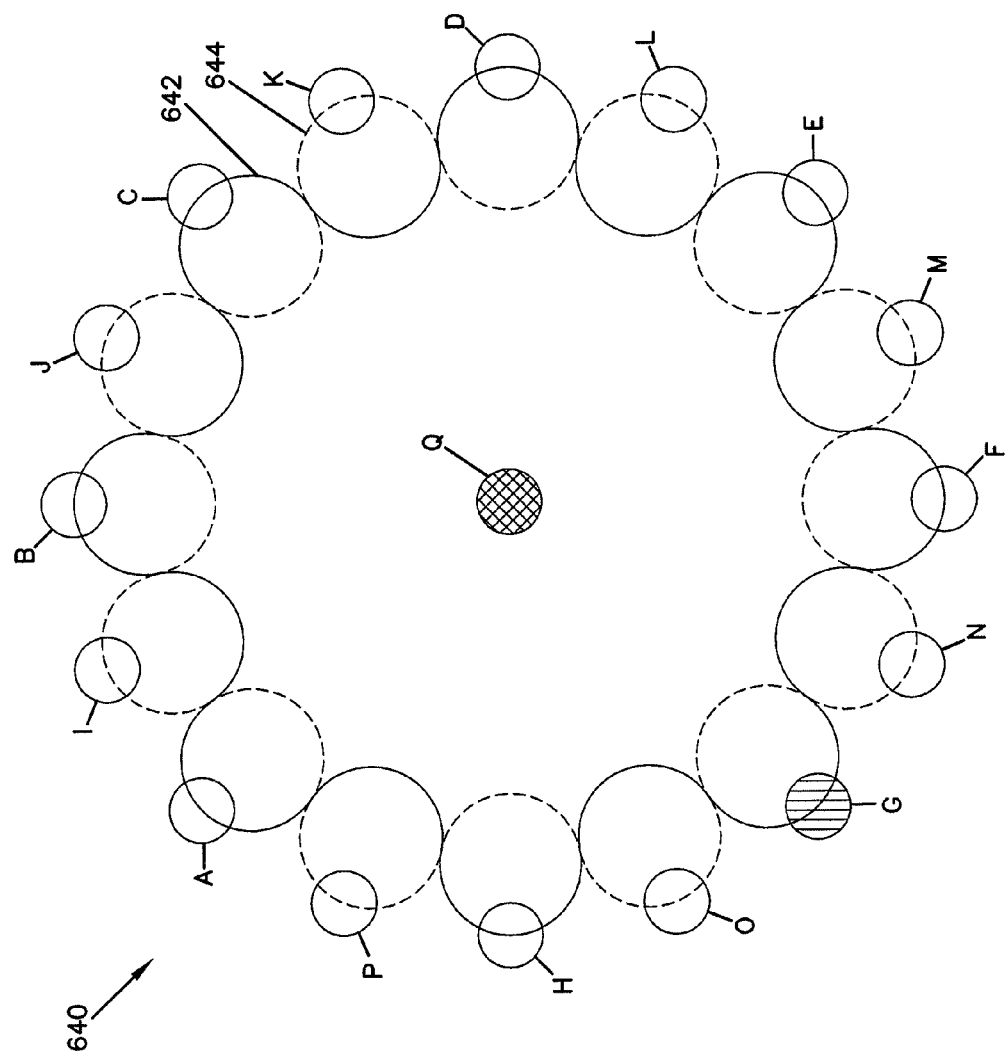
FIG. 61 is a top diagrammatic view of a 16 bobbin carrier and track.

FIGS. 60 and 61 are diagrams schematically illustrating an example path 640 of a set of bobbin carriers 640 configured to produce a surgical braid with a core, such as illustrated in FIGS. 50-53. The path 640 includes two endless paths 642 and 644 to manufacture a surgical braid with the 612. As depicted, the bobbin carriers are illustrated as 16 carriers A-P. The bobbin carriers A-H are positioned on a first endless path 642, and the bobbin carriers I-P are positioned on a second endless path 644. In operation, the bobbin carriers A-H move along the first endless path 642 in a direction opposite from the bobbin carriers I-P that move along the second endless path 644, thus creating the 1-over-1 configuration. Additionally, the bobbin carriers include a middle carrier Q for forming the core 612 of the braid 600. As shown in FIG. 56, the bobbin carriers G and Q hold the two trace strands 608 and 611, respectively. In FIG. 60, the bobbin carrier G holds the trace strand 608 that forms the outer wall 610 of the braid 600 and the bobbin carrier Q holds the trace strand 611 that forms the core 612 of the braid 600. In order to transition the trace strands from the outer wall 610 to the core 612 and vice versa, the strands are switched. FIG. 61 illustrates a configuration wherein the trace strands 608 and 611 are switched so that trace strand 608 is placed on bobbin carrier Q, forming the core 612, and trace strand 611 is placed on bobbin carrier G, forming the outer wall 610. Although the example path 640 is illustrated as moving along 16 horn gear assemblies, surgical braids with a core can be made using a path that moves along a different number of horn gear assemblies. For example, the path 640 could be formed around a set of eight horn gear assemblies.

The surgical braids 600, 601, 603, 613, and 620 having a strand that transitions between a core and being braided into the out wall of the braid can be made using an arrangement of active tracks, passive tracks, and gates, including those illustrated in FIGS. 3e and 3f. As illustrated in FIG. 3e, for example, the gate 126 can be moved to the open position and a passive horn gear assembly corresponding to passive track 660 can be rotated to move one bobbin carrier assembly from the active sub-track 208C and another bobbin carrier from the passive track 660 back to the active sub-track 208C. The strand carried by a bobbin carrier assembly positioned along the passive track 660 will form a core of the surgical braid being produced. Switching bobbin carrier assemblies between the active sub-track 208C and the passive track 660 transitions strands between being positioned as the core and being braided into the outer wall of the surgical braid. In another alternative as illustrated in FIG. 3f, the gates 126 can be opened to move one of the bobbin carrier assemblies from the active sub-track 208C to the passive sub-tracks 662 and 661, and also move another bobbin carrier from the passive sub-tracks 661 and 662 back to the active sub-track 208C. Switching bobbin carriers between the active track and the passive track formed by passive sub-tracks 661 and 662 transitions strands between being positioned as the core and being braided into the outer wall of the surgical braid.

Figure 62:
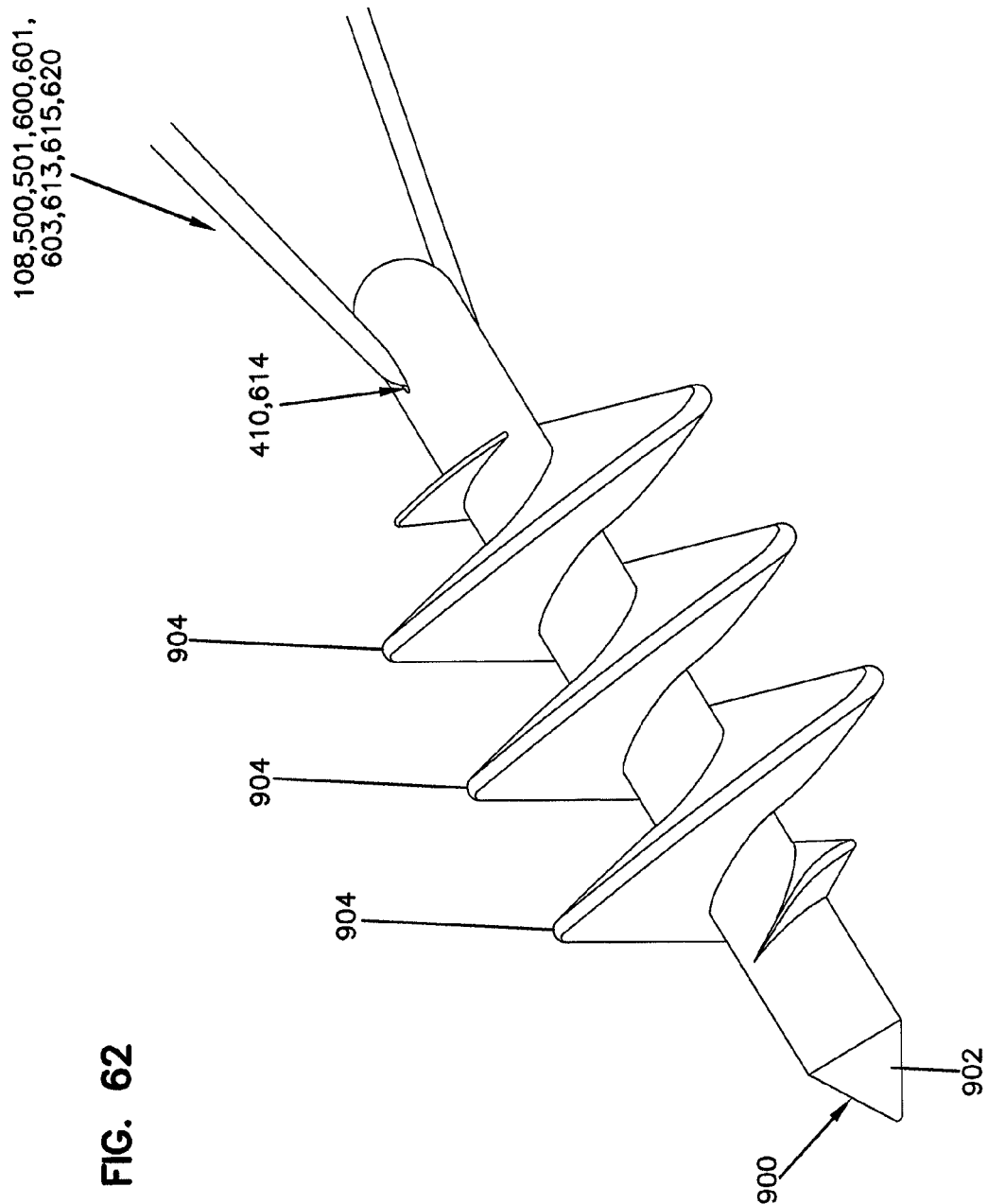
FIG. 62 shows a side view of a surgical braid attached to a surgical orthopedic anchor.

FIG. 62 shows a side view of a braid 108, 500, and 600, as described herein, which is used as a surgical braid. As depicted, the braid 108, 500 and 600 can be anchored to a surgical orthopedic anchor 900. In the depicted example, the surgical braid is anchored to the anchor 900 at, or proximate to, the transition point 410 or 614. In other embodiments, the surgical braid may be anchored at different points, such as a bifurcated section or an end of the surgical braid. As shown, the surgical anchor 900 includes a shaft 902 and one or more threads 904. In some embodiments, the shaft 902 of the surgical anchor 900 is screwed into a bone using the threads 904. The surgical braid threaded through the anchor 900 is then used for securing ligaments and/or muscles to the bone.

FIGS. 63-81 illustrate yet other possible embodiments of a braider that can be used for braiding various surgical braids including surgical braid having round and flat portions, alternating patterns of colored strands, and alternating cores in tubular sections.

Figure 63:
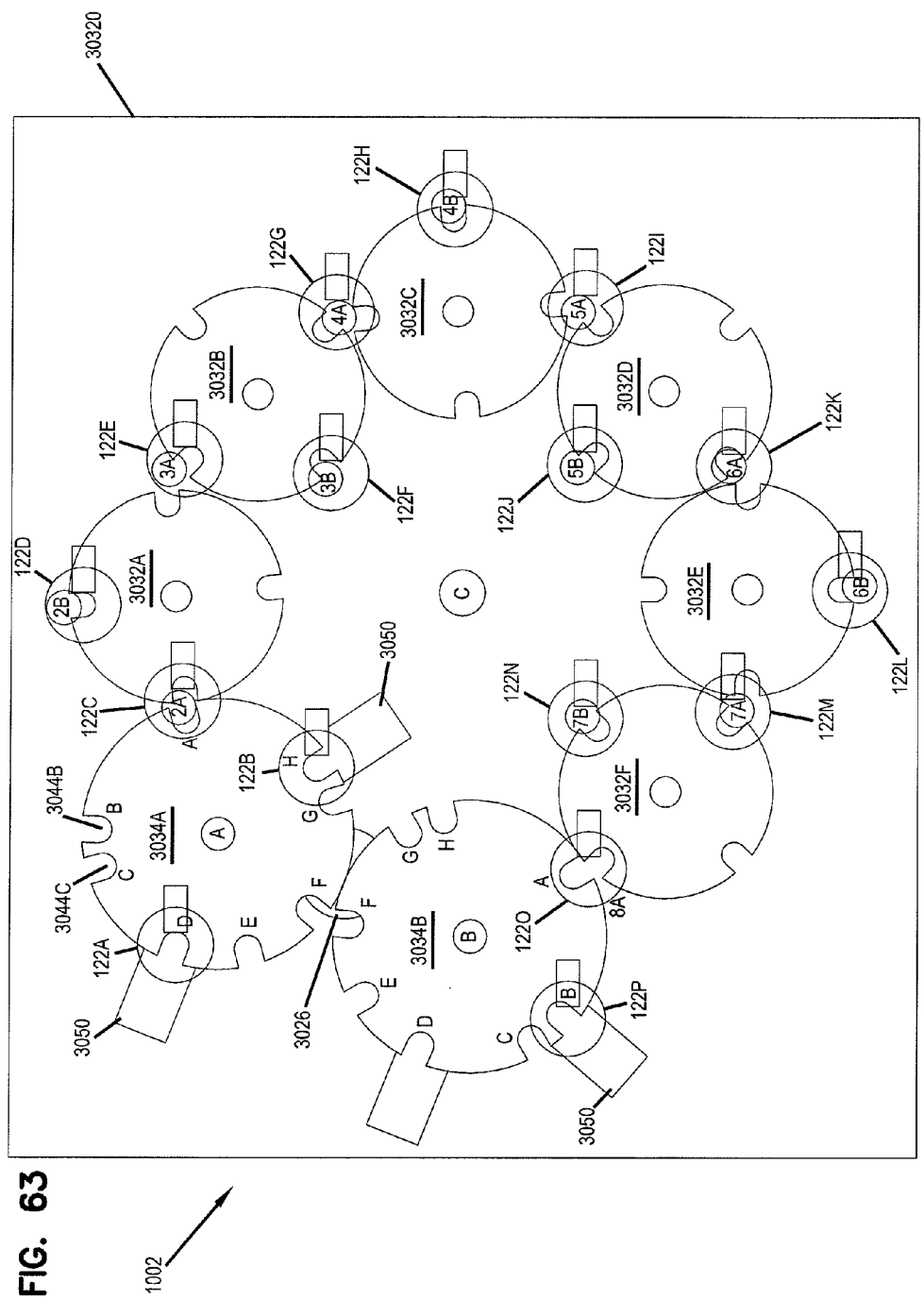
FIG. 63 is a schematic top view of an example braiding assembly.

FIG. 63 illustrates an alternative embodiment of a braiding assembly 3002 that can be used in the braiding machine 102. In this embodiment, the braiding assembly 3002 includes a braiding track plate 3020, a plurality of bobbin carrier assemblies 122 (including 122A-122P), at least a first plurality of horn gear assemblies 3032A-3032F, at least a second plurality of horn gear assemblies 3034A and 3034B, at least one gate 3026, and one or more retraction mechanisms 3050.

As describe in more detail herein, the braiding track plate 3020 is similar to the braiding track plate 120 and defines a track 3102 (e.g., FIGS. 65 and 66) configured to guide the plurality of bobbin carrier assemblies 122A-122P along defined paths. The horn gear assemblies 3032A-3032F and 3034A and 3034B support and drive the bobbin carrier assemblies 122A-122P along the defined paths. In at least some embodiments, the braiding assembly 3002 is configured and operates to produce a braid 108. The one or more gate 3026 is configured to selectively guide the bobbin carrier assemblies 122 to automatically shift the operation of the braiding assembly 3002 between a round section and a flat section of the braid. The structure and operation of the gate 3016 is the same as, or similar to, the gates 126A-126H described herein, except that the dimensions (such as length and curvature) of inter-track and intra-track paths formed in the gate 3026 may be different from those in the gate 126 to match the track 3102 underneath the second horn gear assemblies 3034.

The structure and operation of the horn gear assemblies 3032A-3032F in the first set of horn gears are the same as, or similar to, the horn gear assemblies 132A-132H as described herein. The structure and operation of the horn gear assemblies 3034A and 3034B in the second set of horn gears are also the same as, or similar to, the horn gear assemblies 132A-132H except that the dimensions and number of notches in the horn gear assemblies 3034A and 3034B can be modified as illustrated and described in more detail herein. In the depicted embodiment, the horn gear assemblies 3032A-3032F are arranged adjacent one another. The horn gear assemblies 3034A and 3034B are adjacent to one another and position between horn gear assemblies 3032A and 3032F. In this arrangement, the horn gear assemblies are positioned along the track 3102 and about the machine axis C. In the depicted embodiment, the set of first horn gear assemblies 3032 includes six first horn gear assemblies 3032A-3032F. The horn gear assemblies 3032A-3032F, 3034A, and 3034B are operated so that that the bobbin carrier assemblies 122A-122P move across adjacent horn gear assemblies 3032A-3032H and along the track 3102.

The horn gear assemblies 3032A-3032H, 3034A and 3034B are operated in a manner that two adjacent first horn gear assemblies are rotated in opposite direction. For example, the horn gear assemblies 3032A, 3032C, 3032E, and 3034B are rotated counter-clockwise while the other horn gear assemblies 3032B, 3032D, 3032F, and 3034A are rotated clockwise, or vice versa. In other embodiments, the first horn gear assemblies 3032A-3032F, 3034A, and 3034B can be configured to rotate in different manners. As described in more detail herein, the first horn gear assemblies 3032 can be mechanically linked and operated together.

The gate 3026 can be arranged along the track 3102 between the adjacent second horn gear assemblies 3034A and 3034B. The gate 3026 can be operated to enable at least one of the bobbin carrier assemblies 122A-122P to move between the adjacent second horn gear assemblies 3034A and 3034B. Alternatively, the gate 3026 can be operated to prevent at least one of the bobbin carrier assemblies 122A-122P from crossing between the adjacent second horn gear assemblies 3034A and 3034B and to cause the bobbin carrier assembly to move back to the adjacent horn gear assembly to begin moving in the opposite direction (e.g., transition from clockwise to counterclockwise movement, or vice versa, around machine axis C).

The retraction mechanisms 3050 operates to retract at least one of the bobbin carrier assemblies 122 from the horn gear assemblies 3024A and 3024B. As described in more detail herein, the retraction mechanisms 3050 can cooperate with the gate 3026 to shift between braiding a flat section of a braid and braiding a tubular section of the braid. The retraction mechanisms 3050 also can be used to shift between braiding a surgical braid with a core and braiding the braid without a core, alternate or change the strands used as the core along a braid, or change a pattern or colors of the strands used to form the surgical braid.

In the depicted embodiment, the braiding assembly 3002 includes six first horn gear assemblies 3032A-3032F and two second horn gear assemblies 3034A and 3034B, and includes one gate 3026 along a portion of the track 3102 between the two second horn gear assemblies 3034A and 3034B. Other embodiments can include different number of horn gear assemblies 3032 and 3034 along the track, a different number of gates 3026, or a different number of retraction mechanisms 3050 than illustrated in the exemplary shown in FIG. 2. There can be a different total number of horn gear assemblies 3032 and 3034, more or fewer than two second horn gear assemblies 3034, or more or fewer than six horn gear assemblies 3032, or a different ratio between the number of horn gears 3034 and the number of horn gears 3032. For example, alternative embodiments might include two additional horn gears 3034 either between, or in place of, horn gears 3032C and 3032D with a gate between the two additional horn gears and additional retraction mechanisms. Such alternative embodiments would enable braiding of a bifurcated flat section my moving of some of the bobbin carriers 122 and strands along a path defined from the horn gear 3034A to the additional horn gear located in place of horn gear 3032C, and other bobbin carriers 122 and strands along a path defined from the horn gear 3034B to the additional horn gear located in place of horn gear 3032D, Yet other embodiments might include yet other additional horn gears 3034 position between or in place of the other horn gears 3032A, 3032B, 3032E, or 3032F. Other embodiments might include only horn gears 3034 with associated gates 3026 and retraction mechanisms 3050.

In the depicted embodiment, the braiding assembly 3002 includes 16 bobbin carrier assemblies 122A-122P to produce a 16-end braid 108. Other embodiments can include any suitable number of bobbin carrier assemblies 122 to make braids having any desired numbers of strands. For example, alternative braiding assemblies could have 8, 24, or 32 bobbin carrier assemblies 122, or any other suitable number of bobbin carrier assemblies 122. Further, in the example of FIG. 79, the braiding assembly 3002 includes 17 bobbin carrier assemblies to produce a 17-end braid having 16 strands as a sheath and one strand as a core.

Figure 64A:
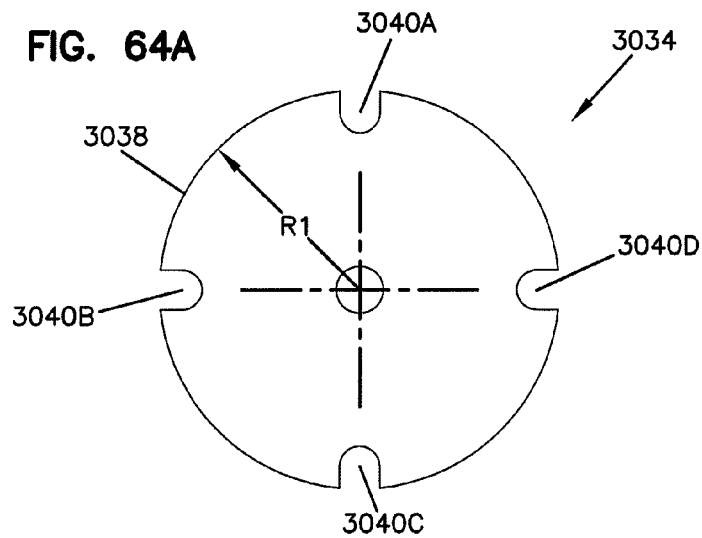
FIG. 64A is a schematic, top view of an example first horn gear assembly.

FIG. 64A is a schematic, top view of an example first horn gear assembly 3032. The first horn gear assembly 3032 is configured as a disk 3038 having a plurality of slots 3040 (including 3040A-3040D). The slots 3040 are configured to engage the bobbin carrier assemblies 1022, respectively. In at some embodiments, the first horn gear assembly 3032 has four slots 3040A-3040D that are evenly spaced apart and formed at the circumference of the disk 3038. In other embodiments, the first horn gear assembly 3032 can has one or more slots 3040 (other than four slots) that are either evenly or unevenly spaced apart around the circumference of the disk 3038.

Figure 64B:
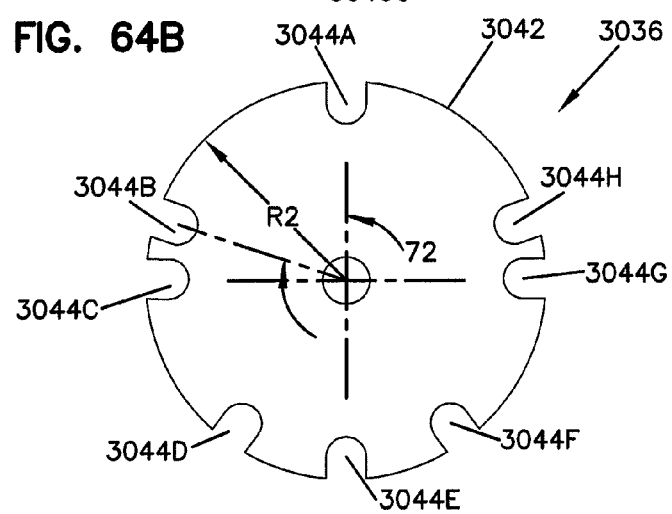
FIG. 64B is a schematic, top view of an example second horn gear assembly.
Figure 64C:
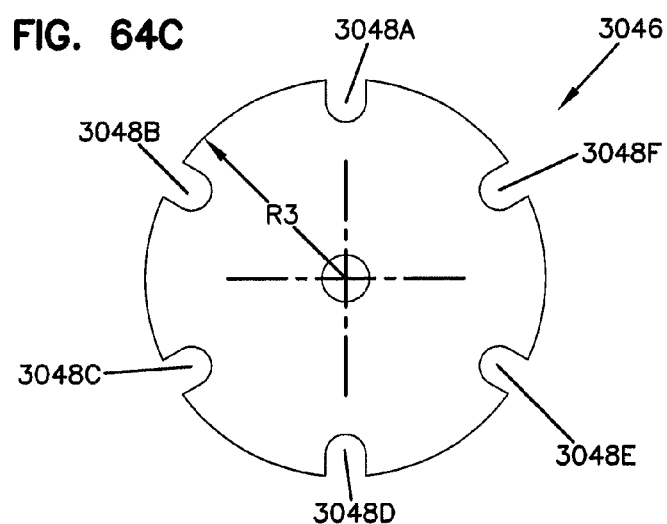
FIG. 64C is a schematic, top view of another example second horn gear assembly.

Referring to FIGS. 64B and 64C, an example second horn gear assembly 3034 is illustrated. The second horn gear assembly 3034 is configured as a disk 3042 or 3046 having a plurality of slots. The plurality of slots is configured to engage the bobbin carrier assemblies 1022, respectively. The plurality of slots are formed at the circumference of the disk and arranged such that at least some of the slots are selectively used to provide either an even number of evenly spaced slots around the disk 3042 or 3046 or an odd number of evenly spaced slots around the disk 3042 or 3046. As described herein, the even number of evenly spaced slots can be used to create a round section of a braid 108, and the odd number of evenly spaced slots can be used to braid a flat section of the braid 108.

FIG. 64B is a schematic, top view of an example second horn gear assembly 3034. In this example, the second horn gear assembly 3034 is shaped as a disk 3042 having eight slots 3044A-3044H. The slots 3044A, 3044C, 3044E, and 3044G are evenly spaced apart in about 90 degree increments around the disk 3042 to form a set of four evenly spaced slots (an even number of slots), although alternative embodiment can have an angular spacing other than 90 degrees. Further, the slots 3044A, 3044B, 3044D, 3044F, and 3044H are evenly spaced apart in about 72 degree increments around the disk 3042 to form a set of five evenly spaced slots (an odd number of slots), although alternative embodiment can have an angular spacing other than 72 degrees. As such, the set of four evenly spaced slots shares one slot (the slot 3044A) with the set of five evenly spaced slots. In at least some embodiments, the disk 3042 of the second horn gear assembly 3034 has a radius R2 that is greater than a radius R1 of the disk 3038.

FIG. 64C is a schematic, top view of another example second horn gear assembly 3034. In this example, the second horn gear assembly 3034 is shaped as a disk 3046 having six slots 3048A-3048F. The slots 3048A, 3048B, 3048C, 3048D, 3048E, and 3048F are evenly spaced apart in about 60 degree increments around the disk 3046 to form a set of six evenly spaced slots (an even number of slots), although alternative embodiment can have an angular spacing other than 60 degrees. Further, the slots 3048A, 3048C, and 3048E are evenly spaced apart in about 120 degree increments around the disk 3046 to form a set of three evenly spaced slots (an odd number of slots), although alternative embodiment can have an angular spacing other than 120 degrees. The set of six evenly spaced slots shares three slots (the slots 3048A, 3048C, and 3048E) with the set of three evenly spaced slots. In at least some embodiments, the disk 3046 of the second horn gear assembly 3034 has a radius R3 that is greater than a radius R1 of the disk 3038.

In other embodiments, the second horn gear assembly 3034 is configured as a disk having a different size and a different number of slots. It is still noted that the slots of the second horn gear assembly 3034 are arranged such that at least some of the slots are selectively used to provide either an even number of evenly spaced slots or an odd number of evenly spaced slots.

Figure 65A:
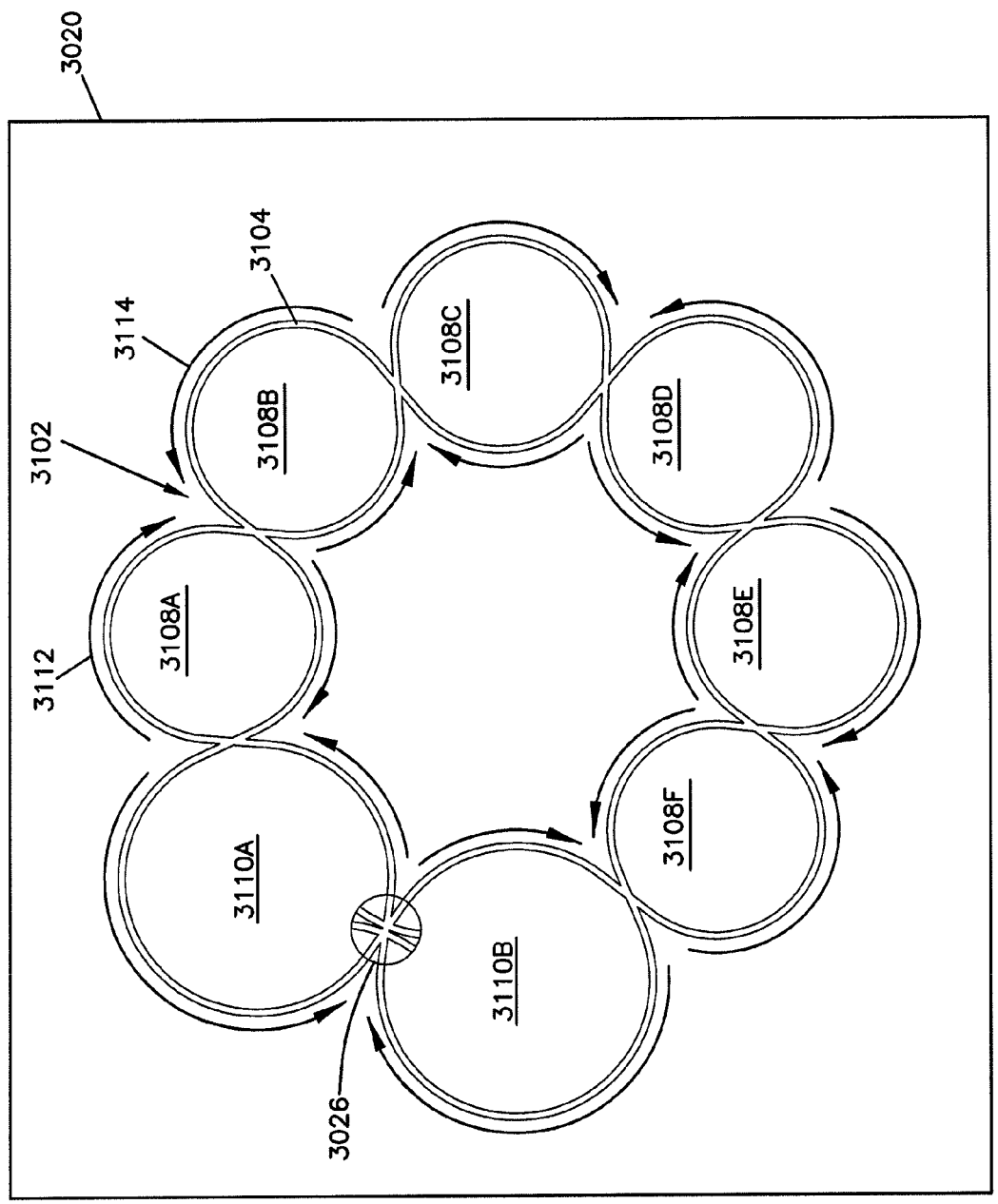
FIG. 65A illustrates an embodiment of a track plate and a track of FIG. 63.

FIG. 65A illustrates the embodiment of the track plate 3020 and the track 3102 as discussed with reference to FIG. 63. In this embodiment, the gate 3026 is in an open position. The track plate 3020 is a plate that defines a plurality of slots or grooves 3104 that form the track 3102. The track 3102 is formed to correspond to the first and second horn gear assemblies 3032A-3032F and 3034A-3034B and guide the bobbin carrier assemblies 122A-122P as they are propelled by the first and second horn gear assemblies 3032A-3032F and 3034A-3034B as explained in more detail herein. The track 3102 includes eight sub-tracks (i.e., six first sub-tracks 3108A-3108F and two second sub-tracks 3110A-3110B), which correspond to the first and second horn gear assemblies 3032A-3032F and 3034A-3034B, respectively. The sub-tracks 3108A-3108F and 3110A-3110B are arranged abutted to each other around the machine axis C so that the bobbin carrier assemblies 1022A-1022P selectively move between adjacent sub-tracks 3108A-3108F and 3110A-3110B as they move along the track 3102.

The gate 3026 is positioned between the second sub-tracks 3110A and 3110B. The gate 3026 has an open position and a closed position and define grooves or slots for guiding the bobbin carrier assemblies 122A-122P either between the second sub-tracks 3110A and 3110B, or along one of the second sub-tracks 3110A and 3110B and pass the other.

Figure 65B:
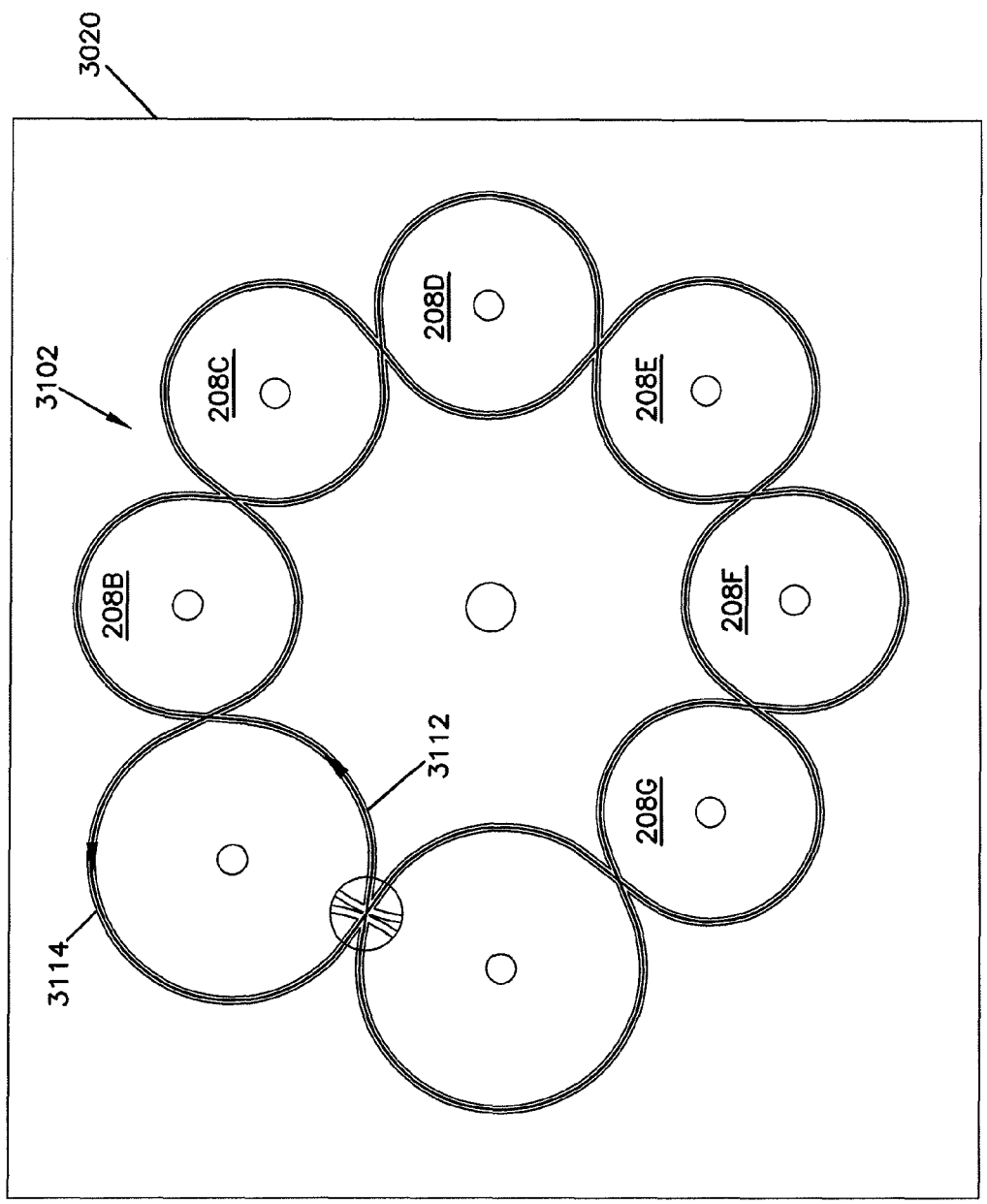
FIG. 65B illustrates an example path of bobbin carrier assemblies along the track of FIG. 65A.
Figure 68:
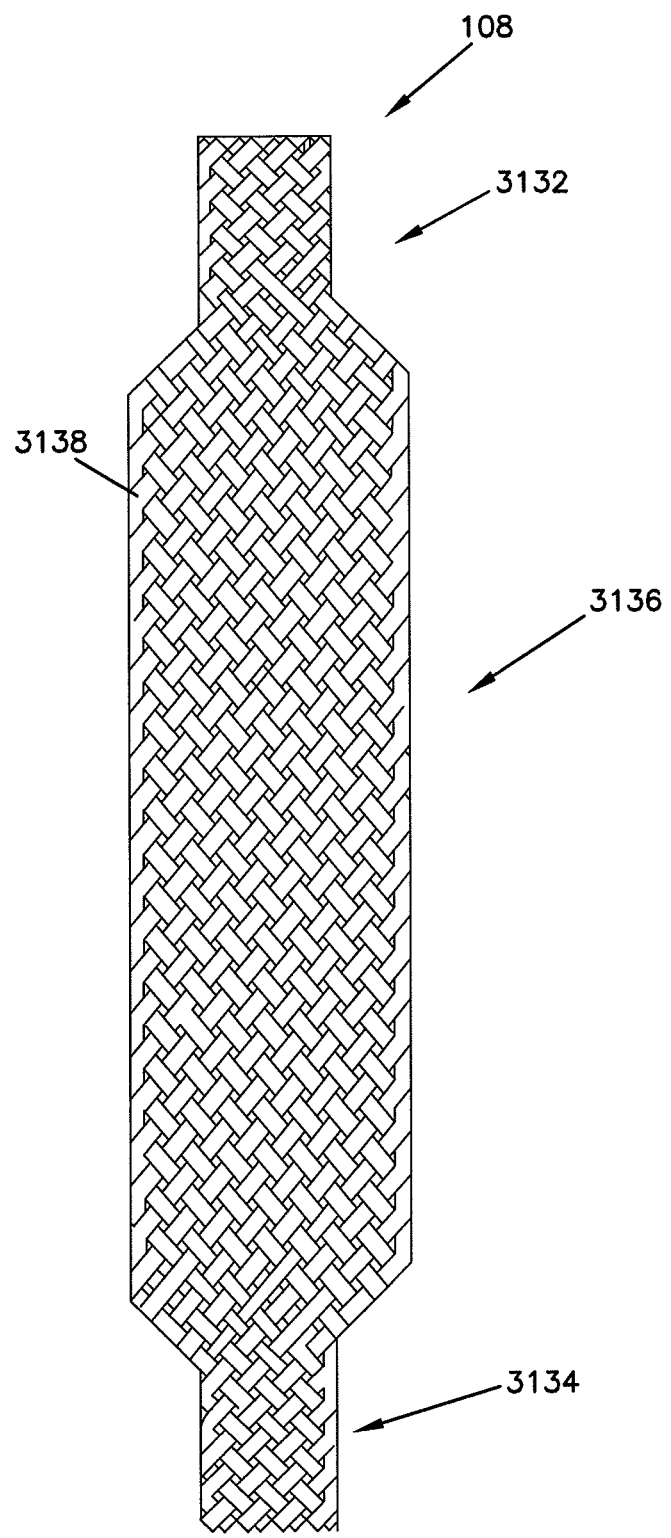
FIG. 68 illustrates an example braid that can be made using the braiding machine with the braiding assembly.

Referring to FIG. 65A, the gate 3026 is in the open position at which the bobbin carrier assemblies 122A-122P are guided by the inter-bridge path of the gate 3026 to move between the second sub-tracks 3110A and 3110B as they are propelled by the second horn gear assemblies 3034A-3034B. Thus, as illustrated in FIG. 65B, the track 3102 provides a clockwise path 3112 and a counter clockwise path 3114, each of which oscillates and is out-of-phase from the other. When the gate 3026 is in the open position, the braiding assembly 3002 operates to carry half of the bobbin carrier assemblies 122 along the clockwise path 3112 and the other half of the bobbin carrier assemblies 122 along the counter clockwise path 3114 in order to braid a non-flat (e.g., round) section of a braid 108, as illustrated in FIG. 68.

Figure 66A:
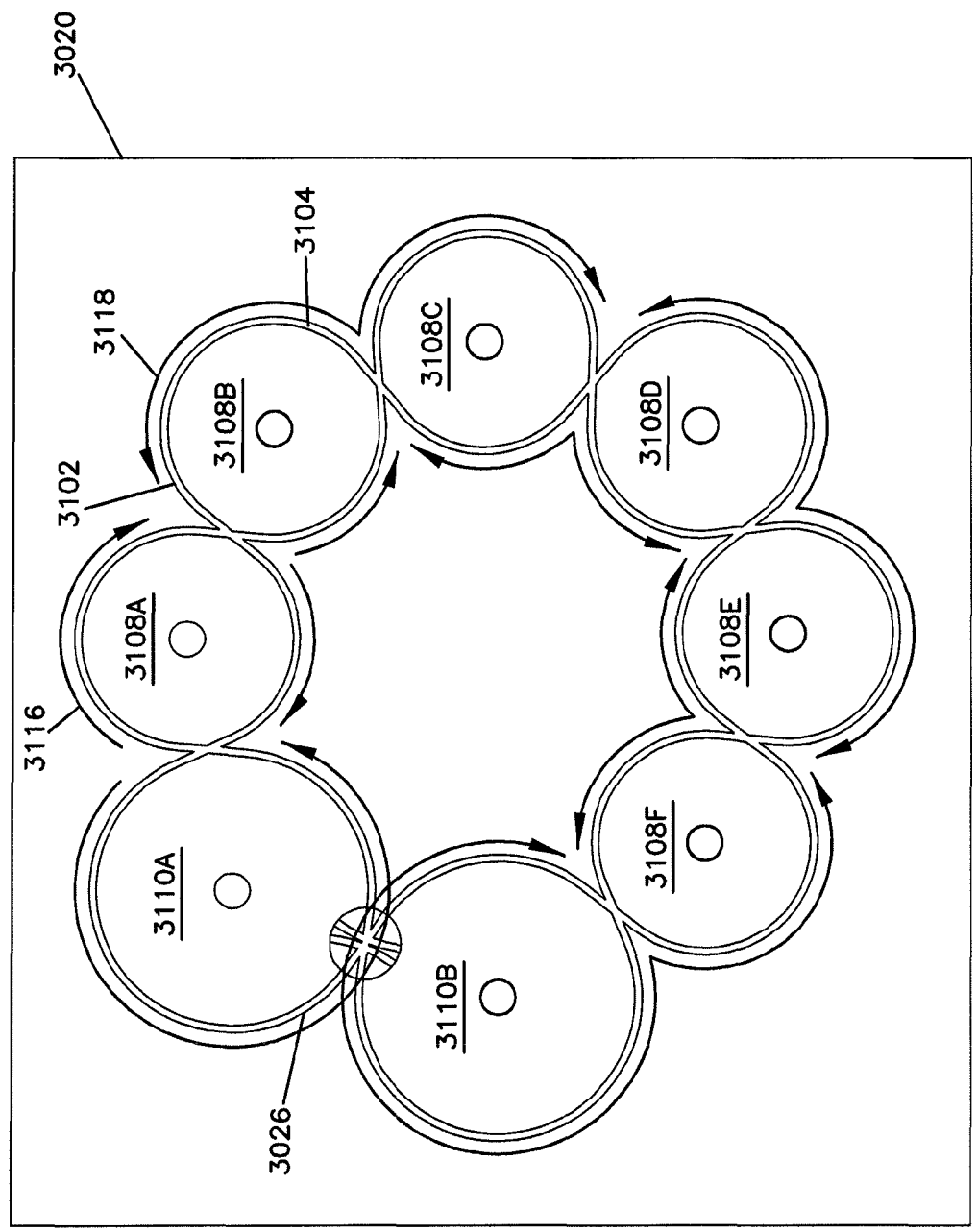
FIG. 66A illustrates an embodiment of the track plate and the track with a gate in the closed position.

FIG. 66A illustrates the embodiment of the track plate 3020 and the track 3102 with the gate 3026 in the closed position. When the gate 3026 is in the closed position, the intra-bridge path of the gate 3026 will guide the bobbin carrier assemblies 122A-122P along clockwise and counter-clockwise paths 3116 and 3118 of the track 3020 (FIG. 66B) such that the bobbin carrier assemblies 122A-122P remain in one of the second sub-tracks 3110A and 3110B, along which they are traveling, and pass the other of the second sub-tracks 3110A and 3110B. The clockwise path 3116 is similar to the clockwise path 3112, and the counterclockwise path 3118 is similar to the clockwise path 3114. However, when the gate 3026 is in the closed position, the bobbin carrier assemblies 122 are prevented from continuing to move along either the clockwise path 3112 or the counterclockwise path 3114 past the gate 3026, and are guided by the gate 3026 to move from the clockwise path 3116 and the counterclockwise path 3118 across the gate 3026, or vice versa. As such, when the gate 3026 is in the closed position, a single oscillating closed, endless path is formed with the clockwise and counterclockwise paths 3116 and 3118. When the gate 3026 is in the closed position, the braiding assembly 3002 operates to braid a flat section of the braid 108, as illustrated in FIG. 68.

Figure 67:
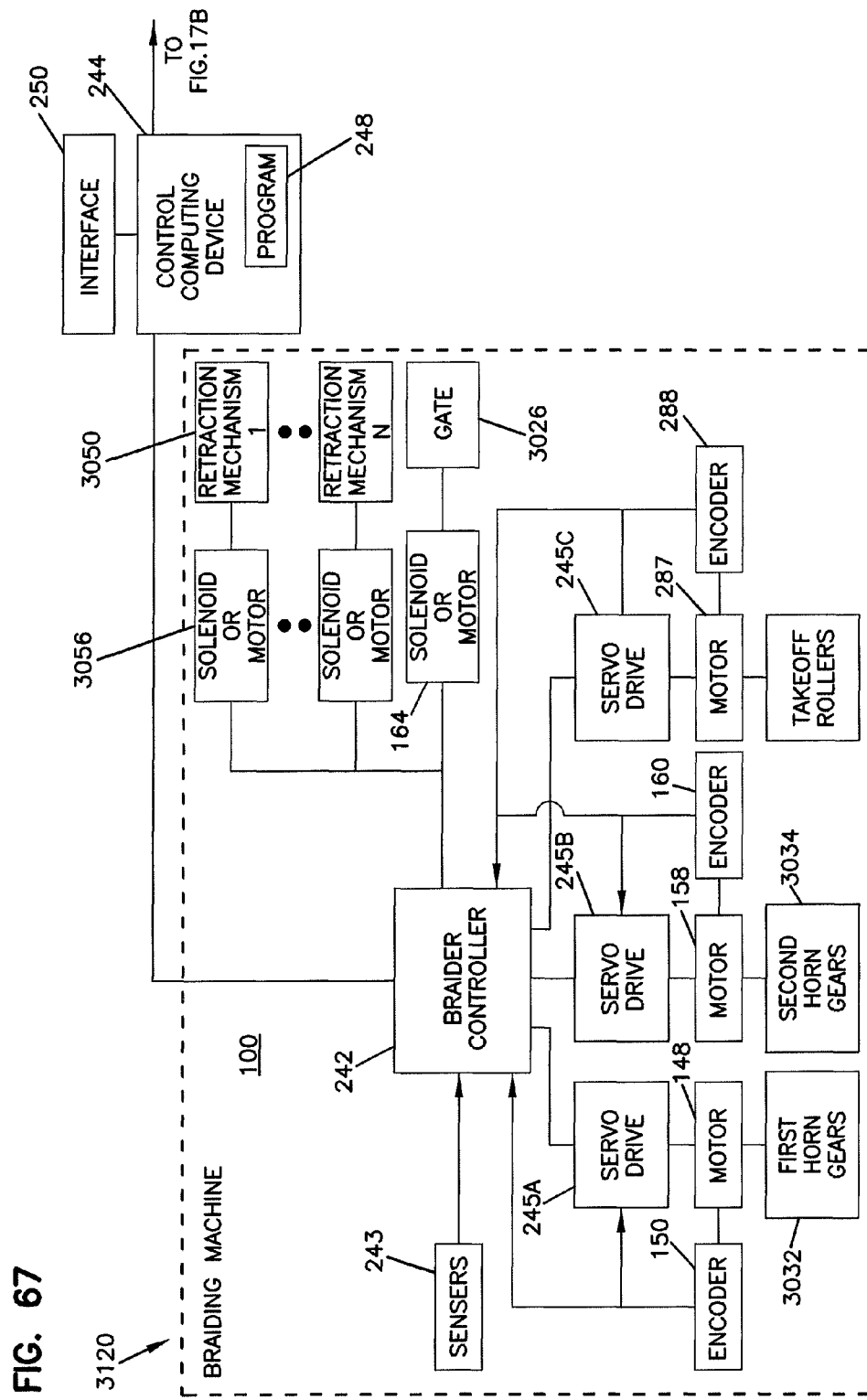
FIG. 67 is a schematic diagram of an example braiding control system for the braiding machine including the braiding assembly.

FIG. 67 is a schematic diagram of an example braiding control system 3120 for the braiding machine 100 including the braiding assembly 3002. In at least some embodiments, the braiding control system 3120 is designed similarly to the control system 240 as illustrated in FIG. 17A. As many of the concepts and features are similar to the embodiment shown in FIG. 17A, the description for the embodiment illustrated in FIG. 17A is hereby incorporated by reference for an embodiment of the braiding control system 3120. Where like or similar features or elements are shown, the same reference numbers will be used where possible. The following description for the braiding control system 3120 will be limited primarily to the differences between the control system 240 and the braiding control system 3120.

As illustrated in FIG. 67, in at least some embodiments, the set of the first horn gear assemblies 3032A-3032F is operated by a first motor 148, and the set of the second horn gear assemblies 3034A and 3034B is operated by a second motor 158. The gate 3026 can be actuated by a gate actuating system 164 (e.g., a solenoid or motor system). The retraction mechanisms 3050 can be actuated by retraction operation systems 3056 (e.g., a solenoid or motor system), respectively. In some embodiments, the retraction mechanisms 3050 can be operated by a single retraction operation system 3056.

FIG. 68 illustrates an example braid 108 that can be made using the braiding machine 100 with the braiding assembly 3002. In at least some embodiments, the braid 108 has two non-flat sections 3132 and 3134 and a flat section 3136 therebetween. The braid 108 can be braided similarly to the braid 500, as explained FIGS. 36 and 41.

In at least some embodiments, the non-flat sections 3132 and 3134 are configured to be out-of-round or cylindrical. In other embodiments, the non-flat sections 3132 and 3134 are round sections. A flat or tape section 3136 is positioned between the two non-flat sections 3132 and 3134. The first and second non-flat sections 3132 and 3134 and the tape section 3136 are formed with a plurality of strands 3138 braided into a continuous braid. In at least some embodiments, there is no interruption in the braiding at the transition between the non-flat sections 3132 and 3134 and the tape section 3136. Nor is there any splicing, gluing, or other fastening between the non-flat sections 3132 and 3134 and the tape section 3136.

The strands 3138 are braided using a 1-over-1 configuration such that the strands 3138 in the non-flat sections 3132 and 3134 follow a generally helical or otherwise spiral path for a full 360°. When the strands 3138 transition to the tape section 3136, the strands 3138 in the braid 108 follow a helical or otherwise spiral path over an arc that is less than 360°. As they are being braided, the strands 3138 in the tape section 3136 reverse direction, relative to the width of the braid, as they reach each end of the arc. In the illustrated embodiment, the surgical braid 108 as illustrated in FIG. 68 does not have any bifurcated sections or gaps in either the non-flat sections 3132 and 3134 or the tape section 3136. Additionally, there is no core running through the non-flat sections 502 and 504 or spine running along or otherwise reinforcing the tape section 506.

Although the braid 108 is illustrated in FIG. 68 to have two non-flat sections 3132 and 3134 and one flat section 3136 therebetween, other embodiments are also possible that the braid 108 has a plurality of flat sections 3136 and a plurality of non-flat sections 3132 and 3134, which are alternately arranged each other.

Figure 69:
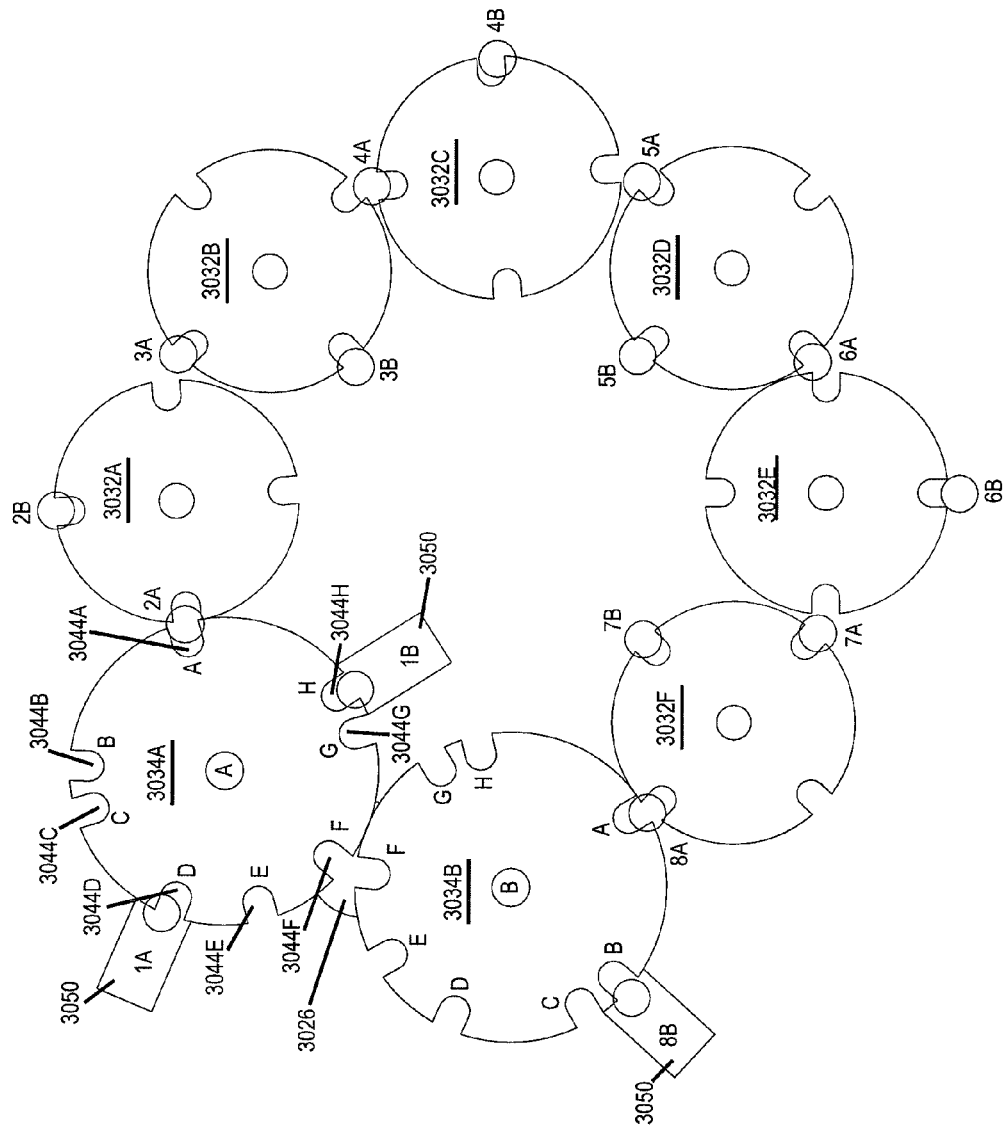
FIG. 69 illustrates example positions of horn gear assemblies of the braiding assembly, which is in a transition start position.
Figure 70:
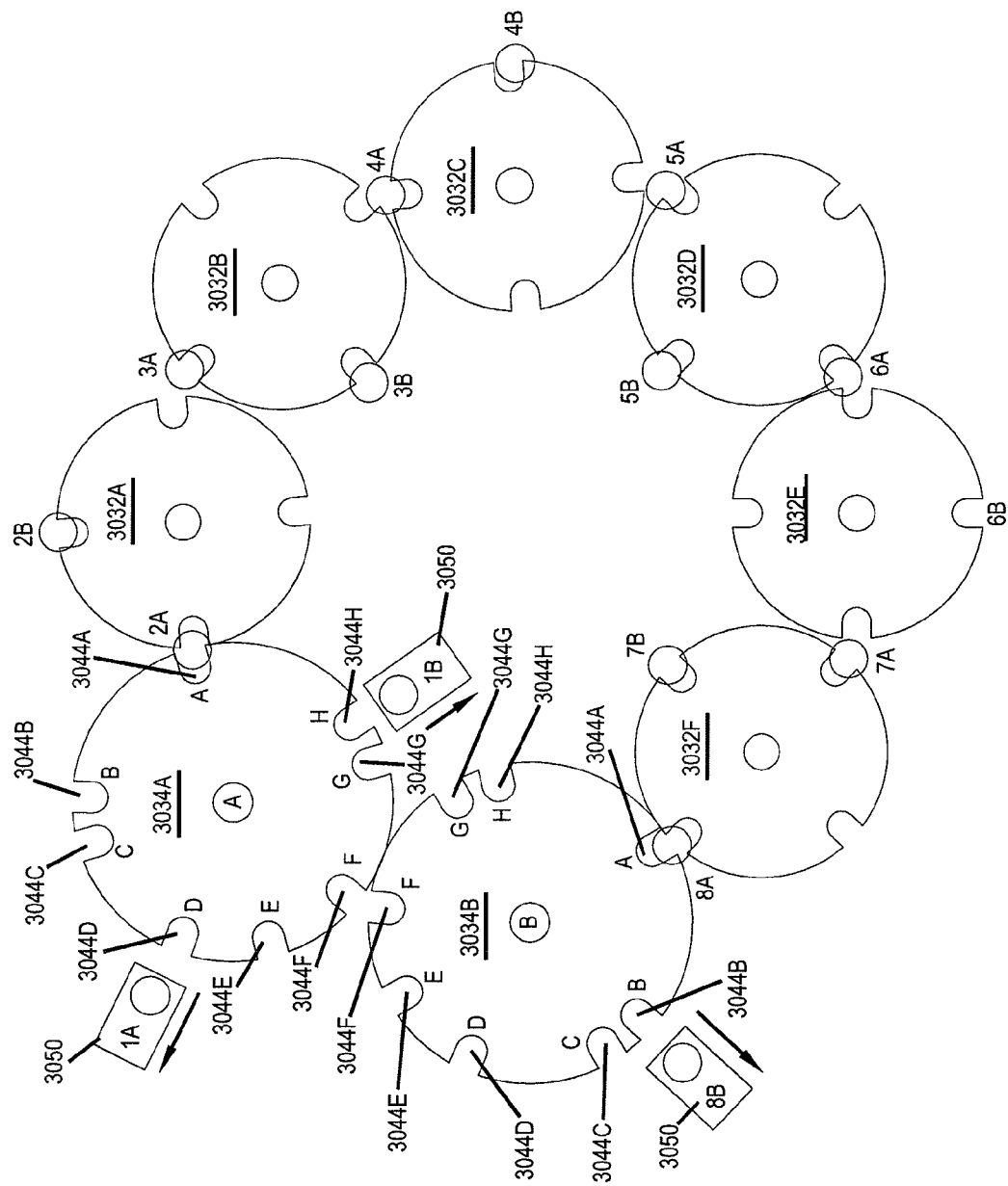
FIG. 70 illustrates example positions of the horn gear assemblies of the braiding assembly, which is in an intermediate transition position.
Figure 71:
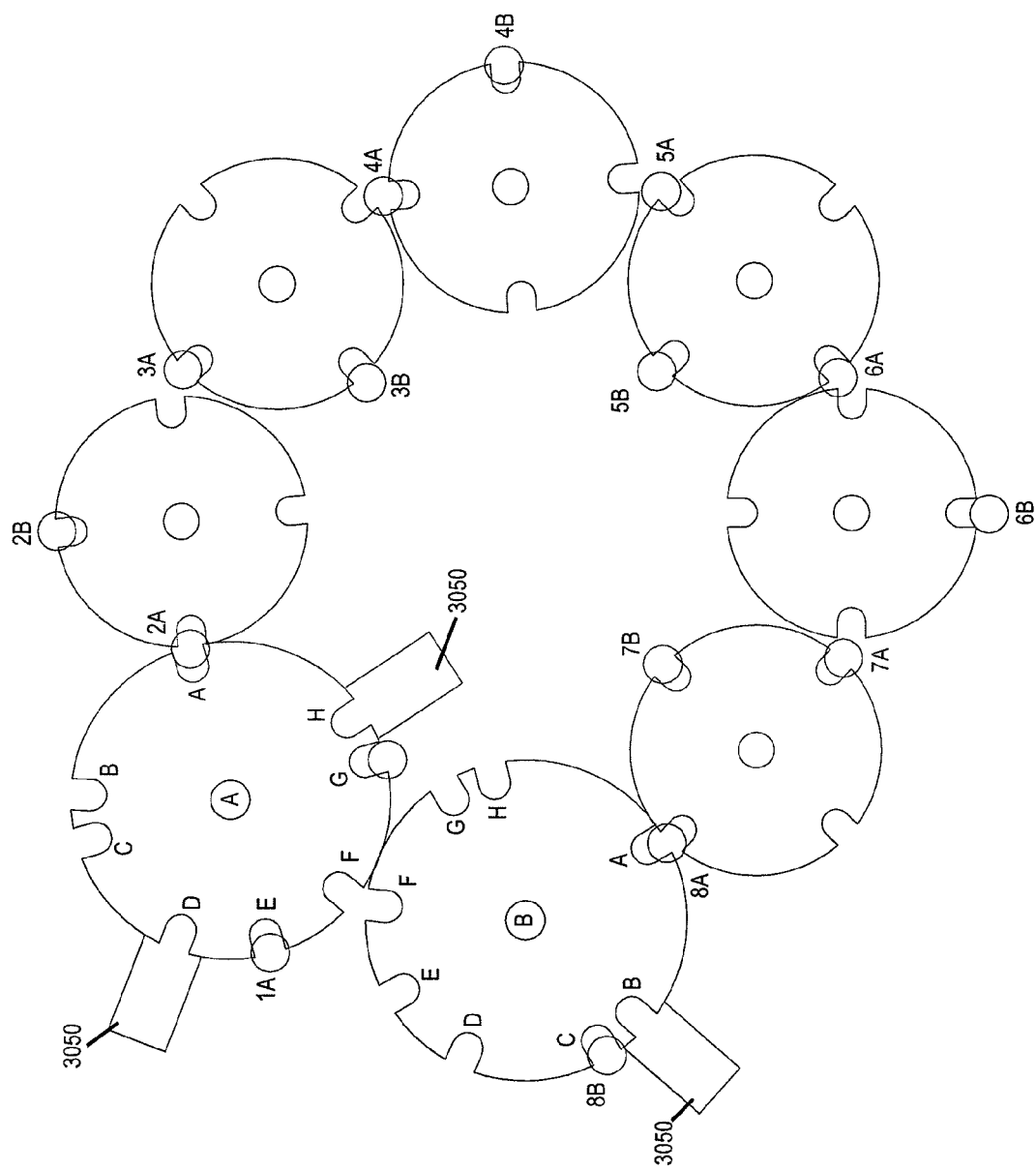
FIG. 71 illustrates example positions of the horn gear assemblies of the braiding assembly, which is in a transition end position.

FIGS. 69-71 illustrate an example operation of the braiding assembly 3002 for transitioning between flat and non-flat sections of the braid 108, which is described in FIG. 68. In particular, FIG. 69 illustrates example positions of the horn gear assemblies 3032A-3032F and 3034A-3034B of the braiding assembly 3002, which is in a transition start position. FIG. 70 illustrates example positions of the horn gear assemblies 3032A-3032F and 3034A-3034B of the braiding assembly 3002, which is in an intermediate transition position. FIG. 71 illustrates example positions of the horn gear assemblies 3032A-3032F and 3034A-3034B of the braiding assembly 3002, which is in a transition end position. As described herein, when the braiding assembly 3002 moves from the transition start position to the transition end portion through the intermediate transition position, the braid 108 transitions from a flat section to a non-flat section. Similarly, the braid 108 can transition from a non-flat section to a flat section when the braiding assembly 3002 operates in the opposite steps (i.e., when the braiding assembly 3002 moves from the transition end position to the transition start position through the intermediate transition position). For purposes of illustration, the steps and bobbin carrier positions in FIGS. 69-71 are shown using the arrangement of the track, horn gear assemblies, and gate illustrated in FIGS. 63-66, although the steps or operations described herein can be implemented with alternative arrangements of the passive track, horn gear assemblies, and one or more gates.

The horn gear assemblies 3032A-3032F and 3034A-3034B operate in a manner similar to the horn gear assemblies 132A-132H, as illustrated in FIGS. 23-31, except for the passive horn gears 134A-134H. The eight horn gear assemblies 3032A-3032F and 3034A-3034B operate to carry bobbin carrier assemblies 1A, 1B, 2A, 2B, 3A, 3B, 4A, 4B, 5A, 5B, 6A, 6B, 7A, 7B, 8A, and 8B, which roughly correspond to the bobbin carrier assemblies 122A-122P. As described below, the horn gear assemblies also operate to selectively transfer at least one of the bobbin carrier assemblies between adjacent horn gear assemblies as the horn gear assemblies rotate. In at least some embodiments, shifts of the bobbin carrier assemblies between adjacent active horn gear assemblies occur at transition positions therebetween. The bobbin carrier assemblies can be selectively shifted between the second horn gear assemblies 3034A and 3034B through a transition mechanism, which can be configured as the gate 3026. In the depicted example of FIG. 69 in which the braiding assembly 3002 operates to braid a flat section of a braid, a first set of bobbin carrier assemblies 1A,2A, 3A, 4A, 5A, 6A, 7A, and 8A moves along one of the clockwise path 3116 and the counterclockwise path 3118, and a second set of bobbin carrier assemblies 1B, 2B, 3B, 4B, 5B, 6B, 7B, and 8B moves along the other of the clockwise path 3116 and the counterclockwise path 3118. In the depicted example of FIG. 71 in which the braiding assembly 3002 operates to braid a non-flat section of a braid, the first set of bobbin carrier assemblies 1A,2A, 3A, 4A, 5A, 6A, 7A, and 8A moves along one of the clockwise path 3112 and the counterclockwise path 3114, and the second set of bobbin carrier assemblies 1B, 2B, 3B, 4B, 5B, 6B, 7B, and 8B moves along the other of the clockwise path 3112 and the counterclockwise path 3114.

Figure 66B:
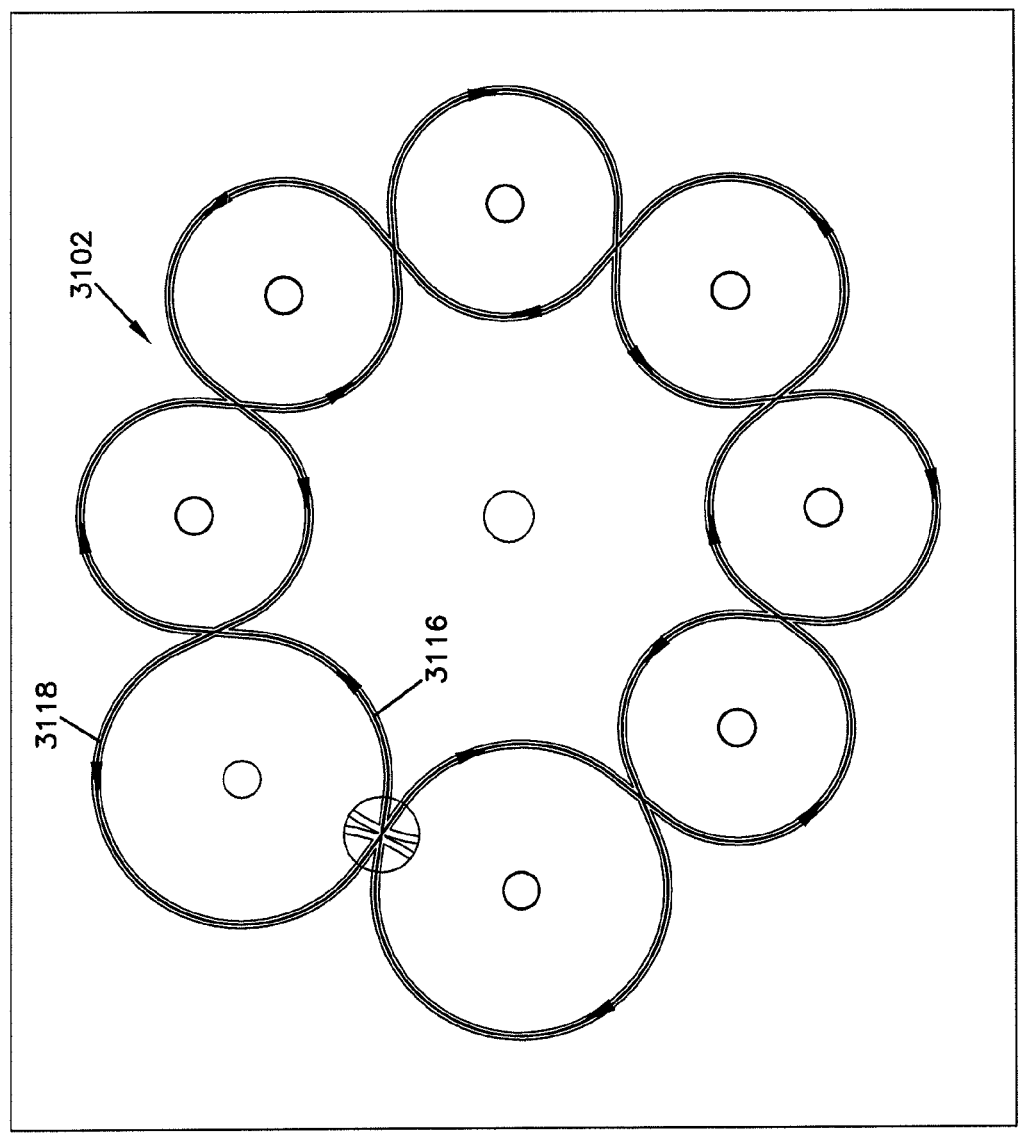
FIG. 66B illustrates an example path of bobbin carrier assemblies along the track of FIG. 66A.

Referring to FIG. 69, the braiding assembly 3002 is in a transition start position at which the braiding assembly 3002 is ready to transition from braiding a flat section 3136 to a non-flat section 3132 or 3134. Until the braiding assembly 3002 reaches the transition start position as depicted in FIG. 69, the braiding assembly 3002 operates to braid a flat section of the braid 108 with a 1-over-1 configuration. In particular, the second horn gear assemblies 3034A and 3034B are operated such that an odd number of evenly spaced slots are used to braid a flat section of the braid 108. In at least some embodiments, five slots 3044A, 3044B, 3044D, 3044F, and 3044H, which are evenly spaced apart in about 72 degree increments, are selected for a flat section braiding, although alternative embodiment can have an angular spacing other than 72 degrees. Further, the gate 3026 is closed between the second horn gear assemblies 3034A and 3034B for braiding a flat section of the braid 108. The horn gear assemblies operate to carry the eight horn gear assemblies along the clockwise path 3116 and the counterclockwise path 3118 of the track 3102 (FIGS. 66A and 66B). The horn gear assemblies 3032A-3032F and 3034A-3034B are configured to have a speed profile that matches the four slots 3040A-3040D of the first horn gear assemblies 3032A-3032F and the five slots 3044A, 3044B, 3044D, 3044F, and 3044H of the second horn gear assemblies 3034A and 3034B between two adjacent ones of the first and second horn gear assemblies 3032A-3032F and 3034A-3034B.

To transition from a flat section braiding to a non-flat section braiding, the braiding assembly 3002 is paused in the transition start position, as illustrated in FIG. 69. Once the braiding assembly 3002 is in the transition start position, the gate 3026 between the second horn gear assemblies 3034A and 3034B is opened. Further, the bobbin carrier assemblies 1A, 1B, and 8B are retracted from the associated second horn gear assemblies 3034A and 3034B, as illustrated in FIG. 70. In some embodiments, the retraction mechanisms 3050 (FIG. 72) are used to retract the bobbin carrier assemblies 1A, 1B, and 8B, as illustrated herein.

Referring to FIG. 70, the bobbin carrier assemblies 1A and 1B are retracted from the associated slots 3044D and 3044H of the second horn gear assembly 3034A, and the bobbin carrier assembly 8B is retracted from the associated slot 3044B of the second horn gear assembly 3034B, such that the braiding assembly 3002 is in an intermediate transition position. In the intermediate transition position, the bobbin carrier assemblies 1A, 1B and 8B, which have been retracted, are clear of the horn gear assemblies when the horn gear assemblies rotate. In at least some embodiments, the retraction mechanism 3050 (FIG. 72) is used to mechanically retract the bobbin carrier assemblies 1A, 1B and 8B from the associated slots of the second horn gear assemblies 3034A and 3034B. An example of the retraction mechanism 3050 is illustrated and described with reference to FIG. 72.

Once the braiding assembly 3002 is in the intermediate transition position (i.e., the bobbin carrier assemblies 1A, 1B, and 8B are retracted from the associated second horn gear assemblies 3034A and 3034B), the horn gear assemblies 3032A-3032F and 3034A-3034B rotate such that the slot 3044C of the second horn gear assembly 3032B is aligned with the bobbin carrier assembly 8B. In the depicted example, the horn gear assemblies 3032A-3032F and 3034A-3034B rotate about 18 degrees, respectively, such that the second horn gear assembly 3034B rotates about 18 degrees in a counterclockwise direction, although alternative embodiment can have an angular movement other than 18 degrees. Then, the bobbin carrier assembly 8B moves toward the horn gear assembly 3034B so as to engage the slot 3044C of the second horn gear assembly 3034B. The bobbin carrier assembly 8B switches from the slot 3044B to the slot 3044C of the second horn gear assembly 3034B. The retraction mechanism 3050 can be used to insert the bobbin carrier assembly 8B into the slot 3044C of the second horn gear assembly 3034B.

Once the horn gear assemblies 3032A-3032F and 3034A-3034B rotate such that the bobbin carrier assembly 8B is switched from the slot 3044B to the slot 3044C of the second horn gear assembly 3032B, the horn gear assemblies 3032A-3032F and 3034A-3034B rotate in the opposite direction such that the slot 3044G of the second horn gear assembly 3034A is aligned with the bobbin carrier assembly 1B. In the depicted example, the horn gear assemblies 3032A-3032F and 3034A-3034B rotate 36 about degrees, respectively, in the opposite direction such that the second horn gear assembly 3034A rotates about 36 degrees in a counterclockwise direction, although alternative embodiment can have an angular movement other than 36 degrees. Then, the bobbin carrier assembly 1B moves toward the horn gear assembly 3034A so as to engage the slot 3044G of the second horn gear assembly 3034A. Therefore, the bobbin carrier assembly 1B switches from the slot 3044H to the slot 3044G of the second horn gear assembly 3034A. Similarly, the retraction mechanism 3050 can be used to insert the bobbin carrier assembly 1B into the slot 3044G of the second horn gear assembly 3034A.

Once the horn gear assemblies 3032A-3032F and 3034A-3034B rotate such that the bobbin carrier assembly 1B is switched from the slot 3044H to the slot 3044G of the second horn gear assembly 3032A, the horn gear assemblies 3032A-3032F and 3034A-3034B rotate such that the slot 3044E of the second horn gear assembly 3034A is aligned with the bobbin carrier assembly 1A. In the depicted example, the horn gear assemblies 3032A-3032F and 3034A-3034B rotate about 54 degrees, respectively, in the direction opposite to the previous rotation such that the second horn gear assembly 3034A rotates about 18 degrees in a clockwise direction, although alternative embodiment can have an angular movement other than 54 or 18 degrees, respectively. Then, the bobbin carrier assembly 1A moves toward the horn gear assembly 3034A so as to engage the slot 3044E of the second horn gear assembly 3034A. Therefore, the bobbin carrier assembly 1A switches from the slot 3044D to the slot 3044E of the second horn gear assembly 3034A. Similarly, the retraction mechanism 3050 can be used to insert the bobbin carrier assembly 1A into the slot 3044E of the second horn gear assembly 3034A. The final positions of the bobbin carrier assemblies relative to the horn gear assemblies are illustrated in FIG. 71.

Referring to FIG. 71, the horn gear assemblies 3032A-3032F and 3034A-3034B of the braiding assembly 3002 is in a transition end position. Beginning from the transition end position, the second horn gear assemblies 3034A and 3034B are operated such that an even number of evenly spaced slots are used to braid a non-flat section of the braid 108. In at least some embodiments, four slots 3044A, 3044C, 3044E, and 3044G, which are evenly spaced apart in about 90 degree increments, are selected for a non-flat section braiding, although alternative embodiment can have an angular spacing other than 90 degrees. Further, the gate 3026 remains open between the second horn gear assemblies 3034A and 3034B for braiding a non-flat section of the braid 108. Therefore, the horn gear assemblies operate to carry the eight horn gear assemblies along the clockwise path 3112 and the counterclockwise path 3114 of the track 3102 (FIG. 65). The horn gear assemblies 3032A-3032F and 3034A-3034B also changes to have a speed profile that matches the four slots 3040A-3040D of the first horn gear assemblies 3032A-3032F and the four slots 3044A, 3044C, 3044E, and 3044G of the second horn gear assemblies 3034A and 3034B between two adjacent ones of the first and second horn gear assemblies 3032A-3032F and 3034A-3034B.

In other embodiments, the steps performed from the transition start position to the transition end position can change as necessary to the extent that the bobbin carrier assemblies engaged in one or more of an odd number of evenly spaced slots of the second horn gear assemblies 3034A and 3034B have shifted to one or more of an even number of evenly spaced slots of the same second horn gear assemblies 3034A and 3034B.

Although it is described that all of the horn gear assemblies 3032A-3032F and 3034A-3034B are operated to rotate together in the transition stage, it is possible to permit only some of the horn gear assemblies 3032A-3032F and 3034A-3034B to rotate as necessary. In the embodiments where the first horn gear assemblies 3032A-3032F are operated together by a single motor and the second horn gear assemblies 3034A-3034B are actuated together by another single motor, the second horn gear assemblies 3034A-3034B can be operated to rotate together, but independently from the first horn gear assemblies 3032A-3032F.

The steps described above with reference to FIGS. 69-71 are reversed to transition from braiding a non-flat section to braiding a flat section of the braid 108.

FIGS. 72-78 schematically illustrate example configuration of a retraction mechanism 3050. The retraction mechanism 3050 is configured to enable a bobbin carrier assembly 122 to switch slots of the second horn gear assembly 3034. For brevity purposes, the bobbin carrier assembly 122 is only partially illustrated to clearly show configuration and operation of the retraction mechanism 3050.

Figure 72:
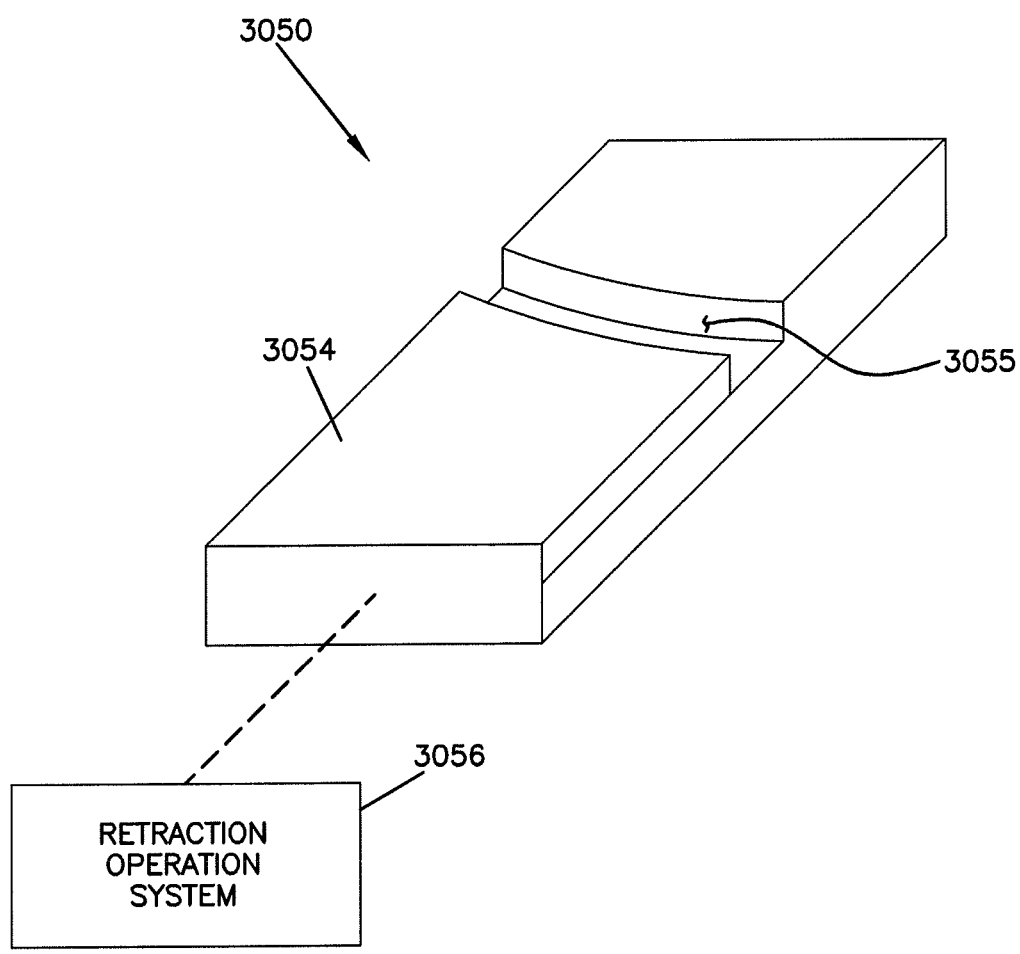
FIG. 72 schematically illustrates an example retraction mechanism.

FIG. 72 is a schematic perspective view of an example retraction mechanism 3050. The retraction mechanism 3050 can include a retraction body 3054 defining a track path 3055. The track path 3055 is configured to receive the carrier guide 176 (e.g., the keels 182A and 182B) of the bobbin carrier assembly 122 that moves along the track 3102 of the braiding track plate 3020. In some embodiments, the track path 3055 has the same dimensions (such as width and curvature) as those of the track 3102 to which the retraction mechanism 3050 is arranged adjacent. In the illustrated example, as the retraction mechanism 3050 is arranged with the second sub-tracks 3110A-3110B, the track path 3055 has the same width and curvature as the groove of the second sub-tracks 3110A-3110B. The track path 3055 is formed in the retraction body 3054 to be aligned with the track 3102 of the braiding track plate 3020 when the retraction mechanism 3050 is in a non-retracted position (FIG. 73). In the non-retracted position, the track path 3055 of the retraction mechanism 3050 functions as a portion of the track 3102 so that the bobbin carrier assemblies continuously moves along the track path 3055 of the retraction mechanism 3050 and the remainder of the track 3102. When the retraction mechanism 3050 is in a retracted position (FIG. 74), the track path 3055 operates to hold the carrier guide 176 of the bobbin carrier assembly 122 out of the track 3102. As described herein, the retraction mechanism 3050 is actuated by the retraction operation system 3056 that includes either a solenoid or a motor.

Figure 73A:
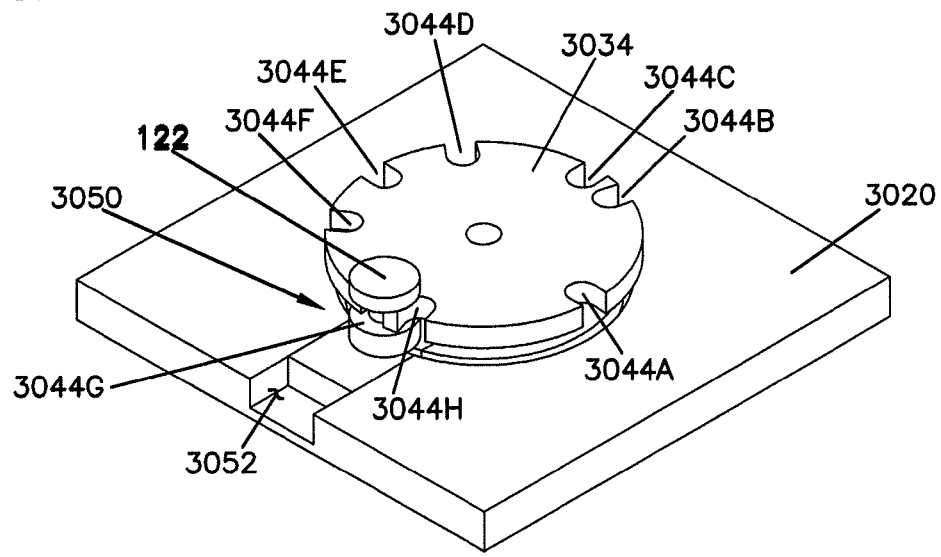
FIG. 73A schematically illustrates the retraction mechanism in a non-retracted position.
Figure 73B:
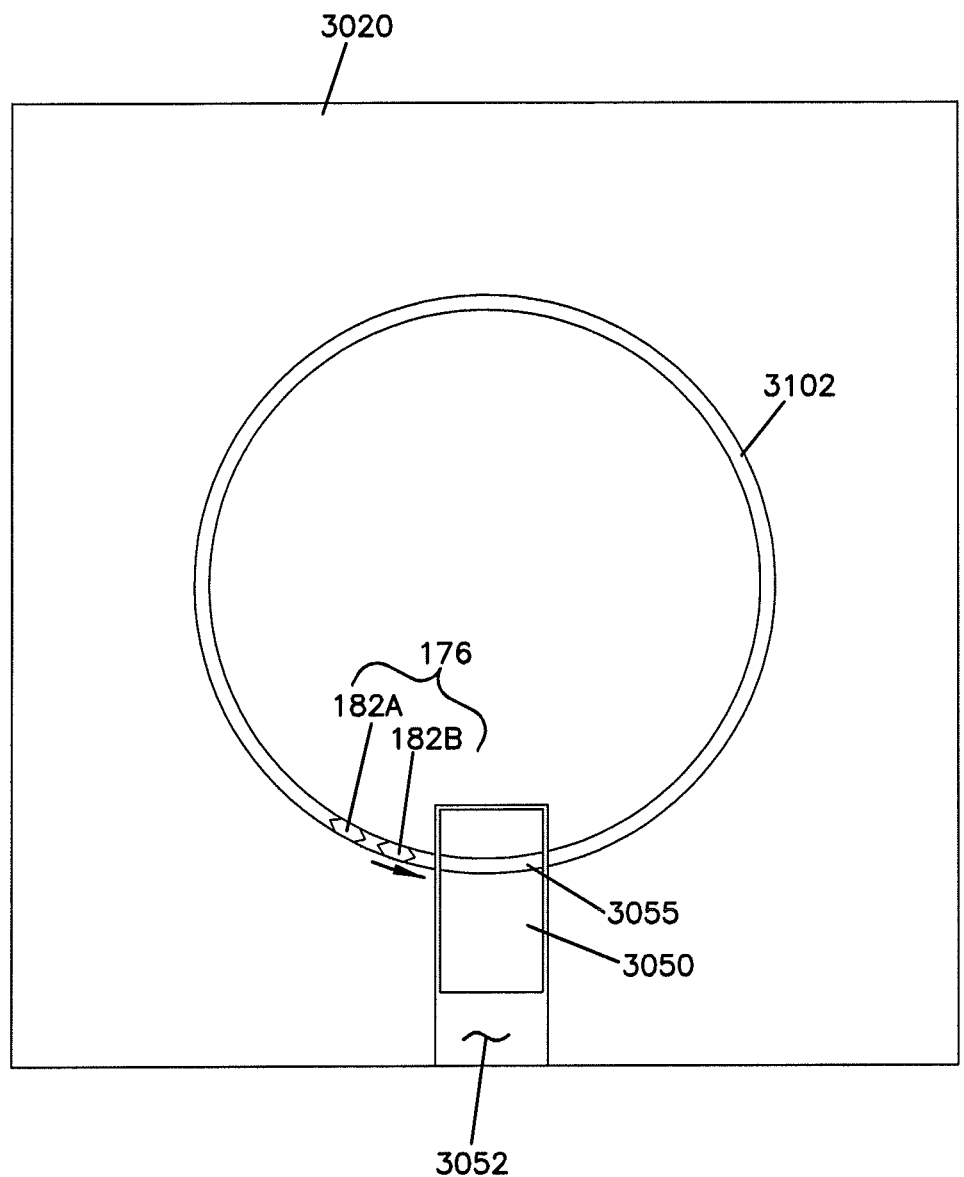
FIG. 73B schematically illustrates an example track with the retraction mechanism in the non-retracted position.
Figure 73C:
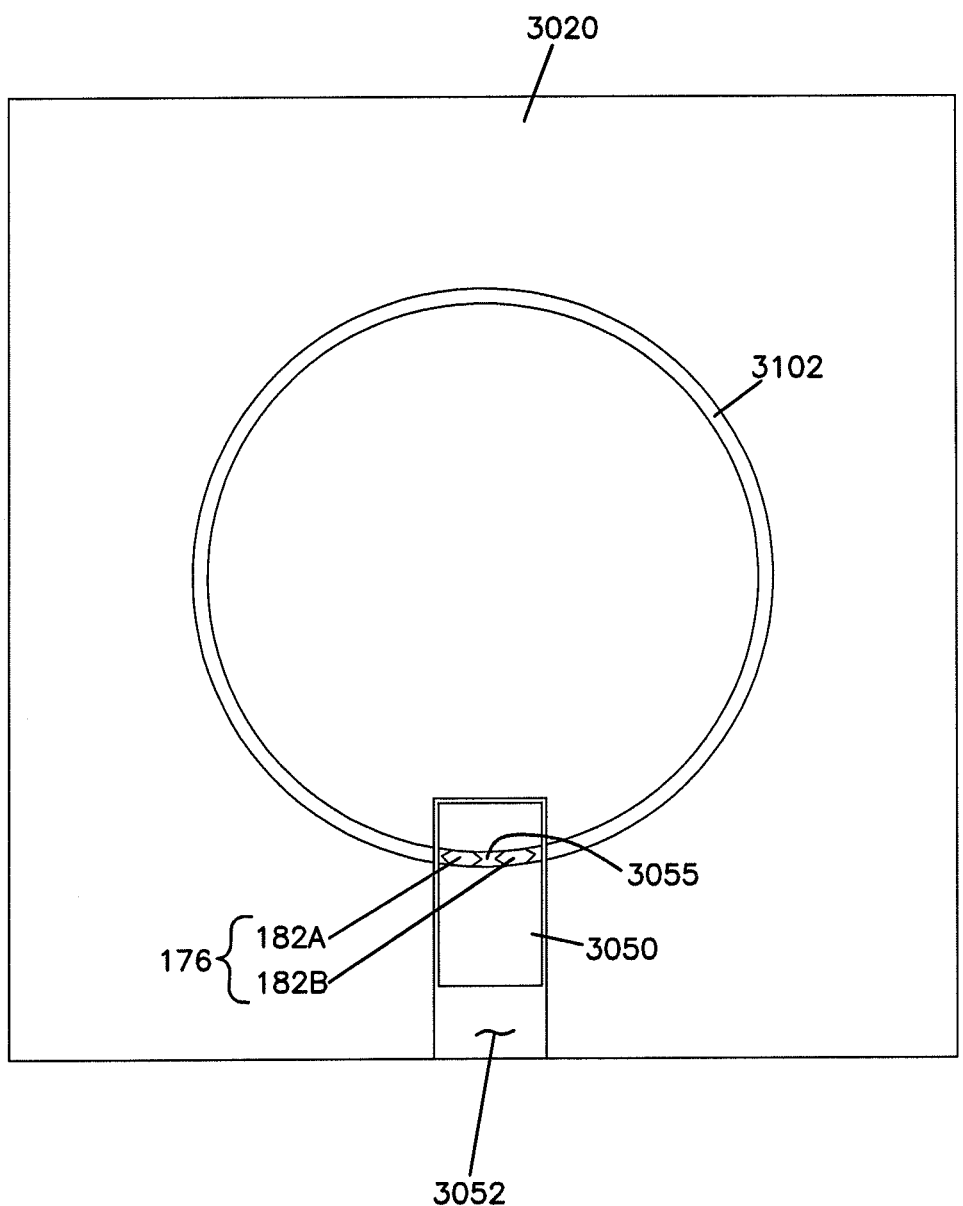
FIG. 73C schematically illustrates the track with the retraction mechanism in the non-retracted position.

FIGS. 73A-73C schematically illustrate an example operation of the retraction mechanism 3050. In FIG. 73A, the retraction mechanism 3050 is in a non-retracted position. In the depicted example of FIG. 73A, the bobbin carrier assembly 122 is inserted in the slot 3044G of the horn gear assembly 3034. As illustrated in FIG. 73B, the bobbin carrier assembly 122 is guided by the associated horn gear assembly 3034 to move along the track 3102 toward the track path 3055 of the retraction mechanism 3050. In particular, the carrier guide 176 (such as the keels 182A and 182B) is guided by the track 3102 toward the track path 3055 that is aligned with the track 3102. Referring to FIG. 73C, the carrier guide 176 of the bobbin carrier assembly 122 slides into the track path 3055 of the retraction mechanism 3050 so that the bobbin carrier assembly 122 is arranged as illustrated in FIG. 73A.

The retraction mechanism 3050 is configured to selectively retract the bobbin carrier assembly 122 from the associated horn gear assembly 3034 so that the retracted bobbin carrier assembly 122 is clear of the spinning horn gear assembly 3034. In at least some embodiments, the retraction mechanism 3050 is configured to slidably move in a radial direction with respect to the horn gear assembly 3034. In at least some embodiments, the track plate 3020 includes a guiding mechanism 3052 (e.g., a groove or channel) configured to guide movement of the retraction mechanism 3050.

Figure 74A:
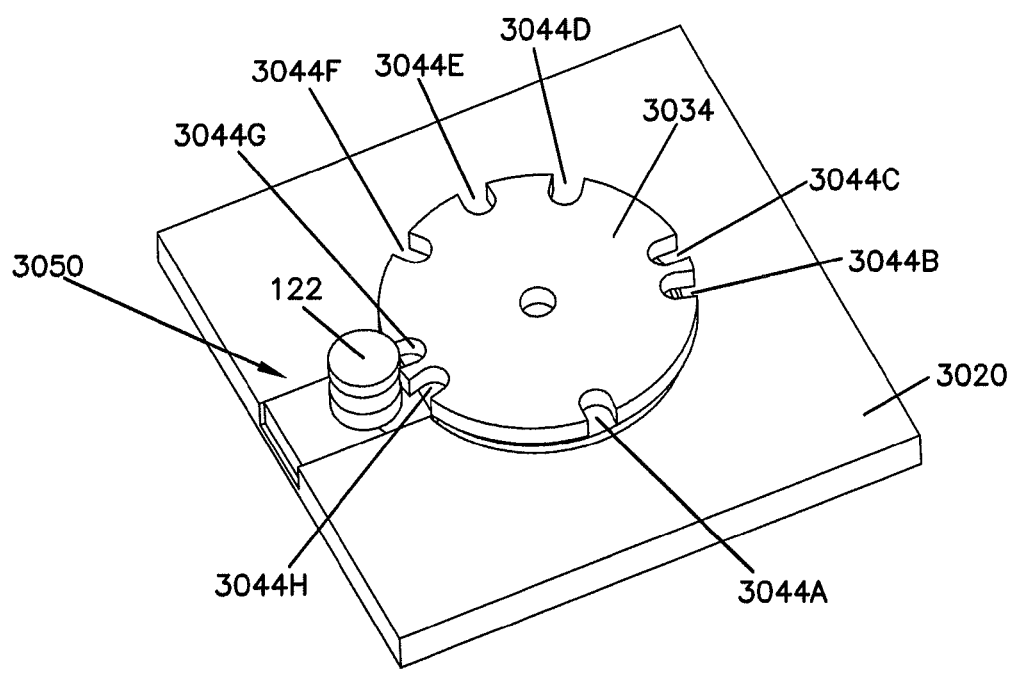
FIGS. 74A, 74B, and 74C schematically illustrate the retraction mechanism of FIGS. 73A-73C when the retraction mechanism retracts a bobbin carrier assembly from a slot of a horn gear assembly.
Figure 74B:
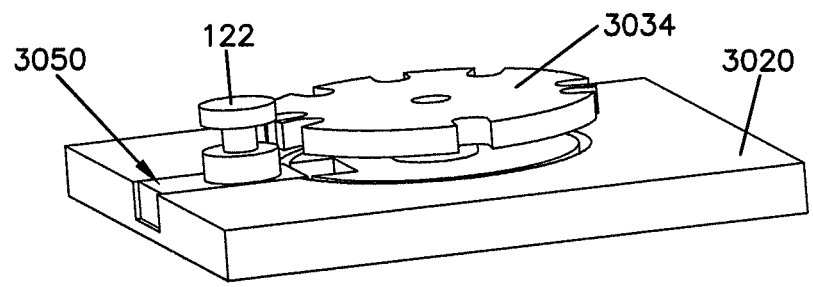
Figure 74C:
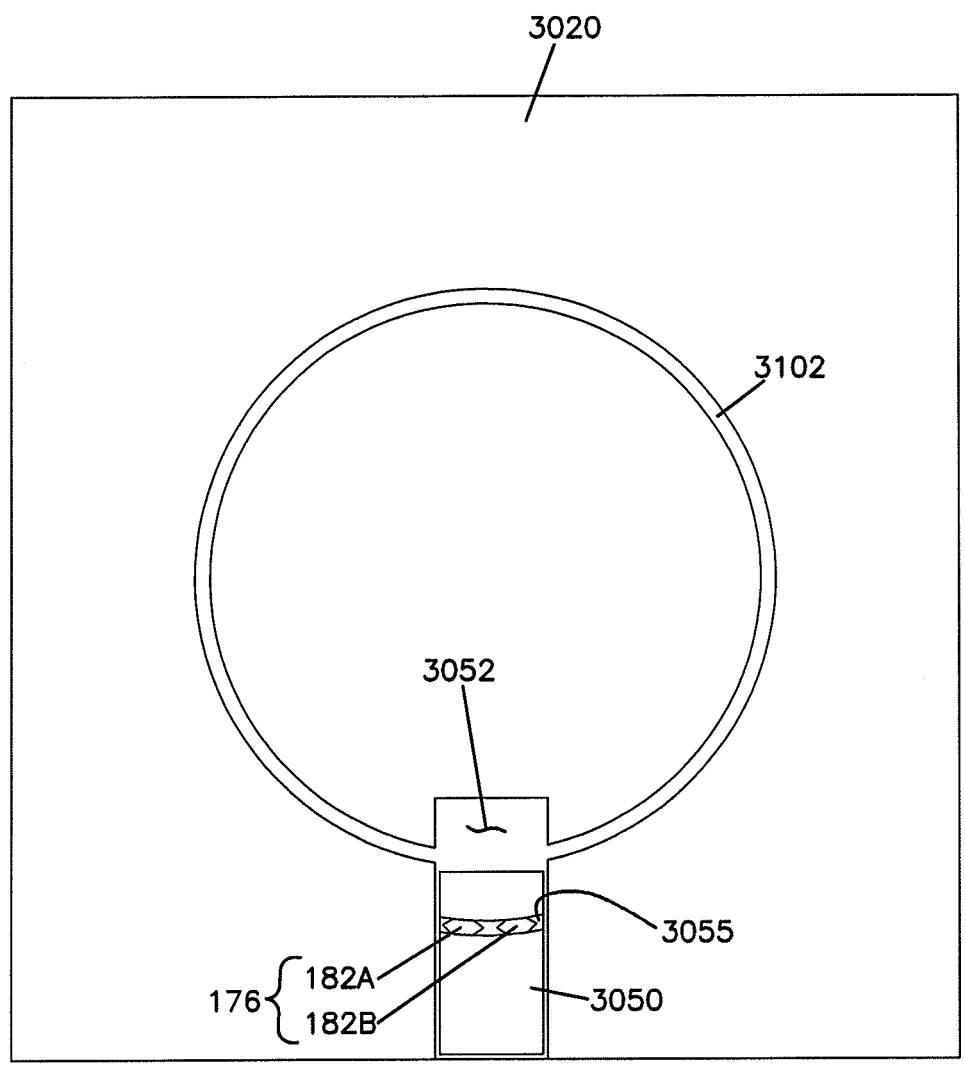

FIGS. 74A-74C schematically illustrate the retraction mechanism 3050 of FIGS. 73A-73C when the retraction mechanism 3050 is in a retracted position, in which the retraction mechanism 3050 retracts the bobbin carrier assembly 122 from the slot 3044G of the horn gear assembly 3034. In this position, the horn gear assembly 3034 can freely rotate and the bobbin carrier assembly 122 does not interfere with the rotation of the horn gear assembly 3034. For example, when the carrier guide 176 (such as the keels 182A and 182B) moves into the track path 3055 of the retraction mechanism 3050, the retraction mechanism 3050 is displaced radially outwardly by the retraction operation system 3056 such that the retracted bobbin carrier assembly 122 is clear of the rotating horn gear assembly 3034. FIG. 74C illustrates the position of the carrier guide 176 of the bobbin carrier assembly 122 relative to the retraction mechanism 3050 and the track 3102.

Figure 75:
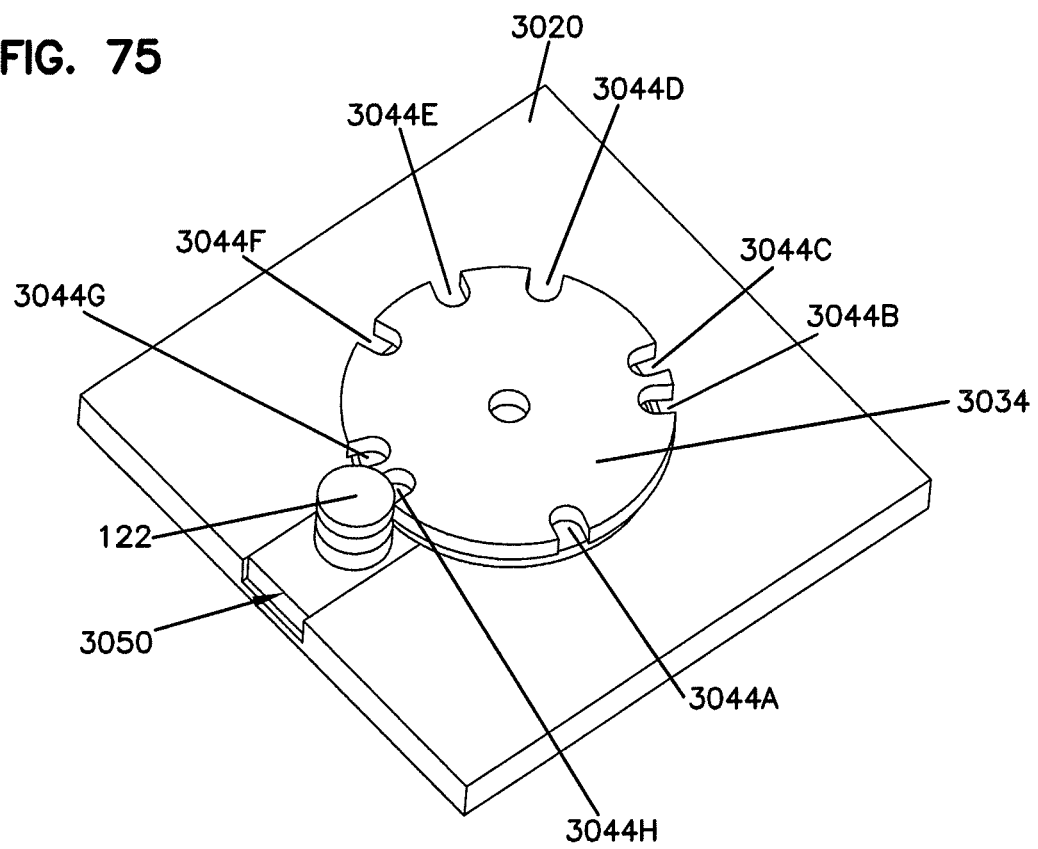
FIG. 75 schematically illustrates the retraction mechanism of FIG. 73A-73C when the horn gear assembly rotates at a predetermined amount of rotation.

FIG. 75 schematically illustrates the retraction mechanism 3050 of FIGS. 73A-73C when the horn gear assembly 3034 rotates at a predetermined amount of rotation. In the depicted example, the horn gear assembly 3034 rotates about 18 degrees clockwise so that the slot 3044H is aligned with the bobbin carrier assembly 122, although alternative embodiment can have an angular movement other than 18 degrees.

Figure 76A:
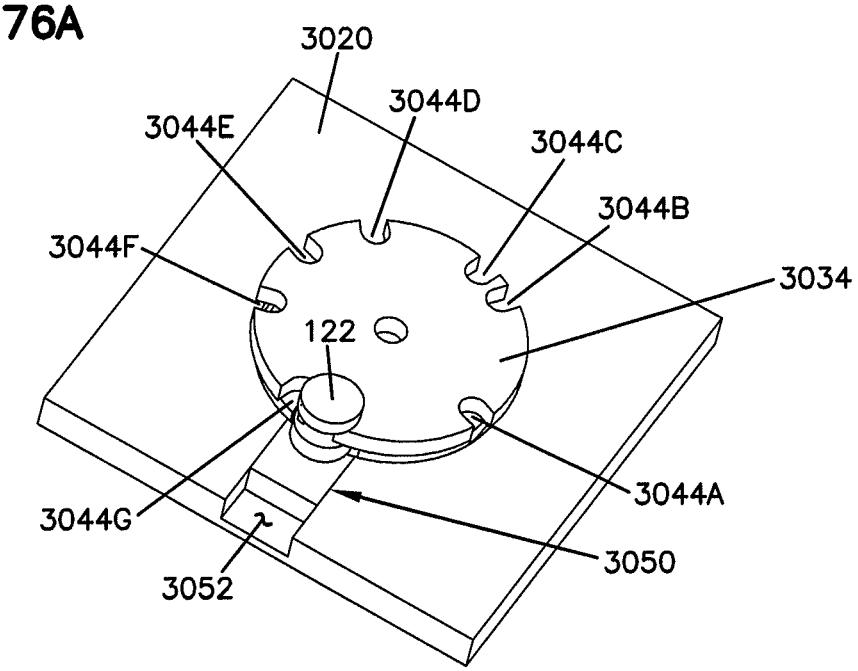
FIG. 76A schematically illustrates the retraction mechanism of FIG. 73A-73C when the retraction mechanism operates to insert the bobbin carrier assembly to the slot of the horn gear assembly.
Figure 76B:
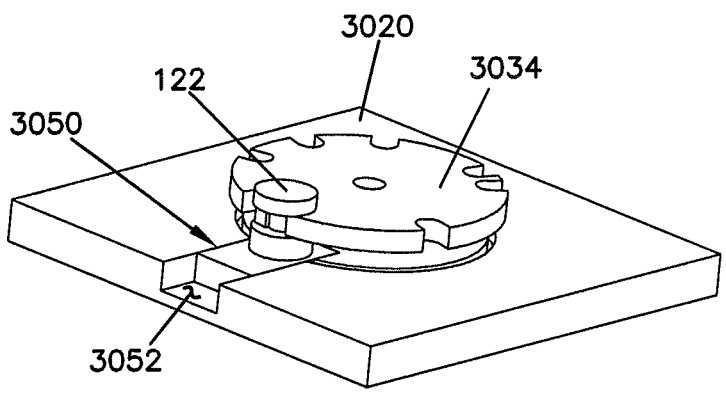
FIG. 76B schematically illustrate the retraction mechanism of FIG. 76A.

FIGS. 76A and 76B schematically illustrate the retraction mechanism 3050 of FIGS. 73A-73C when the retraction mechanism 3050 operates to insert the bobbin carrier assembly 122 to the slot 3044H of the horn gear assembly 3034. In this position, the retraction mechanism 3050 moves toward the horn gear assembly 3034 to carry the bobbin carrier assembly 122 into the slot 3044H when the horn gear assembly 3034 rotates to align the slot 3044H with the bobbin carrier assembly 122.

In at least some embodiments, the braiding assembly 3002 can include one retraction mechanism 3050 configured to selectively retract and insert one or more bobbin carrier assemblies. In other embodiments, the braiding assembly 3002 can include a plurality of retraction mechanisms 3050 for selectively retract and insert one or more bobbin carrier assemblies. For example, there may be four retraction mechanisms 3050 arranged adjacent the second horn gear assemblies 3034A and 3034B.

As illustrated in FIG. 67, the retraction mechanism 3050 can be operated by a retraction operation system 3056. In some embodiments, the retraction operation system 3056 can include one or more solenoids of any type, such as electromechanical solenoids, rotary solenoids, rotary voice coils, pneumatic solenoid valves, and hydraulic solenoid valves. In other embodiments, the retraction operation system 3056 can include a pneumatic operating system. For example, the pneumatic operating system can include a pneumatic indexer, rack and pinion arrangement or a belt. In yet other embodiments, the retraction operation system 3056 can include a motor, such as a servo or stepper motor.

Figure 77:
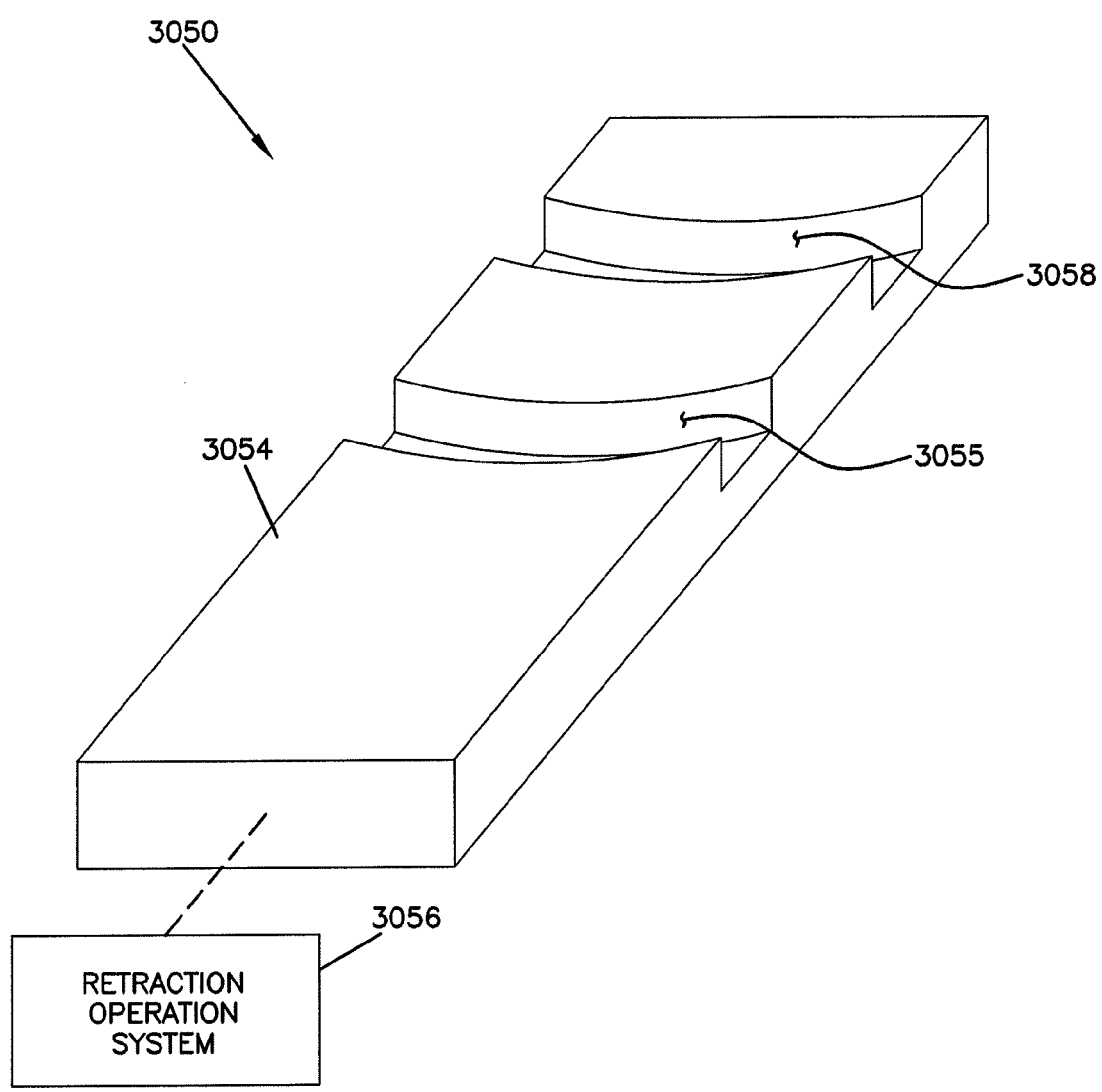
FIG. 77 is a schematic perspective view of another example retraction mechanism 3050.

FIG. 77 is a schematic perspective view of another example retraction mechanism 3050. The retraction mechanism 3050 in this example is substantially the same as the retraction mechanism 3050 as illustrated in FIG. 72 except for a secondary track path 3058. As described herein, the track path 3055 is configured to align the track 3102 of the braiding track plate 3020 when the retraction mechanism 3050 is in the non-retracted position. The secondary track path 3058 is configured to align the track 3102 of the braiding track plate 3020 when the retraction mechanism 3050 is in the retracted position. For doing so, the secondary track path 3058 can have the same dimensions (such as width and curvature) as those of the track 3102 to which the retraction mechanism 3050 is arranged adjacent. When the retraction mechanism 3050 is in the retracted position, the secondary track path 3058 enables the bobbin carrier assemblies to move along the track 3102 across the secondary track path 3058.

Figure 78A:
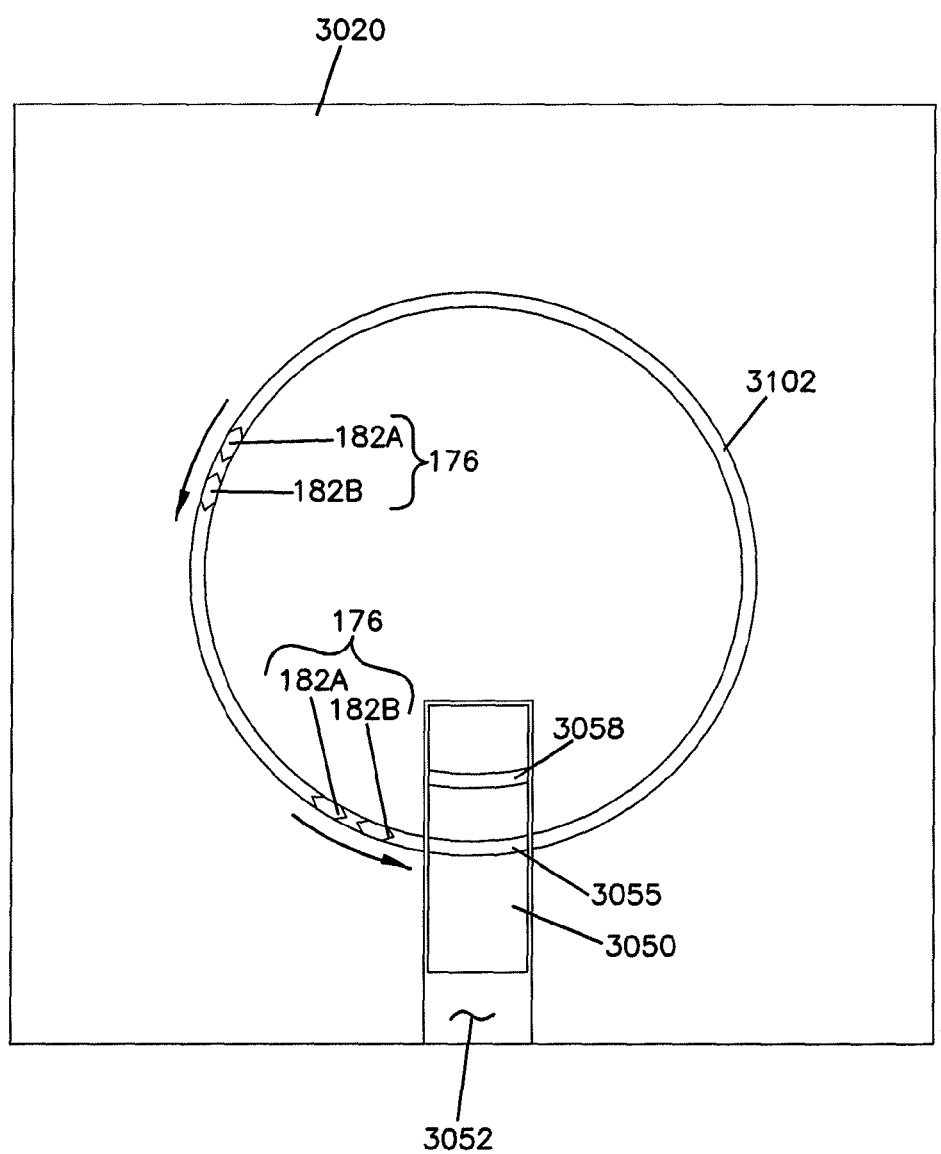
FIGS. 78A-78C schematically illustrate an example operation of the retraction mechanism 3050 of FIG. 77.
Figure 78B:
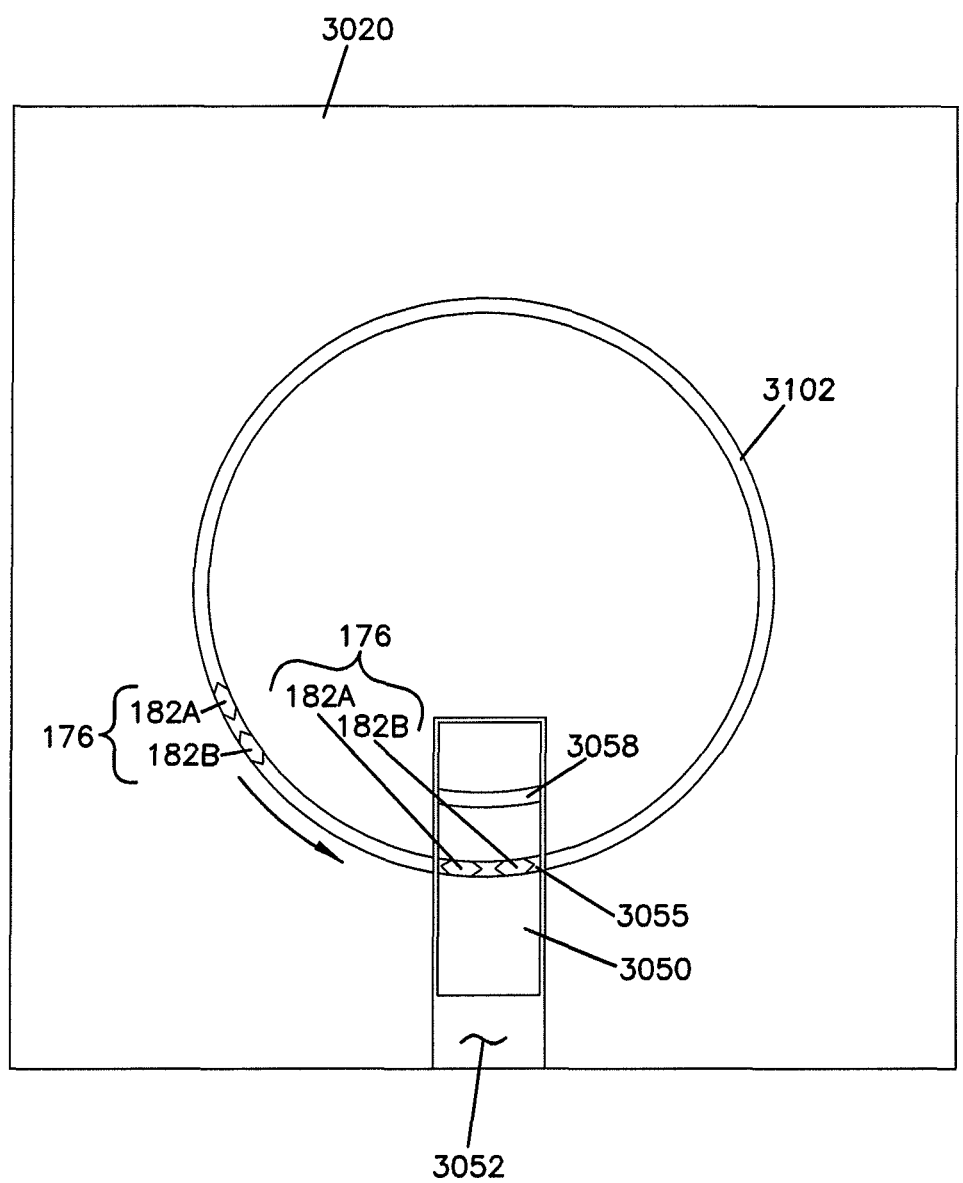
Figure 78C:
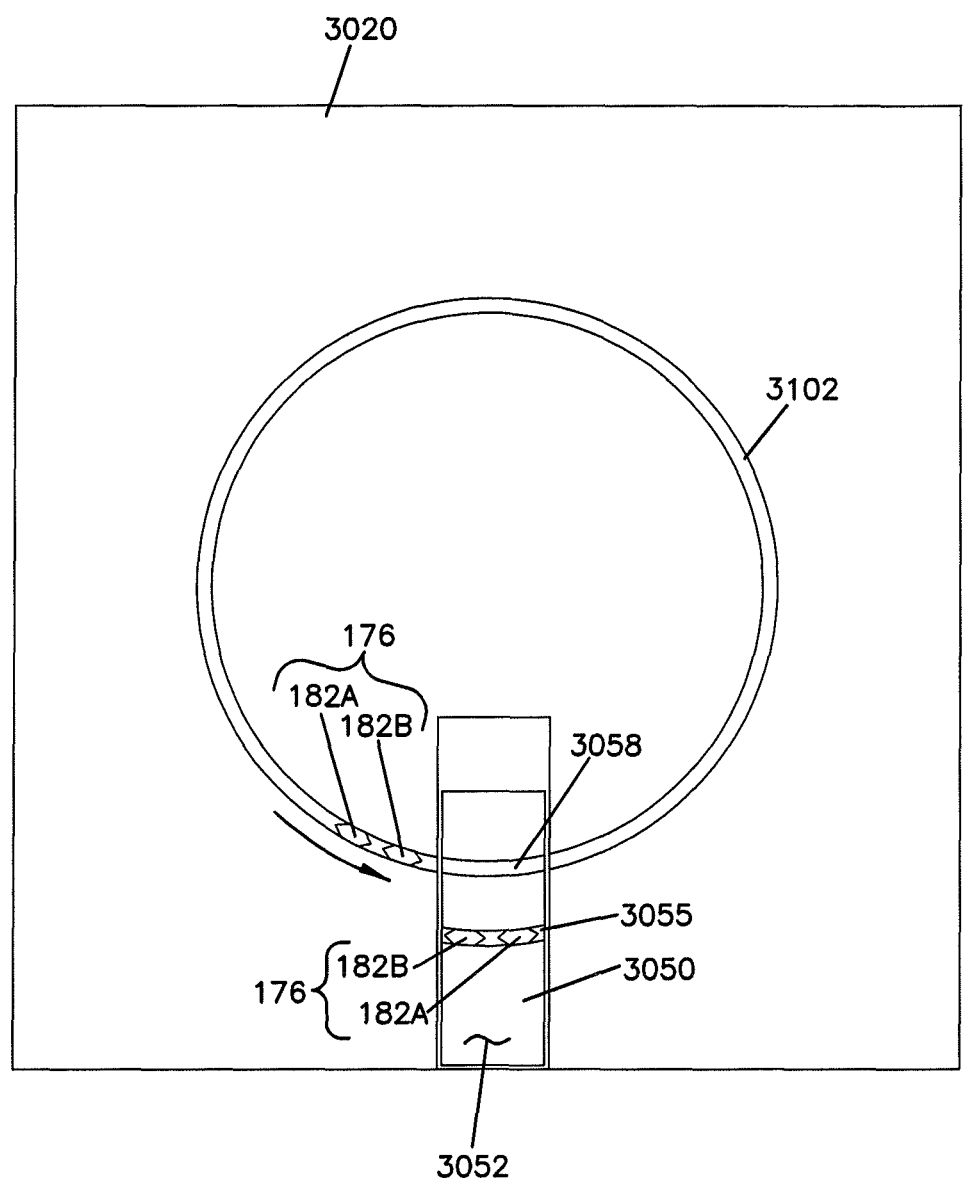

FIGS. 78A-78C schematically illustrate an example operation of the retraction mechanism 3050 of FIG. 77. Referring to FIG. 78A, the retraction mechanism 3050 is in the non-retraction position, and two bobbin carrier assemblies 122 approach the retraction mechanism 3050. In particular, two carrier guides 176 (such as the keels 182A and 182B) of the bobbin carrier assemblies 122 are guided by the track 3102 toward the track path 3055 that is aligned with the track 3102. Referring to FIG. 78B, one of the carrier guides 176 slides into the track path 3055 of the retraction mechanism 3050. Referring to FIG. 78C, the retraction mechanism 3050 is radially outwardly shifted to its retracted position, in which the secondary track path 3058 aligns the track 3102 of the braiding track plate 3020. The other carrier guide 176 of the bobbin carrier assembly 122 can slide into the secondary track path 3058 to pass the retraction mechanism 3050.

Operation of the retraction mechanism 3050 having two paths enables a bobbin carrier to be moved off the track so that another bobbin carrier can move pass it thereby changing the sequence or order of the bobbin carriers and strands as they move around the track. Changing the sequence or order of the bobbin carriers or strands while braiding a surgical braid will change the pattern of the strands forming the braids as described herein. Operations that change the sequence or order of the bobbin carriers and strands to change the pattern of the strands can be performed using the embodiments illustrated in FIGS. 63-81 as well as other embodiments including the other embodiments illustrated and describe herein and other braiders that may not be illustrated or described herein.

Figure 79A:
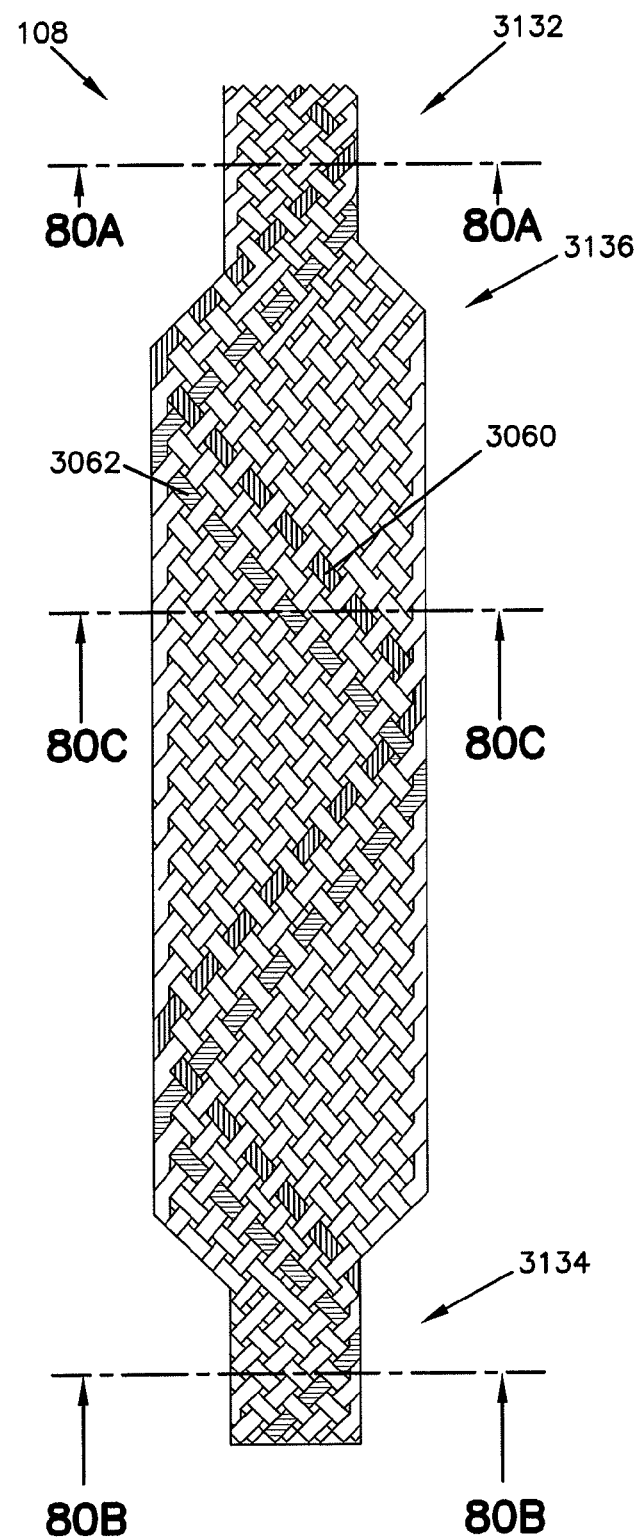
FIGS. 79A-79C illustrates an example braid that can be made using the braiding machine with the braiding assembly.
Figure 79B:
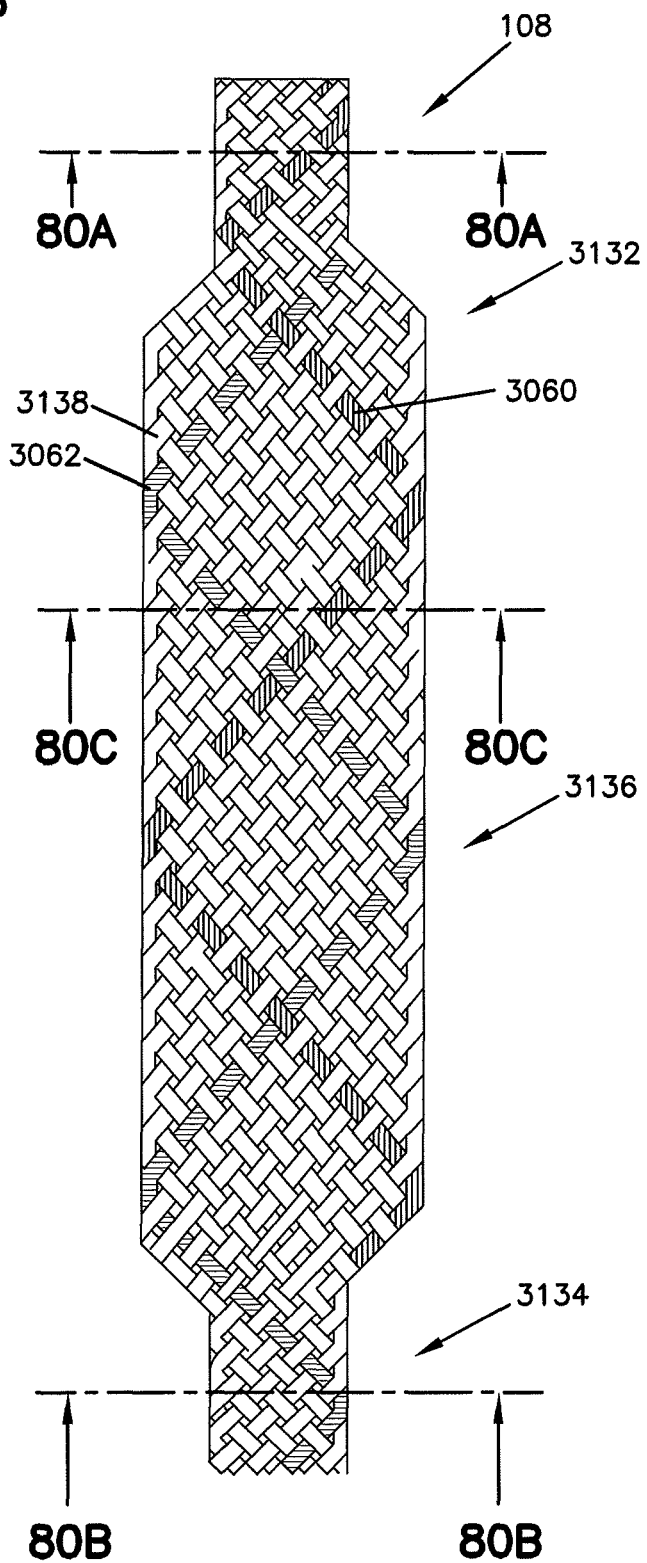
Figure 79C:
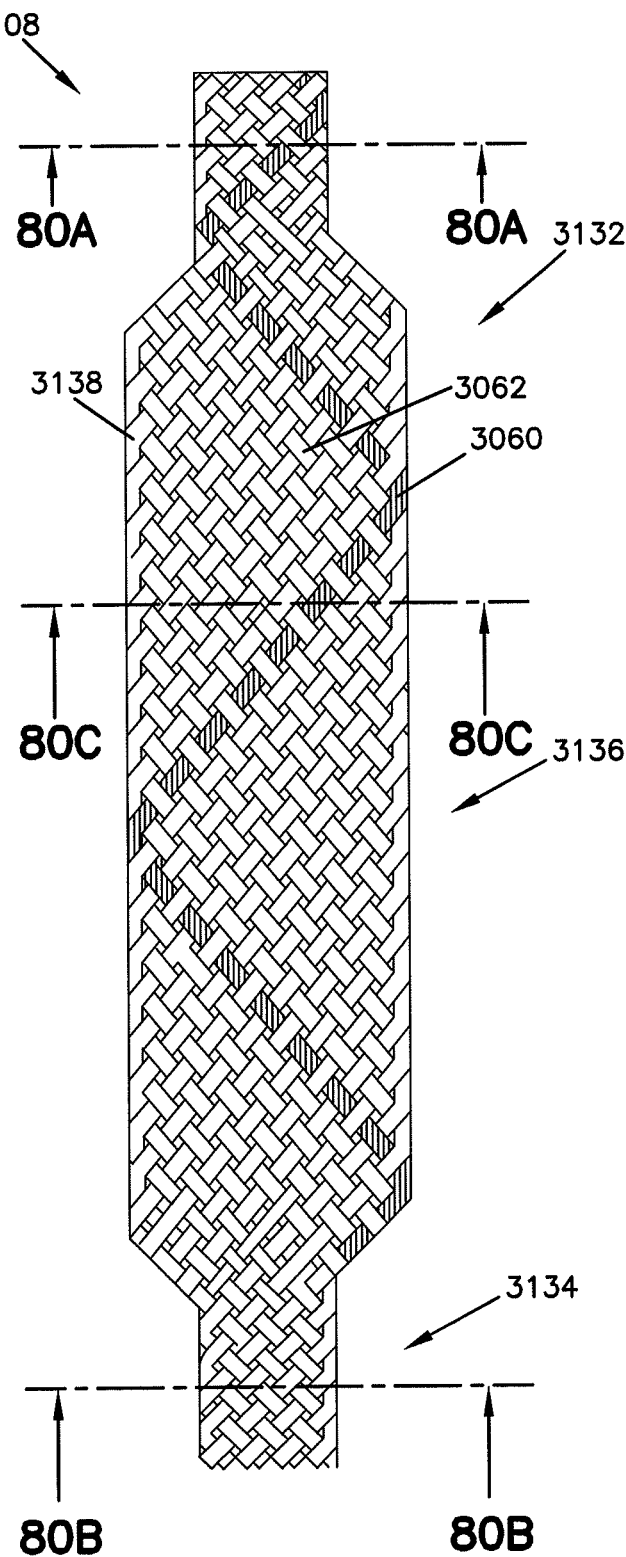

FIGS. 79A-79C illustrates an example braid 108 that can be made using the braiding machine 100 with the braiding assembly 3002. The braid 108 as illustrated in FIGS. 79A-79C is similar to the braid 108 as illustrated in FIG. 68, except for an additional strand 3060 running through the braid 108. The additional strand 3060 can also be referred to herein as a trace strand 3060.

Similarly to the braid 108 in FIG. 68, the braid 108 in this embodiment has two non-flat sections 3132 and 3134 and a flat section 3136 therebetween. The configuration of the non-flat sections 3132 and 3134 and the flat section 3136 of the braid 108 is the same as those of the braid 108 as illustrated in FIG. 68. Although the braid 108 is illustrated in FIG. 68 to have two non-flat sections 3132 and 3134 and one flat section 3136 therebetween, other embodiments are also possible that the braid 108 has a plurality of flat sections 3136 and a plurality of non-flat section 3132 and 3134, which are alternately arranged each other.

As described herein, the braid 108 as illustrated in FIG. 68 is formed of 16 strands interbraided in a 1-over-1 configuration. The trace strand 3060 as illustrated in FIGS. 79A-79C is another strand added into the 16-strand braid. As such, the braid 108 as illustrated in FIGS. 79A-79C is formed of 17 strands.

In some embodiments, the trace strand 3060 is braided into an outer wall of the first non-flat section 3132 to increase visibility of the braid 108, which can be used for medical purposes (e.g., as a surgical braid). The trace strand 3060 then runs through the flat section 3136 of the braid 108 to further add visibility of the braid 108. The trace strand 3060 forms a core 3064 (FIGS. 80A and 80B) running along the second non-flat section 3134. For example, the outer wall of the second non-flat section 3134 is braided around the core 3064, thereby forming a continuous braid. In this configuration, the core 3064 is formed with the trace strand 3060 at the second non-flat section 3134. In other embodiments, braids 108 can be formed using one or more trace strands 3060. In these example embodiments, the trace strand(s) 3060 do not require splicing, gluing or fastening between flat and non-flat sections, however these methods are possible in alternative embodiments.

Referring to FIG. 79A, the braid 108 is formed of 17 strands including a first color strand 3060 and a second color strand 3062. The first and second color strands 3060 and 3062 have different colors from the remaining strands (15 strands). For example, the first color strand 3060 can have blue and the second color strand 3062 can have black while the other strands are white. The colors of the strands can change as necessary. At the first non-flat section 3132, the first color strand 3060 is braided into an outer wall of the first non-flat section 3132, and the second color strand 3062 forms a core 3064. At the second non-flat section 3134, the first color strand 3060 forms a core 3064 and the second color strand 3062 is braided into an outer wall of the second non-flat section 3132. The first and second color strands 3060 and 3062 run through the flat section 3136 so as to be arranged in parallel. The first and second color strands 3060 and 3062 can be spaced at various manners through the flat section 3136. In the illustrated example, the first and second color strands 3060 and 3062 run in parallel with one strand therebetween. In other embodiments, the first and second color strands 3060 and 3062 are spaced with more than one strands therebetween, or arranged to about each other without a strand therebetween. To form the parallel pattern, a bobbin carrier assembly 112 supplying the first color strand 3060 and a bobbin carrier assembly supplying the second color strand 3061 are relatively positioned to travel along the track 3102 in the same direction (either clockwise or counterclockwise).

Referring to FIG. 79B, the braid 108 is formed of 17 strands including the first color strand 3060 and the second color strand 3062. At the first non-flat section 3132, the first color strand 3060 is braided into an outer wall of the first non-flat section 3132, and the second color strand 3062 forms a core 3064. At the second non-flat section 3134, the first color strand 3060 forms a core 3064 and the second color strand 3062 is braided into an outer wall of the second non-flat section 3132. The first and second color strands 3060 and 3062 run through the flat section 3136 so as to form a cross pattern. The first and second color strands 3060 and 3062 can run to cross each other in various manners through the flat section 3136. In the illustrated example, the first and second color strands 3060 and 3062 run to cross each other symmetrically. In other embodiments, other cross patterns are possible. To form the cross pattern, a bobbin carrier assembly 112 supplying the first color strand 3060 and a bobbin carrier assembly supplying the second color strand 3061 are relatively positioned to travel along the track 3102 in the opposite directions. For example, when the bobbin carrier assembly 112 holding the first color strand 3060 moves clockwise along the track 3102, the bobbin carrier assembly 112 holding the second color strand 3062 is configured to travel counterclockwise.

Referring to FIG. 79C, the braid 108 is formed of 17 strands including a single color strand 3060. The color strand 3060 has a color different from that of the other 16 strands. In other words, the second color strand 3062 has the same color as that of the remaining 15 strands. As illustrated, the color strand 3060 is braided into an outer wall of the first non-flat section 3132, runs through the non-flat section 3136, and forms a core 3064 at the second non-flat section 3134. As such, the braid 108 shown in FIG. 79C is a continuous braid having a single trace strand 3060 that transitions from the outer wall of the non-flat section to the core of the next non-flat section with the flat section therebetween.

Figure 80A:
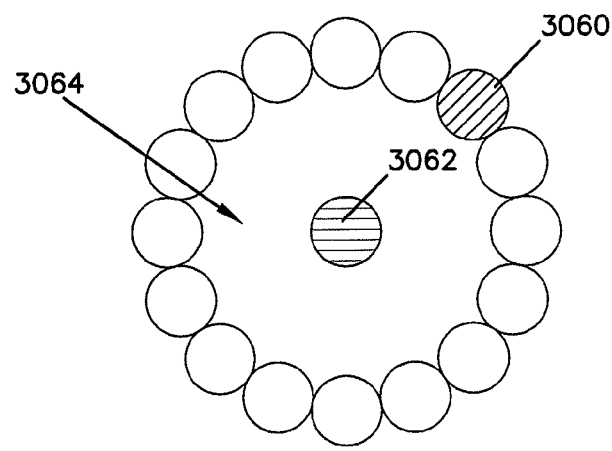
FIG. 80A shows a cross-sectional view of a first non-flat section of the braid illustrated in FIGS. 79A-79C.
Figure 80B:
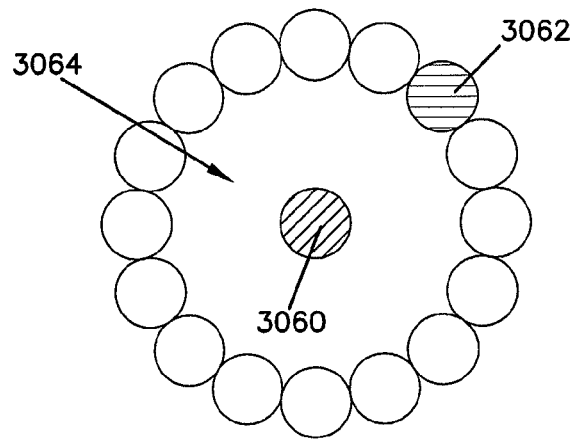
FIG. 80B shows a cross-sectional view of a second non-flat section of the braid illustrated in FIGS. 79A-79C.
Figure 80C:
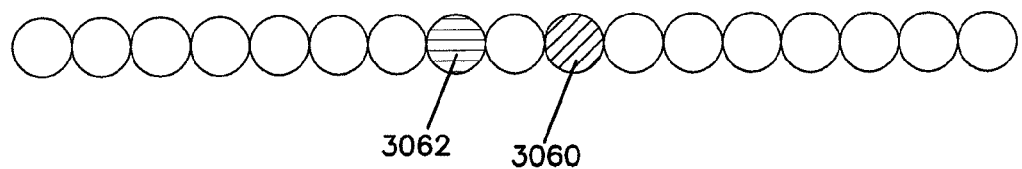
FIG. 80C show a cross-sectional view of a tape section 3136 of the braid illustrated in FIGS. 79A-79C.

FIGS. 80A-80C show cross-sectional views of the first non-flat section 3132, the second non-flat section 3134, and the non-flat section 3136, respectively, of the braid 108 illustrated in FIGS. 79A-79C. As described herein, the non-flat section of the braid 108 is tubular and has a generally round circumference. Other possible embodiments include flattened, oval, or other generally oblong cross-sectional shapes. The first color strand 3060 is braided into the outer wall of the first non-flat section 3132 (FIG. 80A) and runs through the flat section 3136 (FIG. 80C), and is subsequently transitioned to form a core 3064 of the second non-flat section 3134 (FIG. 80B). The second color strand 3062 forms a core 3064 of the first non-flat section 3132 (FIG. 80A), runs through the flat section 3136 (FIG. 80C), and is subsequently transitioned to be braided into the outer wall of the second non-flat section 3134 (FIG. 80B). In the example of FIG. 79C, the second color strand 3062 is white or non-distinguishing color from other 15 strands.

Figure 81:
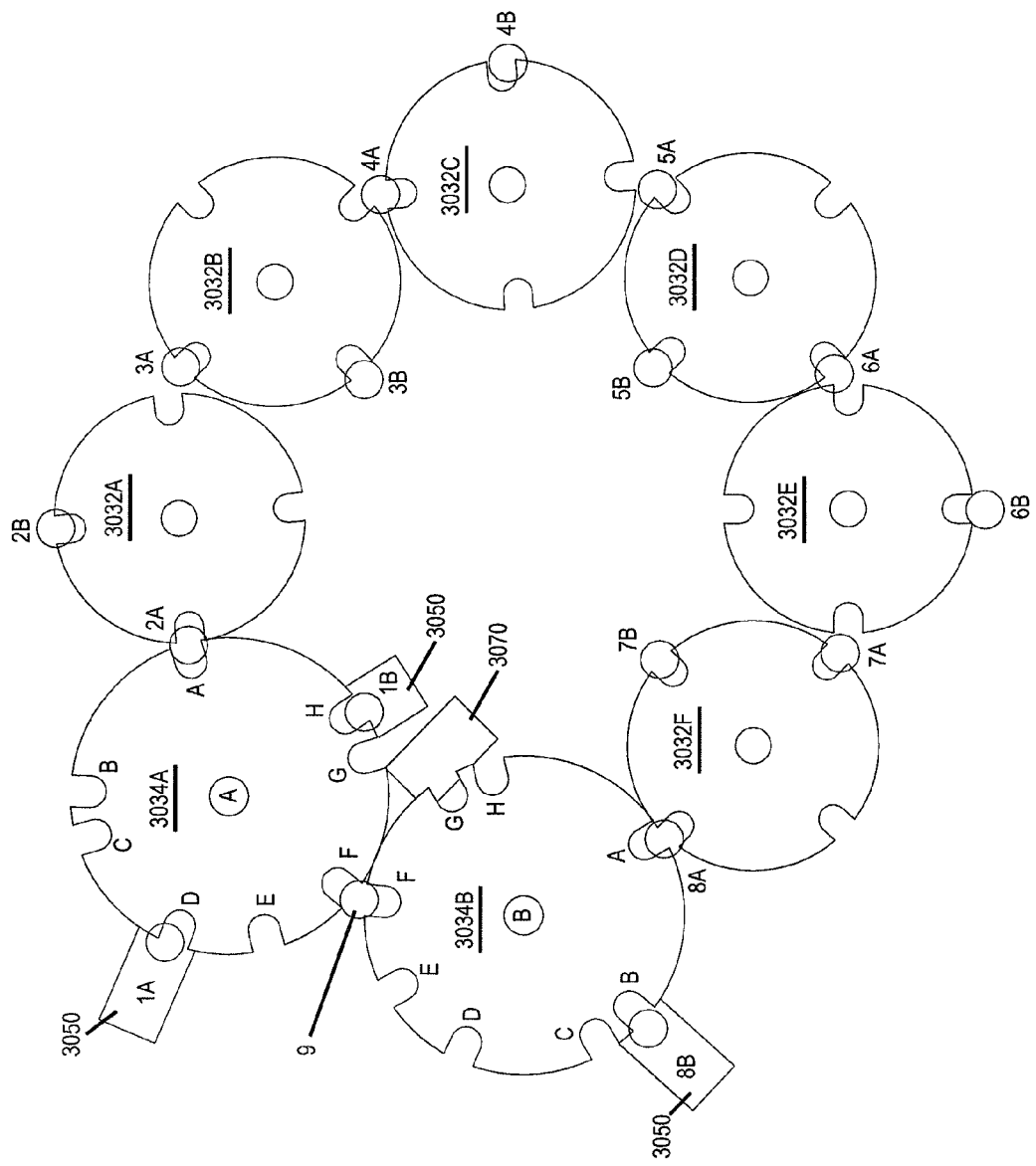
FIG. 81 illustrates example positions of the horn gear assemblies of the braiding assembly for braiding the flat section of the braid with a trace strand.
Figure 82:
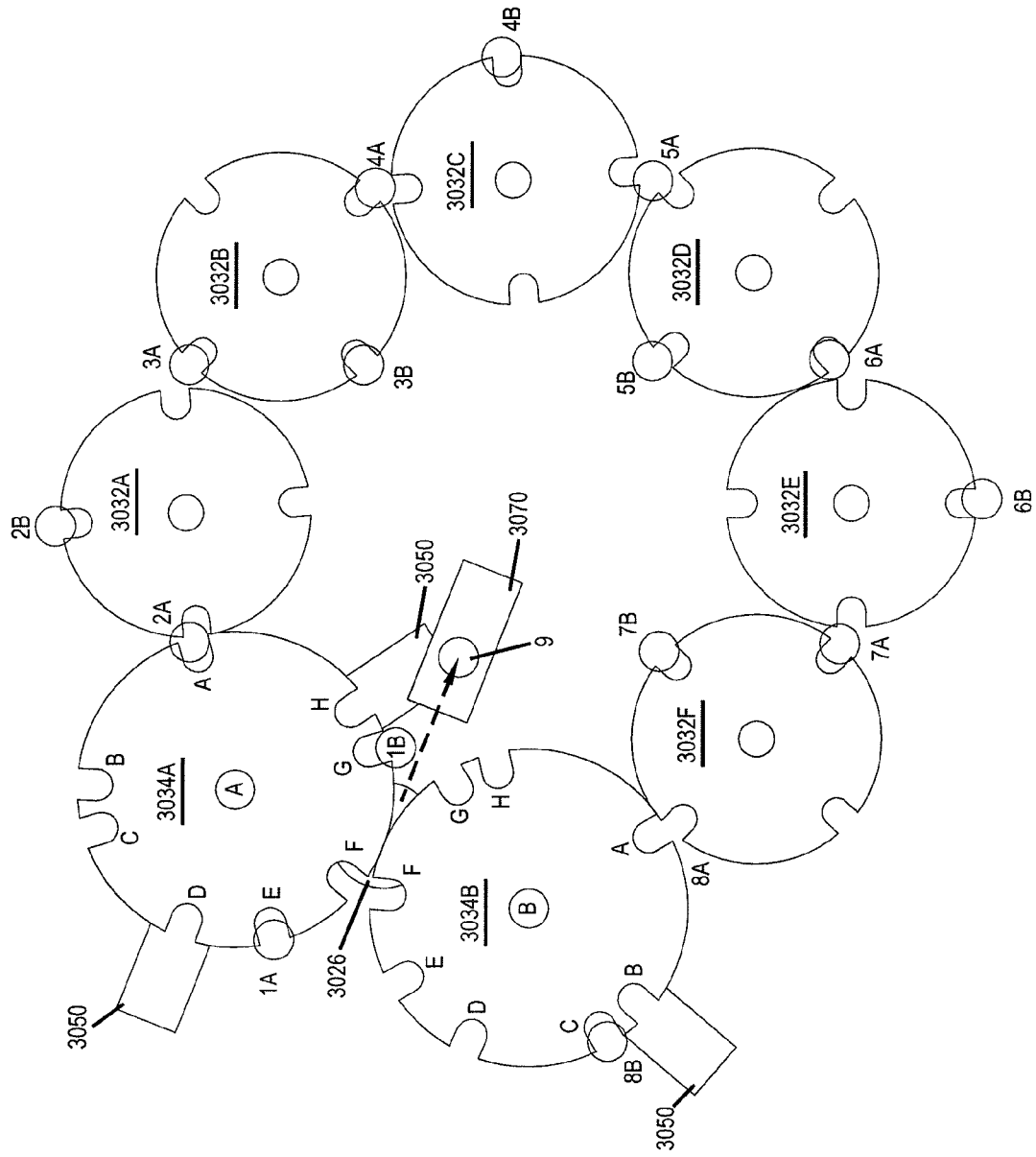
FIG. 82 illustrates example positions of the horn gear assemblies of the braiding assembly for braiding the non-flat section of the braid with a core.

FIGS. 81 and 82 illustrate an example operation of the braiding assembly 3002 for braiding a braid 108 with a trace strand 3060, as described in FIGS. 79-80. In particular, FIG. 81 illustrates example positions of the horn gear assemblies 3032A-3032F and 3034A-3034B of the braiding assembly 3002 for braiding the non-flat section of the braid 108 with a core 3064. FIG. 82 illustrates example positions of the horn gear assemblies 3032A-3032F and 3034A-3034B of the braiding assembly 3002 for braiding the flat section of the braid 108 with a trace strand 3060.

In at least some embodiments, the braiding assembly 3002 for braiding a braid 108 as illustrated in FIGS. 79-80 is operated similarly to the braiding assembly 3002 (FIGS. 69-71) for braiding a braid 108 as illustrated in FIG. 68. As many of the concepts and features are similar to the braiding assembly 3002 of FIGS. 69-72, the description for the braiding assembly 3002 as illustrated in FIGS. 69-72 is hereby incorporated by reference for this embodiment. Where like or similar features or elements are shown, the same reference numbers will be used where possible. The following description for this embodiment will be limited primarily to the differences from the braiding assembly 3002 of FIGS. 69-71.

In this embodiment, the braiding assembly 3002 includes additional bobbin carrier assembly 9, in addition to 16 bobbin carrier assemblies 1A, 1B, 2A, 2B, 3A, 3B, 4A, 4B, 5A, 5B, 6A, 6B, 7A, 7B, 8A, and 8B.

Referring to FIG. 81, when the braiding assembly 3002 operates to braid a flat section (e.g., the flat section 3132, 3134) of the braid 108, the bobbin carrier assembly 9 is carried by the horn gear assemblies 3032A-3032F and 3034A and 3034B, together with the other 16 bobbin carrier assemblies. The bobbin carrier assembly 9 is arranged such that, in the transition start position as depicted in FIG. 79A, the bobbin carrier assembly 9 is inserted in the slot 3044F of the second horn gear assemblies 3034A and 3034B. The bobbin carrier assembly 9 is guided by a core retraction mechanism 3070. In at least some embodiments, the core retraction mechanism 3070 for the bobbin carrier assembly 9 can be configured similarly to the retraction mechanism 3050 as described herein.

Referring to FIG. 82, when the braiding assembly 3002 operates to braid a non-flat section (e.g., the non-flat section 3136) of the braid 108 with a core 3064, the bobbin carrier assembly 9 is retracted from the horn gear assemblies 3032A-3032F and 3034A and 3034B, as illustrated in FIG. 82. The retracted bobbin carrier assembly 9 operates as the core 3064 of the non-flat section of the braid 108. In at least some embodiments, the core retraction mechanism 3070 can be used to selectively retract the bobbin carrier assembly 9.

In accordance with the principles of the present disclosure, many alternative embodiments and arrangements of the braiding assembly 3002 are possible. These alternative embodiments enable greater flexibility for defining different paths for the bobbin carrier assemblies and enable the braiding machine 100 to make a wider variety of different braid structures and configurations. Referring to FIG. 81, for example, the braiding assembly 3002 can include a track plate 3020 having an active track 3102 and a passive track 3202. In at least some embodiments, the active track 3102 is the same as the active track 3102 as illustrated in FIGS. 65 and 66. The passive track 3202 is similar to ones described in FIGS. 3A-3F. For example, the passive track 3202 is formed by grooves or slots 3204 defined in the track plate 3020. The passive track 3202 includes a first set of passive sub-tracks 3210A and 3210B, which are adjacent to the active sub-tracks 3108A and 3108B, a second set of passive sub-tracks 3210C and 3210D, which are adjacent to the active sub-tracks 3108C and 3108D, a third set of passive sub-tracks 3210E and 3210F, which are adjacent to the active sub-tracks 3108E and 3108F, and a fourth set of passive sub-tracks 3210G and 3210H, which are adjacent to the active sub-tracks 3110A and 3110B.

The passive sub-tracks 3210A-3210H correspond to passive horn gear assemblies 134A-134H, respectively, and guide the bobbin carrier assemblies 122 as they are propelled by the passive horn gear assemblies 134A-134H as explained herein. Additionally, the bobbin carrier assemblies 122 can selectively move between the active track 3102 and one or more of the passive tracks 3202 as described herein. A plurality of gates 3026 are arranged between the active and passive tracks 3102 and 3202 for selective transition of the bobbin carrier assemblies 122 therebetween, as described herein. With the passive sub-tracks 3210A-3210H, braids with a variety of color pattern changes can be produced as described herein.

Figure 83:
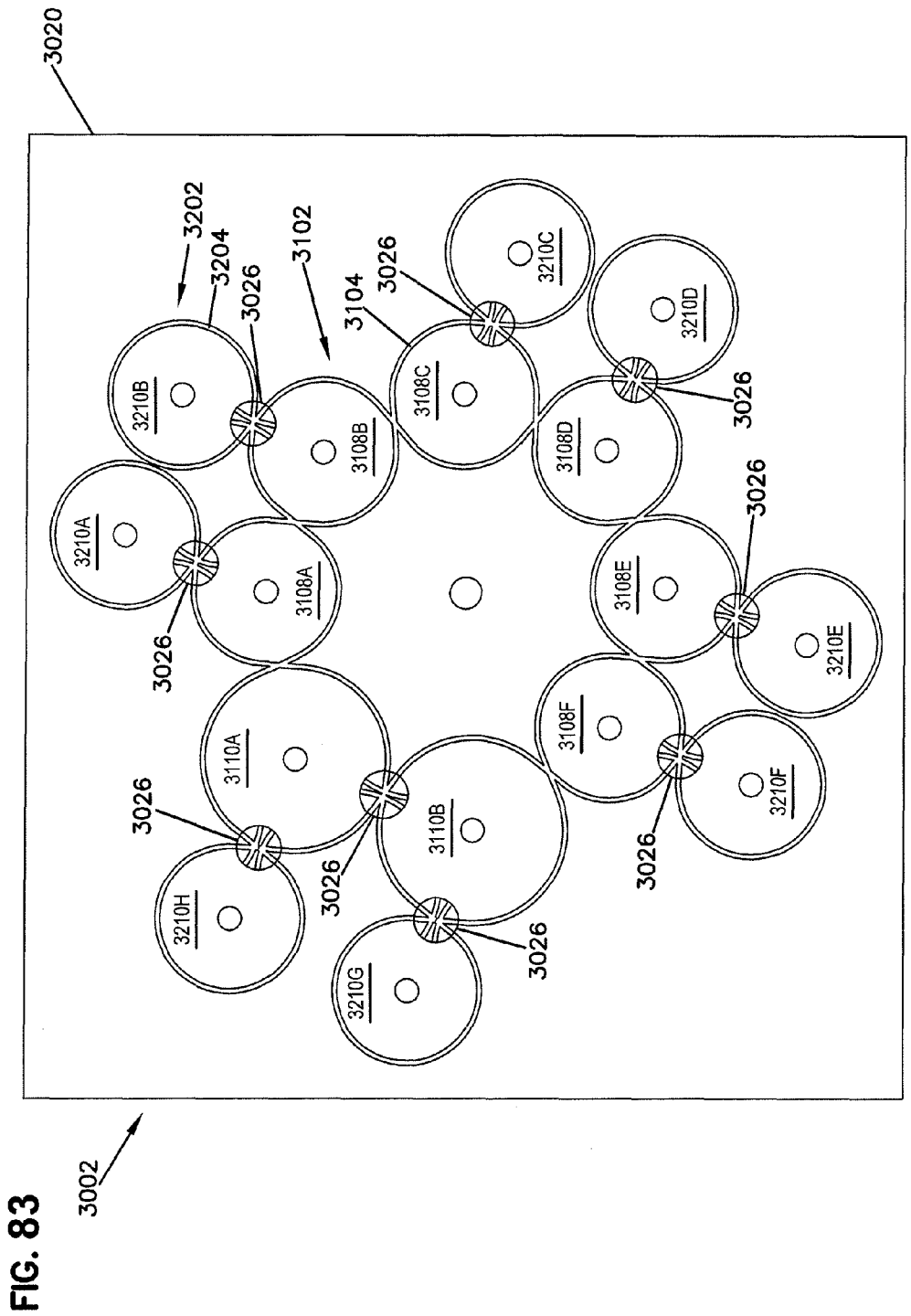
FIG. 83 illustrates an alternative embodiment of the braiding assembly with a passive track.

Other embodiments are possible in the braiding assembly 3002 with the passive track 3202. As illustrated in FIG. 83, for example, configuration of the passive track 3202 can be modified similarly to ones described in FIGS. 3B-3F.

As explain herein, the braiding machine 100 in accordance with the present disclosure has various advantages over other braiding machines. The braiding machine 100 can use a different number of bobbin carrier assemblies with a predetermined number of horn gear assemblies. In the illustrated examples, the braiding machine 100 can use eight horn gear assemblies to carry 16 or 17 bobbin carrier assemblies. In other embodiments, the eight horn gear assemblies of the braiding machine 100 can guide different numbers of bobbin carrier assemblies. In contrast, other braiding machines are designed to use a number of bobbin carrier assemblies with the same number of horn gear assemblies. For example, the other braiding machines carries either bobbin carriers with eight horn gear assemblies, or 16 bobbin carriers with 16 horn gear assemblies. Such other braiding machines can be designed to perform a process for swapping two bobbin carrier assemblies for changing shapes (e.g., non-flat and flat sections) and/or patterns of a braid. For the swapping process, the braiding machines at least two different speed profiles for the horn gear assemblies thereof. For example, at least one of the horn gear assemblies can have a constant speed profile and an acceleration/deceleration profile to swap two bobbin carriers. Such different speed profiles require an actuation system with a higher capacity, such as a motor with a higher capacity. Further, the changing speed of horn gear assemblies in the acceleration/deceleration profile causes associated bobbin carriers to be subjected to a centrifugal force that pulls out the bobbin carriers from the horn gear assemblies, thereby increasing a risk that the bobbin carriers are disengaged from the horn gear assemblies. In contrast, the braiding machine 100 of the present disclosure does not need a process for swapping bobbin carriers during braiding and is configured to maintain a constant speed of the horn gears throughout the braining process.

The braiding machine 100 of the present disclosure is capable of braiding a braid with at least 16 strands in a 1-over-1 configuration, using 8 horn gear assemblies. The braiding machine 100 can thus use strands having a larger diameter to make a braid having a smaller diameter, compared to a braid that is produced by other braiding machines (as described above) and is not truly in a 1-over-1 configuration. Thus, a braid produced by the braiding machine 100 of the present disclosure can have a thicker wall than other braids. For example, a 16-strand braid with size #2 that is braided by the other braiding machines can use 8 strands with 55 dtex and 8 strands with 110 dtex to produce a braid diameter of about 0.024 inches. In contrast, a 16-strand braid with size #2 that is braided by the braiding machine 100 of the present disclosure can use 16 strands with 100 dtex to produce a braid diameter of about 0.024 inches. As such, the braiding machine 100 can perform tight braiding to improve the strength of the braid.

The braiding machine 100 of the present disclosure can also produce a braid with a core and change the configuration of the core in the braid, as illustrated herein. In contrast, the other braiding machines are not configured to selectively change the configuration of a core in a braid. Further, the braiding machine 100 requires one track distance for full rotation while the other braiding machines require two or more time a track distance for full rotation.

The various examples described above are provided by way of illustration only and should not be construed to limit the scope of the present disclosure or the following claims. Those skilled in the art will readily recognize various modifications and changes that may be made without following the example embodiment illustrated and described herein, and without departing from the true spirit and scope of the present disclosure and claims.

What is claimed is:

1. A surgical braid comprising:
   two non-flat sections;
   a tape section, tape section being generally flat, the tape section having a determined number of strands extending from one of the non-flat sections to the other non-flat section; and
   the tape section the comprising a single braid, and the two non-flat sections and the tape section being formed with a continuous and bifurcation-less braid.

2. The surgical braid of claim 1 wherein:
   each non-flat section comprises a circumference, the circumference having a generally non-flat shape; and
   the non-flat shape is a generally oval shape.

3. The surgical braid of claim 2 wherein each non-flat section is non-tubular.

4. The surgical braid of claim 3 wherein each non-flat section is coreless.

5. The surgical braid of claim 2 wherein the tape section is non-tubular.

6. The surgical braid of claim 1 further comprising:
   a plurality of strands braided together;
   first and second transition portions, the first transition portion between one non-flat section and the tape section, the second transition portion between the other non-flat section and the tape section;
   the tape section comprising first and second edge portions extending between the first and second transition portions, the first edge portion oppositely disposed from the second edge portion; and
   the plurality of strands being interlaced into a substantially uniform pattern within the tape section, the substantially uniform pattern extending between the first and second transition portions and between the first and second end portions.

7. The surgical braid of claim 6 further comprising:
   first and second end portions, the first end portion being oppositely disposed from the second end portion; and
   two or more of the strands being continuously braided between the first and second end portions.

8. The surgical braid of claim 7 wherein the tape section is spineless.

9. A surgical braid comprising:
   a plurality of strands comprising a first trace strand, the first trace strand comprising a color distinguished from a color of two or more other strands in the plurality of strands;
   two non-flat sections, each non-flat section has a generally tubular wall and defines a channel;
   a tape section, the tape section being generally flat and being positioned between the two non-flat sections, the tape section comprising a single braid, and the two non-flat sections and the tape section being formed with a continuous and gap-less braid; and
   the first trace strand is braided into the generally tubular wall of one non-flat section, is braided into the substantially uniform pattern of the tape section, and extends through the channel of the other non-flat section.

10. The surgical braid of claim 9 wherein:
    the plurality of strands comprises a second trace strand, the second trace strand comprising a color distinguished from the color of the two or more other strands in the plurality of strands; and
    the second trace strand extends through the channel of the one non-flat section, is braided into the substantially uniform pattern of the tape section, and is braided into the generally tubular wall of the other non-flat section.

11. The surgical braid of claim 10, wherein the color of the first trace strand is different than the color of the second trace strand, and the colors of the trace strands are selected from the group consisting essentially of: blue, green, violet, brown, purple, black, or white.

12. The surgical braid of claim 10 wherein the plurality of strands comprises n strands, each of the two non-flat sections comprises n−1 strands braided into the tubular walls, and the tape section comprises n strands braided into the substantially uniform pattern, wherein n is a whole number.

13. The surgical braid of claim 12 wherein n equals 17.

14. The surgical braid of claim 1 further comprising more than two non-flat sections and more than one tape section, the non-flat sections and the tape sections alternating along the length of the surgical braid.

15. A surgical braid comprising:
    a plurality of strands braided into two non-flat sections and a tape section, the tape section being generally flat and positioned between the two non-flat sections;
    first and second end portions, the first end portion being oppositely disposed from the second end portion, two or more of the strands being continuously braided between the first and second end portions;
    first and second transition portions, the first transition portion between one non-flat section and the tape section, the second transition portion between the other non-flat section and the tape section;
    the tape section comprising first and second edge portions extending between the first and second transition portions, the first edge portion oppositely disposed from the second edge portion; and
    the plurality of strands being interlaced into a single braid and a substantially uniform pattern as they pass through the tape section, the single braid and substantially uniform pattern extending between the first and second transition portions and between the first and second end portions forming a single flat braid between the two non-flat sections.

16. The surgical braid of claim 15 wherein the plurality of strands comprises n strands, each of the two non-flat sections comprises n–1 strands braided into tubular walls, and the tape section comprises n strands braided into the substantially uniform pattern, wherein n is a whole number.

17. The surgical braid of claim 15 wherein each non-flat section is coreless.

18. The surgical braid of claim 15 wherein each non-flat section comprises a circumference, the circumference being generally out-of-round.

19. The surgical braid of claim 15 further comprising more than two non-flat sections and more than one tape section, the non-flat sections and the tape sections alternating along the length of the surgical braid.

\* \* \* \* \*

UNITED STATES PATENT AND TRADEMARK OFFICE
CERTIFICATE OF CORRECTION

PATENT NO. : 9,610,077 B2
APPLICATION NO. : 15/063215
DATED : April 4, 2017
INVENTOR(S) : Brock P. Allen Page 1 of 1

It is certified that error appears in the above-identified patent and that said Letters Patent is hereby corrected as shown below:

In Claim 1, Line 3, "a tape section, tape section" should be "a tape section, the tape section"

In Claim 1, Line 6, "the tape section the comprising" should be "the tape section comprising"

Signed and Sealed this
Thirty-first Day of July, 2018

Andrei Iancu
*Director of the United States Patent and Trademark Office*